US010053706B2

(12) United States Patent
Siegfried et al.

(10) Patent No.: US 10,053,706 B2
(45) Date of Patent: Aug. 21, 2018

(54) PARENTAL RNAI SUPPRESSION OF CHROMATIN REMODELING GENES TO CONTROL COLEOPTERAN PESTS

(71) Applicants: Dow AgroSciences LLC, Zionsville, IN (US); The Board of Regents of the University of Nebraska, Lincoln, NE (US)

(72) Inventors: Blair D. Siegfried, Lincoln, NE (US); Kenneth E. Narva, Zionsville, IN (US); Kanika Arora, Indianapolis, IN (US); Sarah E. Worden, Indianapolis, IN (US); Chitvan Khajuria, Chesterfield, MO (US); Elane Fishilevich, Indianapolis, IN (US); Nicholas P. Storer, Kensington, MD (US); Meghan Frey, Greenwood, IN (US); Ronda L. Hamm, Carmel, IN (US); Ana Velez, Lincoln, NE (US)

(73) Assignees: Dow AgroSciences LLC, Indianapolis, IN (US); The Board of Regents of the University of Nebraska, Lincoln, NE (US)

( * ) Notice: Subject to any disclaimer, the term of this patent is extended or adjusted under 35 U.S.C. 154(b) by 92 days.

(21) Appl. No.: 14/971,515

(22) Filed: Dec. 16, 2015

(65) Prior Publication Data

US 2016/0222408 A1 Aug. 4, 2016

Related U.S. Application Data

(60) Provisional application No. 62/092,747, filed on Dec. 16, 2014.

(51) Int. Cl.

| | |
|---|---|
| ***C12N 15/82*** | (2006.01) |
| ***C12N 15/113*** | (2010.01) |
| ***A01N 57/16*** | (2006.01) |
| ***A01N 63/02*** | (2006.01) |

(52) U.S. Cl.

CPC ......... *C12N 15/8286* (2013.01); *A01N 57/16* (2013.01); *A01N 63/02* (2013.01); *C12N 15/113* (2013.01); *C12N 15/8218* (2013.01); *C12N 2310/14* (2013.01)

(58) Field of Classification Search

CPC .................................................. C12N 15/8286

USPC .......................................................... 800/279

See application file for complete search history.

(56) References Cited

U.S. PATENT DOCUMENTS

| | | | | |
|---|---|---|---|---|
| 2009/0188005 | A1* | 7/2009 | Boukharov ........ | C07K 14/4354 800/279 |
| 2012/0174258 | A1 | 7/2012 | Narva et al. | |
| 2013/0058890 | A1 | 3/2013 | Raemaekers et al. | |
| 2013/0097730 | A1 | 4/2013 | Narva | |
| 2016/0230186 | A1 | 8/2016 | Baum | |

FOREIGN PATENT DOCUMENTS

| | | |
|---|---|---|
| WO | 2007035650 | 3/2007 |

OTHER PUBLICATIONS

Thomas et al. 2001, The Plant Journal 25(4):417-425.*

Yibrah et al. 1993, Hereditas 118:273-2890.*

Thomas et al.; 2001; Plant J. 25:417-425.

Gkhajuria, Chitvan et al., ‘Parental RNA interference of genes involved in embryonic development of the western corn rootworm, *Diabrotica virgifera virgifera* LeConte’, Insect Biochemistry and Molecular Biology, Epub. May 22, 2015, vol. 63, pp. 54-62.

Ho, Lena et al., “Chromatin remodelling during development,”, Nature, Jan. 28, 2010, pp. 474-484, vol. 463, No. 7280 (NIH Public Access Author Manuscript Version internal pp. 1-24).

Mito, Taro et al., “Kruppel acts as a gap gene regulating expression of hunchback and even-skipped in the intermediate germ cricket *G1yllus bimaculatus,*” Developmental Biology, Epub. Apr. 17, 2006, vol. 294, No. 2, pp. 471-481.

NCBI, GenBank accession No. XM_003742362.1 (Jun. 14, 2012).

NCBI, GenBank accession No. XM_007547345.1 (Apr. 22, 2014).

Search Report and Written Opinion for PCT/US2015/066082, dated Apr. 15, 2016.

Search Report and Written Opinion for PCT/US2015/066134, dated Apr. 22, 2016.

* cited by examiner

*Primary Examiner* — Li Zheng

(74) *Attorney, Agent, or Firm* — Sean M. Russell; Magleby Cataxinos & Greenwood

(57) ABSTRACT

This disclosure concerns nucleic acid molecules and methods of use thereof for control of hemipteran pests through RNA interference-mediated inhibition of target coding and transcribed non-coding sequences in hemipteran pests. The disclosure also concerns methods for making transgenic plants that express nucleic acid molecules useful for the control of hemipteran pests, and the plant cells and plants obtained thereby.

31 Claims, 11 Drawing Sheets

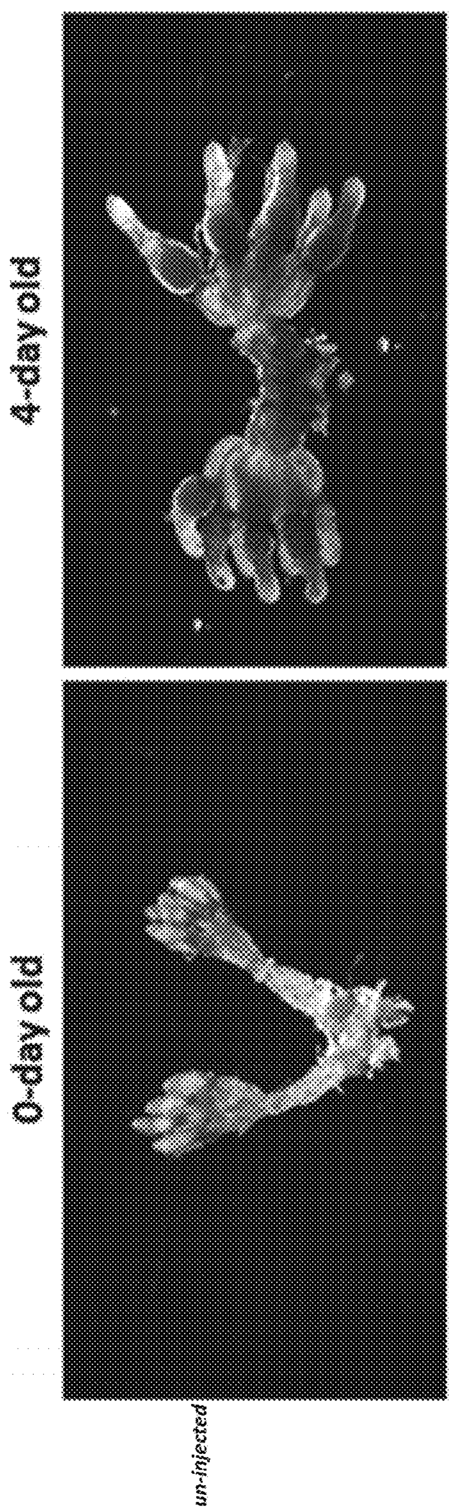
FIG 7A
FIG 7B
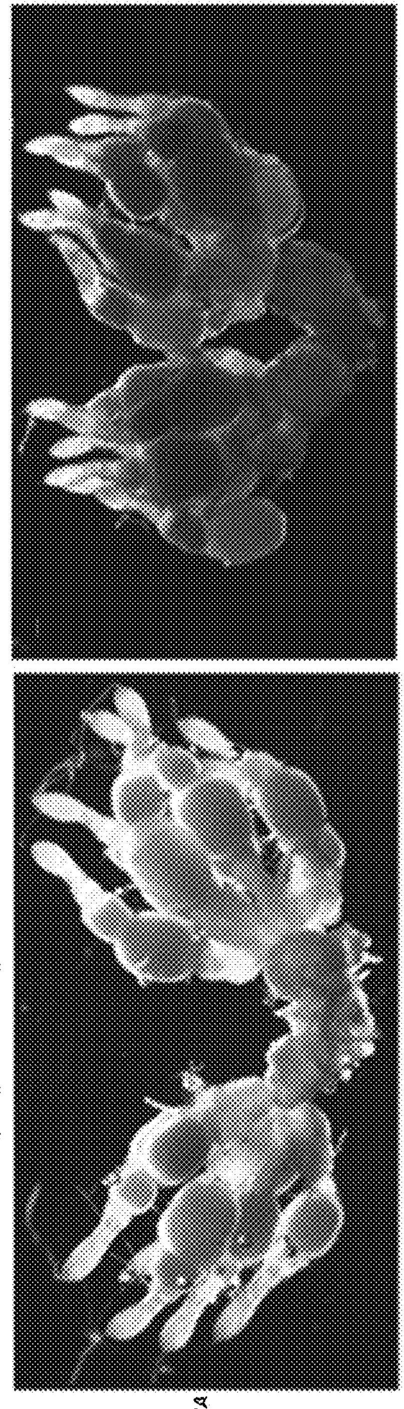
FIG 7C
FIG 7D

*brahma* dsRNA
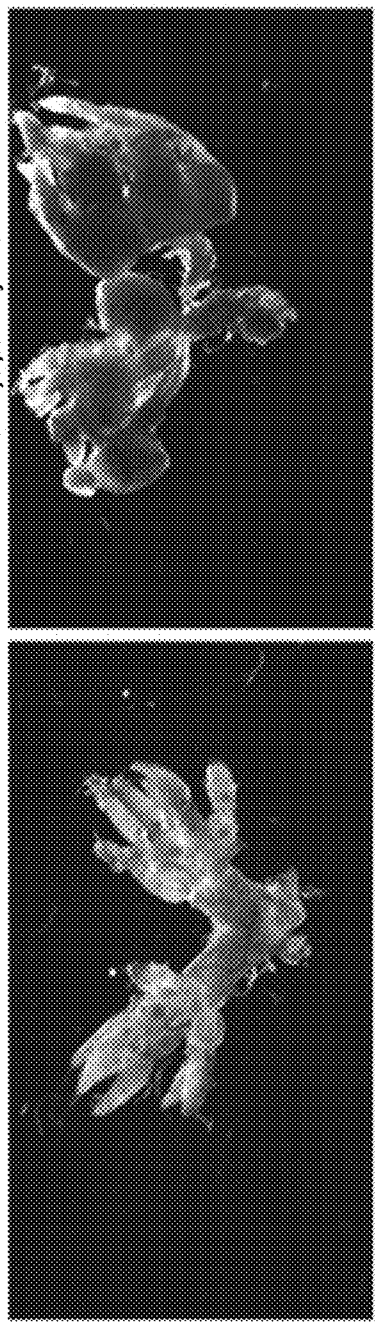
FIG 7E
FIG 7F
*mi-2* dsRNA
9 days post injection
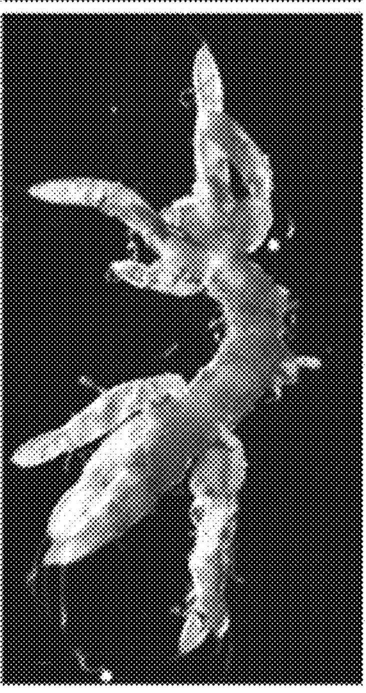
FIG 7G
14 days post injection
2 mm
FIG 7H

SEQUENCE LISTING

```
<160> NUMBER OF SEQ ID NOS: 91

<210> SEQ ID NO 1
<211> LENGTH: 4958
<212> TYPE: DNA
<213> ORGANISM: Euchistus heros

<400> SEQUENCE: 1

cttggctagt actcttccgt gacgtcacgt tcgccatatt gttagagttt gtcttgcctc     60

tggatagtta tgttgattct ttttaagtga ttttgaagat ttcctgacca ttttatcacg    120

aaaaactatt ttaaacagcg ctattgctcc ttataatacg tgtgattcaa caacgatgga    180

cggagacagc ggtggtatgg cgagcccttc gccacagcct cagtcgtcac caatgccccc    240

tccacaagct ccatcaccta tgggcccgcc gcagggcgcc ccatcgccaa tgccccccttc   300

taaccaacag gcggcctcac caatgggtcc accgcaccac ccccacagcc cgacaggtta    360

ccaaggaggg atgccacaca tgaatggacc aaatggtgtt cctcctggta tgcagcaggc    420

tactcaaaca tttcagcctc atcagcaatt gccaccccac cagcaaccac caatgcagac    480

tgctcctggt gggcctgcta gtggtggagg acaagaaaat cttagcgctc tccagcgtgc    540

aatagattct atggaagaga aagggcttca ggaagatcca cgttactcgc agctgcttgc    600

gttgagggca aggcatgcca acatggaacc tccggttagg cctccatctc agcttgttgg    660

gggtgggttc agcggtgagg gtggtgcccc tcctcctgct aaacacagct tcagcgcgaa    720

ccaactgcaa caacttcgag tgcagatcat ggcgtatcgc ctacttgcta ggaaccaacc    780

tctttcccag cagctagctt tggctgtgca aggcaaacgc ctcgacagcc ctggcgagtc    840

caactaccag catcctccta gtgaaggagc aggaggtgtt ggtggagaag gaagtggaga    900

cgggggatcg tcgaacggcc tgatgacgca gccgatgcgt gccccatgcc cccctggtgg    960

ccagcccccca acggcctcac cgatgacagg ccagatggca cctcctactg ggccagctcc  1020

tgtaaggcca cctcctcccg gtgtgtctcc tacacctccg cgccctcctc agcaggttcc   1080

tggtgctccg ggggccccac aaccaaagca aaatagggtt accaccatgc caagaccgca   1140

tggtttagat cccattctta ttctccagga aagagagaat agagtagccg ctaggattgt   1200

acataggatg gaagaattat caaatttacc agctacgatg cctgaagacc ttcgaataaa   1260

agcgcagata gaacttaggg ccttgagggt acttaacttc caaaggcaat taagagcaga   1320

ggtgatagct tgtactagac gcgatacaac attagaaaca gctgtaaatg tgaaagctta   1380

taaacgaacg aagaggcaag gcttacggga agccagagct acggaaaagc ttgaaaaaca   1440

acagaaactt gagacagaaa ggaagaagag acaaaaacac caggaatatc tgagcactat   1500
```

-continued

```
attgcaacat tgcaaagact tcaaagaatt ccatagaaat aatgttgcta aagttggtag   1560
attaaataag gctgtgatga attaccatgc gaatgccgag cgtgaacaga agaaagagca   1620
agaaaggata gaaaaagaac gtatgagaag gcttatggct gaggatgaag agggttacag   1680
gaaactgatt gatcagaaaa aagataagag attggcattc cttctttcac aaactgatga   1740
atatattgcc aatcttactg aaatggtgaa gcagcataaa atggaacaac agcgtaagca   1800
ggaacaagaa gagcaacaaa aacggaagag gaaaaagaaa aagaagaata gggaaggaga   1860
tccagatgat gaaagctctc agatgtcaga tttacatgtt agcgttatag aagcagcaac   1920
tggtcggcag ctgacggggg aggatgctcc attggccagc cagcttggga gctggttgga   1980
ggcacacccg ggctgggagc ctttggaaga tagcgaagat gaagatgatg aagaggacag   2040
cgacgaggaa ggtgatgata acagtagatc aaaaggtggt ttttcaatga taggaaaaga   2100
tgaagctgat agcaagttat ctgttgaaga cgaagctcga gaaatgataa agaaagcgaa   2160
gattgaagat gatgaataca agaacacgac cgaagaacat acatactaca gcatcgctca   2220
caccgtgcat gaaattgtca ccgaacaagc ttcaatcatg attaacggta aattgaaaga   2280
atatcaaatt aaaggtcttg aatggttggt ttctttatac aacaacaact tgaatggaat   2340
cctcgccgac gagatgggcc ttggcaagac aattcaaaca ataggtctca ttacttattt   2400
gatggagaag aagaaagtaa atggtcctta cctcattatt gttcctctgt caacattatc   2460
caattgggtt ttggaattcg agaaatgggc tccttcagtg tttgtggtag cttataaagg   2520
ttctcctgca atgaggagaa ctttacaatc acagatgcgc tcgacgaagt tcaatgtcct   2580
gctcacgacc tacgagtatg tcatcaagga caaggcagta cttgcaaagt tgcattggaa   2640
gtacatgata atcgacgagg gacacaggat gaaaaaccac cattgtaagc tgacgcaggt   2700
gctgaacacc cattatttgg cacctcaccg cctccttctc acgggcacac ctctccagaa   2760
caaactacct gagctctggg ctcttctaaa ctttctcctc ccgtccatct tcaagtcgtg   2820
ttctacgttt gagcaatggt tcaatgcacc atttgctacc actggagaaa aggttgagtt   2880
gaatgaggaa gaaacaattt tgattatcag gcgtttacat aaggtccttc gacctttcct   2940
ccttcgtcga ctgaaaaagg aagtcgaaag tcagttgcca gagaaaattg aatacatcgt   3000
caagtgtgat atgtctggtc tccaacgtgt actttatagg cacatgcaga gtaaaggagt   3060
cctgcttacc gatggttctg agaagggcaa gcagggtaaa ggaggagcta aagcgctaat   3120
gaacacgatc gtccaattga ggaagctttg caatcatcct ttcatgttcc atcatattga   3180
agaaaaatat tgtgatcacg ttggccagaa caacgttgtc acagggcctg atctgttccg   3240
agtttctggt aaatttgaat tcctcgatcg tatattgcca aaactgaagg ccacgagcca   3300
tagggtactt cttttctgtc aaatgactca gctgatgacc atcatggagg attatttgtc   3360
ttggagaggg ttctcctacc ttcgtcttga tggtacgacc aaatctgaag accgaggaga   3420
tcttctgaaa aaattcaaca atccagaaag tgaatatttt attttcttgc tctcaaccag   3480
agctggaggt ctcggattga acttacaggc tgcagatact gtcattatat ttgattcaga   3540
ttggaaccct catcaggatt tacaagctca agacagagct cataggattg gacagcaaaa   3600
cgaagttcgt gttttgcggc taatgacagt aaattctgtt gaggagcgta ttcttgcagc   3660
tgctcggtac aagctgaata tggatgagaa agtcattcag gctggtatgt ttgaccagaa   3720
atctacagga accgagaggc agaaatttct gcaaaacatc cttcatcaag atgatgcaga   3780
tgatgaggaa aatgaagttc cagatgatga aatggttaat cgtatgattg cgcgaacaga   3840
agatgaattc aacctcttcc agaaaatcga tttagaaagg aggagggaag aggctaaact   3900
```

```
tggacctaac aggaagtcaa ggcttgtaga agaggcggaa ttacctgact ggcttgtaaa   3960
gaatgacgat gagattgaga agtggactta tgaagaaacc gaggtccaaa tgggaagagg   4020
taataggcag aggaaggaag tagattatac agatagtttg actgaaaaag aatggttaaa   4080
ggccattgat gacaatgtag atgattttga tgacgatgaa gaggaagagg taaaaacaaa   4140
gaaaagaggc aagagaagaa gaaggggaga ggatgatgaa gaagatgcaa gtacttcaaa   4200
gagaaggaaa tattctccat ctgaaaacaa actgaggagg cgtatgcgta acctcatgaa   4260
cattgttgtt aagtatactg acagtgactc gagagtactc agtgaaccat tcatgaaact   4320
tccctctcgc cataagtacc cagactacta tgagttgatc aagaaaccta tagacatcaa   4380
gaggatattg gccaaagtag aagagtgtaa atatgctgac atggatgaat tagaaaagga   4440
ttttatgcaa ctttgtaaaa atgctcagac atacaatgag gaggcctcat tgatctatga   4500
agattcgata gtattagaaa gtgttttctc taatgctcgt caaaaagtag agcaggataa   4560
tgattcagat gatgatgaaa gtaaaggtga ccaagaagat gctgcatcag acacttcatc   4620
cgtcaaaatg aaattgaaac taaagcctgg gaggacccga gggagtggag ctggtggtaa   4680
aaggaggaga agaaaatata tctctgaaga tgaagacgaa gaccatagcg aagtttcctt   4740
aatgtaatgc ctcttcactg tcctttgtaa ttattagttt tcatcggtgt tcggtacctg   4800
tcagtcaagg gagaagctaa gctttttagt tgactattga agaatttagg actgagttct   4860
gtttttgttt tttttgtttg ttttttttg gataaatgta tttaatagat aaaatgtttc   4920
gcttatatat atatttttta ctggttttgt aattggcc                          4958
```

<210> SEQ ID NO 2
<211> LENGTH: 1523
<212> TYPE: PRT
<213> ORGANISM: Euchistus heros

<400> SEQUENCE: 2

```
Met Asp Gly Asp Ser Gly Gly Met Ala Ser Pro Ser Pro Gln Pro Gln
1               5                   10                  15

Ser Ser Pro Met Pro Pro Pro Gln Ala Pro Ser Pro Met Gly Pro Pro
            20                  25                  30

Gln Gly Ala Pro Ser Pro Met Pro Pro Ser Asn Gln Gln Ala Ala Ser
        35                  40                  45

Pro Met Gly Pro Pro His His Pro His Ser Pro Thr Gly Tyr Gln Gly
    50                  55                  60

Gly Met Pro His Met Asn Gly Pro Asn Gly Val Pro Pro Gly Met Gln
65                  70                  75                  80

Gln Ala Thr Gln Thr Phe Gln Pro His Gln Gln Leu Pro Pro His Gln
                85                  90                  95

Gln Pro Pro Met Gln Thr Ala Pro Gly Gly Pro Ala Ser Gly Gly Gly
            100                 105                 110

Gln Glu Asn Leu Ser Ala Leu Gln Arg Ala Ile Asp Ser Met Glu Glu
        115                 120                 125

Lys Gly Leu Gln Glu Asp Pro Arg Tyr Ser Gln Leu Leu Ala Leu Arg
    130                 135                 140

Ala Arg His Ala Asn Met Glu Pro Pro Val Arg Pro Pro Ser Gln Leu
145                 150                 155                 160

Val Gly Gly Gly Phe Ser Gly Glu Gly Gly Ala Pro Pro Pro Ala Lys
                165                 170                 175

His Ser Phe Ser Ala Asn Gln Leu Gln Gln Leu Arg Val Gln Ile Met
```

```
            180                 185                 190

Ala Tyr Arg Leu Leu Ala Arg Asn Gln Pro Leu Ser Gln Gln Leu Ala
        195                 200                 205

Leu Ala Val Gln Gly Lys Arg Leu Asp Ser Pro Gly Glu Ser Asn Tyr
    210                 215                 220

Gln His Pro Pro Ser Glu Gly Ala Gly Gly Val Gly Gly Glu Gly Ser
225                 230                 235                 240

Gly Asp Gly Gly Ser Ser Asn Gly Leu Met Thr Gln Pro Met Arg Ala
                245                 250                 255

Pro Cys Pro Pro Gly Gly Gln Pro Pro Thr Ala Ser Pro Met Thr Gly
            260                 265                 270

Gln Met Ala Pro Pro Thr Gly Pro Ala Pro Val Arg Pro Pro Pro Pro
        275                 280                 285

Gly Val Ser Pro Thr Pro Pro Arg Pro Pro Gln Gln Val Pro Gly Ala
    290                 295                 300

Pro Gly Ala Pro Gln Pro Lys Gln Asn Arg Val Thr Thr Met Pro Arg
305                 310                 315                 320

Pro His Gly Leu Asp Pro Ile Leu Ile Leu Gln Glu Arg Glu Asn Arg
                325                 330                 335

Val Ala Ala Arg Ile Val His Arg Met Glu Glu Leu Ser Asn Leu Pro
            340                 345                 350

Ala Thr Met Pro Glu Asp Leu Arg Ile Lys Ala Gln Ile Glu Leu Arg
        355                 360                 365

Ala Leu Arg Val Leu Asn Phe Gln Arg Gln Leu Arg Ala Glu Val Ile
    370                 375                 380

Ala Cys Thr Arg Arg Asp Thr Thr Leu Glu Thr Ala Val Asn Val Lys
385                 390                 395                 400

Ala Tyr Lys Arg Thr Lys Arg Gln Gly Leu Arg Glu Ala Arg Ala Thr
                405                 410                 415

Glu Lys Leu Glu Lys Gln Gln Lys Leu Glu Thr Glu Arg Lys Lys Arg
            420                 425                 430

Gln Lys His Gln Glu Tyr Leu Ser Thr Ile Leu Gln His Cys Lys Asp
        435                 440                 445

Phe Lys Glu Phe His Arg Asn Asn Val Ala Lys Val Gly Arg Leu Asn
    450                 455                 460

Lys Ala Val Met Asn Tyr His Ala Asn Ala Glu Arg Glu Gln Lys Lys
465                 470                 475                 480

Glu Gln Glu Arg Ile Glu Lys Glu Arg Met Arg Arg Leu Met Ala Glu
                485                 490                 495

Asp Glu Glu Gly Tyr Arg Lys Leu Ile Asp Gln Lys Lys Asp Lys Arg
            500                 505                 510

Leu Ala Phe Leu Leu Ser Gln Thr Asp Glu Tyr Ile Ala Asn Leu Thr
        515                 520                 525

Glu Met Val Lys Gln His Lys Met Glu Gln Gln Arg Lys Gln Glu Gln
    530                 535                 540

Glu Glu Gln Gln Lys Arg Lys Arg Lys Lys Lys Lys Lys Asn Arg Glu
545                 550                 555                 560

Gly Asp Pro Asp Asp Glu Ser Ser Gln Met Ser Asp Leu His Val Ser
                565                 570                 575

Val Ile Glu Ala Ala Thr Gly Arg Gln Leu Thr Gly Glu Asp Ala Pro
            580                 585                 590

Leu Ala Ser Gln Leu Gly Ser Trp Leu Glu Ala His Pro Gly Trp Glu
        595                 600                 605
```

```
Pro Leu Glu Asp Ser Glu Asp Glu Asp Asp Glu Glu Asp Ser Asp Glu
    610                 615                 620

Glu Gly Asp Asp Asn Ser Arg Ser Lys Gly Gly Phe Ser Met Ile Gly
625                 630                 635                 640

Lys Asp Glu Ala Asp Ser Lys Leu Ser Val Glu Asp Glu Ala Arg Glu
                645                 650                 655

Met Ile Lys Lys Ala Lys Ile Glu Asp Asp Glu Tyr Lys Asn Thr Thr
            660                 665                 670

Glu Glu His Thr Tyr Tyr Ser Ile Ala His Thr Val His Glu Ile Val
        675                 680                 685

Thr Glu Gln Ala Ser Ile Met Ile Asn Gly Lys Leu Lys Glu Tyr Gln
    690                 695                 700

Ile Lys Gly Leu Glu Trp Leu Val Ser Leu Tyr Asn Asn Asn Leu Asn
705                 710                 715                 720

Gly Ile Leu Ala Asp Glu Met Gly Leu Gly Lys Thr Ile Gln Thr Ile
                725                 730                 735

Gly Leu Ile Thr Tyr Leu Met Glu Lys Lys Lys Val Asn Gly Pro Tyr
            740                 745                 750

Leu Ile Ile Val Pro Leu Ser Thr Leu Ser Asn Trp Val Leu Glu Phe
        755                 760                 765

Glu Lys Trp Ala Pro Ser Val Phe Val Val Ala Tyr Lys Gly Ser Pro
    770                 775                 780

Ala Met Arg Arg Thr Leu Gln Ser Gln Met Arg Ser Thr Lys Phe Asn
785                 790                 795                 800

Val Leu Leu Thr Thr Tyr Glu Tyr Val Ile Lys Asp Lys Ala Val Leu
                805                 810                 815

Ala Lys Leu His Trp Lys Tyr Met Ile Ile Asp Glu Gly His Arg Met
            820                 825                 830

Lys Asn His His Cys Lys Leu Thr Gln Val Leu Asn Thr His Tyr Leu
        835                 840                 845

Ala Pro His Arg Leu Leu Leu Thr Gly Thr Pro Leu Gln Asn Lys Leu
    850                 855                 860

Pro Glu Leu Trp Ala Leu Leu Asn Phe Leu Leu Pro Ser Ile Phe Lys
865                 870                 875                 880

Ser Cys Ser Thr Phe Glu Gln Trp Phe Asn Ala Pro Phe Ala Thr Thr
                885                 890                 895

Gly Glu Lys Val Glu Leu Asn Glu Glu Glu Thr Ile Leu Ile Ile Arg
            900                 905                 910

Arg Leu His Lys Val Leu Arg Pro Phe Leu Leu Arg Arg Leu Lys Lys
        915                 920                 925

Glu Val Glu Ser Gln Leu Pro Glu Lys Ile Glu Tyr Ile Val Lys Cys
    930                 935                 940

Asp Met Ser Gly Leu Gln Arg Val Leu Tyr Arg His Met Gln Ser Lys
945                 950                 955                 960

Gly Val Leu Leu Thr Asp Gly Ser Glu Lys Gly Lys Gln Gly Lys Gly
                965                 970                 975

Gly Ala Lys Ala Leu Met Asn Thr Ile Val Gln Leu Arg Lys Leu Cys
            980                 985                 990

Asn His Pro Phe Met Phe His His  Ile Glu Glu Lys Tyr  Cys Asp His
        995                 1000                1005

Val Gly  Gln Asn Asn Val Val  Thr Gly Pro Asp Leu  Phe Arg Val
    1010                1015                1020
```

```
Ser Gly  Lys Phe Glu Phe Leu  Asp Arg Ile Leu Pro  Lys Leu Lys
    1025                 1030                 1035

Ala Thr  Ser His Arg Val Leu  Leu Phe Cys Gln Met  Thr Gln Leu
    1040                 1045                 1050

Met Thr  Ile Met Glu Asp Tyr  Leu Ser Trp Arg Gly  Phe Ser Tyr
    1055                 1060                 1065

Leu Arg  Leu Asp Gly Thr Thr  Lys Ser Glu Asp Arg  Gly Asp Leu
    1070                 1075                 1080

Leu Lys  Lys Phe Asn Asn Pro  Glu Ser Glu Tyr Phe  Ile Phe Leu
    1085                 1090                 1095

Leu Ser  Thr Arg Ala Gly Gly  Leu Gly Leu Asn Leu  Gln Ala Ala
    1100                 1105                 1110

Asp Thr  Val Ile Ile Phe Asp  Ser Asp Trp Asn Pro  His Gln Asp
    1115                 1120                 1125

Leu Gln  Ala Gln Asp Arg Ala  His Arg Ile Gly Gln  Gln Asn Glu
    1130                 1135                 1140

Val Arg  Val Leu Arg Leu Met  Thr Val Asn Ser Val  Glu Glu Arg
    1145                 1150                 1155

Ile Leu  Ala Ala Ala Arg Tyr  Lys Leu Asn Met Asp  Glu Lys Val
    1160                 1165                 1170

Ile Gln  Ala Gly Met Phe Asp  Gln Lys Ser Thr Gly  Thr Glu Arg
    1175                 1180                 1185

Gln Lys  Phe Leu Gln Asn Ile  Leu His Gln Asp Asp  Ala Asp Asp
    1190                 1195                 1200

Glu Glu  Asn Glu Val Pro Asp  Asp Glu Met Val Asn  Arg Met Ile
    1205                 1210                 1215

Ala Arg  Thr Glu Asp Glu Phe  Asn Leu Phe Gln Lys  Ile Asp Leu
    1220                 1225                 1230

Glu Arg  Arg Arg Glu Glu Ala  Lys Leu Gly Pro Asn  Arg Lys Ser
    1235                 1240                 1245

Arg Leu  Val Glu Glu Ala Glu  Leu Pro Asp Trp Leu  Val Lys Asn
    1250                 1255                 1260

Asp Asp  Glu Ile Glu Lys Trp  Thr Tyr Glu Glu Thr  Glu Val Gln
    1265                 1270                 1275

Met Gly  Arg Gly Asn Arg Gln  Arg Lys Glu Val Asp  Tyr Thr Asp
    1280                 1285                 1290

Ser Leu  Thr Glu Lys Glu Trp  Leu Lys Ala Ile Asp  Asp Asn Val
    1295                 1300                 1305

Asp Asp  Phe Asp Asp Asp Glu  Glu Glu Glu Val Lys  Thr Lys Lys
    1310                 1315                 1320

Arg Gly  Lys Arg Arg Arg Arg  Gly Glu Asp Asp Glu  Glu Asp Ala
    1325                 1330                 1335

Ser Thr  Ser Lys Arg Arg Lys  Tyr Ser Pro Ser Glu  Asn Lys Leu
    1340                 1345                 1350

Arg Arg  Arg Met Arg Asn Leu  Met Asn Ile Val Val  Lys Tyr Thr
    1355                 1360                 1365

Asp Ser  Asp Ser Arg Val Leu  Ser Glu Pro Phe Met  Lys Leu Pro
    1370                 1375                 1380

Ser Arg  His Lys Tyr Pro Asp  Tyr Tyr Glu Leu Ile  Lys Lys Pro
    1385                 1390                 1395

Ile Asp  Ile Lys Arg Ile Leu  Ala Lys Val Glu Glu  Cys Lys Tyr
    1400                 1405                 1410

Ala Asp  Met Asp Glu Leu Glu  Lys Asp Phe Met Gln  Leu Cys Lys
```

```
    1415                1420                1425

Asn Ala  Gln Thr Tyr Asn Glu  Glu Ala Ser Leu Ile  Tyr Glu Asp
    1430                1435                1440

Ser Ile  Val Leu Glu Ser Val  Phe Ser Asn Ala Arg  Gln Lys Val
    1445                1450                1455

Glu Gln  Asp Asn Asp Ser Asp  Asp Asp Glu Ser Lys  Gly Asp Gln
    1460                1465                1470

Glu Asp  Ala Ala Ser Asp Thr  Ser Ser Val Lys Met  Lys Leu Lys
    1475                1480                1485

Leu Lys  Pro Gly Arg Thr Arg  Gly Ser Gly Ala Gly  Gly Lys Arg
    1490                1495                1500

Arg Arg  Arg Lys Tyr Ile Ser  Glu Asp Glu Asp Glu  Asp His Ser
    1505                1510                1515

Glu Val  Ser Leu Met
    1520
```

<210> SEQ ID NO 3
<211> LENGTH: 499
<212> TYPE: DNA
<213> ORGANISM: Euchistus heros

<400> SEQUENCE: 3

```
gatgatgaag aagatgcaag tacttcaaag agaaggaaat attctccatc tgaaaacaaa     60

ctgaggaggc gtatgcgtaa cctcatgaac attgttgtta agtatactga cagtgactcg    120

agagtactca gtgaaccatt catgaaactt ccctctcgcc ataagtaccc agactactat    180

gagttgatca agaaacctat agacatcaag aggatattgg ccaaagtaga agagtgtaaa    240

tatgctgaca tggatgaatt agaaaaggat tttatgcaac tttgtaaaaa tgctcagaca    300

tacaatgagg aggcctcatt gatctatgaa gattcgatag tattagaaag tgttttctct    360

aatgctcgtc aaaaagtaga gcaggataat gattcagatg atgatgaaag taaaggtgac    420

caagaagatg ctgcatcaga cacttcatcc gtcaaaatga aattgaaact aaagcctggg    480

aggacccgag ggagtggag                                                  499
```

<210> SEQ ID NO 4
<211> LENGTH: 20
<212> TYPE: DNA
<213> ORGANISM: Artificial Sequence
<220> FEATURE:
<223> OTHER INFORMATION: T7 phage promoter

<400> SEQUENCE: 4

```
taatacgact cactataggg                                                  20
```

<210> SEQ ID NO 5
<211> LENGTH: 301
<212> TYPE: DNA
<213> ORGANISM: Artificial Sequence
<220> FEATURE:
<223> OTHER INFORMATION: YFPv2 dsRNA sense strand encoding sequence

<400> SEQUENCE: 5

```
catctggagc acttctcttt catgggaaga ttccttacgt tgtggagatg gaagggaatg     60

ttgatggcca cacctttagc atacgtggga aaggctacgg agatgcctca gtgggaaagg    120

ttgatgcaca gttcatctgc acaactggtg atgttcctgt gccttggagc acacttgtca    180

ccactctcac ctatggagca cagtgctttg ccaagtatgg tccagagttg aaggacttct    240
```

```
acaagtcctg tatgccagat ggctatgtgc aagagcgcac aatcaccttt gaaggagatg    300

g                                                                    301


<210> SEQ ID NO 6
<211> LENGTH: 47
<212> TYPE: DNA
<213> ORGANISM: Artificial Sequence
<220> FEATURE:
<223> OTHER INFORMATION: Primer YFPv2-F

<400> SEQUENCE: 6

ttaatacgac tcactatagg gagagcatct ggagcacttc tctttca                   47


<210> SEQ ID NO 7
<211> LENGTH: 46
<212> TYPE: DNA
<213> ORGANISM: Artificial Sequence
<220> FEATURE:
<223> OTHER INFORMATION: Primer YFPv2-R

<400> SEQUENCE: 7

ttaatacgac tcactatagg gagaccatct ccttcaaagg tgattg                    46


<210> SEQ ID NO 8
<211> LENGTH: 6346
<212> TYPE: DNA
<213> ORGANISM: Euchistus heros

<400> SEQUENCE: 8

atctcggtgc tgtggatcgt ccttagtgat tgttttctaa tatagtttgt aattatatag     60

tgttttatgc gttgatatcg gtgatattag tgaataatag tgaagtgttg atgttttatt    120

tctaatggcg tctgaagaag aagttgacga gtgtttacca gttgacgatg aagttgacac    180

tagtgttgtt caacaagaag gcactgaaga aaattcacct gacagtgatg aaagaagtag    240

gatagaggaa gaagatgacg agtatgaccc tgaggatgcg aggaaaaaaa agaaaggtaa    300

aaagagaaaa gccaaagggg aaagcaaaaa agaaaagaaa cgtaaaaaaa ggaagaagaa    360

tgatagtgct gaagaaagtg agggaggcgg ggaagaagaa ggcgattccg attatggaag    420

aaaatctaag aagtctaaag gaacttcaca accaaaacca gtgcagcaag attcttctgg    480

aggtgtacct tcagtagaag aagtttgcag cctttttgga cttacagatg tacagattga    540

ctataccgaa gatgattacc aaaatctgac tacgtataaa ctttttcaac aacatgttcg    600

tcctattctt gccaaggaca accagaaggt tcccatcgga aaaatgatga tgctcgtggc    660

tgcaaaatgg agagattttt gcaattccaa tccaaacgct caacaggaac cagatccaga    720

agcttcagaa gaacaggaat attctaaacc taccaggaca cgaccttcac gagtttcaac    780

tacacaaaat gatgatgaag aagacgacga tgctgacgaa cgagggagga aaaagagaag    840

tggacgaagt aaaaagtcat caggaaagaa gtccgctcct ccggccacaa ccaaggtccc    900

taccctcaag atcaagatag gaaaaagaaa acagaattcc gatgaagaag atgaaggttc    960

agttggtgcc gtttctgaaa gggactcaga tgctgaattc gagcaaatgc tcgcagaagc   1020

tgaagaagtt aataaacctg aaggtgttgt agaagaagaa gaaggtgcag aggtggctcc   1080

tgtacctaag aaaaaggcca aaacgaaaat tggtaataaa aagaaaaagga aaaagacacg  1140

gactactaac aagtttccag acagtgaagc tggttatgaa acagatcatc aggactattg   1200

tgaagtttgt caacaaggag gtgaaataat attatgtgat acgtgccctc gagcttatca   1260

tttggtctgt ttggatcccg aattggaaga tacgccagaa ggcaaatggt catgccctca   1320
```

```
ttgtgaaggt gaaggtgtac aggaaaaaga agatgatgtc catcaagaat tttgcagagt   1380
ttgtaaagat ggtggagaac ttttatgctg tgattcttgc ccttctgcat accacacatt   1440
ctgtttgaac cctccattga cagatattcc agatggtgac tggaagtgcc cacgttgttc   1500
ggcgaagcct ttgagaggta aagtgtcaaa gattcttact tggaggtggt tggaatctcc   1560
cagtagtaaa gatgaagaag acaatactaa aaaacgaaac aggcagaggc aaagagaata   1620
tttcgtcaag tgggcagata tgtcttattg gcactgtagt tgggtgtctg aacttcagat   1680
ggatgttttt catactcaaa tgatcaggag ttatattcgt aaatatgata tggacgaacc   1740
tcccaaacta gaagaaccct tggatgaagc agacaataga atgaagagga tacgagaggc   1800
aaatatcaat gagcaagaat tagaagagaa atattacaag tatggtatca aaccagagtg   1860
gcttattgtg cagagggtaa ttaaccatcg cactataagg gatggaagca atctgtacct   1920
cgtcaaatgg agggacctcc cttatgacca ggcgacttgg gaggaagaag tcaccgatat   1980
ccctggcttg aagaaagcta ttgaatatta caatgagatg agggcttgct gtttaggtga   2040
atctaaaaaa ctaaaaaaag gtaaaggtaa aagatcaaag agagatcaag atgatgagga   2100
aggaagcaga agtgcaggaa tgatgggcgt cggtggacca gctactggtc aatacttccc   2160
gcctcctgaa aagcctgtca cagatttgaa aaagaaatac gataaacagc cggactatct   2220
cgacgtctcc ggtatgtgcc ttcatcctta ccaattagaa ggtttaaatt ggttgaggta   2280
ttcctggggg caaggaacag acactattct tgccgatgag atgggtcttg gaaaaaccat   2340
tcagacaatt actttcctct attctcttta caaagagggt cattgtaaag gcccccttcct  2400
tgtgagtgta cccttatcta caattatcaa ttgggaaaga gagttcgaaa cttgggcgcc   2460
agacttctac gttgtcacat atgtcggaga caaagattct cgtgctgtaa tacgtgaaaa   2520
tgaattttca ttcgatgata atgctgttag aggaggaaga ggtgtttcta aagttcgctc   2580
ttctgcaata aagtttcatg tactgctaac atcttatgaa cttatctcta tcgatgtcac   2640
ttgccttgga tcgatcgagt gggcagtgct tgtagtagat gaagcacaca ggctgaaaag   2700
taatcagagc aagttcttta ggcttcttgc ttcataccac attgcttata aacttctgct   2760
gacaggaact ccgttgcaaa acaatctaga agaattgttt catttactta atttccttac   2820
gccggaaaaa ttcaacgacc ttgcgacatt tcaaaacgaa ttcgctgata tttcaaaaga   2880
agaacaagtc aaaagacttc atgagttact cgggccgcat atgttgagga gattaaaagc   2940
tgatgtactc aagaatatgc ctacaaaatc tgagttcatt gttagagttg aactctcccc   3000
gatgcagaag aagtactaca aatatattct cacaaggaat ttcgaagctt taaatccaaa   3060
aggaggcggt caacaagtat ctcttttgaa cattatgatg gatcttaaaa aatgctgtaa   3120
tcatccatac ctgtttcctg ctgcttctca ggaagctcct ttaggaccaa gcggatctta   3180
cgatcttcaa gggttaatca aagcatctgg aaaattgata cttctgtcga aaatgctgag   3240
acggctcaaa gaagagggtc acagagtact gatttttctct caaatgacaa aaatgttgga  3300
cttattagaa gactacctcg agggtgaagg ttataaatat gaacgtattg acggtacgat   3360
caccggtagc ttaagacaag aagctatcga tcggtttaac gcccctggag ctcaacaatt   3420
tgtttttctt ttgtccactc gtgcgggagg tcttggtatt aatctcgcta ctgcagatac   3480
agttattatt tatgactctg actggaatcc tcataacgat attcaggcct tttcgagagc   3540
acacaggata gggcaagcaa acaaggttat gatttatcga tttgtgacac gagcgtctgt   3600
tgaagaaaga gtaacgcaag tggctaagag aaaaatgatg ttaacccatc ttgtcgtacg   3660
```

```
accaggtatg ggtggcaagc aagcaaattt cactaagcaa gaacttgatg atattttaag   3720
gtttggaaca gaagaacttt tcaaagaaga gcagggtaaa gaagatgaag ccattcatta   3780
tgacgataaa gctgttgaag aattacttga ccggtcgaag atgggtattg aacagaaaga   3840
aaactggtct aatgaatatc tttcttcttt caaagtggca agttatgtta ctaaagaaga   3900
agacgaagat gaggaaatag gaacagaggt aataaaacag gaagcagaaa atacagaccc   3960
agcttattgg gtcaaactgt tgaggcacca ttatgagcaa caacaagagg atatttctcg   4020
aactctcggt aaaggaaaaa ggattcgaaa acaggtgaat tacatcgacg gtggagtgat   4080
ggactcaaga gagaacgccg attcgacgtg gcaagacaac ctctctgact ataattcaga   4140
cttctctgct ccttctgatg atgacaagga agacgatgac tttgatgaga aaaatgatga   4200
tggaacgaga aagaagcgta ggccagaaag gagggaggac aaagataggc ctctacctcc   4260
tcttcttgcc cgagtcggtg gaaacattga ggtcctggga ttcaacgcca gacagcgtaa   4320
agcattcttg aatgctatta tgaggtatgg aatgccacct caagatgcat tcaactcgca   4380
gtggcttgtt cgagacctga ggggtaaatc tgagaagcat ttcaaggcat acgtatccct   4440
ctttatgagg catttgtgtg agcctggcgc ggacaatgcc gaaacattcg cggatggtgt   4500
tccaagggaa ggtcttagtc ggcagcatgt tctcacaagg ataggtgtga tgtcactcat   4560
taggaaaaag gttcaagaat ttgagcaaat taatggatat tactcgatgc ctgaaatgtt   4620
gaagaaacca cttgttgatg ccggattgca taaaacaagt gctagcagta taggtgaagg   4680
tgctagtagt tccggtacac ctgcaacatc agctgctcca agtccagctc ctactctttt   4740
ggataagaca caaattgaag atttgagtga aaaagaagat ccgtcaaaga ctgaagataa   4800
aaccaccgat gattccaaac cctcagaaga ggctaaagct gcagatgatg caaataagcc   4860
tcaggctgaa ggagaaaagg cagaaggatc ttctaatgca aaccaaactt ctgaagctga   4920
aggaagcgat gagaaaaaac ccaaagaaga accgatggat gtagatggtg aaggagaggc   4980
taaagatagt gataagacag aaaaacaaga aggtactgac gaaaaagatg tagccctaaa   5040
agaggaagaa aaggatgaag aggtcaacaa agagaaggga gaggaaacag aggaaaagaa   5100
ggttatcgat tttgaagaag acaaatctaa aaggaaattt atgttcaata tcgctgatgg   5160
aggatttact gagctccata ccttatggca aaatgaagag aaagctgcag tacctggtag   5220
ggagtacgag atctggcata ggaggcatga ctattggctg ttgggtggaa tcgttaccca   5280
tggctatggt cggtggcaag atattcaaaa tgatattaga tttgctatta tcaacgaacc   5340
atttaagatg gatgttggaa aaggaaattt cttagaaatt aaaaataaat ttcttgccag   5400
gaggtttaag cttcttgagc aagctctggt gattgaagaa cagttaagac gtgcagctta   5460
tttaaatctg acgcaagatc caaatcaccc agcaatgtca ctgaatgcaa gatttgcaga   5520
ggttgaatgt ctagccgaat ctcaccaaca cctctcgaag gaaagtcttg ctggcaacaa   5580
acctgcaaat gcagtgttac ataaagtatt gaaccaatta gaggagcttc tgtcggatat   5640
gaaatctgac gtatctcgac taccagccac tctagccaga attccacctg tagcccagag   5700
gctacagatg tctgaacggt caatactttc taggttggct gcaactactt ctcctgcgac   5760
gcccaccacg tcccatcaaa ctggtatgat aagcagtcag ttccctgctg gatttcaatc   5820
agggcagttg actggaacgt ttccgaatgc cagttttacc aacttcaggc cccagtattc   5880
agttcctggg caaactgcag cccagggttt tcccggtaat tgataattga aagctggacg   5940
gtaattgtct gcgagtgaat tctccatgag taaataatag gttttttttt tttttaaga    6000
aagaaataaa agaagcgttt tgtttagttt tgttgatagt tctctttatt tctttcaatt   6060
```

```
ttgttttagc ggaaaaaaaa atgttcatta taagtaactt ataaattgga catgctaatt   6120

aaatttccta ttagattatt ttgttatttg taagtttttc ggtattgtaa gaatgtctat   6180

atgtgtaaga ggttgtacaa gattgcctaa ataccttgta ttatttattt ttactattga   6240

ataaaaaaaa aaaataatta acttcgatct taggttaagg gtaataaaaa aaaatgttac   6300

tggaaaaaaa aatagaaaaa ataaaaaaga tagcctttcc ccttac                  6346


<210> SEQ ID NO 9
<211> LENGTH: 1938
<212> TYPE: PRT
<213> ORGANISM: Euchistus heros

<400> SEQUENCE: 9

Met Ala Ser Glu Glu Glu Val Asp Glu Cys Leu Pro Val Asp Asp Glu
1               5                   10                  15

Val Asp Thr Ser Val Val Gln Gln Glu Gly Thr Glu Glu Asn Ser Pro
            20                  25                  30

Asp Ser Asp Glu Arg Ser Arg Ile Glu Glu Glu Asp Asp Glu Tyr Asp
        35                  40                  45

Pro Glu Asp Ala Arg Lys Lys Lys Lys Gly Lys Lys Arg Lys Ala Lys
    50                  55                  60

Gly Glu Ser Lys Lys Glu Lys Lys Arg Lys Lys Arg Lys Lys Asn Asp
65                  70                  75                  80

Ser Ala Glu Glu Ser Glu Gly Gly Gly Glu Glu Glu Gly Asp Ser Asp
                85                  90                  95

Tyr Gly Arg Lys Ser Lys Lys Ser Lys Gly Thr Ser Gln Pro Lys Pro
            100                 105                 110

Val Gln Gln Asp Ser Ser Gly Gly Val Pro Ser Val Glu Glu Val Cys
        115                 120                 125

Ser Leu Phe Gly Leu Thr Asp Val Gln Ile Asp Tyr Thr Glu Asp Asp
    130                 135                 140

Tyr Gln Asn Leu Thr Thr Tyr Lys Leu Phe Gln Gln His Val Arg Pro
145                 150                 155                 160

Ile Leu Ala Lys Asp Asn Gln Lys Val Pro Ile Gly Lys Met Met Met
                165                 170                 175

Leu Val Ala Ala Lys Trp Arg Asp Phe Cys Asn Ser Asn Pro Asn Ala
            180                 185                 190

Gln Gln Glu Pro Asp Pro Glu Ala Ser Glu Glu Gln Glu Tyr Ser Lys
        195                 200                 205

Pro Thr Arg Thr Arg Pro Ser Arg Val Ser Thr Thr Gln Asn Asp Asp
    210                 215                 220

Glu Glu Asp Asp Asp Ala Asp Glu Arg Gly Arg Lys Lys Arg Ser Gly
225                 230                 235                 240

Arg Ser Lys Lys Ser Ser Gly Lys Lys Ser Ala Pro Pro Ala Thr Thr
                245                 250                 255

Lys Val Pro Thr Leu Lys Ile Lys Ile Gly Lys Arg Lys Gln Asn Ser
            260                 265                 270

Asp Glu Glu Asp Glu Gly Ser Val Gly Ala Val Ser Glu Arg Asp Ser
        275                 280                 285

Asp Ala Glu Phe Glu Gln Met Leu Ala Glu Ala Glu Glu Val Asn Lys
    290                 295                 300

Pro Glu Gly Val Val Glu Glu Glu Glu Gly Ala Glu Val Ala Pro Val
305                 310                 315                 320
```

```
Pro Lys Lys Lys Ala Lys Thr Lys Ile Gly Asn Lys Lys Lys Arg Lys
                325                 330                 335

Lys Thr Arg Thr Thr Asn Lys Phe Pro Asp Ser Glu Ala Gly Tyr Glu
            340                 345                 350

Thr Asp His Gln Asp Tyr Cys Glu Val Cys Gln Gln Gly Gly Glu Ile
        355                 360                 365

Ile Leu Cys Asp Thr Cys Pro Arg Ala Tyr His Leu Val Cys Leu Asp
    370                 375                 380

Pro Glu Leu Glu Asp Thr Pro Glu Gly Lys Trp Ser Cys Pro His Cys
385                 390                 395                 400

Glu Gly Glu Gly Val Gln Glu Lys Glu Asp Asp Val His Gln Glu Phe
                405                 410                 415

Cys Arg Val Cys Lys Asp Gly Gly Glu Leu Leu Cys Cys Asp Ser Cys
            420                 425                 430

Pro Ser Ala Tyr His Thr Phe Cys Leu Asn Pro Pro Leu Thr Asp Ile
        435                 440                 445

Pro Asp Gly Asp Trp Lys Cys Pro Arg Cys Ser Ala Lys Pro Leu Arg
    450                 455                 460

Gly Lys Val Ser Lys Ile Leu Thr Trp Arg Trp Leu Glu Ser Pro Ser
465                 470                 475                 480

Ser Lys Asp Glu Glu Asp Asn Thr Lys Lys Arg Asn Arg Gln Arg Gln
                485                 490                 495

Arg Glu Tyr Phe Val Lys Trp Ala Asp Met Ser Tyr Trp His Cys Ser
            500                 505                 510

Trp Val Ser Glu Leu Gln Met Asp Val Phe His Thr Gln Met Ile Arg
        515                 520                 525

Ser Tyr Ile Arg Lys Tyr Asp Met Asp Glu Pro Pro Lys Leu Glu Glu
    530                 535                 540

Pro Leu Asp Glu Ala Asp Asn Arg Met Lys Arg Ile Arg Glu Ala Asn
545                 550                 555                 560

Ile Asn Glu Gln Glu Leu Glu Glu Lys Tyr Tyr Lys Tyr Gly Ile Lys
                565                 570                 575

Pro Glu Trp Leu Ile Val Gln Arg Val Ile Asn His Arg Thr Ile Arg
            580                 585                 590

Asp Gly Ser Asn Leu Tyr Leu Val Lys Trp Arg Asp Leu Pro Tyr Asp
        595                 600                 605

Gln Ala Thr Trp Glu Glu Glu Val Thr Asp Ile Pro Gly Leu Lys Lys
    610                 615                 620

Ala Ile Glu Tyr Tyr Asn Glu Met Arg Ala Cys Cys Leu Gly Glu Ser
625                 630                 635                 640

Lys Lys Leu Lys Lys Gly Lys Gly Lys Arg Ser Lys Arg Asp Gln Asp
                645                 650                 655

Asp Glu Glu Gly Ser Arg Ser Ala Gly Met Met Gly Val Gly Gly Pro
            660                 665                 670

Ala Thr Gly Gln Tyr Phe Pro Pro Pro Glu Lys Pro Val Thr Asp Leu
        675                 680                 685

Lys Lys Lys Tyr Asp Lys Gln Pro Asp Tyr Leu Asp Val Ser Gly Met
    690                 695                 700

Cys Leu His Pro Tyr Gln Leu Glu Gly Leu Asn Trp Leu Arg Tyr Ser
705                 710                 715                 720

Trp Gly Gln Gly Thr Asp Thr Ile Leu Ala Asp Glu Met Gly Leu Gly
                725                 730                 735

Lys Thr Ile Gln Thr Ile Thr Phe Leu Tyr Ser Leu Tyr Lys Glu Gly
```

```
            740                 745                 750

His Cys Lys Gly Pro Phe Leu Val Ser Val Pro Leu Ser Thr Ile Ile
        755                 760                 765

Asn Trp Glu Arg Glu Phe Glu Thr Trp Ala Pro Asp Phe Tyr Val Val
    770                 775                 780

Thr Tyr Val Gly Asp Lys Asp Ser Arg Ala Val Ile Arg Glu Asn Glu
785                 790                 795                 800

Phe Ser Phe Asp Asp Asn Ala Val Arg Gly Gly Arg Gly Val Ser Lys
                805                 810                 815

Val Arg Ser Ser Ala Ile Lys Phe His Val Leu Leu Thr Ser Tyr Glu
            820                 825                 830

Leu Ile Ser Ile Asp Val Thr Cys Leu Gly Ser Ile Glu Trp Ala Val
        835                 840                 845

Leu Val Val Asp Glu Ala His Arg Leu Lys Ser Asn Gln Ser Lys Phe
    850                 855                 860

Phe Arg Leu Leu Ala Ser Tyr His Ile Ala Tyr Lys Leu Leu Leu Thr
865                 870                 875                 880

Gly Thr Pro Leu Gln Asn Asn Leu Glu Glu Leu Phe His Leu Leu Asn
                885                 890                 895

Phe Leu Thr Pro Glu Lys Phe Asn Asp Leu Ala Thr Phe Gln Asn Glu
            900                 905                 910

Phe Ala Asp Ile Ser Lys Glu Glu Gln Val Lys Arg Leu His Glu Leu
        915                 920                 925

Leu Gly Pro His Met Leu Arg Arg Leu Lys Ala Asp Val Leu Lys Asn
    930                 935                 940

Met Pro Thr Lys Ser Glu Phe Ile Val Arg Val Glu Leu Ser Pro Met
945                 950                 955                 960

Gln Lys Lys Tyr Tyr Lys Tyr Ile Leu Thr Arg Asn Phe Glu Ala Leu
                965                 970                 975

Asn Pro Lys Gly Gly Gly Gln Gln Val Ser Leu Leu Asn Ile Met Met
            980                 985                 990

Asp Leu Lys Lys Cys Cys Asn His  Pro Tyr Leu Phe Pro  Ala Ala Ser
        995                 1000                1005

Gln Glu  Ala Pro Leu Gly Pro  Ser Gly Ser Tyr Asp  Leu Gln Gly
    1010                1015                1020

Leu Ile  Lys Ala Ser Gly Lys  Leu Ile Leu Leu Ser  Lys Met Leu
    1025                1030                1035

Arg Arg  Leu Lys Glu Glu Gly  His Arg Val Leu Ile  Phe Ser Gln
    1040                1045                1050

Met Thr  Lys Met Leu Asp Leu  Leu Glu Asp Tyr Leu  Glu Gly Glu
    1055                1060                1065

Gly Tyr  Lys Tyr Glu Arg Ile  Asp Gly Thr Ile Thr  Gly Ser Leu
    1070                1075                1080

Arg Gln  Glu Ala Ile Asp Arg  Phe Asn Ala Pro Gly  Ala Gln Gln
    1085                1090                1095

Phe Val  Phe Leu Leu Ser Thr  Arg Ala Gly Gly Leu  Gly Ile Asn
    1100                1105                1110

Leu Ala  Thr Ala Asp Thr Val  Ile Ile Tyr Asp Ser  Asp Trp Asn
    1115                1120                1125

Pro His  Asn Asp Ile Gln Ala  Phe Ser Arg Ala His  Arg Ile Gly
    1130                1135                1140

Gln Ala  Asn Lys Val Met Ile  Tyr Arg Phe Val Thr  Arg Ala Ser
    1145                1150                1155
```

```
Val Glu Glu Arg Val Thr Gln Val Ala Lys Arg Lys Met Met Leu
    1160                1165                1170

Thr His Leu Val Val Arg Pro Gly Met Gly Gly Lys Gln Ala Asn
    1175                1180                1185

Phe Thr Lys Gln Glu Leu Asp Asp Ile Leu Arg Phe Gly Thr Glu
    1190                1195                1200

Glu Leu Phe Lys Glu Glu Gln Gly Lys Glu Asp Glu Ala Ile His
    1205                1210                1215

Tyr Asp Asp Lys Ala Val Glu Glu Leu Leu Asp Arg Ser Lys Met
    1220                1225                1230

Gly Ile Glu Gln Lys Glu Asn Trp Ser Asn Glu Tyr Leu Ser Ser
    1235                1240                1245

Phe Lys Val Ala Ser Tyr Val Thr Lys Glu Glu Asp Glu Asp Glu
    1250                1255                1260

Glu Ile Gly Thr Glu Val Ile Lys Gln Glu Ala Glu Asn Thr Asp
    1265                1270                1275

Pro Ala Tyr Trp Val Lys Leu Leu Arg His His Tyr Glu Gln Gln
    1280                1285                1290

Gln Glu Asp Ile Ser Arg Thr Leu Gly Lys Gly Lys Arg Ile Arg
    1295                1300                1305

Lys Gln Leu Tyr Lys Val Asn Tyr Ile Asp Gly Gly Val Met Asp
    1310                1315                1320

Ser Arg Glu Asn Ala Asp Ser Thr Trp Gln Asp Asn Leu Ser Asp
    1325                1330                1335

Tyr Asn Ser Asp Phe Ser Ala Pro Ser Asp Asp Asp Lys Glu Asp
    1340                1345                1350

Asp Asp Phe Asp Glu Lys Asn Asp Asp Gly Thr Arg Lys Lys Arg
    1355                1360                1365

Arg Pro Glu Arg Arg Glu Asp Lys Asp Arg Pro Leu Pro Pro Leu
    1370                1375                1380

Leu Ala Arg Val Gly Gly Asn Ile Glu Val Leu Gly Phe Asn Ala
    1385                1390                1395

Arg Gln Arg Lys Ala Phe Leu Asn Ala Ile Met Arg Tyr Gly Met
    1400                1405                1410

Pro Pro Gln Asp Ala Phe Asn Ser Gln Trp Cys Ser Arg Leu Val
    1415                1420                1425

Arg Asp Leu Arg Gly Lys Ser Glu Lys His Phe Lys Ala Tyr Val
    1430                1435                1440

Ser Leu Phe Met Arg His Leu Cys Glu Pro Gly Ala Asp Asn Ala
    1445                1450                1455

Glu Thr Phe Ala Asp Gly Val Pro Arg Glu Gly Leu Ser Arg Gln
    1460                1465                1470

His Val Leu Thr Arg Ile Gly Val Met Ser Leu Ile Arg Lys Lys
    1475                1480                1485

Val Gln Glu Phe Glu Gln Ile Asn Gly Tyr Tyr Ser Met Pro Glu
    1490                1495                1500

Met Leu Lys Lys Pro Leu Val Asp Ala Gly Leu His Lys Thr Ser
    1505                1510                1515

Ala Ser Ser Ile Gly Glu Gly Ala Ser Ser Ser Gly Thr Pro Ala
    1520                1525                1530

Thr Ser Ala Ala Pro Ser Pro Ala Pro Thr Leu Leu Asp Lys Thr
    1535                1540                1545
```

```
Gln Ile  Glu Asp Leu Ser Glu  Lys Glu Asp Pro Ser  Lys Thr Glu
    1550                 1555                 1560

Asp Lys  Thr Thr Asp Asp Ser  Lys Pro Ser Glu Glu  Ala Lys Ala
    1565                 1570                 1575

Ala Asp  Asp Ala Asn Lys Pro  Gln Ala Glu Gly Glu  Lys Ala Glu
    1580                 1585                 1590

Gly Ser  Ser Asn Ala Asn Gln  Thr Ser Glu Ala Glu  Gly Ser Asp
    1595                 1600                 1605

Glu Lys  Lys Pro Lys Glu Glu  Pro Met Asp Val Asp  Gly Glu Gly
    1610                 1615                 1620

Glu Ala  Lys Asp Ser Asp Lys  Thr Glu Lys Gln Glu  Gly Thr Asp
    1625                 1630                 1635

Glu Lys  Asp Val Ala Leu Lys  Glu Glu Glu Lys Asp  Glu Glu Val
    1640                 1645                 1650

Asn Lys  Glu Lys Gly Glu Glu  Thr Glu Glu Lys Lys  Val Ile Asp
    1655                 1660                 1665

Phe Glu  Glu Asp Lys Ser Lys  Arg Lys Phe Met Phe  Asn Ile Ala
    1670                 1675                 1680

Asp Gly  Gly Phe Thr Glu Leu  His Thr Leu Trp Gln  Asn Glu Glu
    1685                 1690                 1695

Lys Ala  Ala Val Pro Gly Arg  Glu Tyr Glu Ile Trp  His Arg Arg
    1700                 1705                 1710

His Asp  Tyr Trp Leu Leu Gly  Gly Ile Val Thr His  Gly Tyr Gly
    1715                 1720                 1725

Arg Trp  Gln Asp Ile Gln Asn  Asp Ile Arg Phe Ala  Ile Ile Asn
    1730                 1735                 1740

Glu Pro  Phe Lys Met Asp Val  Gly Lys Gly Asn Phe  Leu Glu Ile
    1745                 1750                 1755

Lys Asn  Lys Phe Leu Ala Arg  Arg Phe Lys Leu Leu  Glu Gln Ala
    1760                 1765                 1770

Leu Val  Ile Glu Glu Gln Leu  Arg Arg Ala Ala Tyr  Leu Asn Leu
    1775                 1780                 1785

Thr Gln  Asp Pro Asn His Pro  Ala Met Ser Leu Asn  Ala Arg Phe
    1790                 1795                 1800

Ala Glu  Val Glu Cys Leu Ala  Glu Ser His Gln His  Leu Ser Lys
    1805                 1810                 1815

Glu Ser  Leu Ala Gly Asn Lys  Pro Ala Asn Ala Val  Leu His Lys
    1820                 1825                 1830

Val Leu  Asn Gln Leu Glu Glu  Leu Leu Ser Asp Met  Lys Ser Asp
    1835                 1840                 1845

Val Ser  Arg Leu Pro Ala Thr  Leu Ala Arg Ile Pro  Pro Val Ala
    1850                 1855                 1860

Gln Arg  Leu Gln Met Ser Glu  Arg Ser Ile Leu Ser  Arg Leu Ala
    1865                 1870                 1875

Ala Thr  Thr Ser Pro Ala Thr  Pro Thr Thr Ser His  Gln Thr Gly
    1880                 1885                 1890

Met Ile  Ser Ser Gln Phe Pro  Ala Gly Phe Gln Ser  Gly Gln Leu
    1895                 1900                 1905

Thr Gly  Thr Phe Pro Asn Ala  Ser Phe Thr Asn Phe  Arg Pro Gln
    1910                 1915                 1920

Tyr Ser  Val Pro Gly Gln Thr  Ala Ala Gln Gly Phe  Pro Gly Asn
    1925                 1930                 1935
```

<210> SEQ ID NO 10
<211> LENGTH: 3391
<212> TYPE: DNA
<213> ORGANISM: Euchistus heros

<400> SEQUENCE: 10

```
agagggggta ggcgcacagc tttcctcaca tcgaacaata tcttagtgaa tgaatggctt     60
tattggccgg ttcaaaatct tgttaaatgt tggtttgata tatatttata ctaacgttat    120
ttaacgcagc tcacaccaat aaaaatgtcg aagccaaatg aagttagttt ggatacaaca    180
gatactgttg aaatttctaa tgaatcttcg ggagacacag agtcgtccaa gggtaaaaat    240
gaagattttg aaacaaaaat tgaaactgac cgttctagaa gatttgagtt tctgttgaag    300
cagacagaaa ttttttcaca ttttatgaca aatcaaggaa agtcgaacag ccctgcaaag    360
cctaaagtcg gccgtcctag aaaggaaact aataaattgg caccagccgg tggtgatggt    420
tctgccgacc atcggcatcg tatgaccgag caggaagaag atgaagaact gcttgctgaa    480
agtaatactt cttcaaaatc cttagcaagg tttgacgctt ctccttttta tattaaaagc    540
ggagagttga gggattacca gatacgtggt ttgaattgga tgatatccct ctacgaacac    600
ggtataaatg gtatacttgc tgatgagatg ggtttaggta aaactctcca aactatttct    660
ctccttggtt acatgaagca ttatagaaat ataccagggc cacatatggt catcgtacca    720
aaatcaacat tagctaattg gatgaatgaa tttaaaaagt ggtgcccaac cctgcgtgct    780
gtctgtttaa tcggagatca ggaaacgagg aatgcgttca tcagagacac tcttatgccg    840
ggtgaatggg atgtctgcgt tacatcttat gaaatgatca tacgagaaaa gagcgttttc    900
aagaagttca actggaggta tatggtcatt gacgaagccc acaggatcaa gaatgaaaaa    960
tccaaactct ccgagattgt gagagagttc aaaacgacga atcgattact cctgaccggt   1020
actcctttac aaaataacct ccacgaattg tggtctcttc ttaacttcct cttaccagat   1080
gttttcaatt catcagatga ttttgattca tggtttaata ccaatacctt ccttggcgat   1140
aattctcttg tcgagagatt acatgctgta ctgagacctt tcctcctaag aagattgaaa   1200
tctgaggtag agaaaaaact caaaccgaag aaagaagtca aaatctacgt tggattgagt   1260
aaaatgcaga gagaatggta tactaaagtt ctaatgaaag atatagacat tgtaaacggt   1320
gctggccgag tcgaaaaaat gcgcctccaa aacatcctca tgcagttgag gaagtgcagt   1380
aatcaccctt atctcttcga cggagctgaa ccaggtccac cttactcaac tgatgagcat   1440
ctggtatata acagtggaaa aatggtaata ttagacaagc ttcttcctaa attgcaagaa   1500
caaggatcac gagttctggt tttcagccaa atgacaagga tgattgatat tctcgaagat   1560
tactgttatt ggagaggata taattactgt cgtcttgatg gtaatacacc tcatgaggat   1620
aggcagagac agattaatga gttcaacgaa gaagacagta agaaattcat tttcatgttg   1680
tcgactcgtg cgggtggttt gggtatcaat ttagccaccg cagatgtagt cattttgtac   1740
gattcggatt ggaaccctca aatggatctc caggctatgg atcgtgctca tcgtattggt   1800
caaaagaaac aagtcaaagt gttcaggatg ataactgaaa acacagttga agagaaaatt   1860
gttgagagag ctgaaataaa actccgcctc gataagttgg tcatccaaca aggcaggctg   1920
gtagacaata aaacggcact caacaaagat gaaatgttga atatgatccg tcacggtgcc   1980
aatcatgtat ttgccagtaa agattctgaa atcaccgatg aagacattga cactattttg   2040
gaaaaaggcg aagcaaggac ggaagaaatg aataaaaaac ttgaacaact cggtgattct   2100
aatttgaaag acttcatgat ggaaaccccg actgagtcag tttaccaatt cgaaggagag   2160
```

```
gattacaggg aaaagcagaa agttttagga ataggaagtt ggatagaacc tccaaaaaga   2220

gaacgtaaag ctaattacgc tgtcgatgcc tattttaggg aagcattgag agtatcagaa   2280

cctaaagctc ccaaggcacc gaggcctcct aaacagccta tagttcaaga tttccaattc   2340

tttcctcctc gtctctttga gctattggac caggagatct attacttcag gaaaactgtg   2400

ggctacaaag ttcctaaaaa tcctgaatta ggttctgatg catcacgtgt ccaaaaggaa   2460

gaacaaagaa agatagatga ggcagaacct ttatcagaag aagaactcgc tgaaaaggaa   2520

aaacttctta cgcagggttt taccaattgg actaaaagag atttcaacca gtttattaaa   2580

gctaatgaaa aatatggtcg tgatgatatt gacaatattt caaaagaagt agaaggaaaa   2640

actccagaag aagtaagagc ttattcagaa gtgttctggg aacgatgtaa cgaattgcag   2700

gacatagatc gtatcatggg gcagatcgac aggggagagg ctaaaattca aaggagagca   2760

agtattaaga aagctctcga tacaaagatg agccggtaca gagccccatt tcatcaactt   2820

cgcatctcct acggtacgaa taagggtaag aactataccg aggaagaaga tagattcctt   2880

gtctgtatgt tgcataagct tggttttgac aaggaaaatg tgtacgaaga acttagagcg   2940

atggtcaggt gtgcgcctca gttcagattc gactggttca tcaaatcgag aacagccatg   3000

gaattgcaga ggcgttgtaa tactctaatt actctcatcg aaagagaaaa tcaggaactt   3060

gaggagaggg aaagagccga gaagaggaaa ggaagaggaa gtgggcgtgg tcctggttcc   3120

ggtaaaagga aaggagacgg ttccatttca tctcccccctc ctgtccctgg ccaaggggat   3180

aagaacagcc ccgccagaaa aaagaaaaaa atgtagtttc acctcctcat gaaaggaact   3240

cattttaaga tatctttttc tagatattta ttttgtgaaa actgtgatgt attttatatc   3300

cgttccgaaa agctctactg ttttgacagt tttattaatt agtggggtgg ggaggaaata   3360

tagccccctc accccccaat aattcataaa t                                  3391
```

```
<210> SEQ ID NO 11
<211> LENGTH: 1023
<212> TYPE: PRT
<213> ORGANISM: Euchistus heros

<400> SEQUENCE: 11

Met Ser Lys Pro Asn Glu Val Ser Leu Asp Thr Thr Asp Thr Val Glu
1               5                   10                  15

Ile Ser Asn Glu Ser Ser Gly Asp Thr Glu Ser Ser Lys Gly Lys Asn
            20                  25                  30

Glu Asp Phe Glu Thr Lys Ile Glu Thr Asp Arg Ser Arg Arg Phe Glu
        35                  40                  45

Phe Leu Leu Lys Gln Thr Glu Ile Phe Ser His Phe Met Thr Asn Gln
    50                  55                  60

Gly Lys Ser Asn Ser Pro Ala Lys Pro Lys Val Gly Arg Pro Arg Lys
65                  70                  75                  80

Glu Thr Asn Lys Leu Ala Pro Ala Gly Gly Asp Gly Ser Ala Asp His
                85                  90                  95

Arg His Arg Met Thr Glu Gln Glu Glu Asp Glu Glu Leu Leu Ala Glu
            100                 105                 110

Ser Asn Thr Ser Ser Lys Ser Leu Ala Arg Phe Asp Ala Ser Pro Phe
        115                 120                 125

Tyr Ile Lys Ser Gly Glu Leu Arg Asp Tyr Gln Ile Arg Gly Leu Asn
    130                 135                 140

Trp Met Ile Ser Leu Tyr Glu His Gly Ile Asn Gly Ile Leu Ala Asp
145                 150                 155                 160
```

```
Glu Met Gly Leu Gly Lys Thr Leu Gln Thr Ile Ser Leu Leu Gly Tyr
                165                 170                 175

Met Lys His Tyr Arg Asn Ile Pro Gly Pro His Met Val Ile Val Pro
            180                 185                 190

Lys Ser Thr Leu Ala Asn Trp Met Asn Glu Phe Lys Lys Trp Cys Pro
        195                 200                 205

Thr Leu Arg Ala Val Cys Leu Ile Gly Asp Gln Glu Thr Arg Asn Ala
    210                 215                 220

Phe Ile Arg Asp Thr Leu Met Pro Gly Glu Trp Asp Val Cys Val Thr
225                 230                 235                 240

Ser Tyr Glu Met Ile Ile Arg Glu Lys Ser Val Phe Lys Lys Phe Asn
                245                 250                 255

Trp Arg Tyr Met Val Ile Asp Glu Ala His Arg Ile Lys Asn Glu Lys
            260                 265                 270

Ser Lys Leu Ser Glu Ile Val Arg Glu Phe Lys Thr Thr Asn Arg Leu
        275                 280                 285

Leu Leu Thr Gly Thr Pro Leu Gln Asn Asn Leu His Glu Leu Trp Ser
    290                 295                 300

Leu Leu Asn Phe Leu Leu Pro Asp Val Phe Asn Ser Ser Asp Asp Phe
305                 310                 315                 320

Asp Ser Trp Phe Asn Thr Asn Thr Phe Leu Gly Asp Asn Ser Leu Val
                325                 330                 335

Glu Arg Leu His Ala Val Leu Arg Pro Phe Leu Leu Arg Arg Leu Lys
            340                 345                 350

Ser Glu Val Glu Lys Lys Leu Lys Pro Lys Lys Glu Val Lys Ile Tyr
        355                 360                 365

Val Gly Leu Ser Lys Met Gln Arg Glu Trp Tyr Thr Lys Val Leu Met
    370                 375                 380

Lys Asp Ile Asp Ile Val Asn Gly Ala Gly Arg Val Glu Lys Met Arg
385                 390                 395                 400

Leu Gln Asn Ile Leu Met Gln Leu Arg Lys Cys Ser Asn His Pro Tyr
                405                 410                 415

Leu Phe Asp Gly Ala Glu Pro Gly Pro Pro Tyr Ser Thr Asp Glu His
            420                 425                 430

Leu Val Tyr Asn Ser Gly Lys Met Val Ile Leu Asp Lys Leu Leu Pro
        435                 440                 445

Lys Leu Gln Glu Gln Gly Ser Arg Val Leu Val Phe Ser Gln Met Thr
    450                 455                 460

Arg Met Ile Asp Ile Leu Glu Asp Tyr Cys Tyr Trp Arg Gly Tyr Asn
465                 470                 475                 480

Tyr Cys Arg Leu Asp Gly Asn Thr Pro His Glu Asp Arg Gln Arg Gln
                485                 490                 495

Ile Asn Glu Phe Asn Glu Glu Asp Ser Lys Lys Phe Ile Phe Met Leu
            500                 505                 510

Ser Thr Arg Ala Gly Gly Leu Gly Ile Asn Leu Ala Thr Ala Asp Val
        515                 520                 525

Val Ile Leu Tyr Asp Ser Asp Trp Asn Pro Gln Met Asp Leu Gln Ala
    530                 535                 540

Met Asp Arg Ala His Arg Ile Gly Gln Lys Lys Gln Val Lys Val Phe
545                 550                 555                 560

Arg Met Ile Thr Glu Asn Thr Val Glu Glu Lys Ile Val Glu Arg Ala
                565                 570                 575
```

```
Glu Ile Lys Leu Arg Leu Asp Lys Leu Val Ile Gln Gln Gly Arg Leu
            580                 585                 590

Val Asp Asn Lys Thr Ala Leu Asn Lys Asp Glu Met Leu Asn Met Ile
        595                 600                 605

Arg His Gly Ala Asn His Val Phe Ala Ser Lys Asp Ser Glu Ile Thr
    610                 615                 620

Asp Glu Asp Ile Asp Thr Ile Leu Glu Lys Gly Glu Ala Arg Thr Glu
625                 630                 635                 640

Glu Met Asn Lys Lys Leu Glu Gln Leu Gly Asp Ser Asn Leu Lys Asp
                645                 650                 655

Phe Met Met Glu Thr Pro Thr Glu Ser Val Tyr Gln Phe Glu Gly Glu
            660                 665                 670

Asp Tyr Arg Glu Lys Gln Lys Val Leu Gly Ile Gly Ser Trp Ile Glu
        675                 680                 685

Pro Pro Lys Arg Glu Arg Lys Ala Asn Tyr Ala Val Asp Ala Tyr Phe
    690                 695                 700

Arg Glu Ala Leu Arg Val Ser Glu Pro Lys Ala Pro Lys Ala Pro Arg
705                 710                 715                 720

Pro Pro Lys Gln Pro Ile Val Gln Asp Phe Gln Phe Phe Pro Pro Arg
                725                 730                 735

Leu Phe Glu Leu Leu Asp Gln Glu Ile Tyr Tyr Phe Arg Lys Thr Val
            740                 745                 750

Gly Tyr Lys Val Pro Lys Asn Pro Glu Leu Gly Ser Asp Ala Ser Arg
        755                 760                 765

Val Gln Lys Glu Glu Gln Arg Lys Ile Asp Glu Ala Glu Pro Leu Ser
    770                 775                 780

Glu Glu Glu Leu Ala Glu Lys Glu Lys Leu Leu Thr Gln Gly Phe Thr
785                 790                 795                 800

Asn Trp Thr Lys Arg Asp Phe Asn Gln Phe Ile Lys Ala Asn Glu Lys
                805                 810                 815

Tyr Gly Arg Asp Asp Ile Asp Asn Ile Ser Lys Glu Val Glu Gly Lys
            820                 825                 830

Thr Pro Glu Glu Val Arg Ala Tyr Ser Glu Val Phe Trp Glu Arg Cys
        835                 840                 845

Asn Glu Leu Gln Asp Ile Asp Arg Ile Met Gly Gln Ile Asp Arg Gly
    850                 855                 860

Glu Ala Lys Ile Gln Arg Arg Ala Ser Ile Lys Lys Ala Leu Asp Thr
865                 870                 875                 880

Lys Met Ser Arg Tyr Arg Ala Pro Phe His Gln Leu Arg Ile Ser Tyr
                885                 890                 895

Gly Thr Asn Lys Gly Lys Asn Tyr Thr Glu Glu Glu Asp Arg Phe Leu
            900                 905                 910

Val Cys Met Leu His Lys Leu Gly Phe Asp Lys Glu Asn Val Tyr Glu
        915                 920                 925

Glu Leu Arg Ala Met Val Arg Cys Ala Pro Gln Phe Arg Phe Asp Trp
    930                 935                 940

Phe Ile Lys Ser Arg Thr Ala Met Glu Leu Gln Arg Arg Cys Asn Thr
945                 950                 955                 960

Leu Ile Thr Leu Ile Glu Arg Glu Asn Gln Glu Leu Glu Glu Arg Glu
                965                 970                 975

Arg Ala Glu Lys Arg Lys Gly Arg Gly Ser Gly Arg Gly Pro Gly Ser
            980                 985                 990

Gly Lys Arg Lys Gly Asp Gly Ser  Ile Ser Ser Pro Pro  Pro Val Pro
```

```
        995                 1000                 1005

Gly Gln  Gly Asp Lys Asn Ser  Pro Ala Arg Lys Lys  Lys Lys Met
    1010                 1015                 1020
```

```
<210> SEQ ID NO 12
<211> LENGTH: 1316
<212> TYPE: DNA
<213> ORGANISM: Euchistus heros

<400> SEQUENCE: 12

aatgaataaa aaacttgaac aacttggtgt tgattcatca ttaaaagatt tcatgatgga     60

ggctcccact gagtctgtct atcagtttga aggcgaagat tatagagaaa agcaaaaagt    120

ttttggaatt ggaaattgga ttgaaccacc aaaacgagaa cgtaaagcaa attatgcagt    180

agatgcctat tttagagaag cactgagagt ttcagaacct aaagctccaa aggcccctag    240

gccaccaaag caacccatag ttcaagattt ccaatttttc ccacctcgtc tgtttgagct    300

gttagatcaa gaaatatact attttcgaaa aactgtttgc tacaaggttc ctaaaaatcc    360

ggagttagga tcagatgctt ctcgtataca aagggaagag caaagaaaaa ttgatgaagc    420

tgagccgttg actgaggaag agctagctga gaaagaaaac ttattgaccc agggttttac    480

taattggact aaaagagatt ttaaccagtt cataaaagct aatgaaaaat atggacgtga    540

tgatattgat aatatctcaa aagatgttga agggaagact ccagaagaag tacgagcata    600

ctctgaagta ttttgggaaa ggtgcaatga actacaggcc atagatcgta tcatggggca    660

gattgataga ggtgaagcga aaattcaaag aagagccagt attaaaaaag ctttagatac    720

aaagatgagt cgatatagag caccgtttca tcaactacga attgcttatg gtacgaacaa    780

ggggaaaaat tacacagaag aagaagacag attccttgtg tgcatgctac ataagcttgg    840

ctttgataaa gaaaatgtgt atgaggaact tagggcgatg gtgaggtgtg ctcctcagtt    900

taggtttgat tggttcatca agtctcgaac agctttggaa ttgcaaagac gttgtaatac    960

tctaatcacg ttaattgaaa gggaaaacca agaattagaa gaaagggaaa aagtagaaaa   1020

aaggaaaagt cgaggcagta atgggcgtgg tcccagttct ggtaaacgta agggagatgg   1080

atctatttca tctccacctg tctctgtaca gagtgataaa agcagccctg ctcggaaaaa   1140

gaaaaagtat atctctgttg agtaaattta tcttaaaact gggagtagat acccaattct   1200

cattatcggg tgatcaagga atcaatctca tataggagcc taaaacttca ttagtttgta   1260

attgaatatt taatttacat ctctagtttc caaatattgt ttcttttaca tctgta       1316
```

```
<210> SEQ ID NO 13
<211> LENGTH: 387
<212> TYPE: PRT
<213> ORGANISM: Euchistus heros

<400> SEQUENCE: 13

Met Asn Lys Lys Leu Glu Gln Leu Gly Val Asp Ser Ser Leu Lys Asp
1               5                   10                  15

Phe Met Met Glu Ala Pro Thr Glu Ser Val Tyr Gln Phe Glu Gly Glu
            20                  25                  30

Asp Tyr Arg Glu Lys Gln Lys Val Phe Gly Ile Gly Asn Trp Ile Glu
        35                  40                  45

Pro Pro Lys Arg Glu Arg Lys Ala Asn Tyr Ala Val Asp Ala Tyr Phe
    50                  55                  60

Arg Glu Ala Leu Arg Val Ser Glu Pro Lys Ala Pro Lys Ala Pro Arg
65                  70                  75                  80
```

```
Pro Pro Lys Gln Pro Ile Val Gln Asp Phe Gln Phe Phe Pro Pro Arg
                85                  90                  95

Leu Phe Glu Leu Leu Asp Gln Glu Ile Tyr Tyr Phe Arg Lys Thr Val
            100                 105                 110

Cys Tyr Lys Val Pro Lys Asn Pro Glu Leu Gly Ser Asp Ala Ser Arg
        115                 120                 125

Ile Gln Arg Glu Glu Gln Arg Lys Ile Asp Glu Ala Glu Pro Leu Thr
    130                 135                 140

Glu Glu Glu Leu Ala Glu Lys Glu Asn Leu Leu Thr Gln Gly Phe Thr
145                 150                 155                 160

Asn Trp Thr Lys Arg Asp Phe Asn Gln Phe Ile Lys Ala Asn Glu Lys
                165                 170                 175

Tyr Gly Arg Asp Asp Ile Asp Asn Ile Ser Lys Asp Val Glu Gly Lys
            180                 185                 190

Thr Pro Glu Glu Val Arg Ala Tyr Ser Glu Val Phe Trp Glu Arg Cys
        195                 200                 205

Asn Glu Leu Gln Ala Ile Asp Arg Ile Met Gly Gln Ile Asp Arg Gly
    210                 215                 220

Glu Ala Lys Ile Gln Arg Arg Ala Ser Ile Lys Lys Ala Leu Asp Thr
225                 230                 235                 240

Lys Met Ser Arg Tyr Arg Ala Pro Phe His Gln Leu Arg Ile Ala Tyr
                245                 250                 255

Gly Thr Asn Lys Gly Lys Asn Tyr Thr Glu Glu Glu Asp Arg Phe Leu
            260                 265                 270

Val Cys Met Leu His Lys Leu Gly Phe Asp Lys Glu Asn Val Tyr Glu
        275                 280                 285

Glu Leu Arg Ala Met Val Arg Cys Ala Pro Gln Phe Arg Phe Asp Trp
    290                 295                 300

Phe Ile Lys Ser Arg Thr Ala Leu Glu Leu Gln Arg Arg Cys Asn Thr
305                 310                 315                 320

Leu Ile Thr Leu Ile Glu Arg Glu Asn Gln Glu Leu Glu Glu Arg Glu
                325                 330                 335

Lys Val Glu Lys Arg Lys Ser Arg Gly Ser Asn Gly Arg Gly Pro Ser
            340                 345                 350

Ser Gly Lys Arg Lys Gly Asp Gly Ser Ile Ser Ser Pro Pro Val Ser
        355                 360                 365

Val Gln Ser Asp Lys Ser Ser Pro Ala Arg Lys Lys Lys Lys Tyr Ile
    370                 375                 380

Ser Val Glu
385


<210> SEQ ID NO 14
<211> LENGTH: 1827
<212> TYPE: DNA
<213> ORGANISM: Euchistus heros

<400> SEQUENCE: 14

gataaatatg aataagaaaa ttttaaattt atttgtttca ttaaaaaatt atcttatggg      60

tttattgatt ataaattggt tcaatcataa aatacgagat acataagatt gtattatcat     120

aacaaaccca atctctagta tcgtcatcct gctgttctgg ttcactctga gtttctttat     180

cttcatcaaa agcaaaactt gcaactttaa aagcagaaag taattcatca ccaacagtgg     240

ctggtccttc atctctggtt tcagctcttc tcaaaatttc gtcaatgtca caagttggtt     300
```

```
cttcatcacc atcttcttca tctttaaata attcttcagc cccaaatttt aaaatagcag    360
taagttcttc tttgttaaaa ggcgcactgg atgaagaatt ttttttatcc aggacagttc    420
tacctgtagt atccattctt tgtataacta aatgatctaa gaccattttt tgtttggccc    480
gctcgacaat attttcctca acagaacttt tagtaacaag tctgtatatg ttcacctgat    540
ttttctgacc gattctatga gctctagctt gtgcttgcaa atcattttgt ggattccaat    600
cagagtcaaa tataatgaca gtatcagctg ttgctaaatt aatgcccaaa ccaccagcac    660
gagttgataa taagaaacag aaatctggtg aattttcagc attgaaatga tcgagggctt    720
gctttctcaa ttcaccttta attgaaccgt ctaaacgttg gaaagggaaa tgtctcattt    780
gaagatactc agccagtata tccaacattc gtaccatttg agaaaatata agtactctat    840
gcccagtttc tttaaggcga acaagcaact tgtccaacag aagtaatttc cctgagcctt    900
ttaacaattg ctgtaagtag tcttcagttt ttgcttcatt ttctaatggt tttattagat    960
gtgcatgatt acagcatttt tttaattcaa taacaatatt tataaatgta ctaggagaac   1020
ctttgactcc ttttcgaaga gcagaataat ttttggacaa aatccacctg taatactgct   1080
tctgtacaga tgtcatttca acacgtaata tttgttccac tttagctggt aaagatttct   1140
caacatcctt cttaactcgt cgtagaatat atggttccag ctgtctgtgc aacttagtat   1200
agcctttatt agcagagttg tcatgttctt tttcaaattc ttcccagtta ttaaatctgt   1260
tgggcataat aaagtgaagc aacgcccaaa gctctttaag actattttgc aaaggagtgc   1320
ctgttataag aagcctatgg ttggtatcaa actctttcaa tgttttgtat aataatgaat   1380
catcattttt caatctgtgt gcttcatcaa ccataaggat agcccagctt atactaccca   1440
aaaatgcttt gtctttaaga acaatttcat atgtagtaag aatggcattg aattttaacc   1500
ttttcgaacc tgaatagcac cattcataat tacgtataac atcacgggag tttatatcac   1560
caatataagt tacaacattc atttctggag cccataatga aaactccctc tgccatgaag   1620
tcatcgtaga taaagggaca acaattaaaa atggtccata caactggtga gtatgaaata   1680
aataatacaa actgcagata gtctgaatag ttttaccaag acccatttca tcagccaaaa   1740
taatagaatt ttctttacac cacgaatgaa ccaaccaatt caaaccactg atttgataat   1800
ctctcaaaac caatacctgg tcaccac                                       1827
```

```
<210> SEQ ID NO 15
<211> LENGTH: 1454
<212> TYPE: PRT
<213> ORGANISM: Euchistus heros

<400> SEQUENCE: 15

Met Pro Gln Lys Asp Gly Ser Glu Asp Ser Ala Ser Glu Ser Asp Lys
1               5                   10                  15

Asp Gln Gly Asn Gln Glu Glu Ser Asp Asn Ser Ser Ser Glu Ser Gly
            20                  25                  30

Ser Gly Ser Glu Ser Asp Ser Ala Ser Ser Ala Ser Ser Ser Ser Lys
        35                  40                  45

Ser Ser Asp Ser Gly Ser Asp Tyr Lys Ser Lys Thr Ser Asn Ser Ser
    50                  55                  60

Arg Gly Lys Asn Asp Ile Lys Gln Tyr Trp Glu Glu Asn Pro Asp Val
65                  70                  75                  80

Tyr Gly Ile Arg Arg Ser Asn Arg Gln Arg Lys Glu Pro Ser Arg Leu
                85                  90                  95

Asn Thr Gly Asp Ser Asp Ser Ser Glu Lys Thr Lys Arg Ser Val Lys
```

```
            100                 105                 110

Arg Ser Ser Pro Lys Ser Trp Asn Ser Asp Thr Ser Tyr Asp Ser Glu
        115                 120                 125

Thr Asp Lys Glu Ser Lys Arg Pro Pro Pro Ser Lys Pro Pro Gly Gly
    130                 135                 140

Arg Arg Arg Pro Ala Lys Thr Thr Arg Lys Pro Lys Ser Arg Ile Arg
145                 150                 155                 160

Asn Arg Ala Tyr Ser Asp Ser Ser Glu Ser Ser Tyr Glu Ser Glu Asp
                165                 170                 175

Asp Asn Asn Arg Arg Thr Lys Ser Arg Arg Gly Val Thr Ser Val Ser
            180                 185                 190

Tyr Lys Glu Ala Ser Asp Glu Lys Thr Asp Ser Asp Glu Leu Leu Glu
        195                 200                 205

Pro Asp Pro Glu Pro Val Glu Pro Ala Pro Pro Asp Thr Ser Glu Thr
    210                 215                 220

Ile Glu Lys Val Leu Ala Gln Arg Ile Gly Lys Lys Gly Val Val Gly
225                 230                 235                 240

Asn Gln Thr Thr Val Tyr Ala Val Glu Glu Asn Gly Asp Pro Asn Ser
                245                 250                 255

Asn Tyr Glu Ser Leu Asp Lys Asp Glu Thr Glu Val Gln Tyr Leu Ile
            260                 265                 270

Lys Trp Lys Gly Trp Ser His Ile His Asn Thr Trp Glu Ser Glu Leu
        275                 280                 285

Ser Leu Lys Glu Gln Lys Val Lys Gly Val Lys Lys Leu Glu Asn Phe
    290                 295                 300

Val Lys Arg Glu Glu Asp Ile Arg Phe Trp Lys Glu His Thr Thr Pro
305                 310                 315                 320

Glu Asp Ile Glu Tyr Tyr Glu Cys Gln Leu Glu Leu Gln Gln Glu Leu
                325                 330                 335

Leu Lys Ser Tyr Asn Arg Val Glu Arg Ile Ile Ala Val Ser Lys Thr
            340                 345                 350

Asp Gly Gln Val Glu Tyr Tyr Val Lys Trp Glu Ser Leu Pro Tyr Ser
        355                 360                 365

Glu Ala Thr Trp Glu Asp Ser Gly Leu Ile Glu Lys Lys Trp Pro Lys
    370                 375                 380

Lys Ile Lys Glu Phe Lys Glu Arg Glu Asp Ser Lys Arg Thr Pro Ser
385                 390                 395                 400

Lys Leu Cys Arg Val Leu Lys Ala Arg Pro Lys Phe Ile Lys Ile Glu
                405                 410                 415

Asp Gln Pro Glu Tyr Met Gly Gly Asp Gln Val Leu Val Leu Arg Asp
            420                 425                 430

Tyr Gln Ile Ser Gly Leu Asn Trp Leu Val His Ser Trp Cys Lys Glu
        435                 440                 445

Asn Ser Ile Ile Leu Ala Asp Glu Met Gly Leu Gly Lys Thr Ile Gln
    450                 455                 460

Thr Ile Cys Ser Leu Tyr Tyr Leu Phe His Thr His Gln Leu Tyr Gly
465                 470                 475                 480

Pro Phe Leu Ile Val Val Pro Leu Ser Thr Met Thr Ser Trp Gln Arg
                485                 490                 495

Glu Phe Ser Leu Trp Ala Pro Glu Met Asn Val Val Thr Tyr Ile Gly
            500                 505                 510

Asp Ile Asn Ser Arg Asp Val Ile Arg Asn Tyr Glu Trp Cys Tyr Ser
        515                 520                 525
```

```
Gly Ser Lys Arg Leu Lys Phe Asn Ala Ile Leu Thr Thr Tyr Glu Ile
    530                 535                 540

Val Leu Lys Asp Lys Ala Phe Leu Gly Ser Ile Ser Trp Ala Ile Leu
545                 550                 555                 560

Met Val Asp Glu Ala His Arg Leu Lys Asn Asp Asp Ser Leu Leu Tyr
                565                 570                 575

Lys Thr Leu Lys Glu Phe Asp Thr Asn His Arg Leu Leu Ile Thr Gly
            580                 585                 590

Thr Pro Leu Gln Asn Ser Leu Lys Glu Leu Trp Ala Leu Leu His Phe
        595                 600                 605

Ile Met Pro Asn Arg Phe Asn Asn Trp Glu Glu Phe Glu Lys Glu His
    610                 615                 620

Asp Asn Ser Ala Asn Lys Gly Tyr Thr Lys Leu His Arg Gln Leu Glu
625                 630                 635                 640

Pro Tyr Ile Leu Arg Arg Val Lys Lys Asp Val Glu Lys Ser Leu Pro
                645                 650                 655

Ala Lys Val Glu Gln Ile Leu Arg Val Glu Met Thr Ser Val Gln Lys
            660                 665                 670

Gln Tyr Tyr Arg Trp Ile Leu Ser Lys Asn Tyr Ser Ala Leu Arg Lys
        675                 680                 685

Gly Val Lys Gly Ser Pro Ser Thr Phe Ile Asn Ile Val Ile Glu Leu
    690                 695                 700

Lys Lys Cys Cys Asn His Ala His Leu Ile Lys Pro Leu Glu Asn Glu
705                 710                 715                 720

Ala Lys Thr Glu Asp Tyr Leu Gln Gln Leu Leu Lys Gly Ser Gly Lys
                725                 730                 735

Leu Leu Leu Leu Asp Lys Leu Leu Val Arg Leu Lys Glu Thr Gly His
            740                 745                 750

Arg Val Leu Ile Phe Ser Gln Met Val Arg Met Leu Asp Ile Leu Ala
        755                 760                 765

Glu Tyr Leu Gln Met Arg His Phe Pro Phe Gln Arg Leu Asp Gly Ser
    770                 775                 780

Ile Lys Gly Glu Leu Arg Lys Gln Ala Leu Asp His Phe Asn Ala Glu
785                 790                 795                 800

Asn Ser Pro Asp Phe Cys Phe Leu Leu Ser Thr Arg Ala Gly Gly Leu
                805                 810                 815

Gly Ile Asn Leu Ala Thr Ala Asp Thr Val Ile Ile Phe Asp Ser Asp
            820                 825                 830

Trp Asn Pro Gln Asn Asp Leu Gln Ala Gln Ala Arg Ala His Arg Ile
        835                 840                 845

Gly Gln Lys Asn Gln Val Asn Ile Tyr Arg Leu Val Thr Lys Ser Ser
    850                 855                 860

Val Glu Glu Asn Ile Val Glu Arg Ala Lys Gln Lys Met Val Leu Asp
865                 870                 875                 880

His Leu Val Ile Gln Arg Met Asp Thr Thr Gly Arg Thr Val Leu Asp
                885                 890                 895

Lys Lys Asn Ser Ser Ser Ser Ala Pro Phe Asn Lys Glu Glu Leu Thr
            900                 905                 910

Ala Ile Leu Lys Phe Gly Ala Glu Glu Leu Phe Lys Asp Glu Glu Asp
        915                 920                 925

Gly Asp Glu Glu Pro Thr Cys Asp Ile Asp Glu Ile Leu Arg Arg Ala
    930                 935                 940
```

```
Glu Thr Arg Asp Glu Gly Pro Ala Thr Val Gly Asp Glu Leu Leu Ser
945                 950                 955                 960

Ala Phe Lys Val Ala Ser Phe Ala Phe Asp Glu Asp Lys Glu Thr Gln
                965                 970                 975

Ser Glu Pro Glu Gln Gln Asp Asp Asp Thr Arg Asp Trp Asp Glu Ile
            980                 985                 990

Ile Pro Glu Thr Tyr Arg Gln Lys  Val Glu Glu Glu Glu  Arg Ala Lys
        995                 1000                 1005

Glu Met  Glu Asp Leu Tyr Leu  Pro Pro Arg Ser Arg  Lys Thr Leu
    1010                 1015                 1020

Gln Gln  Ile Asn His Ser Glu  Ser Asp Ala Asp Gly  Lys Ala Asn
    1025                 1030                 1035

Lys Lys  Lys Arg Lys Lys Gly  Glu Glu Asn Glu Thr  Thr Glu Glu
    1040                 1045                 1050

Gly Ser  Asp Glu Glu Lys Pro  Arg Lys Arg Gly Arg  Pro Arg Gly
    1055                 1060                 1065

Asn Lys  Gly Ser Ser Lys Glu  Val Ile Lys Gly Phe  Asn Asp Ala
    1070                 1075                 1080

Glu Ile  Arg Arg Phe Ile Arg  Ser Phe Lys Lys Phe  Pro Ala Pro
    1085                 1090                 1095

Leu Lys  Arg Leu Asp Ala Ile  Ala Cys Asp Ala Glu  Leu Gln Glu
    1100                 1105                 1110

Lys Pro  Leu Ala Glu Leu Arg  Lys Leu Gly Asp Met  Leu Lys Gln
    1115                 1120                 1125

Arg Cys  Lys Ala Cys Leu Gly  Asp Gln Thr Lys Glu  Asn Leu Thr
    1130                 1135                 1140

Asp Ala  Asn Glu Glu Asn Thr  Gly Thr Ser Gly Arg  Lys Arg Gly
    1145                 1150                 1155

Arg Gly  Pro Ser Ala Lys Leu  Gly Gly Val Ser Val  Asn Ala Lys
    1160                 1165                 1170

Ser Leu  Leu Ala Cys Glu Lys  Glu Leu Glu Pro Leu  Asp Ile Glu
    1175                 1180                 1185

Ile Pro  Leu Asp Pro Asn Glu  Arg Asn Lys Trp Val  Leu Asp Val
    1190                 1195                 1200

Arg Val  Lys Pro Ala Asn Phe  Asp Cys Asp Trp Asp  Val Asn Asp
    1205                 1210                 1215

Asp Ser  Ala Leu Leu Arg Gly  Val Tyr Gln Tyr Gly  Met Gly Ser
    1220                 1225                 1230

Trp Glu  Ala Ile Lys Met Asp  Pro Ser Ile Gly Ile  Ser Asp Lys
    1235                 1240                 1245

Ile Leu  Ser Asn Asn Gly Ser  Lys Pro Gln Thr Lys  His Leu Ala
    1250                 1255                 1260

Ser Arg  Ala Glu Tyr Leu Leu  Lys Val Leu Lys Lys  Ser Ile Asp
    1265                 1270                 1275

Gln Arg  Gln Gly Ser Thr Val  Lys Thr Lys Arg Gln  Arg Lys Arg
    1280                 1285                 1290

Asp Asn  Lys Ala Thr Ser Arg  Glu Ile Ile Glu Asp  Lys Asp Asp
    1295                 1300                 1305

Ser Ser  Gly Gly Glu Leu Pro  Ala Glu Ser Val Ser  Thr Pro Ser
    1310                 1315                 1320

Gln Asp  Ser Phe Asn His Lys  Asp Ile Lys Leu Glu  Glu Asn Glu
    1325                 1330                 1335

Glu Asp  Lys Lys Lys Gly Lys  Lys Lys Glu Thr Gln  Lys Lys Lys
```

```
    1340                1345                1350

Lys Lys  Asn Glu Ser Gly Pro  Met His Phe Thr Ala  Asn Ser Glu
    1355                1360                1365

Pro Arg  Ala Leu Asp Val Leu  Gly Asp Leu Glu Pro  Ser Ile Phe
    1370                1375                1380

Asn Glu  Cys Lys Glu Lys Met  Arg Pro Val Lys Lys  Ala Leu Lys
    1385                1390                1395

Ala Leu  Asp Asn Pro Asp Gln  Ser Leu Gly Pro Gln  Glu Gln Val
    1400                1405                1410

Asn His  Thr Arg Gln Cys Leu  Val Gln Ile Gly Asp  Gln Ile Asn
    1415                1420                1425

Lys Cys  Leu Met Glu Tyr Lys  Glu Ser Asp Ile Ile  Lys Gln Trp
    1430                1435                1440

Arg Arg  Cys Val Ser Ser Asn  Phe Val Ile Val
    1445                1450
```

<210> SEQ ID NO 16
<211> LENGTH: 496
<212> TYPE: DNA
<213> ORGANISM: Euchistus heros

<400> SEQUENCE: 16

```
gactacctcg agggtgaagg ttataaatat gaacgtattg acggtacgat caccggtagc     60

ttaagacaag aagctatcga tcggtttaac gcccctggag ctcaacaatt tgtttttctt    120

ttgtccactc gtgcgggagg tcttggtatt aatctcgcta ctgcagatac agttattatt    180

tatgactctg actggaatcc tcataacgat attcaggcct tttcgagagc acacaggata    240

gggcaagcaa acaaggttat gatttatcga tttgtgacac gagcgtctgt tgaagaaaga    300

gtaacgcaag tggctaagag aaaaatgatg ttaacccatc ttgtcgtacg accaggtatg    360

ggtggcaagc aagcaaattt cactaagcaa gaacttgatg atattttaag gtttggaaca    420

gaagaacttt tcaaagaaga gcagggtaaa gaagatgaag ccattcatta tgacgataaa    480

gctgttgaag aattac                                                    496
```

<210> SEQ ID NO 17
<211> LENGTH: 481
<212> TYPE: DNA
<213> ORGANISM: Euchistus heros

<400> SEQUENCE: 17

```
caaaaattga aactgaccgt tctagaagat ttgagtttct gttgaagcag acagaaattt     60

tttcacattt tatgacaaat caaggaaagt cgaacagccc tgcaaagcct aaagtcggcc    120

gtcctagaaa ggaaactaat aaattggcac cagccggtgg tgatggttct gccgaccatc    180

ggcatcgtat gaccgagcag gaagaagatg aagaactgct tgctgaaagt aatacttctt    240

caaaatcctt agcaaggttt gacgcttctc ctttttatat taaaagcgga gagttgaggg    300

attaccagat acgtggtttg aattggatga tatccctcta cgaacacggt ataaatggta    360

tacttgctga tgagatgggt ttaggtaaaa ctctccaaac tatttctctc cttggttaca    420

tgaagcatta tagaaatata ccagggccac atatggtcat cgtaccaaaa tcaacattag    480

c                                                                    481
```

<210> SEQ ID NO 18
<211> LENGTH: 490
<212> TYPE: DNA

<213> ORGANISM: Euchistus heros

<400> SEQUENCE: 18

```
gttcaagatt tccaattttt cccacctcgt ctgtttgagc tgttagatca agaaatatac     60
tattttcgaa aaactgtttg ctacaaggtt cctaaaaatc cggagttagg atcagatgct    120
tctcgtatac aaagggaaga gcaaagaaaa attgatgaag ctgagccgtt gactgaggaa    180
gagctagctg agaaagaaaa cttattgacc cagggtttta ctaattggac taaaagagat    240
tttaaccagt tcataaaagc taatgaaaaa tatggacgtg atgatattga taatatctca    300
aaagatgttg aagggaagac tccagaagaa gtacgagcat actctgaagt attttgggaa    360
aggtgcaatg aactacaggc catagatcgt atcatggggc agattgatag aggtgaagcg    420
aaaattcaaa gaagagccag tattaaaaaa gctttagata caaagatgag tcgatataga    480
gcaccgtttc                                                           490
```

<210> SEQ ID NO 19
<211> LENGTH: 496
<212> TYPE: DNA
<213> ORGANISM: Euchistus heros

<400> SEQUENCE: 19

```
cagctggaac catatattct acgacgagtt aagaaggatg ttgagaaatc tttaccagct     60
aaagtggaac aaatattacg tgttgaaatg acatctgtac agaagcagta ttacaggtgg    120
attttgtcca aaaattattc tgctcttcga aaaggagtca aaggttctcc tagtacattt    180
ataaatattg ttattgaatt aaaaaaatgc tgtaatcatg cacatctaat aaaaccatta    240
gaaaatgaag caaaaactga agactactta cagcaattgt taaaaggctc agggaaatta    300
cttctgttgg acaagttgct tgttcgcctt aaagaaactg ggcatagagt acttatattt    360
tctcaaatgg tacgaatgtt ggatatactg gctgagtatc ttcaaatgag acatttccct    420
ttccaacgtt tagacggttc aattaaaggt gaattgagaa agcaagccct cgatcatttc    480
aatgctgaaa attcac                                                    496
```

<210> SEQ ID NO 20
<211> LENGTH: 38
<212> TYPE: DNA
<213> ORGANISM: Artificial Sequence
<220> FEATURE:
<223> OTHER INFORMATION: Primer Mi2.T7.F

<400> SEQUENCE: 20

```
taatacgact cactataggg aagaaggcat agaacaga                             38
```

<210> SEQ ID NO 21
<211> LENGTH: 39
<212> TYPE: DNA
<213> ORGANISM: Artificial Sequence
<220> FEATURE:
<223> OTHER INFORMATION: Primer Mi2.T7.R

<400> SEQUENCE: 21

```
taatacgact cactataggg tcagaatggt aatcagaga                            39
```

<210> SEQ ID NO 22
<211> LENGTH: 38
<212> TYPE: DNA
<213> ORGANISM: Artificial Sequence
<220> FEATURE:
<223> OTHER INFORMATION: Primer ISWI30.T7.F

<400> SEQUENCE: 22
taatacgact cactataggg tgaatcagtc taccaatt 38

<210> SEQ ID NO 23
<211> LENGTH: 38
<212> TYPE: DNA
<213> ORGANISM: Artificial Sequence
<220> FEATURE:
<223> OTHER INFORMATION: Primer ISWI30.T7.R

<400> SEQUENCE: 23
taatacgact cactataggg ggttctgact catctatt 38

<210> SEQ ID NO 24
<211> LENGTH: 39
<212> TYPE: DNA
<213> ORGANISM: Artificial Sequence
<220> FEATURE:
<223> OTHER INFORMATION: Primer ISWI2.T7.F

<400> SEQUENCE: 24
taatacgact cactataggg ttgctcaatc ctacataca 39

<210> SEQ ID NO 25
<211> LENGTH: 38
<212> TYPE: DNA
<213> ORGANISM: Artificial Sequence
<220> FEATURE:
<223> OTHER INFORMATION: Primer ISWI2.T7.R

<400> SEQUENCE: 25
taatacgact cactataggg gaataccaac aggctact 38

<210> SEQ ID NO 26
<211> LENGTH: 38
<212> TYPE: DNA
<213> ORGANISM: Artificial Sequence
<220> FEATURE:
<223> OTHER INFORMATION: Primer KSMT.T7.F

<400> SEQUENCE: 26
taatacgact cactataggg gatcaaattc aagcaact 38

<210> SEQ ID NO 27
<211> LENGTH: 38
<212> TYPE: DNA
<213> ORGANISM: Artificial Sequence
<220> FEATURE:
<223> OTHER INFORMATION: Primer KSMT.T7.R

<400> SEQUENCE: 27
taatacgact cactataggg ttcttcctaa accatgtt 38

<210> SEQ ID NO 28
<211> LENGTH: 38
<212> TYPE: DNA
<213> ORGANISM: Artificial Sequence
<220> FEATURE:
<223> OTHER INFORMATION: Primer CHD1.T7.F

<400> SEQUENCE: 28
taatacgact cactataggg tttgcttcct tctttcaa 38

<210> SEQ ID NO 29

<211> LENGTH: 39
<212> TYPE: DNA
<213> ORGANISM: Artificial Sequence
<220> FEATURE:
<223> OTHER INFORMATION: Primer CHD1.T7.R

<400> SEQUENCE: 29
taatacgact cactataggg cttctttgtt aaacggatt 39

<210> SEQ ID NO 30
<211> LENGTH: 4493
<212> TYPE: DNA
<213> ORGANISM: Euchistus heros

<400> SEQUENCE: 30
gcatatacag aaacaatcaa aagatcaaat ctaactcgtt caaacagcag gatgaagaaa 60
actaggaaga attctcgacc tttatttgtg gctggtggtt ttgcagcggc agctgagaag 120
atgcctgagt aggcctgatt gagagtgcag gtacggatgg ctttcttccc ggtcctctca 180
gtcctctggg gccacgtgag ccaatatgac cagggccgac gggcctcaac cgtggcctcc 240
ctggacctcg acgattgctt cggttgctta aagcaggcat gaaaggcctc gaaatttttg 300
gtggtgtctg gctgataggt tcctcctggt cggtgttgtt atcattggag tcttggctcg 360
atttcataac gtccgtgccc ttcggactct cagctggtga tttcacacct tggtaaactt 420
caacgacccc atcttcagtc ttcatatgtt tcaccgtgtc cttgtaattt cctagagcat 480
tttttctttt tctttctctt tccctgtaga tatcttgcct tgattcttca agttgtctcc 540
tctctgcttg cttctgccga tatttctgtt ctatttctgc atcatcaagc aatagagaaa 600
caacctcttt cggtttaaga gtgtctggtt tgaaattacc cccactgatg acaacccttt 660
ggatttcact tttttcttga gctctctgca agatcctttc ttcgatggtc cctttacaaa 720
tgagccgata gactgtgact tgtttcgttt gtccaagacg atgggcacgg tccatcgctt 780
gttggtcaac agtagggttc caatcactgt catagaatat cacagtatca gctgcggtaa 840
ggttgattcc aagacctcca gctcgcgtac tcaacaggaa tacaaatatg tcctctcttg 900
tttgaaagtc agcaaccata tcccttctgt ctgatatctt tgaagaacca tctaacctca 960
tatatgtgtg ctttctgtac cacatatatt cctctaacaa gtcgatcatc cttgtcatct 1020
gggagtaaat tagagctcga tgcccttgtt ccttcagcct ggtgagaagc ccatccaaga 1080
cgtacagctt tccagcatca gttaccagtg tctgtttgtc aggtatgact atactcgacc 1140
agccagtgat tggtcgaaga ctgagtaggc caagaggagg tgggcactgg aacccaggtt 1200
cttgtttatc cccttcccaa agaacctgcc acagtctccc gtcctccccc cagaggtgag 1260
aagagatcca gctccacctt cggttcgagc tgtacagccg tctgcttttc tttatctcca 1320
ccttgacagt aggagtgaag aggaatggag gtaaatagac tggctgacat gagagaatct 1380
gaggcttcct cacaatatgt ggcaatgctg gtaataagtt agcactatct tctccaccgc 1440
actctccctt agccttcttc gacctgacta tgcgatgttc tatcgtttca ggcatacttt 1500
ctatcctcac ggtggaatgg gaaaacactt ggttggaata agtggtgaac acaagattgt 1560
ttgggtagct cctgtcttca atgattccga cgagtttcct tctcactcct tgcctccttg 1620 ctataaatatt gtgccacctg aaataaatcc caaaaaacat tagcttatac agttctccta 1680
cagataacct caacagtcga gtgaaagaaa atgaactatc cctctcggat gagtcatcac 1740
tgaataaaga tctatgagaa tgaaaaggat taaaaggcga taagtagttc atgagaagat 1800
gaagtttatc cccagggaac acagcatctg tgatgagagc aggcacaatg taatcttccg 1860

```
tagccatgga aaaaggggat cgaggttccc ttcgctcgaa tagttcaggg tgattacaga   1920
ccttacgaaa ttgcatcacg aggttcatca aatttgaagt gatactctga gctgattggt   1980
aagaagatcc agaagagtgt agcaaatctt caattcgaat cttctttttc acagctgaat   2040
ataacatctt ctgcctcgtc gtcagaggac agtacaccat gatttctatt ttatctgaca   2100
gttcattctc cacatctgtt tttactctcc gcaacatgaa tggttttagg atcatatgta   2160
aacgggacaa atgcttttca tcaatactgg ttttatgctc tgcatgactt tctatatctt   2220
ttgaaaacca ttcattgaac tcatcgtgtg aatcaaacat tgagggcatt atgaaatgaa   2280
gaagagccca aagttcagcc attgagtttt gaataggtgt tccactcaga agtaatctgt   2340
tgcggcaatt gaatccaaga agcaatttcc aacgcatgct tgtagtgctt ttgatagcct   2400
gagcttcgtc tagaattaaa tactgccatt ttatcctatt gaagtatttt atatcagtaa   2460
ttacaagctg atagcttgtg atcacaacat ggaaactggc atctttagta tgtaaacctt   2520
tttgatccca aaattgacgt aatattttcc tttcctgctg atttccccaa taaggcacaa   2580
ctttgaaatc aggtacaaaa cgctgcattt cttgctgcca attatgtaat gtagaagcgg   2640
gcgatattat gagaaatgga ccccaaacag agtatttttc agcaatatgg caaagaaagg   2700
ctatcgattg gactgtcttt cccaatccca tttcatctgc caagattcca ttaatacctt   2760
ggtcatataa attcacaagc catgtcattc cctttatttg atatcccttg agagtaccac   2820
ggaatatctg cggttggggt ttatcttcac caacatctcc atcctcttcc attttctggc   2880
ttactccaaa ttctcttgct cgtgcttctt ccagaaaaaa caccttttca actttctttc   2940
gtactttttc tttctctgcc tcgcaatcgt agtcatccaa aggtaggagt ctaggattag   3000
cttcctcttc aagttggctc aggattcgaa gttgatcttc agtcgttccg ccaccgagct   3060
tacgggacat aaagtgagca tagagttctg tttgagttat gaggaaattt aattttcttt   3120
gctgcctctt agcctccatc agttctacat ccaacttcct ttgttcctct gcttctttct   3180
ccattcttct tcttgtttcc ctttccaccc tctcaaatct tttccagtat acttgcattt   3240
cccgtgtcaa tctttttgct ctccaaataa cctctttcat attcttttgc gattgcattg   3300
cacgttgtcg acagtgcctc atacagttag tagcagctcg cctgcaagct gttagaattt   3360
ctttatggtt acttatccta tagcgctgaa cctttccaat ttcttttttc gccatgttgg   3420
cccaaatttt acgcctgcga tgtgccatga tttcggcagc tttgttttgg gctgattttt   3480
ttctaaggct catttccttt ttagaccttg acattatttg taggtctggt tcttctttga   3540
tttttctttt ctttttttct acactaaaac tttcatgtgg ttgatcttgt tttttcaact   3600
tttctttttt ttgaaaaaca aatttctttt tcttaacaaa accagaactt gaactctgat   3660
gctcaggata cttatcgaaa ttggagagga gtcctgtgcc atagtacata tactcttggt   3720
ttttagaatt gtggtagaat tttttttat atttgtttct aagtacatgt tcacggagca   3780
tgtcttgtaa gtcctcttca gttatttctt catcatcaga ggaatctgat gtgtcagtca   3840
atagaacatc aactaaccac tgcctatcta agcttacatt actcaagttg taaagcctct   3900
tcttgtcagc tatcctatct tctttagttg ctgttatacc attccatacc gtttctccgg   3960
tataggcatc aacaccagct aattccgtgt cagaatcact ggaggcttct ccatcctcac   4020
ctaatggttg ttttaaaaag tcttcaacat atgttaggaa aggagctatg tccaagcttt   4080
tttctagctt ttgataataa agaggtttgg caatttctgt tttcactacc atgtttgttt   4140
tatcatcact catactgcaa aaatcaatga catcaaaaga tatctctgca tcccagttag   4200
```

```
aaaatattac taaactgaaa tgtaaaactt atatagaatc atatttaaaa tgagttgaac   4260

aaactattac gcttgtcaca tttttagtaa accacaccca aattaatatc tacttttata   4320

cataaaccta atcagaatat cagtcagtcc atactagacg attgtaaaaa tgtgctaggg   4380

gtcaaataaa aaaggaaagt gaaattaggt tagtatatat tgaaagacgc atctcctttt   4440

cagagattca gtgaaatatt tcagccagct gggttagcct gacagaattc aag          4493


<210> SEQ ID NO 31
<211> LENGTH: 1363
<212> TYPE: PRT
<213> ORGANISM: Euchistus heros

<400> SEQUENCE: 31

Met Ser Asp Asp Lys Thr Asn Met Val Val Lys Thr Glu Ile Ala Lys
1               5                   10                  15

Pro Leu Tyr Tyr Gln Lys Leu Glu Lys Ser Leu Asp Ile Ala Pro Phe
            20                  25                  30

Leu Thr Tyr Val Glu Asp Phe Leu Lys Gln Pro Leu Gly Glu Asp Gly
        35                  40                  45

Glu Ala Ser Ser Asp Ser Asp Thr Glu Leu Ala Gly Val Asp Ala Tyr
    50                  55                  60

Thr Gly Glu Thr Val Trp Asn Gly Ile Thr Ala Thr Lys Glu Asp Arg
65                  70                  75                  80

Ile Ala Asp Lys Lys Arg Leu Tyr Asn Leu Ser Asn Val Ser Leu Asp
                85                  90                  95

Arg Gln Trp Leu Val Asp Val Leu Leu Thr Asp Thr Ser Asp Ser Ser
            100                 105                 110

Asp Asp Glu Glu Ile Thr Glu Glu Asp Leu Gln Asp Met Leu Arg Glu
        115                 120                 125

His Val Leu Arg Asn Lys Tyr Lys Lys Lys Phe Tyr His Asn Ser Lys
    130                 135                 140

Asn Gln Glu Tyr Met Tyr Tyr Gly Thr Gly Leu Leu Ser Asn Phe Asp
145                 150                 155                 160

Lys Tyr Pro Glu His Gln Ser Ser Ser Ser Gly Phe Val Lys Lys Lys
                165                 170                 175

Lys Phe Val Phe Gln Lys Lys Glu Lys Leu Lys Lys Gln Asp Gln Pro
            180                 185                 190

His Glu Ser Phe Ser Val Glu Lys Lys Lys Arg Lys Ile Lys Glu Glu
        195                 200                 205

Pro Asp Leu Gln Ile Met Ser Arg Ser Lys Lys Glu Met Ser Leu Arg
    210                 215                 220

Lys Lys Ser Ala Gln Asn Lys Ala Ala Glu Ile Met Ala His Arg Arg
225                 230                 235                 240

Arg Lys Ile Trp Ala Asn Met Ala Lys Lys Glu Ile Gly Lys Val Gln
                245                 250                 255

Arg Tyr Arg Ile Ser Asn His Lys Glu Ile Leu Thr Ala Cys Arg Arg
            260                 265                 270

Ala Ala Thr Asn Cys Met Arg His Cys Arg Gln Arg Ala Met Gln Ser
        275                 280                 285

Gln Lys Asn Met Lys Glu Val Ile Trp Arg Ala Lys Arg Leu Thr Arg
    290                 295                 300

Glu Met Gln Val Tyr Trp Lys Arg Phe Glu Arg Val Glu Arg Glu Thr
305                 310                 315                 320

Arg Arg Arg Met Glu Lys Glu Ala Glu Glu Gln Arg Lys Leu Asp Val
```

```
                325                 330                 335

Glu Leu Met Glu Ala Lys Arg Gln Gln Arg Lys Leu Asn Phe Leu Ile
            340                 345                 350

Thr Gln Thr Glu Leu Tyr Ala His Phe Met Ser Arg Lys Leu Gly Gly
        355                 360                 365

Gly Thr Thr Glu Asp Gln Leu Arg Ile Leu Ser Gln Leu Glu Glu Glu
    370                 375                 380

Ala Asn Pro Arg Leu Leu Pro Leu Asp Asp Tyr Asp Cys Glu Ala Glu
385                 390                 395                 400

Lys Glu Lys Val Arg Lys Lys Val Glu Lys Val Phe Phe Leu Glu Glu
                405                 410                 415

Ala Arg Ala Arg Glu Phe Gly Val Ser Gln Lys Met Glu Glu Asp Gly
            420                 425                 430

Asp Val Gly Glu Asp Lys Pro Gln Pro Gln Ile Phe Arg Gly Thr Leu
        435                 440                 445

Lys Gly Tyr Gln Ile Lys Gly Met Thr Trp Leu Val Asn Leu Tyr Asp
    450                 455                 460

Gln Gly Ile Asn Gly Ile Leu Ala Asp Glu Met Gly Leu Gly Lys Thr
465                 470                 475                 480

Val Gln Ser Ile Ala Phe Leu Cys His Ile Ala Glu Lys Tyr Ser Val
                485                 490                 495

Trp Gly Pro Phe Leu Ile Ile Ser Pro Ala Ser Thr Leu His Asn Trp
            500                 505                 510

Gln Gln Glu Met Gln Arg Phe Val Pro Asp Phe Lys Val Val Pro Tyr
        515                 520                 525

Trp Gly Asn Gln Gln Glu Arg Lys Ile Leu Arg Gln Phe Trp Asp Gln
    530                 535                 540

Lys Gly Leu His Thr Lys Asp Ala Ser Phe His Val Val Ile Thr Ser
545                 550                 555                 560

Tyr Gln Leu Val Ile Thr Asp Ile Lys Tyr Phe Asn Arg Ile Lys Trp
                565                 570                 575

Gln Tyr Leu Ile Leu Asp Glu Ala Gln Ala Ile Lys Ser Thr Thr Ser
            580                 585                 590

Met Arg Trp Lys Leu Leu Leu Gly Phe Asn Cys Arg Asn Arg Leu Leu
        595                 600                 605

Leu Ser Gly Thr Pro Ile Gln Asn Ser Met Ala Glu Leu Trp Ala Leu
    610                 615                 620

Leu His Phe Ile Met Pro Ser Met Phe Asp Ser His Asp Glu Phe Asn
625                 630                 635                 640

Glu Trp Phe Ser Lys Asp Ile Glu Ser His Ala Glu His Lys Thr Ser
                645                 650                 655

Ile Asp Glu Lys His Leu Ser Arg Leu His Met Ile Leu Lys Pro Phe
            660                 665                 670

Met Leu Arg Arg Val Lys Thr Asp Val Glu Asn Glu Leu Ser Asp Lys
        675                 680                 685

Ile Glu Ile Met Val Tyr Cys Pro Leu Thr Thr Arg Gln Lys Met Leu
    690                 695                 700

Tyr Ser Ala Val Lys Lys Lys Ile Arg Ile Glu Asp Leu Leu His Ser
705                 710                 715                 720

Ser Gly Ser Ser Tyr Gln Ser Ala Gln Ser Ile Thr Ser Asn Leu Met
                725                 730                 735

Asn Leu Val Met Gln Phe Arg Lys Val Cys Asn His Pro Glu Leu Phe
            740                 745                 750
```

```
Glu Arg Arg Glu Pro Arg Ser Pro Phe Ser Met Ala Thr Glu Asp Tyr
        755                 760                 765

Ile Val Pro Ala Leu Ile Thr Asp Ala Val Phe Pro Gly Asp Lys Leu
    770                 775                 780

His Leu Leu Met Asn Tyr Leu Ser Pro Phe Asn Pro Phe His Ser His
785                 790                 795                 800

Arg Ser Leu Phe Ser Asp Asp Ser Ser Glu Arg Asp Ser Ser Phe Ser
                805                 810                 815

Phe Thr Arg Leu Leu Arg Leu Ser Val Gly Glu Leu Tyr Lys Leu Met
            820                 825                 830

Phe Phe Gly Ile Tyr Phe Arg Trp His Asn Ile Ile Ala Arg Arg Gln
        835                 840                 845

Gly Val Arg Arg Lys Leu Val Gly Ile Ile Glu Asp Arg Ser Tyr Pro
    850                 855                 860

Asn Asn Leu Val Phe Thr Thr Tyr Ser Asn Gln Val Phe Ser His Ser
865                 870                 875                 880

Thr Val Arg Ile Glu Ser Met Pro Glu Thr Ile Glu His Arg Ile Val
                885                 890                 895

Arg Ser Lys Lys Ala Lys Gly Glu Cys Gly Gly Glu Asp Ser Ala Asn
            900                 905                 910

Leu Leu Pro Ala Leu Pro His Ile Val Arg Lys Pro Gln Ile Leu Ser
        915                 920                 925

Cys Gln Pro Val Tyr Leu Pro Pro Phe Leu Phe Thr Pro Thr Val Lys
    930                 935                 940

Val Glu Ile Lys Lys Ser Arg Arg Leu Tyr Ser Ser Asn Arg Arg Trp
945                 950                 955                 960

Ser Trp Ile Ser Ser His Leu Trp Gly Glu Asp Gly Arg Leu Trp Gln
                965                 970                 975

Val Leu Trp Glu Gly Asp Lys Gln Glu Pro Gly Phe Gln Cys Pro Pro
            980                 985                 990

Pro Leu Gly Leu Leu Ser Leu Arg  Pro Ile Thr Gly Trp  Ser Ser Ile
        995                 1000                 1005

Val Ile  Pro Asp Lys Gln Thr  Leu Val Thr Asp Ala  Gly Lys Leu
    1010                 1015                 1020

Tyr Val  Leu Asp Gly Leu Leu  Thr Arg Leu Lys Glu  Gln Gly His
    1025                 1030                 1035

Arg Ala  Leu Ile Tyr Ser Gln  Met Thr Arg Met Ile  Asp Leu Leu
    1040                 1045                 1050

Glu Glu  Tyr Met Trp Tyr Arg  Lys His Thr Tyr Met  Arg Leu Asp
    1055                 1060                 1065

Gly Ser  Ser Lys Ile Ser Asp  Arg Arg Asp Met Val  Ala Asp Phe
    1070                 1075                 1080

Gln Thr  Arg Glu Asp Ile Phe  Val Phe Leu Leu Ser  Thr Arg Ala
    1085                 1090                 1095

Gly Gly  Leu Gly Ile Asn Leu  Thr Ala Ala Asp Thr  Val Ile Phe
    1100                 1105                 1110

Tyr Asp  Ser Asp Trp Asn Pro  Thr Val Asp Gln Gln  Ala Met Asp
    1115                 1120                 1125

Arg Ala  His Arg Leu Gly Gln  Thr Lys Gln Val Thr  Val Tyr Arg
    1130                 1135                 1140

Leu Ile  Cys Lys Gly Thr Ile  Glu Glu Arg Ile Leu  Gln Arg Ala
    1145                 1150                 1155
```

```
Gln Glu  Lys Ser Glu Ile Gln  Arg Val Val Ile Ser  Gly Gly Asn
    1160                 1165                 1170

Phe Lys  Pro Asp Thr Leu Lys  Pro Lys Glu Val Val  Ser Leu Leu
    1175                 1180                 1185

Leu Asp  Asp Ala Glu Ile Glu  Gln Lys Tyr Arg Gln  Lys Gln Ala
    1190                 1195                 1200

Glu Arg  Arg Gln Leu Glu Glu  Ser Arg Gln Asp Ile  Tyr Arg Glu
    1205                 1210                 1215

Arg Glu  Arg Lys Arg Lys Asn  Ala Leu Gly Asn Tyr  Lys Asp Thr
    1220                 1225                 1230

Val Lys  His Met Lys Thr Glu  Asp Gly Val Val Glu  Val Tyr Gln
    1235                 1240                 1245

Gly Val  Lys Ser Pro Ala Glu  Ser Pro Lys Gly Thr  Asp Val Met
    1250                 1255                 1260

Lys Ser  Ser Gln Asp Ser Asn  Asp Asn Asn Thr Asp  Gln Glu Glu
    1265                 1270                 1275

Pro Ile  Ser Gln Thr Pro Pro  Lys Ile Ser Arg Pro  Phe Met Pro
    1280                 1285                 1290

Ala Leu  Ser Asn Arg Ser Asn  Arg Arg Gly Pro Gly  Arg Pro Arg
    1295                 1300                 1305

Leu Arg  Pro Val Gly Pro Gly  His Ile Gly Ser Arg  Gly Pro Arg
    1310                 1315                 1320

Gly Leu  Arg Gly Pro Gly Arg  Lys Pro Ser Val Pro  Ala Leu Ser
    1325                 1330                 1335

Ile Arg  Pro Thr Gln Ala Ser  Ser Gln Leu Pro Leu  Gln Asn His
    1340                 1345                 1350

Gln Pro  Gln Ile Lys Val Glu  Asn Ser Ser
    1355                 1360
```

<210> SEQ ID NO 32
<211> LENGTH: 6108
<212> TYPE: DNA
<213> ORGANISM: Euchistus heros

<400> SEQUENCE: 32

```
acaggcttat atcatctaac aattatgaat gtcatgagat caaaaatatt atccgaacta     60

aattaaaaac acaaaaacga atgacagaaa gatcggcctg aatcagttta aattagtcct    120

ttgattgtga aaaattttaa agctttgaat ccttaattat aataataaac tattaaccgg    180

cagtgtatca tgaagctaaa cttgtactta tagtcaatgg aacaacatct gatggacgct    240

ttgttttact taaccgacca actttcttgc tgaccttact aatctcatta cttgaggcag    300

cagaagctct tctagtacga attacaaggt tagggttcga ataaggtggt gggggaggat    360

taggaggagg gggaggtgta ctacgccgtt taccactctt aaattttcta ctttgccctg    420

atgagggttt ccccccattt tgaggactgt catctaaagt ccacagatca attgaaacac    480

gaccatgaga tctagtcctt ggagtgccct cctcgatact acttccacta tgacaatttc    540

ttcccccgcc cccactagct cttgttttat tgacctgatt tcgcgaatca acgccagagt    600

aagtgagaac agcttccgac tcagcttccc cagaaggtga ttttctatct ccttgcagag    660

cagccagtct accagcctcc cactcttttt tttgttgttc gatttctgct tcagctgcag    720

ccaactgctc ttttgaccaa gcagcatcat tttcttccat gaatttcatg gcatacctct    780

caacagcaga aagctgttgc ataagattgt gaagttctaa ttctgccttg ctcatttctt    840

gcccaactcc ttcatgggta tcaataggta tattttcatc gaactctgcc aactcagcag    900
```

```
cagcttctgc tttagcaacc ttggctgccg caacatcgga ttcatcctca gcttgggcca    960
ttgcactctc gagcgcacca attgctactt tctcatcaga gttcgcaacc atctgtgtgt   1020
cttcaggatt ctgagcagtt ttatcactat tatgaagaac ttctgccatc cttctggaag   1080
catcattctc ggaggtgtca acattaaaca gatcttgaat tgttgaactc ttaaagtaag   1140
ctgtagtaaa gtttcctcct tcaatggcta catctcccag cattctcttt tggttcgctt   1200
ttttaagtat attttcctca acagtttttt cgctgatcaa tctataaata tgtacatctc   1260
tcgtttggcc gattctgtgg catcgatctt gagcttgggc atccatggta ggattccaat   1320
cactatcata aaatataaca gtgtctgcac cagttaaatt aataccaact cctccagatc   1380
ttgtggatag aataaagcaa aatattctct tgtcagcatt aaagcgttcc attaagagct   1440
gtctctgatc tactttcgtt gttccatcaa gacgaagata tatgtgcccg tgaaagttaa   1500
gaaatgcttc cagtacgtct aacattctag tcatttgtgt aaatattaat atccgatgat   1560
ggtcagcttt caatcttcga agaagcttgt ctaatgattg aagctttcca cagtcatact   1620
gtattagtct tctatcaggg aactgcgtac tcattgctga tgatatgcta tgaagtaatc   1680
gaagtttagg tcttagccaa gtatcaacta atgatagcct cttctcttct tggaacatct   1740
ttgaaggtgg cggatgtggc acatgtaaac ggacaggttg gctggaaaca gccggtacgt   1800
acaaaacaaa cctagagaat atatcagaca actccgcaac tcggtcttcg atggaatgaa   1860
tagctgctgt gagagcatga gtctgattcc aaaataacaa ggggtttgaa gataaagcat   1920
tcttacagtg aactgttcca atgcagtctt tagtttcatc aggagcatca tccaatgtta   1980
aagatgatag aaggtcagaa ccataaattg gaagggcctg acacctttgt tcattgattc   2040
taacaatcag ttccaacttc tcctttcgcc gttttttttct aagattttct aggtattcat   2100
ctctcaaatc ttcattcgga ttagattctt ctttgttatt tttatttgag ttcaaagtac   2160
tttgtcttgt tactttttta agagaaggta atgaattgac gttcgatcca tttccttgag   2220
ctggctctga cgatatgctc acaggtgaat tgtttacagt agtcaaactg ttttgaacaa   2280
cagtagctgc agaagtgatg tttaatggag gtaccctcat gataggccga tttgaattta   2340
tttgggtcac agaagtaggg ttgactagtt tagctacatt gcttccctgt ttggatacca   2400
cagttaatct ttgcccagta gtagtcatta cagtagtagc acctccttga ggagtaataa   2460
ccggttgtgg agagagtacc agctgcctac cggtaggggt attaactaat tgtgcaaatt   2520
gagggaccat acgaccagca ttgccttcat ttttaaccac gcctccacta gtagttgtta   2580
atgaagccac tgagattgct ttcatggcac caggttgtaa taactgaagg taattaggaa   2640
tctgaccaga agtaggattc gccagtctta aagttacact ctggctagca ttttgtccaa   2700
gctttatcaa tggtgatgtt ccaacttttg ttgaaaaaga agaaatccga tgattattac   2760
taacttgtac aattggccta acagggctag aaacctgagg tggttggggc aatatccgtt   2820
tcttgacatt aattttaacc cttcctttag ggcaaggtgg tagatcagga ggtgcagaat   2880
caattgtgcg aatgaagtca ggattaactt tgtatttacg agctctgtga gcaacaaatg   2940
ctaataacca tagttcaaat tcaattatcc gcaaatttag gaaaactaga tcgacatgtt   3000
taaacggatc ataatctaaa gcactccaaa ctatagaagg aacatggtat tcaagagaat   3060
ccatttgaaa cggagacacg gtagggcgaa cttcgaacag gttaggatga ttacacactt   3120
tcctcagctg catcagtaca ttaatgacac tcaataaact accagaagca agtgtttctt   3180
ttgttttagc tctagacatg aaatcatcat ataaatatcg ttgcctgttg gataaccgac   3240
```

```
acattactat atgttcatat ttctttggca tttgcgtttc tacttcacac tttaatcttc   3300
ttaacagaaa cggacgcaac actttatgaa gtcttttaat aatagtgtca ttgtactcag   3360
aattcccttc aatcatgcct gttactggat tagaaaacca ttctttaaat tcacgatgcg   3420
attcaaaaac attaggcata agaaaatgca ttaatgacca gagttccata agattatttt   3480
gtaatggagt accagtgagt agtaaccgcc tttgagtttg aaaattcaat aagagttgcc   3540
aacgttgtga tttaaaattt ttgatatttt gagcttcatc taaaattaaa tatttccatt   3600
tttttctacg aaaactctga tgatcctgta taactaactt ataagaggta atgcagatat   3660
ggaatgcatt aggttttgtc caccctgatc gtttcaattt ccgttctttt tgagttccat   3720
aataagttaa tattttgaat gctggacacc attttttaaa ctccatttcc cagtttaaca   3780
tgacagacgt agggacaatg attaaatgag gtccccaatt acctttttca caagcaagat   3840
gagctattaa tgctatggtt tgaattgtct ttccgagacc catttcgtca gcaagtatac   3900
catttagttt cctatcatac atagtaacta accagtctaa cccaatgtgc tgatattctc   3960
ttaagggatg tttaagaaga aaaggaactt tcgtaacaac acttgtagat gatagagtgt   4020
ttcctttagg ctgaagactt tcagctatag cagcaacatc atttatttcc ttgtctttgt   4080
cttggttccc ttcctctaca tgatgcgagt catttatgag agccttcaaa gtcgaatctt   4140
ccttgtcact tgaagaactg tcttcttctt cttcttcttc actaacttca tcttcaaaat   4200
cttcttcttc tgaggcttca tcagattctt cattcaggat ttctttcctt tttcttgatc   4260
tttgggaact gggatctccg ttcgaaggta aaggttcgga cgggagctcg ataccatatt   4320
ttgctctaag ttgttctatg ctcatatttc cttcctcctt taaatcatct atttcttgtt   4380
tataatccac tgttccttca gtcttttctt gttccagaat tgtttcttca tcatctgaag   4440
aatcaccaga atcttgatat tccatgtcat catcctcaac atcttcatcc atgctgacag   4500
gagttgatat agaatccctt tgagcaaggt agttggaaag tagatcttca agtggaagct   4560
cgctctcttt tttcagaaga tccacttcat cttgattatc acatttatca tcattagcag   4620
aaagtgcttc ttccttagca atcgtctctt catcgtcgtc agacggatct tctggctcaa   4680
attcatcgtc agagtgatgc ctgggagaag ttggtcttga agtgttcatg ctttcagcaa   4740
caagacttga atacttttca gtttgatcaa caataaaact taagtgttga tcaagtgctt   4800
tttttctctt ttcttctaac ctagtttgtt gtttgaattc aactagcttt tcaacatttg   4860
accagaactg tttgatttct ttcgcaataa aagaagctat gcgttttaac tgcatttctt   4920
gagctttgat agctttctgt actagagctt ctttttcttg aaaatgtttt tgaaccattc   4980
ttgcacactt ttttgcagct gctttcttcc atttcctctc ctgggcaaaa tctgcagcca   5040
gccaagccat ttcttctagc agataatccc aatgagcttt agcccttggc aattcatgga   5100
ctttaggtaa tcttttctct ggccataatc catccttttg taactctcct accctttgca   5160
ttacatacgc ctcttgttta gctctttcaa caatttgttc ctggctattg actccatcca   5220
ccggagaagc atttttttaca gctgatttca ctgtagtcag tttttggaat ttggaagata   5280
attctgcttt ggtaggacta gcagatgatg gaacccgtac atcagtattg cttcctggcc   5340
tgttcccagt aagagcagat tgtagaagag agtgattttg tgattgcaga accttataca   5400
gatcctctcc gtcattacca ggatctaact tatttgtttt tagaaatgtc tgtaaaggaa   5460
ctacaggcaa acgagacctc cacggactga agtctgagag gtttccattt gcctgtagat   5520
aacagagaag agcacatctc tctgcaaact ttgtctgaaa tcttttattt ttattatcgt   5580
ttaaatcttt tattcttttt ctaaaggaat tatattcatc aagcggcagc ttgcgttttc   5640
```

```
ttgttgaaga tgacgacaaa cttaatgaaa gtgatggttg agggttacct tggctaggag   5700

gttggagatt ggtcatcata ggagaatcgg acaggataga agtcggggag gagcggactt   5760

ggagtcgccc cccttggctc gagtttgcca accttgtcat tgatggtgaa ccctgttgca   5820

gggttggcaa gagaggagcc aaggggagca cttgagatcc agcacaaggt ttttcaagaa   5880

ctggcttttc aaagccaagt tgaagattgt tcatatcaaa ttcattgtgt tatcacaatt   5940

ttcttcgtcc atcaacaata aaatcaagaa aatgatcttc ggtaacgaac tttaggaaag   6000

aactcatttt actaatttat tagccaatta attctgattt tattcaaatt ccgtggagaa   6060

atattcctat gccacattct cttcaatgca acatggcgtt aggttcag                6108
```

<210> SEQ ID NO 33
<211> LENGTH: 1790
<212> TYPE: PRT
<213> ORGANISM: Euchistus heros

<400> SEQUENCE: 33

```
Met Asn Asn Leu Gln Leu Gly Phe Glu Lys Pro Val Leu Glu Lys Pro
1               5                   10                  15

Cys Ala Gly Ser Gln Val Leu Pro Leu Ala Pro Leu Leu Pro Thr Leu
            20                  25                  30

Gln Gln Gly Ser Pro Ser Met Thr Arg Leu Ala Asn Ser Ser Gln Gly
        35                  40                  45

Gly Arg Leu Gln Val Arg Ser Ser Pro Thr Ser Ile Leu Ser Asp Ser
    50                  55                  60

Pro Met Met Thr Asn Leu Gln Pro Pro Ser Gln Gly Ser Asn Thr Asp
65                  70                  75                  80

Val Arg Val Pro Ser Ser Ala Ser Pro Thr Lys Ala Glu Leu Ser Ser
                85                  90                  95

Lys Phe Gln Lys Leu Thr Thr Val Lys Ser Ala Val Lys Asn Ala Ser
            100                 105                 110

Pro Val Asp Gly Val Asn Ser Gln Glu Gln Ile Val Glu Arg Ala Lys
        115                 120                 125

Gln Glu Ala Tyr Val Met Gln Arg Val Gly Glu Leu Gln Lys Asp Gly
    130                 135                 140

Leu Trp Pro Glu Lys Arg Leu Pro Lys Val His Glu Leu Pro Arg Ala
145                 150                 155                 160

Lys Ala His Trp Asp Tyr Leu Leu Glu Glu Met Ala Trp Leu Ala Ala
                165                 170                 175

Asp Phe Ala Gln Glu Arg Lys Trp Lys Lys Ala Ala Ala Lys Lys Cys
            180                 185                 190

Ala Arg Met Val Gln Lys His Phe Gln Glu Lys Glu Ala Leu Val Gln
        195                 200                 205

Lys Ala Ile Lys Ala Gln Glu Met Gln Leu Lys Arg Ile Ala Ser Phe
    210                 215                 220

Ile Ala Lys Glu Ile Lys Gln Phe Trp Ser Asn Val Glu Lys Leu Val
225                 230                 235                 240

Glu Phe Lys Gln Gln Thr Arg Leu Glu Glu Lys Arg Lys Lys Ala Leu
                245                 250                 255

Asp Gln His Leu Ser Phe Ile Val Asp Gln Thr Glu Lys Tyr Ser Ser
            260                 265                 270

Leu Val Ala Glu Ser Met Asn Thr Ser Arg Pro Thr Ser Pro Arg His
        275                 280                 285
```

```
His Ser Asp Asp Glu Phe Glu Pro Glu Asp Pro Ser Asp Asp Asp Glu
    290                 295                 300

Glu Thr Ile Ala Lys Glu Glu Ala Leu Ser Ala Asn Asp Asp Lys Cys
305                 310                 315                 320

Asp Asn Gln Asp Glu Val Asp Leu Leu Lys Lys Glu Ser Glu Leu Pro
                325                 330                 335

Leu Glu Asp Leu Leu Ser Asn Tyr Leu Ala Gln Arg Asp Ser Ile Ser
            340                 345                 350

Thr Pro Val Ser Met Asp Glu Asp Val Glu Asp Asp Asp Met Glu Tyr
        355                 360                 365

Gln Asp Ser Gly Asp Ser Ser Asp Asp Glu Glu Thr Ile Leu Glu Gln
    370                 375                 380

Glu Lys Thr Glu Gly Thr Val Asp Tyr Lys Gln Glu Ile Asp Asp Leu
385                 390                 395                 400

Lys Glu Glu Gly Asn Met Ser Ile Glu Gln Leu Arg Ala Lys Tyr Gly
                405                 410                 415

Ile Glu Leu Pro Ser Glu Pro Leu Pro Ser Asn Gly Asp Pro Ser Ser
            420                 425                 430

Gln Arg Ser Arg Lys Arg Lys Glu Ile Leu Asn Glu Glu Ser Asp Glu
        435                 440                 445

Ala Ser Glu Glu Glu Asp Phe Glu Asp Glu Val Ser Glu Glu Glu Glu
    450                 455                 460

Glu Glu Asp Ser Ser Ser Ser Asp Lys Glu Asp Ser Thr Leu Lys Ala
465                 470                 475                 480

Leu Ile Asn Asp Ser His His Val Glu Glu Gly Asn Gln Asp Lys Asp
                485                 490                 495

Lys Glu Ile Asn Asp Val Ala Ala Ile Ala Glu Ser Leu Gln Pro Lys
            500                 505                 510

Gly Asn Thr Leu Ser Ser Thr Ser Val Val Thr Lys Val Pro Phe Leu
        515                 520                 525

Leu Lys His Pro Leu Arg Glu Tyr Gln His Ile Gly Leu Asp Trp Leu
    530                 535                 540

Val Thr Met Tyr Asp Arg Lys Leu Asn Gly Ile Leu Ala Asp Glu Met
545                 550                 555                 560

Gly Leu Gly Lys Thr Ile Gln Thr Ile Ala Leu Ile Ala His Leu Ala
                565                 570                 575

Cys Glu Lys Gly Asn Trp Gly Pro His Leu Ile Ile Val Pro Thr Ser
            580                 585                 590

Val Met Leu Asn Trp Glu Met Glu Phe Lys Lys Trp Cys Pro Ala Phe
        595                 600                 605

Lys Ile Leu Thr Tyr Tyr Gly Thr Gln Lys Glu Arg Lys Leu Lys Arg
    610                 615                 620

Ser Gly Trp Thr Lys Pro Asn Ala Phe His Ile Cys Ile Thr Ser Tyr
625                 630                 635                 640

Lys Leu Val Ile Gln Asp His Gln Ser Phe Arg Arg Lys Lys Trp Lys
                645                 650                 655

Tyr Leu Ile Leu Asp Glu Ala Gln Asn Ile Lys Asn Phe Lys Ser Gln
            660                 665                 670

Arg Trp Gln Leu Leu Leu Asn Phe Gln Thr Gln Arg Arg Leu Leu Leu
        675                 680                 685

Thr Gly Thr Pro Leu Gln Asn Asn Leu Met Glu Leu Trp Ser Leu Met
    690                 695                 700

His Phe Leu Met Pro Asn Val Phe Glu Ser His Arg Glu Phe Lys Glu
```

```
705                 710                 715                 720

Trp Phe Ser Asn Pro Val Thr Gly Met Ile Glu Gly Asn Ser Glu Tyr
                725                 730                 735

Asn Asp Thr Ile Ile Lys Arg Leu His Lys Val Leu Arg Pro Phe Leu
            740                 745                 750

Leu Arg Arg Leu Lys Cys Glu Val Glu Thr Gln Met Pro Lys Lys Tyr
        755                 760                 765

Glu His Ile Val Met Cys Arg Leu Ser Asn Arg Gln Arg Tyr Leu Tyr
    770                 775                 780

Asp Asp Phe Met Ser Arg Ala Lys Thr Lys Glu Thr Leu Ala Ser Gly
785                 790                 795                 800

Ser Leu Leu Ser Val Ile Asn Val Leu Met Gln Leu Arg Lys Val Cys
                805                 810                 815

Asn His Pro Asn Leu Phe Glu Val Arg Pro Thr Val Ser Pro Phe Gln
            820                 825                 830

Met Asp Ser Leu Glu Tyr His Val Pro Ser Ile Val Trp Ser Ala Leu
        835                 840                 845

Asp Tyr Asp Pro Phe Lys His Val Asp Leu Val Phe Leu Asn Leu Arg
    850                 855                 860

Ile Ile Glu Phe Glu Leu Trp Leu Leu Ala Phe Val Ala His Arg Ala
865                 870                 875                 880

Arg Lys Tyr Lys Val Asn Pro Asp Phe Ile Arg Thr Ile Asp Ser Ala
                885                 890                 895

Pro Pro Asp Leu Pro Pro Cys Pro Lys Gly Arg Val Lys Ile Asn Val
            900                 905                 910

Lys Lys Arg Ile Leu Pro Gln Pro Pro Gln Val Ser Ser Pro Val Arg
        915                 920                 925

Pro Ile Val Gln Val Ser Asn Asn His Arg Ile Ser Ser Phe Ser Thr
    930                 935                 940

Lys Val Gly Thr Ser Pro Leu Ile Lys Leu Gly Gln Asn Ala Ser Gln
945                 950                 955                 960

Ser Val Thr Leu Arg Leu Ala Asn Pro Thr Ser Gly Gln Ile Pro Asn
                965                 970                 975

Tyr Leu Gln Leu Leu Gln Pro Gly Ala Met Lys Ala Ile Ser Val Ala
            980                 985                 990

Ser Leu Thr Thr Thr Ser Gly Gly  Val Val Lys Asn Glu  Gly Asn Ala
        995                 1000                1005

Gly Arg  Met Val Pro Gln Phe  Ala Gln Leu Val Asn  Thr Pro Thr
    1010                1015                1020

Gly Arg  Gln Leu Val Leu Ser  Pro Gln Pro Val Ile  Thr Pro Gln
    1025                1030                1035

Gly Gly  Ala Thr Thr Val Met  Thr Thr Thr Gly Gln  Arg Leu Thr
    1040                1045                1050

Val Val  Ser Lys Gln Gly Ser  Asn Val Ala Lys Leu  Val Asn Pro
    1055                1060                1065

Thr Ser  Val Thr Gln Ile Asn  Ser Asn Arg Pro Ile  Met Arg Val
    1070                1075                1080

Pro Pro  Leu Asn Ile Thr Ser  Ala Ala Thr Val Val  Gln Asn Ser
    1085                1090                1095

Leu Thr  Thr Val Asn Asn Ser  Pro Val Ser Ile Ser  Ser Glu Pro
    1100                1105                1110

Ala Gln  Gly Asn Gly Ser Asn  Val Asn Ser Leu Pro  Ser Leu Lys
    1115                1120                1125
```

```
Lys Val  Thr Arg Gln Ser Thr  Leu Asn Ser Asn Lys  Asn Asn Lys
    1130                 1135                 1140

Glu Glu  Ser Asn Pro Asn Glu  Asp Leu Arg Asp Glu  Tyr Leu Glu
    1145                 1150                 1155

Asn Leu  Arg Lys Lys Arg Arg  Lys Glu Lys Leu Glu  Leu Ile Val
    1160                 1165                 1170

Arg Ile  Asn Glu Gln Arg Cys  Gln Ala Leu Pro Ile  Tyr Gly Ser
    1175                 1180                 1185

Asp Leu  Leu Ser Ser Leu Thr  Leu Asp Asp Ala Pro  Asp Glu Thr
    1190                 1195                 1200

Lys Asp  Cys Ile Gly Thr Val  His Cys Lys Asn Ala  Leu Ser Ser
    1205                 1210                 1215

Asn Pro  Leu Leu Phe Trp Asn  Gln Thr His Ala Leu  Thr Ala Ala
    1220                 1225                 1230

Ile His  Ser Ile Glu Asp Arg  Val Ala Glu Leu Ser  Asp Ile Phe
    1235                 1240                 1245

Ser Arg  Phe Val Leu Tyr Val  Pro Ala Val Ser Ser  Gln Pro Val
    1250                 1255                 1260

Arg Leu  His Val Pro His Pro  Pro Pro Ser Lys Met  Phe Gln Glu
    1265                 1270                 1275

Glu Lys  Arg Leu Ser Leu Val  Asp Thr Trp Leu Arg  Pro Lys Leu
    1280                 1285                 1290

Arg Leu  Leu His Ser Ile Ser  Ser Ala Met Ser Thr  Gln Phe Pro
    1295                 1300                 1305

Asp Arg  Arg Leu Ile Gln Tyr  Asp Cys Gly Lys Leu  Gln Ser Leu
    1310                 1315                 1320

Asp Lys  Leu Leu Arg Arg Leu  Lys Ala Asp His His  Arg Ile Leu
    1325                 1330                 1335

Ile Phe  Thr Gln Met Thr Arg  Met Leu Asp Val Leu  Glu Ala Phe
    1340                 1345                 1350

Leu Asn  Phe His Gly His Ile  Tyr Leu Arg Leu Asp  Gly Thr Thr
    1355                 1360                 1365

Lys Val  Asp Gln Arg Gln Leu  Leu Met Glu Arg Phe  Asn Ala Asp
    1370                 1375                 1380

Lys Arg  Ile Phe Cys Phe Ile  Leu Ser Thr Arg Ser  Gly Gly Val
    1385                 1390                 1395

Gly Ile  Asn Leu Thr Gly Ala  Asp Thr Val Ile Phe  Tyr Asp Ser
    1400                 1405                 1410

Asp Trp  Asn Pro Thr Met Asp  Ala Gln Ala Gln Asp  Arg Cys His
    1415                 1420                 1425

Arg Ile  Gly Gln Thr Arg Asp  Val His Ile Tyr Arg  Leu Ile Ser
    1430                 1435                 1440

Glu Lys  Thr Val Glu Glu Asn  Ile Leu Lys Lys Ala  Asn Gln Lys
    1445                 1450                 1455

Arg Met  Leu Gly Asp Val Ala  Ile Glu Gly Gly Asn  Phe Thr Thr
    1460                 1465                 1470

Ala Tyr  Phe Lys Ser Ser Thr  Ile Gln Asp Leu Phe  Asn Val Asp
    1475                 1480                 1485

Thr Ser  Glu Asn Asp Ala Ser  Arg Arg Met Ala Glu  Val Leu His
    1490                 1495                 1500

Asn Ser  Asp Lys Thr Ala Gln  Asn Pro Glu Asp Thr  Gln Met Val
    1505                 1510                 1515
```

```
Ala Asn  Ser Asp Glu Lys Val  Ala Ile Gly Ala Leu  Glu Ser Ala
    1520                 1525                 1530

Met Ala  Gln Ala Glu Asp Glu  Ser Asp Val Ala Ala  Ala Lys Val
    1535                 1540                 1545

Ala Lys  Ala Glu Ala Ala Ala  Glu Leu Ala Glu Phe  Asp Glu Asn
    1550                 1555                 1560

Ile Pro  Ile Asp Thr His Glu  Gly Val Gly Gln Glu  Met Ser Lys
    1565                 1570                 1575

Ala Glu  Leu Glu Leu His Asn  Leu Met Gln Gln Leu  Ser Ala Val
    1580                 1585                 1590

Glu Arg  Tyr Ala Met Lys Phe  Met Glu Glu Asn Asp  Ala Ala Trp
    1595                 1600                 1605

Ser Lys  Glu Gln Leu Ala Ala  Ala Glu Ala Glu Ile  Glu Gln Gln
    1610                 1615                 1620

Lys Lys  Glu Trp Glu Ala Gly  Arg Leu Ala Ala Leu  Gln Gly Asp
    1625                 1630                 1635

Arg Lys  Ser Pro Ser Gly Glu  Ala Glu Ser Glu Ala  Val Leu Thr
    1640                 1645                 1650

Tyr Ser  Gly Val Asp Ser Arg  Asn Gln Val Asn Lys  Thr Arg Ala
    1655                 1660                 1665

Ser Gly  Gly Gly Gly Arg Asn  Cys His Ser Gly Ser  Ser Ile Glu
    1670                 1675                 1680

Glu Gly  Thr Pro Arg Thr Arg  Ser His Gly Arg Val  Ser Ile Asp
    1685                 1690                 1695

Leu Trp  Thr Leu Asp Asp Ser  Pro Gln Asn Gly Gly  Lys Pro Ser
    1700                 1705                 1710

Ser Gly  Gln Ser Arg Lys Phe  Lys Ser Gly Lys Arg  Arg Ser Thr
    1715                 1720                 1725

Pro Pro  Pro Pro Pro Asn Pro  Pro Pro Pro Pro Tyr  Ser Asn Pro
    1730                 1735                 1740

Asn Leu  Val Ile Arg Thr Arg  Arg Ala Ser Ala Ala  Ser Ser Asn
    1745                 1750                 1755

Glu Ile  Ser Lys Val Ser Lys  Lys Val Gly Arg Leu  Ser Lys Thr
    1760                 1765                 1770

Lys Arg  Pro Ser Asp Val Val  Pro Leu Thr Ile Ser  Thr Ser Leu
    1775                 1780                 1785

Ala Ser
    1790
```

<210> SEQ ID NO 34
<211> LENGTH: 240
<212> TYPE: DNA
<213> ORGANISM: Artificial Sequence
<220> FEATURE:
<223> OTHER INFORMATION: SNF2-helicase degenerate dsRNA sequence
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t

<400> SEQUENCE: 34

```
cgsythctyy tmacsggyac hcctctvcar aayaarctwc chgarytstg ggcbytdcth     60

aayttyytvc tbccstcbat yttyaarwsb tgytcbacdt tygarcartg gttcaaygcv    120
```

cchttygcha cmacbggmga raargtygar ytdaaygarg argaracvat yytkatyaty 180
mgdcgtytdc ayaargtyyt kcgwccktty ytvytnmgdc gnytvaaaaa rgargtmgar 240

<210> SEQ ID NO 35
<211> LENGTH: 27
<212> TYPE: DNA
<213> ORGANISM: Artificial Sequence
<220> FEATURE:
<223> OTHER INFORMATION: SNF2-helicase degenerate dsRNA sequence
<220> FEATURE:
<221> NAME/KEY: misc_feature
<222> LOCATION: (21)..(21)
<223> OTHER INFORMATION: n is a, c, g, or t

<400> SEQUENCE: 35
mghgcygtbt gyythatygg ngaycar 27

<210> SEQ ID NO 36
<211> LENGTH: 60
<212> TYPE: DNA
<213> ORGANISM: Artificial Sequence
<220> FEATURE:
<223> OTHER INFORMATION: SNF2-helicase degenerate dsRNA sequence

<400> SEQUENCE: 36
tayaarctyc tvytsacmgg machccgytb caraacaayc tmgargaryt rttycatytr 60

<210> SEQ ID NO 37
<211> LENGTH: 61
<212> TYPE: DNA
<213> ORGANISM: Artificial Sequence
<220> FEATURE:
<223> OTHER INFORMATION: SNF2-helicase degenerate dsRNA sequence

<400> SEQUENCE: 37
garttygaya cbaaycaymg rctkcthath acwggbacyc ckytvcaraa ywskytdaar 60
g 61

<210> SEQ ID NO 38
<211> LENGTH: 23
<212> TYPE: DNA
<213> ORGANISM: Artificial Sequence
<220> FEATURE:
<223> OTHER INFORMATION: Bromodomain degenerate dsRNA sequence

<400> SEQUENCE: 38
ytswsygaac crttyatgaa ryt 23

<210> SEQ ID NO 39
<211> LENGTH: 65
<212> TYPE: DNA
<213> ORGANISM: Artificial Sequence
<220> FEATURE:
<223> OTHER INFORMATION: HAND-SLIDE degenerate dsRNA sequence

<400> SEQUENCE: 39
gchgtvgatg cytayttymg vgargcwytv mgdgtytchg arccyaargc dccdaargch 60 cchmg 65

<210> SEQ ID NO 40
<211> LENGTH: 36
<212> TYPE: DNA
<213> ORGANISM: Artificial Sequence
<220> FEATURE:
<223> OTHER INFORMATION: Chromodomain degenerate dsRNA sequence
<220> FEATURE:
<221> NAME/KEY: misc_feature
<222> LOCATION: (33)..(33)
<223> OTHER INFORMATION: n is a, c, g, or t

<400> SEQUENCE: 40
mghaartrbg ayatggavga rvvdccbaar ytngar 36

<210> SEQ ID NO 41
<211> LENGTH: 56
<212> TYPE: DNA
<213> ORGANISM: Artificial Sequence
<220> FEATURE:
<223> OTHER INFORMATION: Chromodomain degenerate dsRNA sequence
<220> FEATURE:
<221> NAME/KEY: misc_feature
<222> LOCATION: (29)..(29)
<223> OTHER INFORMATION: n is a, c, g, or t

<400> SEQUENCE: 41
bhggdaarad dggrkkbryb ggmaaymwna chacdrtsta ykmhrtagar gaaaay 56

<210> SEQ ID NO 42
<211> LENGTH: 471
<212> TYPE: DNA
<213> ORGANISM: Artificial Sequence
<220> FEATURE:
<223> OTHER INFORMATION: YFPv2 hpRNA encoding sequence

<400> SEQUENCE: 42
atgtcatctg gagcacttct ctttcatggg aagattcctt acgttgtgga gatggaaggg 60
aatgttgatg gccacacctt tagcatacgt gggaaaggct acggagatgc ctcagtggga 120
aaggactagt accggttggg aaaggtatgt ttctgcttct acctttgata tatatataat 180
aattatcact aattagtagt aatatagtat ttcaagtatt tttttcaaaa taaaagaatg 240
tagtatatag ctattgcttt tctgtagttt ataagtgtgt atattttaat ttataacttt 300
tctaatatat gaccaaaaca tggtgatgtg caggttgatc cgcggttact ttcccactga 360
ggcatctccg tagcctttcc cacgtatgct aaaggtgtgg ccatcaacat tcccttccat 420
ctccacaacg taaggaatct tcccatgaaa gagaagtgct ccagatgaca t 471

<210> SEQ ID NO 43
<211> LENGTH: 4958
<212> TYPE: RNA
<213> ORGANISM: Euchistus heros

<400> SEQUENCE: 43
cuuggcuagu acucuuccgu gacgucacgu ucgccauauu guuagaguuu gucuugccuc 60
uggauaguua uguugauucu uuuuaaguga uuuugaagau uuccugacca uuuuaucacg 120
aaaaacuauu uuaaacagcg cuauugcucc uuauaauacg ugugauucaa caacgaugga 180
cggagacagc ggugguaugg cgagcccuuc gccacagccu cagucgucac caaugccccc 240
uccacaagcu ccaucaccua ugggcccgcc gcagggcgcc ccaucgccaa ugcccccuuc 300
uaaccaacag gcggccucac caaugggucc accgcaccac ccccacagcc cgacagguua 360
ccaaggaggg augccacaca ugaauggacc aaauggugu ccuccuggua ugcagcaggc 420
uacucaaaca uuucagccuc aucagcaauu gccaccccac cagcaaccac caaugcagac 480
ugcuccuggu gggccugcua guggugggagg acaagaaaau cuuagcgcuc uccagcgugc 540
aauagauucu auggaagaga aagggcuuca ggaagaucca cguuacucgc agcugcuugc 600

```
guugagggca aggcaugcca acauggaacc uccgguuagg ccuccaucuc agcuuguugg    660

gggugggguuc agcggugagg guggugcccc uccuccugcu aaacacagcu ucagcgcgaa    720

ccaacugcaa caacuucgag ugcagaucau ggcguaucgc cuacuugcua ggaaccaacc    780

ucuuucccag cagcuagcuu uggcugugca aggcaaacgc cucgacagcc cuggcgaguc    840

caacuaccag cauccuccua gugaaggagc aggagguguu gguggagaag gaaguggaga    900

cgggggaucg ucgaacggcc ugaugacgca gccgaugcgu gccccaugcc ccccuggugg    960

ccagcccccca acggccucac cgaugacagg ccagauggca ccuccuacug ggccagcucc   1020

uguaaggcca ccuccucccg gugugucucc uacaccuccg cgcccuccuc agcagguucc   1080

uggugcuccg ggggccccac aaccaaagca aaauaggguu accaccaugc caagaccgca   1140

ugguuuagau cccauucuua uucuccagga aagagagaau agaguagccg cuaggauugu   1200

acauaggaug gaagaauuau caaauuuacc agcuacgaug ccugaagacc uucgaauaaa   1260

agcgcagaua gaacuuaggg ccuugagggu acuuaacuuc caaaggcaau uaagagcaga   1320

ggugauagcu uguacuagac gcgauacaac auuagaaaca gcuguaaaug ugaaagcuua   1380

uaaacgaacg aagaggcaag gcuuacggga agccagagcu acggaaaagc uugaaaaaca   1440

acagaaacuu gagacagaaa ggaagaagag acaaaaacac caggaauauc ugagcacuau   1500

auugcaacau ugcaaagacu ucaaagaauu ccauagaaau aauguugcua aaguugguag   1560

auuaaauaag gcugugauga auuaccaugc gaaugccgag cgugaacaga agaaagagca   1620

agaaaggaua gaaaaagaac guaugagaag gcuuauggcu gaggaugaag aggguuacag   1680

gaaacugauu gaucagaaaa aagauaagag auuggcauuc cuucuuucac aaacugauga   1740

auauauugcc aaucuuacug aaauggugaa gcagcauaaa auggaacaac agcguaagca   1800

ggaacaagaa gagcaacaaa aacggaagag gaaaaagaaa aagaagaaua gggaaggaga   1860

uccagaugau gaaagcucuc agaugucaga uuuacauguu agcguuauag aagcagcaac   1920

uggucggcag cugacggggg aggaugcucc auuggccagc cagcuuggga gcugguugga   1980

ggcacacccg ggcugggagc cuuuggaaga uagcgaagau gaagaugaug aagaggacag   2040

cgacgaggaa ggugaugaua acaguagauc aaaaggugu uuuucaauga uaggaaaaga   2100

ugaagcugau agcaaguuau cuguugaaga cgaagcucga gaaaugauaa agaaagcgaa   2160

gauugaagau gaugaauaca agaacacgac cgaagaacau acauacuaca gcaucgcuca   2220

caccgugcau gaaauuguca ccgaacaagc uucaaucaug auuaacggua aauugaaaga   2280

auaucaaauu aaaggucuug aaugguuggu uucuuuauac aacaacaacu ugaauggaau   2340

ccucgccgac gagaugggcc uuggcaagac aauucaaaca auaggucuca uuacuuauuu   2400

gauggagaag aagaaaguaa augguccuua ccucauuauu guuccucugu caacauuauc   2460

caauuggguu uuggaauucg agaaaugggc uccuucagug uuugugguag cuuauaaagg   2520

uucuccugca augaggagaa cuuuacaauc acagaugcgc ucgacgaagu ucaauguccu   2580

gcucacgacc uacgaguaug ucaucaagga caaggcagua cuugcaaagu ugcauuggaa   2640

guacaugaua aucgacgagg gacacaggau gaaaaaccac cauuguaagc ugacgcaggu   2700

gcugaacacc cauuauuugg caccucaccg ccuccuucuc acgggcacac cucuccagaa   2760

caaacuaccu gagcucuggg cucuucuaaa cuuucuccuc ccguccaucu ucaagucgug   2820

uucuacguuu gagcaauggu ucaaugcacc auuugcuacc acuggagaaa agguugaguu   2880

gaaugaggaa gaaacaauuu ugauuaucag gcguuuacau aagguccuuc gaccuuuccu   2940

ccuucgucga cugaaaaagg aagucgaaag ucaguugcca gagaaaauug aauacaucgu   3000
```

```
caagugugau augucugguc uccaacgugu acuuuauagg cacaugcaga guaaaggagu   3060

ccugcuuacc gaugguucug agaagggcaa gcaggguaaa ggaggagcua aagcgcuaau   3120

gaacacgauc guccaauuga ggaagcuuug caaucauccu uucauguucc aucauauuga   3180

agaaaaauau ugugaucacg uuggccagaa caacguuguc acagggccug aucuguuccg   3240

aguuucuggu aaauuugaau ucccucgaucg uauauugcca aaacugaagg ccacgagcca   3300

uaggguacuu cuuuucuguc aaaugacuca gcugaugacc aucauggagg auuauuuguc   3360

uuggagaggg uucuccuacc uucgucuuga ugguacgacc aaaucugaag accgaggaga   3420

ucuucugaaa aaauucaaca auccagaaag ugaauauuuu auuuucuugc ucucaaccag   3480

agcuggaggu cucggauuga acuuacaggc ugcagauacu gucauuauau uugauucaga   3540

uuggaacccu caucaggauu uacaagcuca agacagagcu cauaggauug gacagcaaaa   3600

cgaaguucgu guuuugcggc uaaugacagu aaauucuguu gaggagcgua uucuugcagc   3660

ugcucgguac aagcugaaua uggaugagaa agucauucag gcugguaugu uugaccagaa   3720

aucuacagga accgagaggc agaaauuucu gcaaaacauc cuucaucaag augaugcaga   3780

ugaugaggaa aaugaaguuc cagaugauga aaugguuaau cguaugauug cgcgaacaga   3840

agaugaauuc aaccucuucc agaaaaucga uuuagaaagg aggagggaag aggcuaaacu   3900

uggaccuaac aggaagucaa ggcuuguaga agaggcggaa uuaccugacu ggcuuguaaa   3960

gaaugacgau gagauugaga aguggacuua ugaagaaacc gagguccaaa ugggaagagg   4020

uaauaggcag aggaaggaag uagauuauac agauaguuug acugaaaaag aaugguuaaa   4080

ggccauugau gacaauguag augauuuuga ugacgaugaa gaggaagagg uaaaaaacaaa   4140

gaaaagaggc aagagaagaa gaaggggaga ggaugaugaa gaagaugcaa guacuucaaa   4200

gagaaggaaa uauucuccau cugaaaacaa acugaggagg cguaugcgua accucaugaa   4260

cauuguuguu aaguauacug acagugacuc gagaguacuc agugaaccau ucaugaaacu   4320

ucccucucgc cauaaguacc cagacuacua ugaguugauc aagaaaccua uagacaucaa   4380

gaggauauug gccaaaguag aagaguguaa auaugcugac auggaugaau uagaaaagga   4440

uuuuaugcaa cuuuguaaaa augcucagac auacaaugag gaggccucau ugaucuauga   4500

agauucgaua guauuagaaa guguuuucuc uaaugcucgu caaaaaguag agcaggauaa   4560

ugauucagau gaugaugaaa guaaagguga ccaagaagau gcugcaucag acacuucauc   4620

cgucaaaaug aaauugaaac uaaagccugg gaggacccga gggaguggag cugguggu aa   4680

aaggaggaga agaaaauaua ucucugaaga ugaagacgaa gaccauagcg aaguuuccuu   4740

aauguaaugc cucuucacug uccuuuguaa uuauuaguuu ucaucggugu ucgguaccug   4800

ucagucaagg gagaagcuaa gcuuuuuagu ugacuauuga agaauuuagg acugaguucu   4860

guuuuuguuu uuuuuguuug uuuuuuuuug gauaaaugua uuuaauagau aaaauguuuc   4920

gcuuauauau auauuuuuua cugguuuugu aauuggcc                             4958
```

<210> SEQ ID NO 44
<211> LENGTH: 499
<212> TYPE: RNA
<213> ORGANISM: Euchistus heros

<400> SEQUENCE: 44

```
gaugaugaag aagaugcaag uacuucaaag agaaggaaau auucuccauc ugaaaacaaa     60

cugaggaggc guaugcguaa ccucaugaac auuguuguua aguauacuga cagugacucg    120
```

```
agaguacuca gugaaccauu caugaaacuu cccucucgcc auaaguaccc agacuacuau    180

gaguugauca agaaaccuau agacaucaag aggauauugg ccaaaguaga agaguguaaa    240

uaugcugaca uggaugaauu agaaaaggau uuuaugcaac uuuguaaaaa ugcucagaca    300

uacaaugagg aggccucauu gaucuaugaa gauucgauag uauuagaaag uguuuucucu    360

aaugcucguc aaaaaguaga gcaggauaau gauucagaug augaugaaag uaaaggugac    420

caagaagaug cugcaucaga cacuucaucc gucaaaauga aauugaaacu aaagccuggg    480

aggacccgag ggaguggag                                                 499
```

<210> SEQ ID NO 45
<211> LENGTH: 6346
<212> TYPE: RNA
<213> ORGANISM: Euchistus heros

<400> SEQUENCE: 45

```
aucucggugc uguggaucgu ccuuagugau uguuuucuaa uauaguuugu aauuauauag     60

uguuuuaugc guugauaucg gugauauuag ugaauaauag ugaaguguug auguuuuauu    120

ucuaauggcg ucugaagaag aaguugacga guguuuacca guugacgaug aaguugacac    180

uaguguuguu caacaagaag gcacugaaga aaauucaccu gacagugaug aaagaaguag    240

gauagaggaa gaagaugacg aguaugaccc ugaggaugcg aggaaaaaaa agaaagguaa    300

aaagagaaaa gccaaagggg aaagcaaaaa agaaaagaaa cguaaaaaaa ggaagaagaa    360

ugauagugcu gaagaaagug agggaggcgg ggaagaagaa ggcgauuccg auuauggaag    420

aaaaucuaag aagucuaaag gaacuucaca accaaaacca gugcagcaag auucuucugg    480

agguguaccu ucaguagaag aaguuugcag ccuuuuugga cuuacagaug uacagauuga    540

cuauaccgaa gaugauuacc aaaaucugac uacguauaaa cuuuuucaac aacauguucg    600

uccuauucuu gccaaggaca accagaaggu ucccaucgga aaaaugauga ugcucguggc    660

ugcaaaaugg agagauuuuu gcaauuccaa uccaaacgcu caacaggaac cagauccaga    720

agcuucagaa gaacaggaau auucuaaacc uaccaggaca cgaccuucac gaguuucaac    780

uacacaaaau gaugaugaag aagacgacga ugcugacgaa cgagggagga aaaagagaag    840

uggacgaagu aaaaagucau caggaaagaa guccgcuccu ccggccacaa ccaagguccc    900

uacccucaag aucaagauag gaaaaagaaa acagaauucc gaugaagaag augaagguuc    960

aguuggugcc guuucugaaa gggacucaga ugcugaauuc gagcaaaugc ucgcagaagc   1020

ugaagaaguu aauaaaccug aagguguugu agaagaagaa gaaggugcag agguggcucc   1080

uguaccuaag aaaaaggcca aaacgaaaau ugguaauaaa aagaaaagga aaaagacacg   1140

gacuacuaac aaguuuccag acagugaagc ugguuaugaa acagaucauc aggacuauug   1200

ugaaguuugu caacaaggag gugaaauaau auuaugugau acgugcccuc gagcuuauca   1260

uuuggucugu uuggaucccg aauuggaaga uacgccagaa ggcaaauggu caugccccuca   1320

uugugaaggu gaagguguac aggaaaaaga agaugauguc caucaagaau uuugcagagu   1380

uuguaaagau gguggagaac uuuuaugcug ugauucuugc ccuucugcau accacacauu   1440

cuguuugaac ccuccauuga cagauauucc agauggugac uggaagugcc cacguuguuc   1500

ggcgaagccu uugagaggua aagugucaaa gauucuuacu uggaggugguu uggaaucucc   1560

caguaguaaa gaugaagaag acaauacuaa aaaacgaaac aggcagaggc aaagagaaua   1620

uuucgucaag ugggcagaua ugucuuauug gcacuguagu ugggugucug aacuucagau   1680

ggauguuuuu cauacucaaa ugaucaggag uuauauucgu aaauaugaua uggacgaacc   1740
```

```
ucccaaacua gaagaacccu uggaugaagc agacaauaga augaagagga uacgagaggc   1800
aaauaucaau gagcaagaau uagaagagaa auauuacaag uaugguauca aaccagagug   1860
gcuuauugug cagaggguaa uuaaccaucg cacuauaagg gauggaagca aucuguaccu   1920
cgucaaaugg agggaccucc cuuaugacca ggcgacuugg gaggaagaag ucaccgauau   1980
cccuggcuug aagaaagcua uugaauauua caaugagaug agggcuugcu guuuaggu ga   2040
aucuaaaaaa cuaaaaaaag guaaagguaa aagaucaaag agagaucaag augaugagga   2100
aggaagcaga agugcaggaa ugaugggcgu cgguggacca gcuacugguc aauacuuccc   2160
gccuccugaa aagccuguca cagauuugaa aaagaaauac gauaaacagc cggacuaucu   2220
cgacgucucc gguaugugcc uucauccuua ccaauuagaa gguuuaaauu gguugaggua   2280
uuccuggggg caaggaacag acacuauucu ugccgaugag augggucuug gaaaaaccau   2340
ucagacaauu acuuuccucu auucucuuua caaagagggu cauuguaaag gccccuuccu   2400
ugugagugua cccuuaucua caauuaucaa uugggaaaga gaguucgaaa cuugggcgcc   2460
agacuucuac guugucacau augucggaga caaagauucu cgugcuguaa uacgugaaaa   2520
ugaauuuuca uucgaugaua augcuguuag aggaggaaga gguguuucua aaguucgcuc   2580
uucugcaaua aaguuucaug uacugcuaac aucuuaugaa cuuaucucua ucgaugucac   2640
uugccuugga ucgaucgagu gggcagugcu uguaguagau gaagcacaca ggcugaaaag   2700
uaaucagagc aaguucuuua ggcuucuugc uucauaccac auugcuuaua aacuucugcu   2760
gacaggaacu ccguugcaaa acaaucuaga agaauuguuu cauuuacuua auuuccuuac   2820
gccggaaaaa uucaacgacc uugcgacauu ucaaaacgaa uucgcugaua uuucaaaaga   2880
agaacaaguc aaaagacuuc augaguuacu cgggccgcau auguugagga gauuaaaagc   2940
ugauguacuc aagaauaugc cuacaaaauc ugaguucauu guuagaguug aacucucccc   3000
gaugcagaag aaguacuaca aauauauucu cacaaggaau uucgaagcuu uaaauccaaa   3060
aggaggcggu caacaaguau cucuuuugaa cauuaugaug gaucuuaaaa aaugcuguaa   3120
ucauccauac cuguuuccug cugcuucuca ggaagcuccu uuaggaccaa gcggaucuua   3180
cgaucuucaa ggguuaauca aagcaucugg aaaauugaua cuucugucga aaaugcugag   3240
acggcucaaa gaagaggguc acagaguacu gauuuucucu caaaugacaa aaauguugga   3300
cuuauuagaa gacuaccucg agggugaagg uuauaaauau gaacguauug acgguacgau   3360
caccgguagc uuaagacaag aagcuaucga ucgguuuaac gccccuggag cucaacaauu   3420
uguuuuucuu uuguccacuc gugcgggagg ucuugguauu aaucucgcua cugcagauac   3480
aguuauuauu uaugacucug acuggaaucc ucauaacgau auucaggccu uuucgagagc   3540
acacaggaua gggcaagcaa acaagguuau gauuuaucga uuugugacac gagcgucugu   3600
ugaagaaaga guaacgcaag uggcuaagag aaaaaugaug uuaacccauc uugucguacg   3660
accagguaug gguggcaagc aagcaaauuu cacuaagcaa gaacuugaug auauuuuaag   3720
guuuggaaca gaagaacuuu ucaaagaaga gcaggguaaa gaagaugaag ccauucauua   3780
ugacgauaaa gcuguugaag aauuacuuga ccggucgaag augggguauug aacagaaaga   3840
aaacuggucu aaugaauauc uuucuucuuu caaaguggca aguuauguua cuaaagaaga   3900
agacgaagau gaggaaauag gaacagaggu aauaaaaacag gaagcagaaa auacagaccc   3960
agcuuauugg gucaaacugu ugaggcacca uuaugagcaa caacaagagg auauuucucg   4020
aacucucggu aaaggaaaaa ggauucgaaa acaggugaau uacaucgacg guggagugau   4080
```

```
ggacucaaga gagaacgccg auucgacgug gcaagacaac cucucugacu auaauucaga   4140
cuucucugcu ccuucugaug augacaagga agacgaugac uuugaugaga aaaaugauga   4200
uggaacgaga aagaagcgua ggccagaaag gagggaggac aaagauaggc cucuaccucc   4260
ucuucuugcc cgagucggug gaaacauuga gguccuggga uucaacgcca gacagcguaa   4320
agcauucuug aaugcuauua ugagguaugg aaugccaccu caagaugcau ucaacucgca   4380
guggcuuguu cgagaccuga gggguaaauc ugagaagcau uucaaggcau acguaucccu   4440
cuuuaugagg cauuugugug agccuggcgc ggacaaugcc gaaacauucg cggauggugu   4500
uccaagggaa ggucuuaguc ggcagcaugu ucucacaagg auaggugugu ugucacucau   4560
uaggaaaaag guucaagaau uugagcaaau uaauggauau uacucgaugc cugaaauguu   4620
gaagaaacca cuuguugaug ccggauugca uaaaacaagu gcuagcagua uaggugaagg   4680
ugcuaguagu uccgguacac cugcaacauc agcugcucca aguccagcuc cuacucuuuu   4740
ggauaagaca caaauugaag auuugaguga aaaagaagau ccgucaaaga cugaagauaa   4800
aaccaccgau gauuccaaac ccucagaaga ggcuaaagcu gcagaugaug caaauaagcc   4860
ucaggcugaa ggagaaaagg cagaaggauc uucuaaugca aaccaaacuu cugaagcuga   4920
aggaagcgau gagaaaaaac ccaaagaaga accgauggau guagauggug aaggagaggc   4980
uaaagauagu gauaagacag aaaaacaaga agguacugac gaaaaagaug uagcccuaaa   5040
agaggaagaa aaggaugaag aggucaacaa agagaaggga gaggaaacag aggaaaagaa   5100
gguuaucgau uuugaagaag acaaaucuaa aaggaaauuu auguucaaua ucgcugaugg   5160
aggauuuacu gagcuccaua ccuuauggca aaaugaagag aaagcugcag uaccugguag   5220
ggaguacgag aucuggcaua ggaggcauga cuauuggcug uuggguggaa ucguuaccca   5280
uggcuauggu cgguggcaag auauucaaaa ugauauuaga uuugcuauua ucaacgaacc   5340
auuuaagaug gauguuggaa aaggaaauuu cuuagaaauu aaaaauaaau uucuugccag   5400
gagguuuaag cuucuugagc aagcucuggu gauugaagaa caguuaagac gugcagcuua   5460
uuuaaaucug acgcaagauc caaaucaccc agcaauguca cugaaugcaa gauuugcaga   5520
gguugaaugu cuagccgaau cucaccaaca ccucucgaag gaaagucuug cuggcaacaa   5580
accugcaaau gcaguguuac auaaaguauu gaaccaauua gaggagcuuc ugucggauau   5640
gaaaucugac guaucucgac uaccagccac ucuagccaga auuccaccug uagcccagag   5700
gcuacagaug ucugaacggu caauacuuuc uagguuggcu gcaacuacuu cuccugcgac   5760
gcccaccacg ucccaucaaa cugguaugau aagcagucag uucccugcug gauuucaauc   5820
agggcaguug acuggaacgu uuccgaaugc caguuuuacc aacuucaggc cccaguauuc   5880
aguuccuggg caaacugcag cccagggguu ucccgguaau ugauaauuga aagcuggacg   5940
guaauugucu gcgagugaau ucuccaugag uaaauaauag guuuuuuuuu uuuuuuaaga   6000
aagaaauaaa agaagcguuu uguuuaguuu uguugauagu ucucuuuauu ucuuucaauu   6060
uuguuuuagc ggaaaaaaaa auguucauua uaaguaacuu auaaaauugga caugcuaauu   6120
aaauuuccua uuagauuauu uuguuauuug uaaguuuuuc gguauuguaa gaaugucuau   6180
auguguaaga gguuguacaa gauugccuaa auaccuugua uuauuuauuu uuacuauuga   6240
auaaaaaaaa aaaauaauua acuucgaucu uagguuaagg guaauaaaaa aaaauguuac   6300
uggaaaaaaa aauagaaaaa auaaaaaaga uagccuuucc ccuuac                 6346
```

<210> SEQ ID NO 46
<211> LENGTH: 3391

<212> TYPE: RNA
<213> ORGANISM: Euchistus heros

<400> SEQUENCE: 46

```
agagggggua ggcgcacagc uuuccucaca ucgaacaaua ucuuagugaa ugaauggcuu     60
uauuggccgg uucaaaaucu uguuaaaugu ugguuugaua uauauuuaua cuaacguuau    120
uuaacgcagc ucacaccaau aaaaaugucg aagccaaaug aaguuaguuu ggauacaaca    180
gauacuguug aaauuucuaa ugaaucuucg ggagacacag agucguccaa ggguaaaaau    240
gaagauuuug aaacaaaaau ugaaacugac cguucuagaa gauuugaguu ucuguugaag    300
cagacagaaa uuuuuucaca uuuuaugaca aaucaaggaa agucgaacag cccugcaaag    360
ccuaaagucg gccguccuag aaaggaaacu aauaaaauugg caccagccgg uggugauggu    420
ucugccgacc aucggcaucg uaugaccgag caggaagaag augaagaacu gcuugcugaa    480
aguaaauacuu cuucaaaauc cuuagcaagg uuugacgcuu cuccuuuuua uauuaaaagc    540
ggagaguuga gggauuacca gauacguggu uugaauugga ugauaucccu cuacgaacac    600
gguauaaaug guauacuugc ugaugagaug gguuuaggua aaacucucca aacuauuucu    660
cuccuugguu acaugaagca uuauagaaau auaccagggc cacauauggu caucguacca    720
aaaucaacau uagcuaauug gaugaaugaa uuuaaaaagu ggugcccaac ccugcgugcu    780
gucuguuuaa ucggagauca ggaaacgagg aaugcguuca ucagagacac ucuuaugccg    840
ggugaauggg augucugcgu uacaucuuau gaaaugauca uacgagaaaa gagcguuuuc    900
aagaaguuca acuggaggua uauggucauu gacgaagccc acaggaucaa gaaugaaaaa    960
uccaaacucu ccgagauugu gagagaguuc aaaacgacga aucgauuacu ccugaccggu   1020
acuccuuuac aaaauaaccu ccacgaauug uggucucuuc uuaacuuccu cuuaccagau   1080
guuuucaauu caucagauga uuuugauuca ugguuuaaua ccaauaccuu ccuuggcgau   1140
aauucucuug ucgagagauu acaugcugua cugagaccuu uccuccuaag aagauugaaa   1200
ucugagguag agaaaaaacu caaaccgaag aaagaaguca aaaucuacgu uggauugagu   1260
aaaaugcaga gagaauggua uacuaaaguu cuaaugaaag auauagacau uguaaacggu   1320
gcuggccgag ucgaaaaaau gcgccuccaa aacauccuca ugcaguugag gaagugcagu   1380
aaucacccuu aucucuucga cggagcugaa ccagguccac cuuacucaac ugaugagcau   1440
cugguauaua acaguggaaa aaugguaaua uuagacaagc uucuuccuaa auugcaagaa   1500
caaggaucac gaguucuggu uuucagccaa augacaagga ugauugauau ucucgaagau   1560
uacuguuauu ggagaggaua uaauuacugu cgucuugaug guaauacacc ucaugaggau   1620
aggcagagac agauuaauga guucaacgaa gaagacagua agaaauucau uuucauguug   1680
ucgacucgug cgggugguuu ggguaucaau uuagccaccg cagauguagu cauuuuguac   1740
gauucggauu ggaacccuca aauggaucuc caggcuaugg aucgugcuca ucguauuggu   1800
caaaagaaac aagucaaagu guucaggaug auaacugaaa acacaguuga agagaaaauu   1860
guugagagag cugaaauaaa acuccgccuc gauaaguugg ucauccaaca aggcaggcug   1920
guagacaaua aaacggcacu caacaaagau gaaauguuga auaugauccg ucacggugcc   1980
aaucauguau uugccaguaa agauucugaa aucaccgaug aagacauuga cacuauuuug   2040
gaaaaaggcg aagcaaggac ggaagaaaug aauaaaaaac uugaacaacu cggugauucu   2100
aauuugaaag acuucaugau ggaaaccccg acugagucag uuuaccaauu cgaaggagag   2160
gauuacaggg aaaagcagaa aguuuuagga auaggaaguu ggauagaacc uccaaaaaga   2220
```

```
gaacguaaag cuaauuacgc ugucgaugcc uauuuuaggg aagcauugag aguaucagaa   2280
ccuaaagcuc ccaaggcacc gaggccuccu aaacagccua uaguucaaga uuuccaauuc   2340
uuuccuccuc gucucuuuga gcuauuggac caggagaucu auuacuucag gaaaacugug   2400
ggcuacaaag uuccuaaaaa uccugaauua gguucugaug caucacgugu ccaaaaggaa   2460
gaacaaagaa agauagauga ggcagaaccu uuaucagaag aagaacucgc ugaaaaggaa   2520
aaacuucuua cgcagggguu uaccaauugg acuaaaaagag auuucaacca guuuauuaaa   2580
gcuaaugaaa aauauggucg ugaugauauu gacaauauuu caaaagaagu agaaggaaaa   2640
acuccagaag aaguaagagc uuauucagaa guguucuggg aacgauguaa cgaauugcag   2700
gacauagauc guaucauggg gcagaucgac aggggagagg cuaaaauuca aaggagagca   2760
aguauuaaga aagcucucga uacaaagaug agccgguaca gagccccauu ucaucaacuu   2820
cgcaucuccu acgguacgaa uaaggguaag aacuauaccg aggaagaaga uagauuccuu   2880
gucuguaugu ugcauaagcu ugguuuugac aaggaaaaug uguacgaaga acuuagagcg   2940
auggucaggu gugcgccuca guucagauuc gacugguuca ucaaaucgag aacagccaug   3000
gaauugcaga ggcguuguaa uacucuaauu acucucaucg aaagagaaaa ucaggaacuu   3060
gaggagaggg aaagagccga gaagaggaaa ggaagaggaa gugggcgugg uccugguucc   3120
gguaaaagga aaggagacgg uuccauuuca ucuccccccuc cugucccugg ccaaggggau   3180
aagaacagcc ccgccagaaa aaagaaaaaa auguaguuuc accuccucau gaaaggaacu   3240
cauuuuaaga uaucuuuuuc uagauauuua uuuugugaaa acugugaugu auuuuauauc   3300
cguuccgaaa agcucuacug uuuugacagu uuuauuaauu agugggggugg ggaggaaaua   3360
uagcccccuc acccccccaau aauucauaaa u                                  3391
```

```
<210> SEQ ID NO 47
<211> LENGTH: 1316
<212> TYPE: RNA
<213> ORGANISM: Euchistus heros

<400> SEQUENCE: 47

aaugaauaaa aaacuugaac aacuuggugu ugauucauca uuaaaagauu ucaugaugga     60
ggcucccacu gagucugucu aucaguuuga aggcgaagau uauagagaaa agcaaaaagu    120
uuuuggaauu ggaaauugga uugaaccacc aaaacgagaa cguaaagcaa auuaugcagu    180
agaugccuau uuuagagaag cacugagagu uucagaaccu aaagcuccaa aggccccuag    240
gccaccaaag caacccauag uucaagauuu ccaauuuuuc ccaccucguc uguuugagcu    300
guuagaucaa gaaauauacu auuuucgaaa aacuguuugc uacaagguuc cuaaaaaucc    360
ggaguuagga ucagaugcuu cucguauaca aagggaagag caaagaaaaa uugaugaagc    420
ugagccguug acugaggaag agcuagcuga gaaagaaaac uuauugaccc aggguuuuac    480
uaauuggacu aaaagagauu uuaaccaguu cauaaaagcu aaugaaaaau auggacguga    540
ugauauugau aauaucucaa aagauguuga agggaagacu ccagaagaag uacgagcaua    600
cucugaagua uuuugggaaa ggugcaauga acuacaggcc auagaucgua ucaugggca    660
gauugauaga ggugaagcga aaauucaaag aagagccagu auuaaaaaag cuuuagauac    720
aaagaugagu cgauauagag caccguuuca ucaacuacga auugcuuaug guacgaacaa    780
ggggaaaaau uacacagaag aagaagacag auuccuugug ugcaugcuac auaagcuugg    840
cuuugauaaa gaaaaugugu augaggaacu uagggcgaug gugaggugug cuccucaguu    900
uagguuugau ugguucauca agucucgaac agcuuuggaa uugcaaagac guuguaauac    960
```

ucuaaucacg uuaauugaaa gggaaaacca agaauuagaa gaaagggaaa aaguagaaaa 1020
aaggaaaagu cgaggcagua augggcgugg ucccaguucu gguaaacgua agggagaugg 1080
aucuauuuca ucuccaccug ucucuguaca gagugauaaa agcagcccug cucggaaaaa 1140
gaaaaaguau aucucuguug aguaaauuua ucuuaaaacu gggaguagau acccaauucu 1200
cauuaucggg ugaucaagga aucaaucuca uauaggagcc uaaaacuuca uuaguuugua 1260
auugaauauu uaauuuacau cucuaguuuc caaauauugu uucuuuuaca ucugua 1316

<210> SEQ ID NO 48
<211> LENGTH: 1827
<212> TYPE: RNA
<213> ORGANISM: Euchistus heros

<400> SEQUENCE: 48
gauaaauaug aauaagaaaa uuuuaaauuu auuuguuuca uuaaaaaauu aucuuauggg 60
uuuauugauu auaaauuggu ucaaucauaa aauacgagau acauaagauu guauuaucau 120
aacaaaccca aucucuagua ucgucauccu gcuguucugg uucacucuga guuucuuuau 180
cuucaucaaa agcaaaacuu gcaacuuuaa aagcagaaag uaauucauca ccaacagugg 240
cugguccuuc aucucugguu ucagcucuuc ucaaaauuuc gucaauguca caaguugguu 300
cuucaucacc aucuucuuca ucuuuaaaua auucuucagc cccaaauuuu aaaauagcag 360
uaaguucuuc uuuguuaaaa ggcgcacugg augaagaauu uuuuuuaucc aggacaguuc 420
uaccuguagu auccauucuu uguauaacua aaugaucuaa gaccauuuuu uguuuggccc 480
gcucgacaau auuuuccuca acagaacuuu uaguaacaag ucuguauaug uucaccugau 540
uuuucugacc gauucuauga gcucuagcuu gugcuugcaa aucauuuugu ggauuccaau 600
cagagucaaa uauaaugaca guaucagcug uugcuaaauu aaugcccaaa ccaccagcac 660
gaguugauaa uaagaaacag aaaucuggug aauuuucagc auugaaauga ucgagggcuu 720
gcuuucucaa uucaccuuua auugaaccgu cuaaacguug gaaagggaaa ugucucauuu 780
gaagauacuc agccaguaua uccaacauuc guaccauuug agaaaauaua aguacucuau 840
gcccaguuuc uuuaaggcga acaagcaacu uguccaacag aaguaauuuc ccugagccuu 900
uuaacaauug cuguaaguag ucuucaguuu uugcuucauu uucuaauggu uuuauuagau 960
gugcaugauu acagcauuuu uuuaauucaa uaacaauauu uauaaaugua cuaggagaac 1020
cuuugacucc uuuucgaaga gcagaauaau uuuuggacaa aauccaccug uaauacugcu 1080
ucuguacaga ugucauuuca acacguaaua uuuguuccac uuuagcuggu aaagauuucu 1140
caacauccuu cuuaacucgu cguagaauau augguuccag cugucugugc aacuuaguau 1200
agccuuuauu agcagaguug ucauguucuu uuucaaauuc uucccaguua uuaaaucugu 1260
ugggcauaau aaagugaagc aacgcccaaa gcucuuuaag acuauuuugc aaaggagugc 1320
cuguuauaag aagccuaugg uugguaucaa acucuuucaa uguuuuguau aauaaugaau 1380
caucauuuuu caaucugugu gcuucaucaa ccauaaggau agcccagcuu auacuaccca 1440
aaaaugcuuu gucuuuaaga acaauuucau auguaguaag aauggcauug aauuuuaacc 1500
uuuucgaacc ugaauagcac cauucauaau uacguauaac aucacgggag uuuauaucac 1560
caauauaagu uacaacauuc auuucuggag cccauaauga aaacucccuc ugccaugaag 1620
ucaucguaga uaaagggaca acaauuaaaa augguccaua caacugguga guaugaaaua 1680
aauaauacaa acugcagaua gucugaauag uuuuaccaag acccauuuca ucagccaaaa 1740
uauuagaauu uucuuuacac cacgaaugaa ccaaccaauu caaaccacug auuugauaau 1800
cucucaaaac caauaccugg ucaccac 1827

<210> SEQ ID NO 49
<211> LENGTH: 496
<212> TYPE: RNA
<213> ORGANISM: Euchistus heros

<400> SEQUENCE: 49
gacuaccucg agggugaagg uuauaaauau gaacguauug acgguacgau caccgguagc 60
uuaagacaag aagcuaucga ucgguuuaac gccccuggag cucaacaauu uguuuuucuu 120
uuguccacuc gugcgggagg ucuugguauu aaucucgcua cugcagauac aguuauuauu 180
uaugacucug acuggaaucc ucauaacgau auucaggccu uuucgagagc acacaggaua 240
gggcaagcaa acaagguuau gauuuaucga uuugugacac gagcgucugu ugaagaaaga 300
guaacgcaag uggcuaagag aaaaaugaug uuaacccauc uugucguacg accagguaug 360
gguggcaagc aagcaaauuu cacuaagcaa gaacuugaug auauuuuaag guuuggaaca 420
gaagaacuuu ucaaagaaga gcaggguaaa gaagaugaag ccauucauua ugacgauaaa 480
gcuguugaag aauuac 496

<210> SEQ ID NO 50
<211> LENGTH: 481
<212> TYPE: RNA
<213> ORGANISM: Euchistus heros

<400> SEQUENCE: 50
caaaaauuga aacugaccgu ucuagaagau uugaguuucu guugaagcag acagaaauuu 60
uuucacauuu uaugacaaau caaggaaagu cgaacagccc ugcaaagccu aaagucggcc 120
guccuagaaa ggaaacuaau aaauuggcac cagccggugg ugaugguucu gccgaccauc 180
ggcaucguau gaccgagcag gaagaagaug aagaacugcu ugcugaaagu aauacuucuu 240
caaaauccuu agcaagguuu gacgcuucuc cuuuuuauau uaaaagcgga gaguugaggg 300
auuaccagau acgugguuug aauuggauga uaucccucua cgaacacggu auaaauggua 360
uacuugcuga ugagaugggu uuagguaaaa cucuccaaac uauuucucuc cuugguuaca 420
ugaagcauua uagaaauaua ccagggccac auauggucau cguaccaaaa ucaacauuag 480
c 481

<210> SEQ ID NO 51
<211> LENGTH: 490
<212> TYPE: RNA
<213> ORGANISM: Euchistus heros

<400> SEQUENCE: 51
guucaagauu uccaauuuuu cccaccucgu cuguuugagc uguuagauca agaaauauac 60
uauuuucgaa aaacuguuug cuacaagguu ccuaaaaauc cggaguuagg aucagaugcu 120
ucucguauac aaagggaaga gcaaagaaaa auugaugaag cugagccguu gacugaggaa 180
gagcuagcug agaaagaaaa cuuauugacc cagggguuua cuaauuggac uaaaagagau 240
uuuaaccagu ucauaaaagc uaaugaaaaa uauggacgug augauauuga uaauaucuca 300
aaagauguug aagggaagac uccagaagaa guacgagcau acucugaagu auuuugggaa 360
aggugcaaug aacuacaggc cauagaucgu aucauggggc agauugauag aggugaagcg 420
aaaauucaaa gaagagccag uauuaaaaaa gcuuuagaua caaagaugag ucgauauaga 480
gcaccguuuc 490

<210> SEQ ID NO 52
<211> LENGTH: 496
<212> TYPE: RNA
<213> ORGANISM: Euchistus heros

<400> SEQUENCE: 52
cagcuggaac cauauauucu acgacgaguu aagaaggaug uugagaaauc uuuaccagcu 60
aaaguggaac aaauauuacg uguugaaaug acaucuguac agaagcagua uuacaggugg 120
auuuugucca aaaauuauuc ugcucuucga aaaggaguca aagguucucc uaguacauuu 180
auaaauauug uuauugaauu aaaaaaaugc uguaaucaug cacaucuaau aaaaccauua 240
gaaaaugaag caaaaacuga agacuacuua cagcaauugu uaaaaggcuc agggaaauua 300
cuucuguugg acaaguugcu uguucgccuu aaagaaacug ggcauagagu acuuauauuu 360
ucucaaaugg uacgaauguu ggauauacug gcugaguauc uucaaaugag acauuucccu 420
uuccaacguu uagacgguuc aauuaaaggu gaauugagaa agcaagcccu cgaucauuuc 480
aaugcugaaa auucac 496

<210> SEQ ID NO 53
<211> LENGTH: 4493
<212> TYPE: RNA
<213> ORGANISM: Euchistus heros

<400> SEQUENCE: 53
gcauauacag aaacaaucaa aagaucaaau cuaacucguu caaacagcag gaugaagaaa 60
acuaggaaga auucucgacc uuuauuugug gcuggugguu uugcagcggc agcugagaag 120
augccugagu aggccugauu gagagugcag guacggaugg cuuucuuccc gguccucuca 180
guccucuggg gccacgugag ccaauaugac cagggccgac gggccucaac cguggccucc 240
cuggaccucg acgauugcuu cgguugcuua aagcaggcau gaaaggccuc gaaauuuuug 300
guggugucug gcugauaggu uccuccuggu cgguguuguu aucauuggag ucuuggcucg 360
auuucauaac guccgugccc uucggacucu cagcugguga uuucacaccu ugguaaacuu 420
caacgacccc aucuucaguc uucauauguu ucaccguguc cuuguaauuu ccuagagcau 480
uuuuucuuuu ucuuucucuu ucccuguaga uaucuugccu ugauucuuca aguugucucc 540
ucucugcuug cuucugccga uauuucuguu cuauuucugc aucaucaagc aauagagaaa 600
caaccucuuu cgguuuaaga gugucugguu ugaaauuacc cccacugaug acaacccuuu 660
ggauuucacu uuuuucuuga gcucucugca agauccuuuc uucgaugguc ccuuuacaaa 720
ugagccgaua gacugugacu uguuucguuu guccaagacg augggcacgg uccaucgcuu 780
guuggucaac aguaggguuc caaucacugu cauagaauau cacaguauca gcugcgguaa 840
gguugauucc aagaccucca gcucgcguac ucaacaggaa uacaaauaug uccucucuug 900
uuugaaaguc agcaaccaua ucccuucugu cugauaucuu ugaagaacca ucuaaccuca 960
uauaugugug cuuucuguac cacauauauu ccucuaacaa gucgaucauc cuugucaucu 1020
gggaguaaau uagagcucga ugcccuuguu ccuucagccu ggugagaagc ccauccaaga 1080
cguacagcuu uccagcauca guuaccagug ucuguuuguc agguaugacu auacucgacc 1140
agccagugau uggucgaaga cugaguaggc caagaggagg ugggcacugg aacccagguu 1200
cuuguuuauc cccuucccaa agaaccugcc acagucuccc guccuccccc cagaggugag 1260

```
aagagaucca gcuccaccuu cgguucgagc uguacagccg ucugcuuuuc uuuaucucca   1320
ccuugacagu aggagugaag aggaauggag guaaauagac uggcugacau gagagaaucu   1380
gaggcuuccu cacaauaugu ggcaaugcug guaauaaguu agcacuaucu ucuccaccgc   1440
acucucccuu agccuucuuc gaccugacua ugcgauguuc uaucguuuca ggcauacuuu   1500
cuauccucac gguggaaugg gaaaacacuu gguuggaaua agguggugaac acaagauugu  1560
uugguagcu ccugucuuca augauuccga cgaguuuccu ucucacuccu ugccuccuug    1620
cuauaauauu gugccaccug aaauaaaucc caaaaaacau uagcuuauac aguucuccua   1680
cagauaaccu caacagucga gugaaagaaa augaacuauc ccucucggau gagucaucac   1740
ugaauaaaga ucuaugagaa ugaaaaggau uaaaaggcga uaaguaguuc augagaagau   1800
gaaguuuauc cccagggaac acagcaucug ugaugagagc aggcacaaug uaaucuuccg   1860
uagccaugga aaaaggggau cgagguuccc uucgcucgaa uaguucaggg ugauuacaga   1920
ccuuacgaaa uugcaucacg agguucauca aauuugaagu gauacucuga gcugauuggu   1980
aagaagaucc agaagagugu agcaaaucuu caauucgaau cuucuuuuuc acagcugaau   2040
auaacaucuu cugccucguc gucagaggac aguacaccau gauuucuauu uuaucugaca   2100
guucauucuc cacaucuguu uuuacucucc gcaacaugaa ugguuuuagg aucauaugua   2160
aacgggacaa augcuuuuca ucaauacugg uuuuaugcuc ugcaugacuu ucuauaucuu   2220
uugaaaacca uucauugaac ucaucgugug aaucaaacau ugagggcauu augaaaugaa   2280
gaagagccca aaguucagcc auugaguuuu gaauaggugu uccacucaga aguaaucugu   2340
ugcggcaauu gaauccaaga agcaauuucc aacgcaugcu uguagugcuu uugauagccu   2400
gagcuucguc uagaauuaaa uacugccauu uuauccuauu gaaguauuuu auaucaguaa   2460
uuacaagcug auagcuugug aucacaacau ggaaacuggc aucuuuagua uguaaaccuu   2520
uuugauccca aaauugacgu aauauuuucc uuuccugcug auuuccccaa uaaggcacaa   2580
cuuugaaauc agguacaaaa cgcugcauuu cuugcugcca auuauguaau guagaagcgg   2640
gcgauauuau gagaaaugga ccccaaacag aguauuuuuc agcaauaugg caaagaaagg   2700
cuaucgauug gacugucuuu cccaauccca uuucaucugc caagauucca uuaauaccuu   2760
ggucauauaa auucacaagc caugucauuc ccuuuauuug auaucccuug agaguaccac   2820
ggaauaucug cgguuggggu uuaucuucac caacaucucc auccucuucc auuuucuggc   2880
uuacuccaaa uucucuugcu cgugcuucuu ccagaaaaaa caccuuuuca acuuucuuuc   2940
guacuuuuuc uuucucugcc ucgcaaucgu agucauccaa agguaggagu cuaggauuag   3000
cuuccucuuc aaguuggcuc aggauucgaa guugaucuuc agucguuccg ccaccgagcu   3060
uacgggacau aaagugagca uagaguucug uuugaguuau gaggaaauuu aauuuucuuu   3120
gcugccucuu agccuccauc aguucuacau ccaacuuccu uuguuccucu gcuucuuucu   3180
ccauucuucu ucuuguuucc cuuuccaccc ucucaaaucu uuuccaguau acuugcauuu   3240
cccgugucaa ucuuuuugcu cuccaaauaa ccucuuucau auucuuuugc gauugcauug   3300
cacguugucg acagugccuc auacaguuag uagcagcucg ccugcaagcu guuagaauuu   3360
cuuuaugguu acuuauccua uagcgcugaa ccuuuccaau uucuuuuuuc gccauguugg   3420
cccaaauuuu acgccugcga ugugccauga uuucggcagc uuuguuuugg gcugauuuuu   3480
uucuaaggcu cauuuccuuu uuagaccuug acauuauuug uaggucuggu ucuucuuuga   3540
uuuuucuuuu cuuuuuuucu acacuaaaac uuucaugugg uugaucuugu uuuuucaacu   3600
uuucuuuuuu uugaaaaaca aauuucuuuu ucuuaacaaa accagaacuu gaacucugau   3660
```

```
gcucaggaua cuuaucgaaa uuggagagga guccugugcc auaguacaua uacucuuggu   3720

uuuuagaauu gugguagaau uuuuuuuuau auuuguuucu aaguacaugu ucacggagca   3780

ugucuuguaa guccucuuca guuauuucuu caucaucaga ggaaucugau gugucaguca   3840

auagaacauc aacuaaccac ugccuaucua agcuuacauu acucaaguug uaaagccucu   3900

ucuugucagc uauccuaucu ucuuuaguug cuguuauacc auuccauacc guuucuccgg   3960

uauaggcauc aacaccagcu aauuccgugu cagaaucacu ggaggcuucu ccauccucac   4020

cuaaugguug uuuuaaaaag ucuucaacau auguuaggaa aggagcuaug uccaagcuuu   4080

uuucuagcuu uugauaauaa agagguuugg caauuucugu uuucacuacc auguuuguuu   4140

uaucaucacu cauacugcaa aaaucaauga caucaaaaga uaucucugca ucccaguuag   4200

aaaauauuac uaaacugaaa uguaaaacuu auauagaauc auauuuaaaa ugaguugaac   4260

aaacuauuac gcuugucaca uuuuuaguaa accacaccca aauuaauauc uacuuuuaua   4320

cauaaaccua aucagaauau cagucagucc auacuagacg auuguaaaaa ugugcuaggg   4380

gucaaauaaa aaaggaaagu gaaauuaggu uaguauauau ugaaagacgc aucuccuuuu   4440

cagagauuca gugaaauauu ucagccagcu ggguuagccu gacagaauuc aag          4493
```

<210> SEQ ID NO 54
<211> LENGTH: 6108
<212> TYPE: RNA
<213> ORGANISM: Euchistus heros

<400> SEQUENCE: 54

```
acaggcuuau aucaucuaac aauuaugaau gucaugagau caaaaauauu auccgaacua     60

aauuaaaaac acaaaaacga augacagaaa gaucggccug aaucaguuua aauuaguccu    120

uugauuguga aaaauuuuaa agcuuugaau ccuuaauuau aauaauaaac uauuaaccgg    180

caguguauca ugaagcuaaa cuuguacuua uagucaaugg aacaacaucu gauggacgcu    240

uuguuuuacu uaaccgacca acuuucuugc ugaccuuacu aaucucauua cuugaggcag    300

cagaagcucu ucuaguacga auuacaaggu uaggguucga auaaggugga gggggaggau    360

uaggaggagg gggaggugua cuacgccguu uaccacucuu aaauuuucua cuuugcccug    420

augaggguuu ccccccauuu ugaggacugu caucuaaagu ccacagauca auugaaacac    480

gaccaugaga ucuaguccuu ggagugcccu ccucgauacu acuuccacua ugacaauuuc    540

uucccccgcc cccacuagcu cuuguuuuau ugaccugauu ucgcgaauca acgccagagu    600

aagugagaac agcuuccgac ucagcuuccc cagaaggaga uuuucuaucu ccuugcagag    660

cagccagucu accagccucc cacucuuuuu uuuguuguuc gauuucugcu ucagcugcag    720

ccaacugcuc uuuugaccaa gcagcaucau uuucuuccau gaauuucaug gcauaccucu    780

caacagcaga aagcuguugc auaagauugu gaaguucuaa uucugccuug cucauuucuu    840

gcccaacucc uucaugggua ucaauaggua uauuuucauc gaacucugcc aacucagcag    900

cagcuucugc uuuagcaacc uuggcugccg caacaucgga uucauccuca gcuugggcca    960

uugcacucuc gagcgcacca auugcuacuu ucucaucaga guucgcaacc aucuguguga   1020

cuucaggauu cugagcaguu uuaucacuau uaugaagaac uucugccauc cuucuggaag   1080

caucauucuc ggaggugaca acauuaaaca gaucuugaau uguugaacuc uuaaaguaag   1140

cuguaguaaa guuuccuccu ucaauggcua caucucccag cauucucuuu ugguucgcuu   1200

uuuuaaguau auuuuccuca acaguuuuuu cgcugaucaa ucuauaaaua uguacaucuc   1260
```

```
ucguuuggcc gauucugugg caucgaucuu gagcuugggc auccauggua ggauuccaau   1320
cacuaucaua aaauauaaca gugucugcac caguuaaauu aauaccaacu ccuccagauc   1380
uuguggauag aauaaagcaa aauauucucu ugucagcauu aaagcguucc auuaagagcu   1440
gucucugauc uacuuucguu guuccaucaa gacgaagaua uaugugcccg ugaaaguuaa   1500
gaaaugcuuc caguacgucu aacauucuag ucauuugugu aaauauuaau auccgaugau   1560
ggucagcuuu caaucuucga agaagcuugu cuaaugauug aagcuuucca cagucauacu   1620
guauuagucu ucuaucaggg aacugcguac ucauugcuga ugauaugcua ugaaguaaac   1680
gaaguuuagg ucuuagccaa guaucaacua augauagccu cuucucuucu uggaacaucu   1740
uugaaggugg cggauguggc acauguaaac ggacagguug gcuggaaaca gccgguacgu   1800
acaaaacaaa ccuagagaau auaucagaca acuccgcaac ucggucuucg auggaaugaa   1860
uagcugcugu gagagcauga gucugauucc aaaauaacaa ggggguuugaa gauaaagcau   1920
ucuuacagug aacuguucca augcagucuu uaguuucauc aggagcauca uccaauguua   1980
aagaugauag aaggucagaa ccauaaauug gaagggccug acaccuuugu ucauugauuc   2040
uaacaaucag uuccaacuuc uccuuucgcc guuuuuuucu aagauuuucu agguauucau   2100
cucucaaauc uucauucgga uuagauucuu cuuuguuauu uuuauuugag uucaaaguac   2160
uuugucuugu uacuuuuuua agagaaggua augaauugac guucgaucca uuuccuugag   2220
cuggcucuga cgauaugcuc acaggugaau uguuuacagu agucaaacug uuuugaacaa   2280
caguagcugc agaagugaug uuuaauggag guacccucau gauaggccga uuugaauuua   2340
uuugggucac agaaguaggg uugacuaguu uagcuacauu gcuucccugu uuggauacca   2400
caguuaaucu uugcccagua guagucauua caguaguagc accuccuuga ggaguaauaa   2460
ccgguugugg agagaguacc agcugccuac cgguaggggu auuaacuaau ugugcaaauu   2520
gagggaccau acgaccagca uugccuucau uuuuaaccac gccuccacua guaguuguua   2580
augaagccac ugagauugcu uucauggcac cagguuguaa uaacugaagg uaauuaggaa   2640
ucugaccaga aguaggauuc gccagucuua aaguuacacu cuggcuagca uuuuguccaa   2700
gcuuuaucaa uggugauguu ccaacuuuug uugaaaaaga agaaauccga ugauuauuac   2760
uaacuuguac aauuggccua acagggcuag aaaccugagg ugguuggggc aauauccguu   2820
ucuugacauu aauuuuaacc cuuccuuuag ggcaaggugg uagaucagga ggugcagaau   2880
caauugugcg aaugaaguca ggauuaacuu uguauuuacg agcucuguga gcaacaaaug   2940
cuaauaacca uaguucaaau ucaauuaucc gcaaauuuag gaaaacuaga ucgacauguu   3000
uaaacggauc auaaucuaaa gcacuccaaa cuauagaagg aacaugguau ucaagagaau   3060
ccauuugaaa cggagacacg guagggcgaa cuucgaacag guuaggauga uuacacacuu   3120
uccucagcug caucaguaca uuaaugacac ucaauaaacu accagaagca aguguuucuu   3180
uuguuuuagc ucuagacaug aaaucaucau auaaauaucg uugccuguug gauaaccgac   3240
acauuacuau auguucauau uucuuuggca uuugcguuuc uacuucacac uuuaaucuuc   3300
uuaacagaaa cggacgcaac acuuuaugaa gucuuuuaau aauaguguca uuguacucag   3360
aauucccuuc aaucaugccu guuacuggau uagaaaacca uucuuuaaau ucacgaugcg   3420
auucaaaaac auuaggcaua agaaaaugca uuaaugacca gaguuccaua agauuauuuu   3480
guaauggagu accagugagu aguaaccgcc uuugaguuug aaaauucaau aagaguugcc   3540
aacguuguga uuuaaaauuu uugauauuuu gagcuucauc uaaaauuaaa uauuuccauu   3600
uuuuucuacg aaaacucuga ugauccugua uaacuaacuu auaagaggua augcagauau   3660
```

```
ggaaugcauu agguuuuguc cacccugauc guuucaauuu ccguucuuuu ugaguuccau   3720
aauaaguuaa uauuuugaau gcuggacacc auuuuuuaaa cuccauuucc caguuuaaca   3780
ugacagacgu agggacaaug auuaaaugag guccccaauu accuuuuuca caagcaagau   3840
gagcuauuaa ugcuaugguu ugaauugucu uuccgagacc cauuucguca gcaaguauac   3900
cauuuaguuu ccuaucauac auaguaacua accagucuaa cccaaugugc ugauauucuc   3960
uuaagggaug uuuaagaaga aaaggaacuu ucguaacaac acuuguagau gauagagugu   4020
uuccuuuagg cugaagacuu ucagcuauag cagcaacauc auuuauuucc uugucuuugu   4080
cuugguuccc uuccucuaca ugaugcgagu cauuuaugag agccuucaaa gucgaaucuu   4140
ccuugucacu ugaagaacug ucuucuucuu cuucuucuuc acuaacuuca ucuucaaaau   4200
cuucuucuuc ugaggcuuca ucagauucuu cauucaggau uucuuuccuu uuucuugauc   4260
uuugggaacu gggaucuccg uucgaaggua aagguucgga cgggagcucg auaccauauu   4320
uugcucuaag uuguucuaug cucauauuuc cuuccuccuu uaaaucaucu auuucuuguu   4380
uauaauccac uguuccuuca gucuuuucuu guuccagaau uguuucuuca ucaucugaag   4440
aaucaccaga aucuugauau uccaugucau cauccucaac aucuucaucc augcugacag   4500
gaguugauau agaaucccuu ugagcaaggu aguuggaaag uagaucuuca aguggaagcu   4560
cgcucucuuu uuucagaaga uccacuucau cuugauuauc acauuuauca ucauuagcag   4620
aaagugcuuc uuccuuagca aucgucucuu caucgucguc agacggaucu ucuggcucaa   4680
auucaucguc agagugaugc cugggagaag uuggucuuga aguguucaug cuuucagcaa   4740
caagacuuga auacuuuuca guuugaucaa caauaaaacu uaaguguuga ucaagugcuu   4800
uuuuucucuu uucuucuaac cuaguuuguu guuugaauuc aacuagcuuu ucaacauuug   4860
accagaacug uuugauuucu uucgcaauaa aagaagcuau gcguuuuaac ugcauuucuu   4920
gagcuuugau agcuuucugu acuagagcuu cuuuuucuug aaaauguuuu ugaaccauuc   4980
uugcacacuu uuuugcagcu gcuuucuucc auuuccucuc cugggcaaaa ucugcagcca   5040
gccaagccau uucuucuagc agauaauccc aaugagcuuu agcccuuggc aauucaugga   5100
cuuuagguaa ucuuuucucu ggccauaauc cauccuuuug uaacucuccu acccuuugca   5160
uuacauacgc cucuuguuua gcucuuucaa caauuuguuc cuggcuauug acuccaucca   5220
ccggagaagc auuuuuuaca gcugauuuca cuguagucag uuuuuggaau uuggaagaua   5280
auucugcuuu gguaggacua gcagaugaug gaacccguac aucaguauug cuuccuggcc   5340
uguucccagu aagagcagau uguagaagag agugauuuug ugauugcaga accuuauaca   5400
gauccucucc gucauuacca ggaucuaacu uauuuguuuu uagaaauguc uguaaaggaa   5460
cuacaggcaa acgagaccuc cacggacuga agucugagag guuuccauuu gccuguagau   5520
aacagagaag agcacaucuc ucugcaaacu uugucugaaa ucuuuuauuu uuauuaucgu   5580
uuaaaucuuu uauucuuuuu cuaaaggaau uauauucauc aagcggcagc uugcguuuuc   5640
uuguugaaga ugacgacaaa cuuaaugaaa gugaugguug aggguuaccu uggcuaggag   5700
guuggagauu ggucaucaua ggagaaucgg acaggauaga agucggggag gagcggacuu   5760
ggagucgccc cccuuggcuc gaguuugcca accuugucau ugauggugaa cccuguugca   5820
ggguuggcaa gagaggagcc aaggggagca cuugagaucc agcacaaggu uuuucaagaa   5880
cuggcuuuuc aaagccaagu ugaagauugu ucauaucaaa uucauugugu uaucacaauu   5940
uucuucgucc aucaacaaua aaaucaagaa aaugaucuuc gguaacgaac uuuaggaaag   6000
```

```
aacucauuuu acuaauuuau uagccaauua auucugauuu uauucaaauu ccguggagaa   6060

auauuccuau gccacauucu cuucaaugca acauggcguu agguucag                6108


<210> SEQ ID NO 55
<211> LENGTH: 240
<212> TYPE: RNA
<213> ORGANISM: Artificial Sequence
<220> FEATURE:
<223> OTHER INFORMATION: SNF2/Helicase degenerate dsRNA sequence
<220> FEATURE:
<221> NAME/KEY: misc_feature
<222> LOCATION: (216)..(216)
<223> OTHER INFORMATION: n is a, c, g, or u
<220> FEATURE:
<221> NAME/KEY: misc_feature
<222> LOCATION: (222)..(222)
<223> OTHER INFORMATION: n is a, c, g, or u

<400> SEQUENCE: 55

cgsyuhcuyy umacsggyac hccucuvcar aayaarcuwc chgaryusug ggcbyudcuh     60

aayuuyyuvc ubccsucbau yuuyaarwsb ugyucbacdu uygarcarug guucaaygcv    120

cchuuygcha cmacbggmga raarguygar yudaaygarg argaracvau yyukauyauy    180

mgdcguyudc ayaarguyyu kcgwcckuuy yuvyunmgdc gnyuvaaaaa rgargumgar    240


<210> SEQ ID NO 56
<211> LENGTH: 27
<212> TYPE: RNA
<213> ORGANISM: Artificial Sequence
<220> FEATURE:
<223> OTHER INFORMATION: SNF2/Helicase degenerate dsRNA sequence
<220> FEATURE:
<221> NAME/KEY: misc_feature
<222> LOCATION: (21)..(21)
<223> OTHER INFORMATION: n is a, c, g, or u

<400> SEQUENCE: 56

mghgcygubu gyyuhauygg ngaycar                                         27


<210> SEQ ID NO 57
<211> LENGTH: 60
<212> TYPE: RNA
<213> ORGANISM: Artificial Sequence
<220> FEATURE:
<223> OTHER INFORMATION: SNF2/Helicase degenerate dsRNA sequence

<400> SEQUENCE: 57

uayaarcuyc uvyusacmgg machccgyub caraacaayc umgargaryu ruuycauyur     60


<210> SEQ ID NO 58
<211> LENGTH: 61
<212> TYPE: RNA
<213> ORGANISM: Artificial Sequence
<220> FEATURE:
<223> OTHER INFORMATION: SNF2/Helicase degenerate dsRNA sequence

<400> SEQUENCE: 58

garuuygaya cbaaycaymg rcukcuhauh acwggbacyc ckyuvcaraa ywskyudaar     60

g                                                                     61


<210> SEQ ID NO 59
<211> LENGTH: 23
<212> TYPE: RNA
<213> ORGANISM: Artificial Sequence
<220> FEATURE:
<223> OTHER INFORMATION: Bromodomain degenerate dsRNA sequence
```

<400> SEQUENCE: 59
yuswsygaac cruuyaugaa ryu 23

<210> SEQ ID NO 60
<211> LENGTH: 65
<212> TYPE: RNA
<213> ORGANISM: Artificial Sequence
<220> FEATURE:
<223> OTHER INFORMATION: HAND-SLIDE degenerate dsRNA sequence

<400> SEQUENCE: 60
gchguvgaug cyuayuuymg vgargcwyuv mgdguyuchg arccyaargc dccdaargch 60 cchmg 65

<210> SEQ ID NO 61
<211> LENGTH: 36
<212> TYPE: RNA
<213> ORGANISM: Artificial Sequence
<220> FEATURE:
<223> OTHER INFORMATION: Chromodomain degenerate dsRNA sequence
<220> FEATURE:
<221> NAME/KEY: misc_feature
<222> LOCATION: (33)..(33)
<223> OTHER INFORMATION: n is a, c, g, or u

<400> SEQUENCE: 61
mghaarurbg ayauggavga rvvdccbaar yungar 36

<210> SEQ ID NO 62
<211> LENGTH: 56
<212> TYPE: RNA
<213> ORGANISM: Artificial Sequence
<220> FEATURE:
<223> OTHER INFORMATION: Chromodomain degenerate dsRNA sequence
<220> FEATURE:
<221> NAME/KEY: misc_feature
<222> LOCATION: (29)..(29)
<223> OTHER INFORMATION: n is a, c, g, or u

<400> SEQUENCE: 62
bhggdaarad dggrkkbryb ggmaaymwna chacdrusua ykmhruagar gaaaay 56

<210> SEQ ID NO 63
<211> LENGTH: 4569
<212> TYPE: DNA
<213> ORGANISM: Euchistus heros

<400> SEQUENCE: 63
atggacggag acagcggtgg tatggcgagc ccttcgccac agcctcagtc gtcaccaatg 60
ccccctccac aagctccatc acctatgggc ccgccgcagg gcgccccatc gccaatgccc 120
ccttctaacc aacaggcggc ctcaccaatg ggtccaccgc accaccccca cagcccgaca 180
ggttaccaag gagggatgcc acacatgaat ggaccaaatg gtgttcctcc tggtatgcag 240
caggctactc aaacatttca gcctcatcag caattgccac cccaccagca accaccaatg 300
cagactgctc ctggtgggcc tgctagtggt ggaggacaag aaaatcttag cgctctccag 360
cgtgcaatag attctatgga agagaaaggg cttcaggaag atccacgtta ctcgcagctg 420
cttgcgttga gggcaaggca tgccaacatg gaacctccgg ttaggcctcc atctcagctt 480
gttgggggtg ggttcagcgg tgagggtggt gcccctcctc ctgctaaaca cagcttcagc 540
gcgaaccaac tgcaacaact tcgagtgcag atcatggcgt atcgcctact tgctaggaac 600

```
caacctcttt cccagcagct agctttggct gtgcaaggca aacgcctcga cagccctggc    660
gagtccaact accagcatcc tcctagtgaa ggagcaggag gtgttggtgg agaaggaagt    720
ggagacgggg gatcgtcgaa cggcctgatg acgcagccga tgcgtgcccc atgcccccct    780
ggtggccagc cccaacggc ctcaccgatg acaggccaga tggcacctcc tactgggcca    840
gctcctgtaa ggccacctcc tcccggtgtg tctcctacac ctccgcgccc tcctcagcag    900
gttcctggtg ctccgggggc cccacaacca aagcaaaata gggttaccac catgccaaga    960
ccgcatggtt tagatcccat tcttattctc caggaaagag agaatagagt agccgctagg   1020
attgtacata ggatggaaga attatcaaat ttaccagcta cgatgcctga agaccttcga   1080
ataaaagcgc agatagaact tagggccttg agggtactta acttccaaag gcaattaaga   1140
gcagaggtga tagcttgtac tagacgcgat acaacattag aaacagctgt aaatgtgaaa   1200
gcttataaac gaacgaagag gcaaggctta cgggaagcca gagctacgga aaagcttgaa   1260
aaacaacaga aacttgagac agaaaggaag aagagacaaa aacaccagga atatctgagc   1320
actatattgc aacattgcaa agacttcaaa gaattccata gaaataatgt tgctaaagtt   1380
ggtagattaa ataaggctgt gatgaattac catgcgaatg ccgagcgtga acagaagaaa   1440
gagcaagaaa ggatagaaaa agaacgtatg agaaggctta tggctgagga tgaagagggt   1500
tacaggaaac tgattgatca gaaaaaagat aagagattgg cattccttct ttcacaaact   1560
gatgaatata ttgccaatct tactgaaatg gtgaagcagc ataaaatgga acaacagcgt   1620
aagcaggaac aagaagagca acaaaaacgg aagaggaaaa agaaaaagaa gaatagggaa   1680
ggagatccag atgatgaaag ctctcagatg tcagatttac atgttagcgt tatagaagca   1740
gcaactggtc ggcagctgac gggggaggat gctccattgg ccagccagct tgggagctgg   1800
ttggaggcac acccgggctg ggagcctttg gaagatagcg aagatgaaga tgatgaagag   1860
gacagcgacg aggaaggtga tgataacagt agatcaaaag gtggtttttc aatgatagga   1920
aaagatgaag ctgatagcaa gttatctgtt gaagacgaag ctcgagaaat gataaagaaa   1980
gcgaagattg aagatgatga atacaagaac acgaccgaag aacatacata ctacagcatc   2040
gctcacaccg tgcatgaaat tgtcaccgaa caagcttcaa tcatgattaa cggtaaattg   2100
aaagaatatc aaattaaagg tcttgaatgg ttggtttctt tatacaacaa caacttgaat   2160
ggaatcctcg ccgacgagat gggccttggc aagacaattc aaacaatagg tctcattact   2220
tatttgatgg agaagaagaa agtaaatggt ccttacctca ttattgttcc tctgtcaaca   2280
ttatccaatt gggttttgga attcgagaaa tgggctcctt cagtgtttgt ggtagcttat   2340
aaaggttctc ctgcaatgag gagaacttta caatcacaga tgcgctcgac gaagttcaat   2400
gtcctgctca cgacctacga gtatgtcatc aaggacaagg cagtacttgc aaagttgcat   2460
tggaagtaca tgataatcga cgagggacac aggatgaaaa accaccattg taagctgacg   2520
caggtgctga acacccatta tttggcacct caccgcctcc ttctcacggg cacacctctc   2580
cagaacaaac tacctgagct ctgggctctt ctaaactttc tcctcccgtc catcttcaag   2640
tcgtgttcta cgtttgagca atggttcaat gcaccatttg ctaccactgg agaaaaggtt   2700
gagttgaatg aggaagaaac aattttgatt atcaggcgtt tacataaggt ccttcgacct   2760
ttcctccttc gtcgactgaa aaaggaagtc gaaagtcagt tgccagagaa aattgaatac   2820
atcgtcaagt gtgatatgtc tggtctccaa cgtgtacttt ataggcacat gcagagtaaa   2880
ggagtcctgc ttaccgatgg ttctgagaag ggcaagcagg gtaaaggagg agctaaagcg   2940
ctaatgaaca cgatcgtcca attgaggaag ctttgcaatc atcctttcat gttccatcat   3000
```

```
attgaagaaa aatattgtga tcacgttggc cagaacaacg ttgtcacagg gcctgatctg   3060
ttccgagttt ctggtaaatt tgaattcctc gatcgtatat tgccaaaact gaaggccacg   3120
agccataggg tacttctttt ctgtcaaatg actcagctga tgaccatcat ggaggattat   3180
ttgtcttgga gagggttctc ctaccttcgt cttgatggta cgaccaaatc tgaagaccga   3240
ggagatcttc tgaaaaaatt caacaatcca gaaagtgaat attttatttt cttgctctca   3300
accagagctg gaggtctcgg attgaactta caggctgcag atactgtcat tatatttgat   3360
tcagattgga accctcatca ggatttacaa gctcaagaca gagctcatag gattggacag   3420
caaaacgaag ttcgtgtttt gcggctaatg acagtaaatt ctgttgagga gcgtattctt   3480
gcagctgctc ggtacaagct gaatatggat gagaaagtca ttcaggctgg tatgtttgac   3540
cagaaatcta caggaaccga gaggcagaaa tttctgcaaa acatccttca tcaagatgat   3600
gcagatgatg aggaaaatga agttccagat gatgaaatgg ttaatcgtat gattgcgcga   3660
acagaagatg aattcaacct cttccagaaa atcgatttag aaaggaggag ggaagaggct   3720
aaacttggac ctaacaggaa gtcaaggctt gtagaagagg cggaattacc tgactggctt   3780
gtaaagaatg acgatgagat tgagaagtgg acttatgaag aaaccgaggt ccaaatggga   3840
agaggtaata ggcagaggaa ggaagtagat tatacagata gtttgactga aaaagaatgg   3900
ttaaaggcca ttgatgacaa tgtagatgat tttgatgacg atgaagagga agaggtaaaa   3960
acaaagaaaa gaggcaagag aagaagaagg ggagaggatg atgaagaaga tgcaagtact   4020
tcaaagagaa ggaaatattc tccatctgaa aacaaactga ggaggcgtat gcgtaacctc   4080
atgaacattg ttgttaagta tactgacagt gactcgagag tactcagtga accattcatg   4140
aaacttccct ctcgccataa gtacccagac tactatgagt tgatcaagaa acctatagac   4200
atcaagagga tattggccaa agtagaagag tgtaaatatg ctgacatgga tgaattagaa   4260
aaggatttta tgcaactttg taaaaatgct cagacataca atgaggaggc ctcattgatc   4320
tatgaagatt cgatagtatt agaaagtgtt ttctctaatg ctcgtcaaaa agtagagcag   4380
gataatgatt cagatgatga tgaaagtaaa ggtgaccaag aagatgctgc atcagacact   4440
tcatccgtca aaatgaaatt gaaactaaag cctgggagga cccgagggag tggagctggt   4500
ggtaaaagga ggagaagaaa atatatctct gaagatgaag acgaagacca tagcgaagtt   4560
tccttaatg                                                           4569
```

<210> SEQ ID NO 64
<211> LENGTH: 6222
<212> TYPE: DNA
<213> ORGANISM: Euchistus heros

<400> SEQUENCE: 64

```
atggcgtctg aagaagaagt tgacgagtgt ttaccagttg acgatgaagt tgacactagt     60
gttgttcaac aagaaggcac tgaagaaaat tcacctgaca gtgatgaaag aagtaggata    120
gaggaagaag atgacgagta tgaccctgag gatgcgagga aaaaaaagaa aggtaaaaag    180
agaaaagcca aggggaaagg caaaaaagaa aagaaacgta aaaaaaggaa gaagaatgat    240
agtgctgaag aaagtgaggg aggcggggaa gaagaaggcg attccgatta tggaagaaaa    300
tctaagaagt ctaaaggaac ttcacaacca aaaccagtgc agcaagattc ttctggaggt    360
gtaccttcag tagaagaagt ttgcagcctt tttggactta cagatgtaca gattgactat    420
accgaagatg attaccaaaa tctgactacg tataaacttt ttcaacaaca tgttcgtcct    480
```

```
attcttgcca aggacaacca gaaggttccc atcggaaaaa tgatgatgct cgtggctgca    540
aaatggagag atttttgcaa ttccaatcca aacgctcaac aggaaccaga tccagaagct    600
tcagaagaac aggaatattc taaacctacc aggacacgac cttcacgagt ttcaactaca    660
caaaatgatg atgaagaaga cgacgatgct gacgaacgag ggaggaaaaa gagaagtgga    720
cgaagtaaaa agtcatcagg aaagaagtcc gctcctccgg ccacaaccaa ggtccctacc    780
ctcaagatca agataggaaa aagaaaacag aattccgatg aagaagatga aggttcagtt    840
ggtgccgttt ctgaaaggga ctcagatgct gaattcgagc aaatgctcgc agaagctgaa    900
gaagttaata aacctgaagg tgttgtagaa gaagaagaag gtgcagaggt ggctcctgta    960
cctaagaaaa aggccaaaac gaaaattggt aataaaaaga aaaggaaaaa gacacggact   1020
actaacaagt ttccagacag tgaagctggt tatgaaacag atcatcagga ctattgtgaa   1080
gtttgtcaac aaggaggtga aataatatta tgtgatacgt gccctcgagc ttatcatttg   1140
gtctgtttgg atcccgaatt ggaagatacg ccagaaggca aatggtcatg ccctcattgt   1200
gaaggtgaag gtgtacagga aaaagaagat gatgtccatc aagaattttg cagagtttgt   1260
aaagatggtg gagaactttt atgctgtgat tcttgccctt ctgcatacca cacattctgt   1320
ttgaaccctc cattgacaga tattccagat ggtgactgga agtgcccacg ttgttcggcg   1380
aagcctttga gaggtaaagt gtcaaagatt cttacttgga ggtggttgga atctcccagt   1440
agtaaagatg aagaagacaa tactaaaaaa cgaaacaggc agaggcaaag agaatatttc   1500
gtcaagtggg cagatatgtc ttattggcac tgtagttggg tgtctgaact tcagatggat   1560
gtttttcata ctcaaatgat caggagttat attcgtaaat atgatatgga cgaacctccc   1620
aaactagaag aacccttgga tgaagcagac aatagaatga agaggatacg agaggcaaat   1680
atcaatgagc aagaattaga agagaaatat tacaagtatg gtatcaaacc agagtggctt   1740
attgtgcaga gggtaattaa ccatcgcact ataagggatg gaagcaatct gtacctcgtc   1800
aaatggaggg acctccctta tgaccaggcg acttgggagg aagaagtcac cgatatccct   1860
ggcttgaaga aagctattga atattacaat gagatgaggg cttgctgttt aggtgaatct   1920
aaaaaactaa aaaaaggtaa aggtaaaaga tcaaagagag atcaagatga tgaggaagga   1980
agcagaagtg caggaatgat gggcgtcggt ggaccagcta ctggtcaata cttcccgcct   2040
cctgaaaagc ctgtcacaga tttgaaaaag aaatacgata aacagccgga ctatctcgac   2100
gtctccggta tgtgccttca tccttaccaa ttagaaggtt taaattggtt gaggtattcc   2160
tgggggcaag gaacagacac tattcttgcc gatgagatgg gtcttggaaa aaccattcag   2220
acaattactt tcctctattc tctttacaaa gagggtcatt gtaaaggccc cttccttgtg   2280
agtgtaccct tatctacaat tatcaattgg gaaagagagt tcgaaacttg ggcgccagac   2340
ttctacgttg tcacatatgt cggagacaaa gattctcgtg ctgtaatacg tgaaaatgaa   2400
ttttcattcg atgataatgc tgttagagga ggaagaggtg tttctaaagt tcgctcttct   2460
gcaataaagt ttcatgtact gctaacatct tatgaactta tctctatcga tgtcacttgc   2520
cttggatcga tcgagtgggc agtgcttgta gtagatgaag cacacaggct gaaaagtaat   2580
cagagcaagt tctttaggct tcttgcttca taccacattg cttataaact tctgctgaca   2640
ggaactccgt tgcaaaacaa tctagaagaa ttgtttcatt tacttaattt ccttacgccg   2700
gaaaaattca acgaccttgc gacatttcaa aacgaattcg ctgatatttc aaaagaagaa   2760
caagtcaaaa gacttcatga gttactcggg ccgcatatgt tgaggagatt aaaagctgat   2820
gtactcaaga atatgcctac aaaatctgag ttcattgtta gagttgaact ctccccgatg   2880
```

```
cagaagaagt actacaaata tattctcaca aggaatttcg aagctttaaa tccaaaagga   2940

ggcggtcaac aagtatctct tttgaacatt atgatggatc ttaaaaaatg ctgtaatcat   3000

ccatacctgt ttcctgctgc ttctcaggaa gctcctttag gaccaagcgg atcttacgat   3060

cttcaagggt taatcaaagc atctggaaaa ttgatacttc tgtcgaaaat gctgagacgg   3120

ctcaaagaag agggtcacag agtactgatt ttctctcaaa tgacaaaaat gttggactta   3180

ttagaagact acctcgaggg tgaaggttat aaatatgaac gtattgacgg tacgatcacc   3240

ggtagcttaa gacaagaagc tatcgatcgg tttaacgccc ctggagctca acaatttgtt   3300

tttcttttgt ccactcgtgc gggaggtctt ggtattaatc tcgctactgc agatacagtt   3360

attatttatg actctgactg gaatcctcat aacgatattc aggccttttc gagagcacac   3420

aggatagggc aagcaaacaa ggttatgatt tatcgatttg tgacacgagc gtctgttgaa   3480

gaaagagtaa cgcaagtggc taagagaaaa atgatgttaa cccatcttgt cgtacgacca   3540

ggtatgggtg gcaagcaagc aaatttcact aagcaagaac ttgatgatat tttaaggttt   3600

ggaacagaag aacttttcaa agaagagcag ggtaaagaag atgaagccat tcattatgac   3660

gataaagctg ttgaagaatt acttgaccgg tcgaagatgg gtattgaaca gaaagaaaac   3720

tggtctaatg aatatctttc ttctttcaaa gtggcaagtt atgttactaa agaagaagac   3780

gaagatgagg aaataggaac agaggtaata aaacaggaag cagaaaatac agacccagct   3840

tattgggtca aactgttgag gcaccattat gagcaacaac aagaggatat ttctcgaact   3900

ctcggtaaag gaaaaaggat tcgaaaacag gtgaattaca tcgacggtgg agtgatggac   3960

tcaagagaga acgccgattc gacgtggcaa gacaacctct ctgactataa ttcagacttc   4020

tctgctcctt ctgatgatga caaggaagac gatgactttg atgagaaaaa tgatgatgga   4080

acgagaaaga agcgtaggcc agaaaggagg gaggacaaag ataggcctct acctcctctt   4140

cttgcccgag tcggtggaaa cattgaggtc ctgggattca acgccagaca gcgtaaagca   4200

ttcttgaatg ctattatgag gtatggaatg ccacctcaag atgcattcaa ctcgcagtgg   4260

cttgttcgag acctgagggg taaatctgag aagcatttca aggcatacgt atccctcttt   4320

atgaggcatt tgtgtgagcc tggcgcggac aatgccgaaa cattcgcgga tggtgttcca   4380

agggaaggtc ttagtcggca gcatgttctc acaaggatag gtgtgatgtc actcattagg   4440

aaaaaggttc aagaatttga gcaaattaat ggatattact cgatgcctga aatgttgaag   4500

aaaccacttg ttgatgccgg attgcataaa acaagtgcta gcagtatagg tgaaggtgct   4560

agtagttccg gtacacctgc aacatcagct gctccaagtc cagctcctac tcttttggat   4620

aagacacaaa ttgaagattt gagtgaaaaa gaagatccgt caaagactga agataaaacc   4680

accgatgatt ccaaaccctc agaagaggct aaagctgcag atgatgcaaa taagcctcag   4740

gctgaaggag aaaaggcaga aggatcttct aatgcaaacc aaacttctga agctgaagga   4800

agcgatgaga aaaaacccaa agaagaaccg atggatgtag atggtgaagg agaggctaaa   4860

gatagtgata agacagaaaa acaagaaggt actgacgaaa aagatgtagc cctaaaagag   4920

gaagaaaagg atgaagaggt caacaaagag aagggagagg aaacagagga aaagaaggtt   4980

atcgattttg aagaagacaa atctaaaagg aaatttatgt tcaatatcgc tgatggagga   5040

tttactgagc tccatacctt atggcaaaat gaagagaaag ctgcagtacc tggtagggag   5100

tacgagatct ggcataggag gcatgactat tggctgttgg gtggaatcgt tacccatggc   5160

tatggtcggt ggcaagatat tcaaaatgat attagatttg ctattatcaa cgaaccattt   5220
```

-continued

```
aagatggatg ttggaaaagg aaatttctta gaaattaaaa ataaatttct tgccaggagg   5280
tttaagcttc ttgagcaagc tctggtgatt gaagaacagt taagacgtgc agcttattta   5340
aatctgacgc aagatccaaa tcacccagca atgtcactga atgcaagatt tgcagaggtt   5400
gaatgtctag ccgaatctca ccaacacctc tcgaaggaaa gtcttgctgg caacaaacct   5460
gcaaatgcag tgttacataa agtattgaac caattagagg agcttctgtc ggatatgaaa   5520
tctgacgtat ctcgactacc agccactcta gccagaattc cacctgtagc ccagaggcta   5580
cagatgtctg aacggtcaat actttctagg ttggctgcaa ctacttctcc tgcgacgccc   5640
accacgtccc atcaaactgg tatgataagc agtcagttcc ctgctggatt tcaatcaggg   5700
cagttgactg gaacgtttcc gaatgccagt tttaccaact tcaggcccca gtattcagtt   5760
cctgggcaaa ctgcagccca gggtttttccc ggtaattgat aattgaaagc tggacggtaa   5820
ttgtctgcga gtgaattctc catgagtaaa taataggttt tttttttttt ttaagaaaga   5880
aataaaagaa gcgttttgtt tagttttgtt gatagttctc tttatttctt tcaattttgt   5940
tttagcggaa aaaaaaatgt tcattataag taacttataa attggacatg ctaattaaat   6000
ttcctattag attattttgt tatttgtaag tttttcggta ttgtaagaat gtctatatgt   6060
gtaagaggtt gtacaagatt gcctaaatac cttgtattat ttatttttac tattgaataa   6120
aaaaaaaaaa taattaactt cgatcttagg ttaagggtaa taaaaaaaaa tgttactgga   6180
aaaaaaaata gaaaaaataa aaaagatagc ctttcccctt ac                      6222
```

<210> SEQ ID NO 65
<211> LENGTH: 3072
<212> TYPE: DNA
<213> ORGANISM: Euchistus heros

<400> SEQUENCE: 65

```
atgtcgaagc caaatgaagt tagtttggat acaacagata ctgttgaaat ttctaatgaa     60
tcttcgggag acacagagtc gtccaagggt aaaaatgaag attttgaaac aaaaattgaa    120
actgaccgtt ctagaagatt tgagtttctg ttgaagcaga cagaaatttt ttcacatttt    180
atgacaaatc aaggaaagtc gaacagccct gcaaagccta aagtcggccg tcctagaaag    240
gaaactaata aattggcacc agccggtggt gatggttctg ccgaccatcg gcatcgtatg    300
accgagcagg aagaagatga agaactgctt gctgaaagta atacttcttc aaaatcctta    360
gcaaggtttg acgcttctcc tttttatatt aaaagcggag agttgaggga ttaccagata    420
cgtggtttga attggatgat atccctctac gaacacggta taaatggtat acttgctgat    480
gagatgggtt taggtaaaac tctccaaact atttctctcc ttggttacat gaagcattat    540
agaaatatac cagggccaca tatggtcatc gtaccaaaat caacattagc taattggatg    600
aatgaattta aaaagtggtg cccaaccctg cgtgctgtct gtttaatcgg agatcaggaa    660
acgaggaatg cgttcatcag agacactctt atgccgggtg aatgggatgt ctgcgttaca    720
tcttatgaaa tgatcatacg agaaaagagc gttttcaaga agttcaactg gaggtatatg    780
gtcattgacg aagcccacag gatcaagaat gaaaaatcca aactctccga gattgtgaga    840
gagttcaaaa cgacgaatcg attactcctg accggtactc ctttacaaaa taacctccac    900
gaattgtggt ctcttcttaa cttcctctta ccagatgttt tcaattcatc agatgatttt    960
gattcatggt ttaataccaa taccttcctt ggcgataatt ctcttgtcga gagattacat   1020
gctgtactga gacctttcct cctaagaaga ttgaaatctg aggtagagaa aaaactcaaa   1080
ccgaagaaag aagtcaaaat ctacgttgga ttgagtaaaa tgcagagaga atggtatact   1140
```

```
aaagttctaa tgaaagatat agacattgta aacggtgctg gccgagtcga aaaaatgcgc   1200
ctccaaaaca tcctcatgca gttgaggaag tgcagtaatc acccttatct cttcgacgga   1260
gctgaaccag gtccacctta ctcaactgat gagcatctgg tatataacag tggaaaaatg   1320
gtaatattag acaagcttct tcctaaattg caagaacaag gatcacgagt tctggttttc   1380
agccaaatga caaggatgat tgatattctc gaagattact gttattggag aggatataat   1440
tactgtcgtc ttgatggtaa tacacctcat gaggataggc agagacagat taatgagttc   1500
aacgaagaag acagtaagaa attcattttc atgttgtcga ctcgtgcggg tggtttgggt   1560
atcaatttag ccaccgcaga tgtagtcatt ttgtacgatt cggattggaa ccctcaaatg   1620
gatctccagg ctatggatcg tgctcatcgt attggtcaaa agaaacaagt caaagtgttc   1680
aggatgataa ctgaaaacac agttgaagag aaaattgttg agagagctga aataaaactc   1740
cgcctcgata agttggtcat ccaacaaggc aggctggtag acaataaaac ggcactcaac   1800
aaagatgaaa tgttgaatat gatccgtcac ggtgccaatc atgtatttgc cagtaaagat   1860
tctgaaatca ccgatgaaga cattgacact attttggaaa aaggcgaagc aaggacggaa   1920
gaaatgaata aaaaacttga acaactcggt gattctaatt tgaaagactt catgatggaa   1980
accccgactg agtcagttta ccaattcgaa ggagaggatt acagggaaaa gcagaaagtt   2040
ttaggaatag gaagttggat agaacctcca aaaagagaac gtaaagctaa ttacgctgtc   2100
gatgcctatt ttagggaagc attgagagta tcagaaccta aagctcccaa ggcaccgagg   2160
cctcctaaac agcctatagt tcaagatttc caattctttc ctcctcgtct ctttgagcta   2220
ttggaccagg agatctatta cttcaggaaa actgtgggct acaaagttcc taaaaatcct   2280
gaattaggtt ctgatgcatc acgtgtccaa aaggaagaac aaagaaagat agatgaggca   2340
gaacctttat cagaagaaga actcgctgaa aaggaaaaac ttcttacgca gggttttacc   2400
aattggacta aaagagattt caaccagttt attaaagcta atgaaaaata tggtcgtgat   2460
gatattgaca atatttcaaa agaagtagaa ggaaaaactc cagaagaagt aagagcttat   2520
tcagaagtgt tctgggaacg atgtaacgaa ttgcaggaca tagatcgtat catggggcag   2580
atcgacaggg gagaggctaa aattcaaagg agagcaagta ttaagaaagc tctcgataca   2640
aagatgagcc ggtacagagc cccatttcat caacttcgca tctcctacgg tacgaataag   2700
ggtaagaact ataccgagga agaagataga ttccttgtct gtatgttgca taagcttggt   2760
tttgacaagg aaaatgtgta cgaagaactt agagcgatgg tcaggtgtgc gcctcagttc   2820
agattcgact ggttcatcaa atcgagaaca gccatggaat tgcagaggcg ttgtaatact   2880
ctaattactc tcatcgaaag agaaaatcag gaacttgagg agagggaaag agccgagaag   2940
aggaaaggaa gaggaagtgg gcgtggtcct ggttccggta aaaggaaagg agacggttcc   3000
atttcatctc cccctcctgt ccctggccaa ggggataaga acagccccgc cagaaaaaag   3060
aaaaaaatgt ag                                                       3072
```

```
<210> SEQ ID NO 66
<211> LENGTH: 1164
<212> TYPE: DNA
<213> ORGANISM: Euchistus heros

<400> SEQUENCE: 66
```

```
atgaataaaa aacttgaaca acttggtgtt gattcatcat taaaagattt catgatggag     60
gctcccactg agtctgtcta tcagtttgaa ggcgaagatt atagagaaaa gcaaaaagtt    120
```

```
tttggaattg gaaattggat tgaaccacca aaacgagaac gtaaagcaaa ttatgcagta    180
gatgcctatt ttagagaagc actgagagtt tcagaaccta aagctccaaa ggcccctagg    240
ccaccaaagc aacccatagt tcaagatttc caatttttcc cacctcgtct gtttgagctg    300
ttagatcaag aaatatacta ttttcgaaaa actgtttgct acaaggttcc taaaaatccg    360
gagttaggat cagatgcttc tcgtatacaa agggaagagc aaagaaaaat tgatgaagct    420
gagccgttga ctgaggaaga gctagctgag aaagaaaact tattgaccca gggttttact    480
aattggacta aaagagattt taaccagttc ataaaagcta atgaaaaata tggacgtgat    540
gatattgata atatctcaaa agatgttgaa gggaagactc cagaagaagt acgagcatac    600
tctgaagtat tttgggaaag gtgcaatgaa ctacaggcca tagatcgtat catggggcag    660
attgatagag gtgaagcgaa aattcaaaga agagccagta ttaaaaaagc tttagataca    720
aagatgagtc gatatagagc accgtttcat caactacgaa ttgcttatgg tacgaacaag    780
gggaaaaatt acacagaaga agaagacaga ttccttgtgt gcatgctaca taagcttggc    840
tttgataaag aaaatgtgta tgaggaactt agggcgatgg tgaggtgtgc tcctcagttt    900
aggtttgatt ggttcatcaa gtctcgaaca gctttggaat tgcaaagacg ttgtaatact    960
ctaatcacgt taattgaaag ggaaaaccaa gaattagaag aaagggaaaa agtagaaaaa   1020
aggaaaagtc gaggcagtaa tgggcgtggt cccagttctg gtaaacgtaa gggagatgga   1080
tctatttcat ctccacctgt ctctgtacag agtgataaaa gcagccctgc tcggaaaaag   1140
aaaaagtata tctctgttga gtaa                                          1164
```

<210> SEQ ID NO 67
<211> LENGTH: 1665
<212> TYPE: DNA
<213> ORGANISM: Euchistus heros

<400> SEQUENCE: 67

```
atgggtcttg gtaaaactat tcagactatc tgcagtttgt attatttatt tcatactcac     60
cagttgtatg gaccattttt aattgttgtc cctttatcta cgatgacttc atggcagagg    120
gagttttcat tatgggctcc agaaatgaat gttgtaactt atattggtga tataaactcc    180
cgtgatgtta tacgtaatta tgaatggtgc tattcaggtt cgaaaaggtt aaaattcaat    240
gccattctta ctacatatga aattgttctt aaagacaaag catttttggg tagtataagc    300
tgggctatcc ttatggttga tgaagcacac agattgaaaa atgatgattc attattatac    360
aaaacattga aagagtttga taccaaccat aggcttctta taacaggcac tcctttgcaa    420
aatagtctta aagagctttg ggcgttgctt cactttatta tgcccaacag atttaataac    480
tgggaagaat ttgaaaaaga acatgacaac tctgctaata aaggctatac taagttgcac    540
agacagctgg aaccatatat tctacgacga gttaagaagg atgttgagaa atctttacca    600
gctaaagtgg aacaaatatt acgtgttgaa atgacatctg tacagaagca gtattacagg    660
tggattttgt ccaaaaatta ttctgctctt cgaaaaggag tcaaaggttc tcctagtaca    720
tttataaata ttgttattga attaaaaaaa tgctgtaatc atgcacatct aataaaacca    780
ttagaaaatg aagcaaaaac tgaagactac ttacagcaat tgttaaaagg ctcagggaaa    840
ttacttctgt tggacaagtt gcttgttcgc cttaaagaaa ctgggcatag agtacttata    900
ttttctcaaa tggtacgaat gttggatata ctggctgagt atcttcaaat gagacatttc    960
cctttccaac gtttagacgg ttcaattaaa ggtgaattga gaaagcaagc cctcgatcat   1020
ttcaatgctg aaaattcacc agatttctgt ttcttattat caactcgtgc tggtggtttg   1080
```

```
ggcattaatt tagcaacagc tgatactgtc attatatttg actctgattg gaatccacaa   1140

aatgatttgc aagcacaagc tagagctcat agaatcggtc agaaaaatca ggtgaacata   1200

tacagacttg ttactaaaag ttctgttgag gaaaatattg tcgagcgggc caaacaaaaa   1260

atggtcttag atcatttagt tatacaaaga atggatacta caggtagaac tgtcctggat   1320

aaaaaaaatt cttcatccag tgcgcctttt aacaaagaag aacttactgc tattttaaaa   1380

tttggggctg aagaattatt taaagatgaa gaagatggtg atgaagaacc aacttgtgac   1440

attgacgaaa ttttgagaag agctgaaacc agagatgaag gaccagccac tgttggtgat   1500

gaattacttt ctgcttttaa agttgcaagt tttgcttttg atgaagataa agaaactcag   1560

agtgaaccag aacagcagga tgacgatact agagattggg tttgttatga taatacaatc   1620

ttatgtatct cgtattttat gattgaacca atttataatc aataa                    1665
```

<210> SEQ ID NO 68
<211> LENGTH: 4569
<212> TYPE: RNA
<213> ORGANISM: Euchistus heros

<400> SEQUENCE: 68

```
auggacggag acagcggugg uauggcgagc ccuucgccac agccucaguc gucaccaaug     60

cccccuccac aagcuccauc accuaugggc ccgccgcagg gcgccccauc gccaaugccc    120

ccuucuaacc aacaggcggc cucaccaaug gguccaccgc accaccccca cagcccgaca    180

gguuaccaag gagggaugcc acacaugaau ggaccaaaug guguuccucc ugguaugcag    240

caggcuacuc aaacauuuca gccucaucag caauugccac cccaccagca accaccaaug    300

cagacugcuc cuggugggcc ugcuaguggu ggaggacaag aaaaucuuag cgcucuccag    360

cgugcaauag auucuaugga agagaaaggg cuucaggaag auccacguua cucgcagcug    420

cuugcguuga gggcaaggca ugccaacaug gaaccuccgg uuaggccucc aucucagcuu    480

guugggggug gguucagcgg ugagggugguu gccccuccuc cugcuaaaca cagcuucagc    540

gcgaaccaac ugcaacaacu ucgagugcag aucauggcgu aucgccuacu ugcuaggaac    600

caaccucuuu cccagcagcu agcuuuggcu gugcaaggca aacgccucga cagcccuggc    660

gaguccaacu accagcaucc uccuagugaa ggagcaggag guguuggugg agaaggaagu    720

ggagacgggg gaucgucgaa cggccugaug acgcagccga ugcgugcccc augccccccu    780

gguggccagc cccaacggc cucaccgaug acaggccaga uggcaccucc uacugggcca    840

gcuccuguaa ggccaccucc ucccggugug ucuccuacac cuccgcgccc uccucagcag    900

guuccuggug cuccgggggc cccacaacca aagcaaaaua ggguuaccac caugccaaga    960

ccgcaugguu uagaucccau ucuuauucuc caggaaagag agaauagagu agccgcuagg   1020

auuguacaua ggauggaaga auuaucaaau uuaccagcua cgaugccuga agaccuucga   1080

auaaaagcgc agauagaacu uagggccuug aggguacuua acuuccaaag gcaauuaaga   1140

gcagagguga uagcuuguac uagacgcgau acaacauuag aaacagcugu aaaugugaaa   1200

gcuuauaaac gaacgaagag gcaaggcuua cgggaagcca gagcuacgga aaagcuugaa   1260

aaacaacaga aacuugagac agaaaggaag aagagacaaa aacaccagga auaucugagc   1320

acuauauugc aacauugcaa agacuucaaa gaauuccaua gaaauaaugu ugcuaaaguu   1380

gguagauuaa auaaggcugu gaugaauuac caugcgaaug ccgagcguga acagaagaaa   1440

gagcaagaaa ggauagaaaa agaacguaug agaaggcuua uggcugagga ugaagagggu   1500
```

```
uacaggaaac ugauugauca gaaaaaagau aagagauugg cauuccuucu uucacaaacu   1560
gaugaauaua uugccaaucu uacugaaaug gugaagcagc auaaaaugga acaacagcgu   1620
aagcaggaac aagaagagca acaaaaacgg aagaggaaaa agaaaaagaa gaauagggaa   1680
ggagauccag augaugaaag cucucagaug ucagauuuac auguuagcgu uauagaagca   1740
gcaacugguc ggcagcugac gggggaggau gcuccauugg ccagccagcu ugggagcugg   1800
uuggaggcac acccgggcug ggagccuuug gaagauagcg aagaugaaga ugaugaagag   1860
gacagcgacg aggaagguga ugauaacagu agaucaaaag gugguuuuuc aaugauagga   1920
aaagaugaag cugauagcaa guuaucuguu gaagacgaag cucgagaaau gauaaagaaa   1980
gcgaagauug aagaugauga auacaagaac acgaccgaag aacauacaua cuacagcauc   2040
gcucacaccg ugcaugaaau ugucaccgaa caagcuucaa ucaugauuaa cgguaaauug   2100
aaagaauauc aaauuaaagg ucuugaaugg uugguuucuu uauacaacaa caacuugaau   2160
ggaauccucg ccgacgagau gggccuuggc aagacaauuc aaacaauagg ucucauuacu   2220
uauuugaugg agaagaagaa aguaaauggu ccuuaccuca uuauuguucc ucugucaaca   2280
uuauccaauu ggguuuugga auucgagaaa ugggcuccuu caguguuugu gguagcuuau   2340
aaagguucuc cugcaaugag gagaacuuua caaucacaga ugcgcucgac gaaguucaau   2400
guccugcuca cgaccuacga guaugucauc aaggacaagg caguacuugc aaaguugcau   2460
uggaaguaca ugauaaucga cgagggacac aggaugaaaa accaccauug uaagcugacg   2520
caggugcuga acacccauua uuuggcaccu caccgccucc uucucacggg cacaccucuc   2580
cagaacaaac uaccugagcu cugggcucuu cuaaacuuuc uccucccguc caucuucaag   2640
ucguguucua cguuugagca augguucaau gcaccauuug cuaccacugg agaaaagguu   2700
gaguugaaug aggaagaaac aauuuugauu aucaggcguu uacauaaggu ccuucgaccu   2760
uuccuccuuc gucgacugaa aaaggaaguc gaaagucagu ugccagagaa aauugaauac   2820
aucgucaagu gugauauguc uggucuccaa cguguacuuu auaggcacau gcagaguaaa   2880
ggaguccugc uuaccgaugg uucugagaag ggcaagcagg guaaaggagg agcuaaagcg   2940
cuaaugaaca cgaucgucca auugaggaag cuuugcaauc auccuuucau guuccaucau   3000
auugaagaaa aauauuguga ucacguuggc cagaacaacg uugucacagg gccugaucug   3060
uuccgaguuu cugguaaauu ugaauuccuc gaucguauau ugccaaaacu gaaggccacg   3120
agccauaggg uacuucuuuu cugucaaaug acucagcuga ugaccaucau ggaggauuau   3180
uugucuugga gaggguucuc cuaccuucgu cuugauggua cgaccaaauc ugaagaccga   3240
ggagaucuuc ugaaaaaauu caacaaucca gaaagugaau auuuuauuuu cuugcucuca   3300
accagagcug gaggucucgg auugaacuua caggcugcag auacugucau uauauuugau   3360
ucagauugga acccucauca ggauuuacaa gcucaagaca gagcucauag gauuggacag   3420
caaaacgaag uucguguuuu gcggcuaaug acaguaaauu cuguugagga gcguauucuu   3480
gcagcugcuc gguacaagcu gaauauggau gagaaaguca uucaggcugg uauguuugac   3540
cagaaaucua caggaaccga gaggcagaaa uuucugcaaa acauccuuca ucaagaugau   3600
gcagaugaug aggaaaauga aguuccagau gaugaaaugg uuaaucguau gauugcgcga   3660
acagaagaug aauucaaccu cuuccagaaa aucgauuuag aaaggaggag ggaagaggcu   3720
aaacuuggac cuaacaggaa gucaaggcuu guagaagagg cggaauuacc ugacuggcuu   3780
guaaagaaug acgaugagau ugagaagugg acuuaugaag aaaccgaggu ccaaauggga   3840
agagguaaua ggcagaggaa ggaaguagau uauacagaua guuugacuga aaaagaaugg   3900
```

```
uuaaaggcca uugaugacaa uguagaugau uuugaugacg augaagagga agagguaaaa   3960

acaaagaaaa gaggcaagag aagaagaagg ggagaggaug augaagaaga ugcaaguacu   4020

ucaaagagaa ggaaauauuc uccaucugaa aacaaacuga ggaggcguau gcguaaccuc   4080

augaacauug uuguuaagua uacugacagu gacucgagag uacucaguga accauucaug   4140

aaacuucccu cucgccauaa guacccagac uacuaugagu ugaucaagaa accuauagac   4200

aucaagagga uauuggccaa aguagaagag uguaaauaug cugacaugga ugaauuagaa   4260

aaggauuuua ugcaacuuug uaaaaaugcu cagacauaca augaggaggc cucauugauc   4320

uaugaagauu cgauaguauu agaaagugu uucucuaaug cucgucaaaa aguagagcag    4380

gauaaugauu cagaugauga ugaaaguaaa ggugaccaag aagaugcugc aucagacacu   4440

ucauccguca aaaugaaauu gaaacuaaag ccugggagga cccgagggag uggagcuggu   4500

gguaaaagga ggagaagaaa auauaucucu gaagaugaag acgaagacca uagcgaaguu   4560

uccuuaaug                                                           4569
```

<210> SEQ ID NO 69
<211> LENGTH: 6222
<212> TYPE: RNA
<213> ORGANISM: Euchistus heros

<400> SEQUENCE: 69

```
auggcgucug aagaagaagu ugacgagugu uuaccaguug acgaugaagu ugacacuagu     60

guuguucaac aagaaggcac ugaagaaaau ucaccugaca gugaugaaag aaguaggaua    120

gaggaagaag augacgagua ugacccugag gaugcgagga aaaaaaagaa agguaaaaag    180

agaaaagcca aaggggaaag caaaaaagaa aagaaacgua aaaaaaggaa gaagaaugau    240

agugcugaag aaagugaggg aggcggggaa gaagaaggcg auuccgauua uggaagaaaa    300

ucuaagaagu cuaaaggaac uucacaacca aaaccagugc agcaagauuc uucuggaggu    360

guaccuucag uagaagaagu uugcagccuu uuuggacuua cagauguaca gauugacuau    420

accgaagaug auuaccaaaa ucugacuacg uauaaacuuu uucaacaaca uguucguccu    480

auucuugcca aggacaacca gaagguuccc aucggaaaaa ugaugaugcu cguggcugca    540

aaauggagag auuuuugcaa uuccaaucca aacgcucaac aggaaccaga uccagaagcu    600

ucagaagaac aggaauauuc uaaaccuacc aggacacgac cuucacgagu uucaacuaca    660

caaaaugaug augaagaaga cgacgaugcu gacgaacgag ggaggaaaaa gagaagugga    720

cgaaguaaaa agucaucagg aaagaagucc gcuccuccgg ccacaaccaa ggucccuacc    780

cucaagauca agauaggaaa aagaaaacag aauuccgaug aagaagauga agguucaguu    840

ggugccguuu cugaaaggga cucagaugcu gaauucgagc aaaugcucgc agaagcugaa    900

gaaguuaaua aaccugaagg uguuguagaa gaagaagaag gugcagaggu ggcuccugua    960

ccuaagaaaa aggccaaaac gaaaauuggu aauaaaaaga aaaggaaaaa gacacggacu   1020

acuaacaagu uuccagacag ugaagcuggu uaugaaacag aucaucagga cuauugugaa   1080

guuugucaac aaggaggug aauaaauauua ugugauacgu gcccucgagc uuaucauuug   1140

gucuguuugg aucccgaauu ggaagauacg ccagaaggca aauggucaug cccucauugu   1200

gaaggugaag guguacagga aaaagaagau gauguccauc aagaauuuug cagaguuugu   1260

aaagauggug gagaacuuuu augcugugau ucuugcccuu cugcauacca cacauucugu   1320

uugaacccuc cauugacaga uauuccagau ggugacugga agugcccacg uuguucggcg   1380
```

-continued

```
aagccuuuga gagguaaagu gucaaagauu cuuacuugga ggugguugga aucucccagu   1440
aguaaagaug aagaagacaa uacuaaaaaa cgaaacaggc agaggcaaag agaauauuuc   1500
gucaaguggg cagauauguc uuauuggcac uguaguuggg ugucugaacu ucagauggau   1560
guuuuucaua cucaaaugau caggaguuau auucguaaau augauaugga cgaaccuccc   1620
aaacuagaag aacccuugga ugaagcagac aauagaauga agaggauacg agaggcaaau   1680
aucaaugagc aagaauuaga agagaaauau uacaaguaug guaucaaacc agaguggcuu   1740
auugugcaga ggguaauuaa ccaucgcacu auaagggaug gaagcaaucu guaccucguc   1800
aaauggaggg accucccuua ugaccaggcg acuugggagg aagaagucac cgauaucccu   1860
ggcuugaaga aagcuauuga auauuacaau gagaugaggg cuugcuguuu aggugaaucu   1920
aaaaaacuaa aaaaagguaa agguaaaaga ucaaagagag aucaagauga ugaggaagga   1980
agcagaagug caggaaugau gggcgucggu ggaccagcua cuggucaaua cuucccgccu   2040
ccugaaaagc cugucacaga uuugaaaaag aaauacgaua aacagccgga cuaucucgac   2100
gucuccggua ugugccuuca uccuuaccaa uuagaagguu uaaauugguu gagguauucc   2160
ugggggcaag gaacagacac uauucuugcc gaugagaugg gucuuggaaa aaccauucag   2220
acaauuacuu ucccucuauuc ucuuuacaaa gagggucauu guaaaggccc cuuccuugug   2280
aguguacccu uaucuacaau uaucaauugg gaaagagagu ucgaaacuug ggcgccagac   2340
uucuacguug ucacauaugu cggagacaaa gauucucgug cuguaauacg ugaaaaugaa   2400
uuuucauucg augauaaugc uguuagagga ggaagaggug uuucuaaagu ucgcucuucu   2460
gcaauaaagu uucauguacu gcuaacaucu uaugaacuua ucucuaucga ugucacuugc   2520
cuuggaucga ucgagugggc agugcuugua guagaugaag cacacaggcu gaaaaguaau   2580
cagagcaagu ucuuuaggcu ucuugcuuca uaccacauug cuuauaaacu ucugcugaca   2640
ggaacuccgu ugcaaaacaa ucuagaagaa uuguuucauu uacuuaauuu ccuuacgccg   2700
gaaaaauuca acgaccuugc gacauuucaa aacgaauucg cugauauuuc aaaagaagaa   2760
caagucaaaa gacuucauga guuacucggg ccgcauaugu ugaggagauu aaaagcugau   2820
guacucaaga auaugccuac aaaaucugag uucauuguua gaguugaacu cuccccgaug   2880
cagaagaagu acuacaaaua uauucucaca aggaauuucg aagcuuuaaa uccaaaagga   2940
ggcggucaac aaguaucucu uuugaacauu augauggauc uuaaaaaaug cuguaaucau   3000
ccauaccugu uuccugcugc uucucaggaa gcuccuuuag gaccaagcgg aucuuacgau   3060
cuucaagggu uaaucaaagc aucuggaaaa uugauacuuc ugucgaaaau gcugagacgg   3120
cucaaagaag agggucacag aguacugauu uucucucaaa ugacaaaaau guuggacuua   3180
uuagaagacu accucgaggg ugaagguuau aaauaugaac guauugacgg uacgaucacc   3240
gguagcuuaa gacaagaagc uaucgaucgg uuuaacgccc cuggagcuca acaauuuguu   3300
uuucuuuugu ccacucgugc gggagguc uu gguauuaauc ucgcuacugc agauacaguu   3360
auuauuuaug acucugacug gaauccucau aacgauauuc aggccuuuuc gagagcacac   3420
aggauagggc aagcaaacaa gguuaugauu uaucgauuug ugacacgagc gucuguugaa   3480
gaaagaguaa cgcaaguggc uaagagaaaa augauguuaa cccaucuugu cguacgacca   3540
gguaugggug gcaagcaagc aaauuucacu aagcaagaac uugaugauau uuuaagguuu   3600
ggaacagaag aacuuuucaa agaagagcag gguaaagaag augaagccau ucauuaugac   3660
gauaaagcug uugaagaauu acuugaccgg ucgaagaugg guauugaaca gaaagaaaac   3720
uggucuaaug aauaucuuuc uucuuucaaa guggcaaguu auguuacuaa agaagaagac   3780
```

```
gaagaugagg aaauaggaac agagguaaua aaacaggaag cagaaaauac agacccagcu   3840
uauuggguca aacuguugag gcaccauuau gagcaacaac aagaggauau uucucgaacu   3900
cucgguaaag gaaaaaggau ucgaaaacag gugaauuaca ucgacggugg agugauggac   3960
ucaagagaga acgccgauuc gacguggcaa gacaaccucu cugacuauaa uucagacuuc   4020
ucugcuccuu cugaugauga caaggaagac gaugacuuug augagaaaaa ugaugaugga   4080
acgagaaaga agcguaggcc agaaaggagg gaggacaaag auaggccucu accuccucuu   4140
cuugcccgag ucgguggaaa cauugagguc cugggauuca acgccagaca gcguaaagca   4200
uucuugaaug cuauuaugag guauggaaug ccaccucaag augcauucaa cucgcagugg   4260
cuuguucgag accugagggg uaaaucugag aagcauuuca aggcauacgu aucccucuuu   4320
augaggcauu ugugugagcc uggcgcggac aaugccgaaa cauucgcgga ugguguucca   4380
agggaagguc uuagucggca gcauguucuc acaaggauag gugugauguc acucauuagg   4440
aaaaagguuc aagaauuuga gcaaauuaau ggauauuacu cgaugccuga aauguugaag   4500
aaaccacuug uugaugccgg auugcauaaa acaagugcua gcaguauagg ugaaggugcu   4560
aguaguuccg guacaccugc aacaucagcu gcuccaaguc cagcuccuac ucuuuuggau   4620
aagacacaaa uugaagauuu gagugaaaaa gaagauccgu caaagacuga agauaaaacc   4680
accgaugauu ccaaacccuc agaagaggcu aaagcugcag augaugcaaa uaagccucag   4740
gcugaaggag aaaaggcaga aggaucuucu aaugcaaacc aaacuucuga agcugaagga   4800
agcgaugaga aaaaacccaa agaagaaccg auggauguag auggugaagg agaggcuaaa   4860
gauagugaua agacagaaaa acaagaaggu acugacgaaa aagauguagc ccuaaaaagag   4920
gaagaaaagg augaagaggu caacaaagag aagggagagg aaacagagga aaagaagguu   4980
aucgauuuug aagaagacaa aucuaaaagg aaauuuaugu ucaauaucgc ugauggagga   5040
uuuacugagc uccauaccuu auggcaaaau gaagagaaag cugcaguacc ugguagggag   5100
uacgagaucu ggcauaggag gcaugacuau uggcuguugg guggaaucgu uacccauggc   5160
uauggucggu ggcaagauau ucaaaaugau auuagauuug cuauuaucaa cgaaccauuu   5220
aagauggaug uuggaaaagg aaauuucuua gaaauuaaaa auaaauuucu ugccaggagg   5280
uuuaagcuuc uugagcaagc ucuggugauu gaagaacagu uaagacgugc agcuuauuua   5340
aaucugacgc aagauccaaa ucacccagca augucacuga augcaagauu ugcagagguu   5400
gaaugucuag ccgaaucuca ccaacaccuc ucgaaggaaa gucuugcugg caacaaaccu   5460
gcaaaugcag uguuacauaa aguauugaac caauuagagg agcuucuguc ggauaugaaa   5520
ucugacguau cucgacuacc agccacucua gccagaauuc caccuguagc ccagaggcua   5580
cagaugucug aacggucaau acuuucuagg uuggcugcaa cuacuucucc ugcgacgccc   5640
accacguccc aucaaacugg uaugauaagc agucaguucc cugcuggauu ucaaucaggg   5700
caguugacug gaacguuucc gaaugccagu uuuaccaacu ucaggcccca guauucaguu   5760
ccugggcaaa cugcagccca ggguuuuccc gguaauugau aauugaaagc uggacgguaa   5820
uugucugcga gugaauucuc caugaguaaa uaauagguuu uuuuuuuuu uuaagaaaga   5880
aauaaaagaa gcguuuuguu uaguuuuguu gauaguucuc uuuauuucuu ucaauuuugu   5940
uuuagcggaa aaaaaaugu ucauuauaag uaacuuauaa auuggacaug cuaauuaaau   6000
uuccuauuag auuauuuugu uauuuguaag uuuuucggua uuguaagaau gucuauaugu   6060
guaagagguu guacaagauu gccuaaauac cuuguauuau uuauuuuuac uauugaauaa   6120
```

aaaaaaaaaa uaauuaacuu cgaucuuagg uuaaggguaa uaaaaaaaaa uguuacugga 6180
aaaaaaaaua gaaaaaauaa aaaagauagc cuuuccccuu ac 6222

<210> SEQ ID NO 70
<211> LENGTH: 3072
<212> TYPE: RNA
<213> ORGANISM: Euchistus heros

<400> SEQUENCE: 70
augucgaagc caaaugaagu uaguuuggau acaacagaua cuguugaaau uucuaaugaa 60
ucuucgggag acacagaguc guccaagggu aaaaaugaag auuuugaaac aaaaauugaa 120
acugaccguu cuagaagauu ugaguuucug uugaagcaga cagaaauuuu uucacauuuu 180
augacaaauc aaggaaaguc gaacagcccu gcaaagccua aagucggccg uccuagaaag 240
gaaacuaaua aauuggcacc agccggugu gaugguucug ccgaccaucg gcaucguaug 300
accgagcagg aagaagauga agaacugcuu gcugaaagua auacuucuuc aaaauccuua 360
gcaagguuug acgcuucucc uuuuuauauu aaaagcggag aguugaggga uuaccagaua 420
cgugguuuga auuggaugau aucccucuac gaacacggua uaaaugguau acuugcugau 480 gagaugggguu uagguaaaac ucuccaaacu auuucucucc uugguuacau gaagcauuau 540
agaaauauac cagggccaca uauggucauc guaccaaaau caacauuagc uaauuggaug 600
aaugaauuua aaaaguggug cccaacccug cgugcugucu guuuaaucgg agaucaggaa 660
acgaggaaug cguucaucag agacacucuu augccgggug aaugggaugu cugcguuaca 720
ucuuaugaaa ugaucauacg agaaaagagc guuuucaaga aguucaacug gagguauaug 780
gucauugacg aagcccacag gaucaagaau gaaaaaucca aacucuccga gauugugaga 840
gaguucaaaa cgacgaaucg auuacuccug accgguacuc cuuuacaaaa uaaccuccac 900
gaauuguggu cucuucuuaa cuuccucuua ccagauguuu ucaauucauc agaugauuuu 960
gauucauggu uuaauaccaa uaccuucccuu ggcgauaauu cucuugucga gagauuacau 1020
gcuguacuga gaccuuuccu ccuaagaaga uugaaaucug agguagagaa aaaacucaaa 1080
ccgaagaaag aagucaaaau cuacguugga uugaguaaaa ugcagagaga augguauacu 1140
aaaguucuaa ugaaagauau agacauugua aacggugcug gccgagucga aaaaaugcgc 1200
cuccaaaaca uccucaugca guugaggaag ugcaguaauc acccuuaucu cuucgacgga 1260
gcugaaccag guccaccuua cucaacugau gagcaucugg uauauaacag uggaaaaaug 1320
guaauauuag acaagcuucu uccuaaauug caagaacaag gaucacgagu ucugguuuuc 1380
agccaaauga caaggaugau ugauauucuc gaagauuacu guuauuggag aggauauaau 1440
uacugucguc uugaugguaa uacaccucau gaggauaggc agagacagau uaaugaguuc 1500
aacgaagaag acaguaagaa auucauuuuc auguugucga cucgugcggg ugguuugggu 1560
aucaauuuag ccaccgcaga uguagucauu uuguacgauu cggauuggaa cccucaaaug 1620
gaucuccagg cuauggaucg ugcucaucgu auuggucaaa agaaacaagu caaaguguuc 1680
aggaugauaa cugaaaacac aguugaagag aaaauuguug agagagcuga aauaaaacuc 1740
cgccucgaua aguuggucau ccaacaaggc aggcugguag acaauaaaac ggcacucaac 1800
aaagaugaaa uguugaauau gauccgucac ggugccaauc auguauuugc caguaaagau 1860
ucugaaauca ccgaugaaga cauugacacu auuuuggaaa aaggcgaagc aaggacggaa 1920
gaaaugaaua aaaaacuuga acaacucggu gauucuaauu ugaaagacuu caugauggaa 1980
accccgacug agucaguuua ccaauucgaa ggagaggauu acagggaaaa gcagaaaguu 2040

```
uuaggaauag gaaguuggau agaaccucca aaaagagaac guaaagcuaa uuacgcuguc   2100
gaugccuauu uuagggaagc auugagagua ucagaaccua aagcucccaa ggcaccgagg   2160
ccuccuaaac agccuauagu ucaagauuuc caauucuuuc cuccucgucu cuuugagcua   2220
uuggaccagg agaucuauua cuucaggaaa acugugggcu acaaaguucc uaaaaauccu   2280
gaauuagguu cugaugcauc acguguccaa aaggaagaac aaagaaagau agaugaggca   2340
gaaccuuuau cagaagaaga acucgcugaa aaggaaaaac uucuuacgca ggguuuuacc   2400
aauuggacua aaagagauuu caaccaguuu auuaaagcua augaaaaaua uggucgugau   2460
gauauugaca auauuucaaa agaaguagaa ggaaaaacuc cagaagaagu aagagcuuau   2520
ucagaagugu ucugggaacg auguaacgaa uugcaggaca uagaucguau cauggggcag   2580
aucgacaggg gagaggcuaa aauucaaagg agagcaagua uuaagaaagc ucucgauaca   2640
aagaugagcc gguacagagc cccauuucau caacuucgca ucuccuacgg uacgaauaag   2700
gguaagaacu auaccgagga agaagauaga uuccuugucu guauguugca uaagcuuggu   2760
uuugacaagg aaaaugugua cgaagaacuu agagcgaugg ucaggugugc gccucaguuc   2820
agauucgacu gguucaucaa aucgagaaca gccauggaau ugcagaggcg uuguaaauacu  2880
cuaauuacuc ucaucgaaag agaaaaucag gaacuugagg agagggaaag agccgagaag   2940
aggaaaggaa gaggaagugg gcgugguccu gguuccggua aaaggaaagg agacgguucc   3000
auuucaucuc cccccuccugu cccuggccaa ggggauaaga acagccccgc cagaaaaaag  3060
aaaaaaaugu ag                                                       3072
```

<210> SEQ ID NO 71
<211> LENGTH: 1164
<212> TYPE: RNA
<213> ORGANISM: Euchistus heros

<400> SEQUENCE: 71

```
augaauaaaa aacuugaaca acuugguguu gauucaucau uaaaagauuu caugauggag     60
gcucccacug agucugucua ucaguuugaa ggcgaagauu auagagaaaa gcaaaaaguu    120
uuuggaauug gaaauuggau ugaaccacca aaacgagaac guaaagcaaa uuaugcagua    180
gaugccuauu uuagagaagc acugagaguu ucagaaccua aagcuccaaa ggccccuagg    240
ccaccaaagc aacccauagu ucaagauuuc caauuuuucc caccucgucu guuugagcug    300
uuagaucaag aaauauacua uuuucgaaaa acuguuugcu acaagguucc uaaaaauccg    360
gaguuaggau cagaugcuuc ucguauacaa agggaagagc aaagaaaaau ugaugaagcu    420
gagccguuga cugaggaaga gcuagcugag aaagaaaacu uauugaccca ggguuuuacu    480
aauuggacua aaagagauuu uaaccaguuc auaaaagcua augaaaaaua uggacgugau    540
gauauugaua auaucucaaa agauguugaa gggaagacuc cagaagaagu acgagcauac    600
ucugaaguau uuugggaaag gugcaaugaa cuacaggcca uagaucguau cauggggcag    660
auugauagag gugaagcgaa aauucaaaga agagccagua uuaaaaaagc uuuagauaca    720
aagaugaguc gauauagagc accguuucau caacuacgaa uugcuuaugg uacgaacaag    780
gggaaaaauu acacagaaga agaagacaga uuccuugugu gcaugcuaca uaagcuuggc    840
uuugauaaag aaaaugugua ugaggaacuu agggcgaugg ugaggugugc uccucaguuu    900
agguuugauu gguucaucaa gucucgaaca gcuuuggaau ugcaaagacg uuguaauacu    960
cuaaucacgu uaauugaaag ggaaaaccaa gaauuagaag aaagggaaaa aguagaaaaa   1020
```

```
aggaaaaguc gaggcaguaa ugggcguggu cccaguucug guaaacguaa gggagaugga   1080

ucuauuucau cuccaccugu cucuguacag agugauaaaa gcagcccugc ucggaaaaag   1140

aaaaaguaua ucucuguuga guaa                                           1164
```

<210> SEQ ID NO 72
<211> LENGTH: 1665
<212> TYPE: RNA
<213> ORGANISM: Euchistus heros

<400> SEQUENCE: 72

```
augggucuug guaaaacuau ucagacuauc ugcaguuugu auuauuuauu ucauacucac     60

caguuguaug gaccauuuuu aauuguuguc ccuuuaucua cgaugacuuc auggcagagg    120

gaguuuucau uaugggcucc agaaaugaau guuguaacuu auauuggugu uauaaacucc    180

cgugauguua uacguaauua ugaauggugc uauucagguu cgaaaagguu aaaauucaau    240

gccauucuua cuacauauga aauuguucuu aaagacaaag cauuuuuggg uaguauaagc    300

ugggcuaucc uuaugguuga ugaagcacac agauugaaaa augaugauuc auuauuauac    360

aaaacauuga aagaguuuga uaccaaccau aggcuucuua uaacaggcac uccuuugcaa    420

aauagucuua aagagcuuug ggcguugcuu cacuuuauua ugcccaacag auuuaauaac    480

ugggaagaau uugaaaaaga acaugacaac ucugcuaaua aaggcuauac uaaguugcac    540

agacagcugg aaccauauau ucuacgacga guuaagaagg auguugagaa aucuuuacca    600

gcuaaagugg aacaaauauu acguguugaa augacaucug uacagaagca guauuacagg    660

uggauuuugu ccaaaaauua uucugcucuu cgaaaaggag ucaaagguuc uccuaguaca    720

uuuauaaaua uuguuauuga auuaaaaaaa ugcuguaauc augcacaucu aauaaaacca    780

uuagaaaaug aagcaaaaac ugaagacuac uuacagcaau uguuaaaagg cucagggaaa    840

uuacuucugu uggacaaguu gcuuguucgc cuuaaagaaa cugggcauag aguacuuaua    900

uuuucucaaa ugguacgaau guuggauaua cuggcugagu aucuucaaau gagacauuuc    960

ccuuuccaac guuuagacgg uucaauuaaa ggugaauuga gaaagcaagc ccucgaucau   1020

uucaaugcug aaaauucacc agauuucugu uucuuauuau caacucgugc ugguggguuug   1080

ggcauuaauu uagcaacagc ugauacuguc auuauauuug acucugauug gaauccacaa   1140

aaugauuugc aagcacaagc uagagcucau agaaucgguc agaaaaauca ggugaacaua   1200

uacagacuug uuacuaaaag uucuguugag gaaaauauug ucgagcgggc caaacaaaaa   1260

auggucuuag aucauuuagu uauacaaaga auggauacua cagguagaac uguccuggau   1320

aaaaaaaauu cuucauccag ugcgccuuuu aacaaagaag aacuuacugc uauuuuaaaa   1380

uuuggggcug aagaauuauu uaaagaugaa gaagauggug augaagaacc aacuugugac   1440

auugacgaaa uuuugagaag agcugaaacc agagaugaag gaccagccac uguuggugau   1500

gaauuacuuu cugcuuuuaa aguugcaagu uuugcuuuug augaagauaa agaaacucag   1560

agugaaccag aacagcagga ugacgauacu agagauuggg uuuguuauga uaauacaauc   1620

uuauguaucu cguauuuuau gauugaacca auuuauaauc aauaa                    1665
```

<210> SEQ ID NO 73
<211> LENGTH: 1134
<212> TYPE: DNA
<213> ORGANISM: Euchistus heros

<400> SEQUENCE: 73

```
tacaaaatgt gtgacgaaga agttgctgct ttagttgtag acaatggatc tggtatgtgc     60
```

```
aaagccggtt tcgctggaga tgatgcaccc cgagctgtat tcccatcaat tgttggcagg    120

cctagacacc agggtgtcat ggttggaatg ggacaaaagg acagttatgt tggagacgaa    180

gcccaaagca agagaggtat cctcaccctg aaatacccca ttgaacacgg tatcatcacc    240

aactgggacg acatggaaaa gatctggcat cacaccttct acaacgagct gcgagtcgct    300

ccagaggaac accccatcct cctgactgag gctcccctca accccaaagc caacagggag    360

aagatgaccc agatcatgtt tgagaccttc aacaccccag ccatgtatgt cgccatccag    420

gctgtactct ccctctatgc ctccggtcgt actaccggta ttgtacttga ctcaggagat    480

ggtgtctccc acaccgtacc catctatgaa ggttatgccc ttccccacgc catcctccgt    540

ctggatcttg ctggacgtga cttgactgac tatcttatga agatcctcac cgagcgtggt    600

tacagcttca ccaccaccgc tgaaagggaa atcgtcaggg acatcaagga aaaactgtgc    660

tatgtcgccc tggactttga gcaggaaatg gccaccgccg ctgcctccac ctccctggag    720

aagtcctatg aacttcccga cggtcaggtc atcaccatcg gtaacgagag gttccgttgc    780

ccagaggctc tcttccagcc ttccttcttg ggtatggaat cttgcggtat ccatgagact    840

gtctacaact ccatcatgaa gtgcgacgtt gacatcagga aggacttgta cgccaacacc    900

gtcctctccg gaggtaccac catgtaccca ggtattgctg acaggatgca gaaggaaatc    960

accgccctcg ctccttcaac catcaagatc aagatcattg ctcccccaga aaggaagtac   1020

tccgtatgga tcggtggttc catcttggct tccctgtcca ccttccagca gatgtggatc   1080

tccaagcagg aatacgacga atccggccca ggcatcgtcc accgcaaatg cttc         1134
```

```
<210> SEQ ID NO 74
<211> LENGTH: 22
<212> TYPE: DNA
<213> ORGANISM: Artificial Sequence
<220> FEATURE:
<223> OTHER INFORMATION: Primer Actin42A-F

<400> SEQUENCE: 74

tcaaggaaaa actgtgctat gt                                               22


<210> SEQ ID NO 75
<211> LENGTH: 20
<212> TYPE: DNA
<213> ORGANISM: Artificial Sequence
<220> FEATURE:
<223> OTHER INFORMATION: Primer Actin42A-R

<400> SEQUENCE: 75

taccgatggt gatgacctga                                                  20


<210> SEQ ID NO 76
<211> LENGTH: 12
<212> TYPE: DNA
<213> ORGANISM: Artificial Sequence
<220> FEATURE:
<223> OTHER INFORMATION: Probe Actin42A-FAM

<400> SEQUENCE: 76

accgccgctg cc                                                          12


<210> SEQ ID NO 77
<211> LENGTH: 19
<212> TYPE: DNA
<213> ORGANISM: Artificial Sequence
<220> FEATURE:
```

<223> OTHER INFORMATION: Probe brm-F

<400> SEQUENCE: 77
tcatcaagga caaggcagt 19

<210> SEQ ID NO 78
<211> LENGTH: 21
<212> TYPE: DNA
<213> ORGANISM: Artificial Sequence
<220> FEATURE:
<223> OTHER INFORMATION: Primer brm-R

<400> SEQUENCE: 78
gacgggagga gaaagtttag a 21

<210> SEQ ID NO 79
<211> LENGTH: 19
<212> TYPE: DNA
<213> ORGANISM: Artificial Sequence
<220> FEATURE:
<223> OTHER INFORMATION: Probe brm-FAM

<400> SEQUENCE: 79
cgacgaggga cacaggatg 19

<210> SEQ ID NO 80
<211> LENGTH: 17
<212> TYPE: DNA
<213> ORGANISM: Artificial Sequence
<220> FEATURE:
<223> OTHER INFORMATION: Primer mi-2-F

<400> SEQUENCE: 80
gatgagggct tgctgtt 17

<210> SEQ ID NO 81
<211> LENGTH: 18
<212> TYPE: DNA
<213> ORGANISM: Artificial Sequence
<220> FEATURE:
<223> OTHER INFORMATION: Primer mi-2-R

<400> SEQUENCE: 81
gaggcgggaa gtattgac 18

<210> SEQ ID NO 82
<211> LENGTH: 22
<212> TYPE: DNA
<213> ORGANISM: Artificial Sequence
<220> FEATURE:
<223> OTHER INFORMATION: Probe mi-2-FAM

<400> SEQUENCE: 82
atgaggaagg aagcagaagt gc 22

<210> SEQ ID NO 83
<211> LENGTH: 23
<212> TYPE: DNA
<213> ORGANISM: Artificial Sequence
<220> FEATURE:
<223> OTHER INFORMATION: Primer iswi-1-F

<400> SEQUENCE: 83
gagttcaacg aagaagacag taa 23

<210> SEQ ID NO 84
<211> LENGTH: 19
<212> TYPE: DNA
<213> ORGANISM: Artificial Sequence
<220> FEATURE:
<223> OTHER INFORMATION: Primer iswi-R

<400> SEQUENCE: 84
cgatgagcac gatccatag 19

<210> SEQ ID NO 85
<211> LENGTH: 22
<212> TYPE: DNA
<213> ORGANISM: Artificial Sequence
<220> FEATURE:
<223> OTHER INFORMATION: Probe iswi-1-FAM

<400> SEQUENCE: 85
ttagccaccg cagatgtagt ca 22

<210> SEQ ID NO 86
<211> LENGTH: 25
<212> TYPE: DNA
<213> ORGANISM: Artificial Sequence
<220> FEATURE:
<223> OTHER INFORMATION: Primer iswi-2-F_MGB

<400> SEQUENCE: 86
acgtaaggga gatggatcta tttca 25

<210> SEQ ID NO 87
<211> LENGTH: 23
<212> TYPE: DNA
<213> ORGANISM: Artificial Sequence
<220> FEATURE:
<223> OTHER INFORMATION: Primer iswi-2-R_MGB

<400> SEQUENCE: 87
cagggctgct tttatcactc tgt 23

<210> SEQ ID NO 88
<211> LENGTH: 15
<212> TYPE: DNA
<213> ORGANISM: Artificial Sequence
<220> FEATURE:
<223> OTHER INFORMATION: Probe iswi-2-FAM_MGB

<400> SEQUENCE: 88
ctccacctgt ctctg 15

<210> SEQ ID NO 89
<211> LENGTH: 20
<212> TYPE: DNA
<213> ORGANISM: Artificial Sequence
<220> FEATURE:
<223> OTHER INFORMATION: Primer chd1-F

<400> SEQUENCE: 89
caacagtggc tggtccttca 20

<210> SEQ ID NO 90
<211> LENGTH: 23
<212> TYPE: DNA
<213> ORGANISM: Artificial Sequence
<220> FEATURE:
<223> OTHER INFORMATION: Primer chd1-R -continued

```
<400> SEQUENCE: 90

accaacttgt gacattgacg aaa                                              23


<210> SEQ ID NO 91
<211> LENGTH: 16
<212> TYPE: DNA
<213> ORGANISM: Artificial Sequence
<220> FEATURE:
<223> OTHER INFORMATION: Probe chd1-FAM

<400> SEQUENCE: 91

tctggtttca gctctt                                                      16
```

PARENTAL RNAI SUPPRESSION OF CHROMATIN REMODELING GENES TO CONTROL COLEOPTERAN PESTS

PRIORITY CLAIM

This application claims the benefit of the filing date of U.S. Provisional Patent Application Ser. No. 62/092,747, filed Dec. 16, 2014, the contents of which are incorporated herein in its entirety by this reference.

FIELD OF THE DISCLOSURE

The present invention relates generally to genetic control of plant damage caused by hemipteran pests. In particular embodiments, the present disclosure relates to identification of target coding and non-coding polynucleotides, and the use of recombinant DNA technologies for post-transcriptionally repressing or inhibiting expression of target coding and non-coding polynucleotides in the cells of a hemipteran pest to provide a plant protective effect.

BACKGROUND

Stink bugs and other hemipteran insects (heteroptera) are an important agricultural pest complex. Worldwide, over 50 closely related species of stink bugs are known to cause crop damage. McPherson & McPherson (2000) *Stink bugs of economic importance in America north of Mexico*, CRC Press. Hemipteran insects are present in a large number of important crops including maize, soybean, fruit, vegetables, and cereals.

Stink bugs go through multiple nymph stages before reaching the adult stage. These insects develop from eggs to adults in about 30-40 days. Both nymphs and adults feed on sap from soft tissues into which they also inject digestive enzymes causing extra-oral tissue digestion and necrosis. Digested plant material and nutrients are then ingested. Depletion of water and nutrients from the plant vascular system results in plant tissue damage. Damage to developing grain and seeds is the most significant as yield and germination are significantly reduced. Multiple generations occur in warm climates resulting in significant insect pressure. Current management of stink bugs relies on insecticide treatment on an individual field basis. Therefore, alternative management strategies are urgently needed to minimize ongoing crop losses.

RNA interference (RNAi) is a process utilizing endogenous cellular pathways, whereby an interfering RNA (iRNA) molecule (e.g., a double stranded RNA (dsRNA) molecule) that is specific for all, or any portion of adequate size, of a target gene results in the degradation of the mRNA encoded thereby. In recent years, RNAi has been used to perform gene "knockdown" in a number of species and experimental systems; for example, *Caenorhabditis elegans*, plants, insect embryos, and cells in tissue culture. See, e.g., Fire et al. (1998) Nature 391:806-11; Martinez et al. (2002) Cell 110:563-74; McManus and Sharp (2002) Nature Rev. Genetics 3:737-47.

RNAi accomplishes degradation of mRNA through an endogenous pathway including the DICER protein complex. DICER cleaves long dsRNA molecules into short fragments of approximately 20 nucleotides, termed small interfering RNA (siRNA). The siRNA is unwound into two single-stranded RNAs: the passenger strand and the guide strand. The passenger strand is degraded, and the guide strand is incorporated into the RNA-induced silencing complex (RISC). Micro inhibitory ribonucleic acids (miRNAs) are structurally very similar molecules that are cleaved from precursor molecules containing a polynucleotide "loop" connecting the hybridized passenger and guide strands, and they may be similarly incorporated into RISC. Post-transcriptional gene silencing occurs when the guide strand binds specifically to a complementary mRNA molecule and induces cleavage by Argonaute, the catalytic component of the RISC complex. This process is known to spread systemically throughout some eukaryotic organisms despite initially limited concentrations of siRNA and/or miRNA such as plants, nematodes, and some insects.

Only transcripts complementary to the siRNA and/or miRNA are cleaved and degraded, and thus the knock-down of mRNA expression is sequence-specific. In plants, several functional groups of DICER genes exist. The gene silencing effect of RNAi persists for days and, under experimental conditions, can lead to a decline in abundance of the targeted transcript of 90% or more, with consequent reduction in levels of the corresponding protein. In insects, there are at least two DICER genes, where DICER1 facilitates miRNA-directed degradation by Argonaute1. Lee et al. (2004) Cell 117 (1):69-81. DICER2 facilitates siRNA-directed degradation by Argonaute2.

The overwhelming majority of sequences complementary to insect DNAs (such as, for example, the 9,000+ sequences identified in U.S. Pat. No. 7,612,194 and U.S. Patent Publication Nos. 2007/0050860, 2010/0192265, and 2011/0154545) do not provide a plant protective effect when used as dsRNA or siRNA. For example, Baum et al. (2007) Nature Biotechnology 25:1322-1326, describe the effects of inhibiting several Western corn rootworm (WCR) gene targets by RNAi. These authors reported that 8 of the 26 target genes they tested were not able to provide experimentally significant coleopteran pest mortality at a very high iRNA (e.g., dsRNA) concentration of more than 520 ng/cm$^2$.

The authors of U.S. Pat. No. 7,612,194 and U.S. Patent Publication No. 2007/0050860 made the first report of in planta RNAi in corn plants targeting the western corn rootworm. Baum et al. (2007) Nat. Biotechnol. 25(11):1322-6. These authors describe a high-throughput in vivo dietary RNAi system to screen potential target genes for developing transgenic RNAi maize. Of an initial gene pool of 290 targets, only 14 exhibited larval control potential. One of the most effective double-stranded RNAs (dsRNA) targeted a gene encoding vacuolar ATPase subunit A (V-ATPase), resulting in a rapid suppression of corresponding endogenous mRNA and triggering a specific RNAi response with low concentrations of dsRNA. Thus, these authors documented for the first time the potential for in planta RNAi as a possible pest management tool, while simultaneously demonstrating that effective targets could not be accurately identified a priori, even from a relatively small set of candidate genes.

Another potential application of RNAi for insect control involves parental RNAi (pRNAi). First described in *Caenorhabditis elegans*, pRNAi was identified by injection of dsRNA into the body cavity (or application of dsRNA via ingestion), causing gene inactivity in offspring embryos. Fire et al. (1998), supra; Timmons and Fire (1998) Nature 395(6705):854. A similar process was described in the model coleopteran, *Tribolium castaneum*, whereby female pupae injected with dsRNA corresponding to three unique genes that control segmentation during embryonic development resulted in knock down of zygotic genes in offspring embryos. Bucher et al. (2002) Curr. Biol. 12(3):R85-6. Nearly all of the offspring larvae in this study displayed gene-specific phenotypes one week after injection. Although injection of dsRNA for functional genomics studies has been successful in a variety of insects, uptake of dsRNA from the gut environment through oral exposure to dsRNA and subsequent down-regulation of essential genes is required in order for RNAi to be effective as a pest management tool. Auer and Frederick (2009) Trends Biotechnol. 27(11):644-51.

Parental RNAi has been used to describe the function of embryonic genes in a number of insect species, including the springtail, *Orchesella cincta* (Konopova and Akam (2014) Evodevo 5(1):2); the brown plant hopper, *Nilaparvata lugens*; the sawfly, *Athalia rosae* (Yoshiyama et al. (2013) J. Insect Physiol. 59(4):400-7); the German cockroach, *Blattella germanica* (Piulachs et al. (2010) Insect Biochem. Mol. Biol. 40:468-75); and the pea aphid, *Acyrthosiphon pisum* (Mao et al. (2013) Arch Insect Biochem Physiol 84(4):209-21). The pRNAi response in all these instances was achieved by injection of dsRNA into the hemocoel of the parental female.

SUMMARY OF THE DISCLOSURE

Disclosed herein are nucleic acid molecules (e.g., target genes, DNAs, dsRNAs, siRNAs, shRNAs, miRNAs, and hpRNAs), and methods of use thereof, for the control of hemipteran pests, including, for example, *Euschistus heros* (Fabr.) (Neotropical Brown Stink Bug, "BSB"); *E. servus* (Say) (Brown Stink Bug); *Nezara viridula* (L.) (Southern Green Stink Bug); *Piezodorus guildinii* (Westwood) (Red-banded Stink Bug); *Halyomorpha halys* (Stål) (Brown Marmorated Stink Bug); *Chinavia hilare* (Say) (Green Stink Bug); *C. marginatum* (Palisot de Beauvois); *Dichelops melacanthus* (Dallas); *D. furcatus* (F.); *Edessa meditabunda* (F.); *Thyanta perditor* (F.) (Neotropical Red Shouldered Stink Bug); *Horcias nobilellus* (Berg) (Cotton Bug); *Taedia stigmosa* (Berg); *Dysdercus peruvianus* (Guérin-Méneville); *Neomegalotomus parvus* (Westwood); *Leptoglossus zonatus* (Dallas); *Niesthrea sidae* (F.); *Lygus hesperus* (Knight) (Western Tarnished Plant Bug); and *L. lineolaris* (Palisot de Beauvois). In particular examples, exemplary nucleic acid molecules are disclosed that may be homologous to at least a portion of one or more nucleic acids in a hemipteran pest. In some embodiments, hemipteran pests are controlled by reducing the capacity of an existing generation of the pest to produce a subsequent generation of the pest. In certain examples, delivery of the nucleic acid molecules to hemipteran pests does not result in significant mortality to the pests, but reduces the number of viable progeny produced therefrom.

In these and further examples, the nucleic acid may be a target gene, the product of which may be, for example and without limitation: involved in a metabolic process; involved in a reproductive process; and/or involved in embryonic and/or nymph development. In some examples, post-transcriptional inhibition of the expression of a target gene by a nucleic acid molecule comprising a polynucleotide homologous thereto may result in reduced growth and/or reproduction of the hemipteran pest. In specific examples, a chromatin remodeling gene is selected as a target gene for post-transcriptional silencing. In particular examples, a target gene useful for post-transcriptional inhibition is the novel chromatin remodeling gene referred to herein as BSB_brahma (SEQ ID NO:1 and SEQ ID NO:63). In particular examples, a target gene useful for post-transcriptional inhibition is the novel chromatin remodeling gene referred to herein as BSB_mi-2 (SEQ ID NO:8 and SEQ ID NO:64). In particular examples, a target gene useful for post-transcriptional inhibition is the novel chromatin remodeling gene referred to herein as BSB_iswi-1 (SEQ ID NO:10 and SEQ ID NO:65). In particular examples, a target gene useful for post-transcriptional inhibition is the novel chromatin remodeling gene referred to herein as BSB_chd1 (SEQ ID NO:14 and SEQ ID NO:67). In particular examples, a target gene useful for post-transcriptional inhibition is the novel chromatin remodeling gene referred to herein as BSB_iswi-2 (SEQ ID NO:12 and SEQ ID NO:66). In particular examples, a target gene useful for post-transcriptional inhibition is the novel chromatin remodeling gene referred to herein as BSB_ino80 (SEQ ID NO:30). In particular examples, a target gene useful for post-transcriptional inhibition is the novel chromatin remodeling gene referred to herein as BSB_domino (SEQ ID NO:32).

An isolated nucleic acid molecule comprising the polynucleotide of SEQ ID NO:1; the complement of SEQ ID NO:1; SEQ ID NO:8; the complement of SEQ ID NO:8; SEQ ID NO:10; the complement of SEQ ID NO:10; SEQ ID NO:12; the complement of SEQ ID NO:12; SEQ ID NO:14; the complement of SEQ ID NO:14; SEQ ID NO:30; the complement of SEQ ID NO:30; SEQ ID NO:32; the complement of SEQ ID NO:32; SEQ ID NO:63; the complement of SEQ ID NO:63; SEQ ID NO:64; the complement of SEQ ID NO:64; SEQ ID NO:65; the complement of SEQ ID NO:65; SEQ ID NO:66; the complement of SEQ ID NO:66; SEQ ID NO:67; the complement of SEQ ID NO:67; and/or fragments of any of the foregoing (e.g., SEQ ID NO:3, SEQ ID NO:16, SEQ ID NO:17, SEQ ID NO:18, and SEQ ID NO:19) is therefore disclosed herein.

Also disclosed are nucleic acid molecules comprising a polynucleotide that encodes a polypeptide that is at least about 85% identical to an amino acid sequence within a target chromatin remodeling gene product (for example, the product of a brahma, mi-2, iswi-1, chd1, iswi-2, ino80, or domino gene). For example, a nucleic acid molecule may comprise a polynucleotide encoding a polypeptide that is at least 85% identical to a polypeptide selected from the group consisting of SEQ ID NO:2 (BSB BRAHMA); an amino acid sequence within a product of BSB brahma; SEQ ID NO:9 (BSB MI-2); an amino acid sequence within a product of BSB mi-2; SEQ ID NO:11 (BSB ISWI-1); an amino acid sequence within a product of BSB iswi-1; SEQ ID NO:15 (BSB CHD1); an amino acid sequence within a product of BSB chd1; SEQ ID NO:13 (BSB ISWI-2); an amino acid sequence within a product of BSB iswi-2; SEQ ID NO:31 (BSB INO80); an amino acid sequence within a product of BSB ino80; SEQ ID NO:33 (BSB DOMINO); and an amino acid sequence within a product of BSB domino. Further disclosed are nucleic acid molecules comprising a polynucleotide that is the reverse complement of a polynucleotide that encodes a polypeptide at least 85% identical to an amino acid sequence within a target chromatin remodeling gene product.

Also disclosed are cDNA polynucleotides that may be used for the production of iRNA (e.g., dsRNA, siRNA, shRNA, miRNA, and hpRNA) molecules that are complementary to all or part of a hemipteran pest target gene, for example, a chromatin remodeling gene. In particular embodiments, dsRNAs, siRNAs, shRNAs, miRNAs, and/or hpRNAs may be produced in vitro or in vivo by a genetically-modified organism, such as a plant or bacterium. In particular examples, cDNA molecules are disclosed that may be used to produce iRNA molecules that are complementary to all or part of mRNA transcribed from BSB_brahma (SEQ ID NO:1 and SEQ ID NO:63), BSB_mi-2

(SEQ ID NO:8 and SEQ ID NO:64), BSB_iswi-1 (SEQ ID NO:10 and SEQ ID NO:65), BSB_chd1 (SEQ ID NO:14 and SEQ ID NO:67), BSB_iswi-2 (SEQ ID NO:12 and SEQ ID NO:66), BSB_ino80 (SEQ ID NO:30), and BSB_domino (SEQ ID NO:32).

Further disclosed are means for inhibiting expression of an essential gene in a hemipteran pest, and means for protecting a plant from a hemipteran pest. A means for inhibiting expression of an essential gene in a hemipteran pest is a single- or double-stranded RNA molecule consisting of a polynucleotide selected from the group consisting of SEQ ID NO:44; SEQ ID NO:49; SEQ ID NO:50; SEQ ID NO:51; SEQ ID NO:52; and the complements thereof. Functional equivalents of means for inhibiting expression of an essential gene in a hemipteran pest include single- or double-stranded RNA molecules that are substantially homologous to all or part of mRNA transcribed from a BSB gene encoding a ATP-dependent remodeling enzyme, such as mRNAs comprising SEQ ID NO:43; SEQ ID NO:45; SEQ ID NO:46; SEQ ID NO:47; SEQ ID NO:48; SEQ ID NO:53; or SEQ ID NO:54. A means for protecting a plant from a hemipteran pest is a DNA molecule comprising a polynucleotide encoding a means for inhibiting expression of an essential gene in a hemipteran pest operably linked to a promoter, wherein the DNA molecule is capable of being integrated into the genome of a soybean plant.

Disclosed are methods for controlling a population of a hemipteran pest, comprising providing to a hemipteran pest an iRNA (e.g., dsRNA, siRNA, shRNA, miRNA, and hpRNA) molecule that functions upon being taken up by the pest to inhibit a biological function within the pest, wherein the iRNA molecule comprises all or part of (e.g., at least 15 contiguous nucleotides of) a polynucleotide selected from the group consisting of: SEQ ID NO:43; the complement of SEQ ID NO:43; SEQ ID NO:44; the complement of SEQ ID NO:44; SEQ ID NO:45; the complement of SEQ ID NO:45; SEQ ID NO:46; the complement of SEQ ID NO:46; SEQ ID NO:47; the complement of SEQ ID NO:47; SEQ ID NO:48; the complement of SEQ ID NO:48; SEQ ID NO:49; the complement of SEQ ID NO:49; SEQ ID NO:50; the complement of SEQ ID NO:50; SEQ ID NO:51; the complement of SEQ ID NO:51; SEQ ID NO:52; the complement of SEQ ID NO:52; SEQ ID NO:53; the complement of SEQ ID NO:53; SEQ ID NO:54; the complement of SEQ ID NO:54; SEQ ID NO:55; the complement of SEQ ID NO:55; SEQ ID NO:56; the complement of SEQ ID NO:56; SEQ ID NO:57; the complement of SEQ ID NO:57; SEQ ID NO:58; the complement of SEQ ID NO:58; SEQ ID NO:59; the complement of SEQ ID NO:59; SEQ ID NO:60; the complement of SEQ ID NO:60; SEQ ID NO:61; the complement of SEQ ID NO:61; SEQ ID NO:62; the complement of SEQ ID NO:62; SEQ ID NO:68; the complement of SEQ ID NO:68; SEQ ID NO:69; the complement of SEQ ID NO:69; SEQ ID NO:70; the complement of SEQ ID NO:70; SEQ ID NO:71; the complement of SEQ ID NO:71; SEQ ID NO:72; the complement of SEQ ID NO:72; a polynucleotide that hybridizes to a coding polynucleotide of a hemipteran organism (e.g., BSB) comprising all or part of any of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67; and the complement of a polynucleotide that hybridizes to a coding polynucleotide of a hemipteran organism comprising all or part of any of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67.

Also disclosed herein are methods wherein dsRNAs, siRNAs, shRNAs, miRNAs, and/or hpRNAs may be provided to a hemipteran pest in a diet-based assay, or in genetically-modified plant cells expressing the dsRNAs, siRNAs, shRNAs, miRNAs, and/or hpRNAs. In these and further examples, the dsRNAs, siRNAs, shRNAs, miRNAs, and/or hpRNAs may be ingested by a hemipteran pest. Ingestion of dsRNAs, siRNA, shRNAs, miRNAs, and/or hpRNAs of the invention may then result in RNAi in the pest, which in turn may result in silencing of a gene essential for a metabolic process; a reproductive process; and/or nymph development. Thus, methods are disclosed wherein nucleic acid molecules comprising exemplary polynucleotide(s) useful for parental control of hemipteran pests are provided to a hemipteran pest. In particular examples, the hemipteran pest controlled by use of nucleic acid molecules of the invention may be BSB. In some examples, delivery of the nucleic acid molecules to hemipteran pests does not result in significant mortality to the pests, but reduces the number of viable progeny produced therefrom. In some examples, delivery of the nucleic acid molecules to hemipteran pests results in significant mortality to the pests, and also reduces the number of viable progeny produced therefrom.

The foregoing and other features will become more apparent from the following Detailed Description of several embodiments, which proceeds with reference to the accompanying Figures.

BRIEF DESCRIPTION OF THE FIGURES

FIG. 4A shows the effects on female survival: twenty females were injected with each dsRNA and survival rate was monitored for 23 days. FIG. 4B shows the effects on oviposition: eggs collected from dsRNA-injected females starting at 9 days post-injection. The oviposition rates plotted are per day per female, based on each week of collection. FIG. 4C shows the effects on egg hatching: eggs hatched based on the numbers of eggs laid in FIG. 4B. Means comparisons were performed with YFP as control using Dunnett's test, † $p<0.001$, ** $p<0.05$.

FIG. 6A shows the effects on oviposition: eggs collected from dsRNA-injected females starting at 1 day post-injection. The number of eggs plotted are per day per female, binned into three-day intervals. FIG. 6B shows the effects on egg hatching: eggs hatched based on the numbers in FIG. 6A. Means comparisons were performed with Dunnett's test using non-injected insects as controls, * indicates significance at $p<0.05$. ** indicates significance at $p<0.001$ FIGS. 7A-7H includes data showing the effects on ovaries of *E. heros* females injected with brm or mi-2 dsRNA. FIGS. 7(A-B) show ovaries of non-injected *E. heros* females at zero and four days after adult molt, provided for developmental comparison. FIGS. 7(C-D) show ovaries of females injected with YFP dsRNA, and FIGS. 7(E-F) show brahma dsRNA ovaries at 9 and 14 days post injection. FIG. 7(E) shows lack of ovariole elongation and lack oocyte development, and FIG. 7(F) shows decaying oocytes. FIGS. 7(G-H) show mi-2 dsRNA at 9 and 14 days post injection. FIG. 7(H) shows lack of ovariole elongation, and FIG. 7(G) shows somewhat elongated ovaries with no mature oocytes.

FIG. 8 illustrates the effect on the rate of increase in allele frequencies for resistance to an insecticidal protein (R) and RNAi (Y) when non-refuge plants express the insecticidal protein and parental active iRNA.

FIG. 9 illustrates the effect on the rate of increase in allele frequencies for resistance to an insecticidal protein (R) and RNAi (Y) when non-refuge plants express the insecticidal protein and both larval active and parental active iRNA molecules.

SEQUENCE LISTING

Figure 1A:
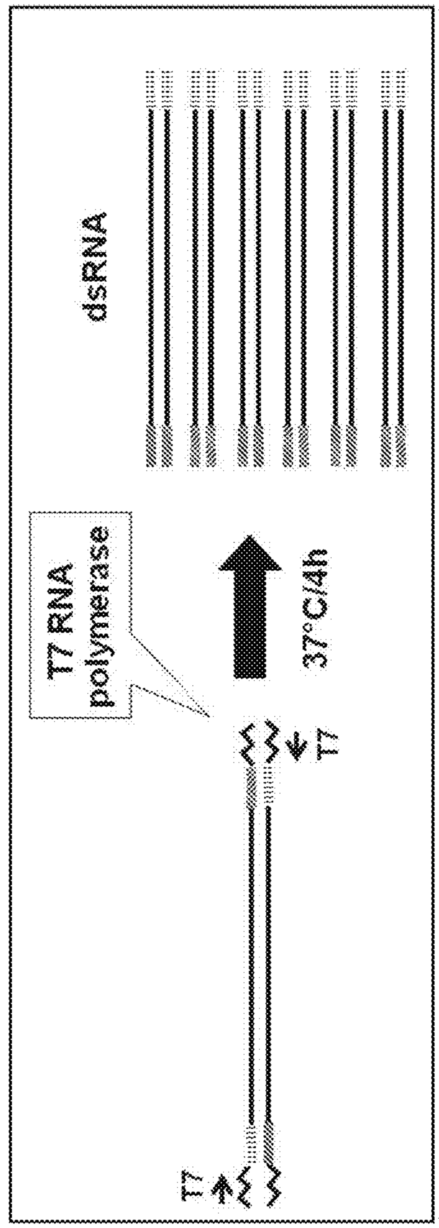
FIG. 1A includes a depiction of the strategy used to generate dsRNA from a single transcription template with a single pair of primers, and from two transcription templates (FIG. 1B).

The nucleic acid sequences listed in the accompanying sequence listing are shown using standard letter abbreviations for nucleotide bases, as defined in 37 C.F.R. § 1.822. The nucleic acid and amino acid sequences listed define molecules (i.e., polynucleotides and polypeptides, respectively) having the nucleotide and amino acid monomers arranged in the manner described. The nucleic acid and amino acid sequences listed also each define a genus of polynucleotides or polypeptides that comprise the nucleotide and amino acid monomers arranged in the manner described. In view of the redundancy of the genetic code, it will be understood that a nucleotide sequence including a coding sequence also describes the genus of polynucleotides encoding the same polypeptide as a polynucleotide consisting of the reference sequence. It will further be understood that an amino acid sequence describes the genus of polynucleotide ORFs encoding that polypeptide.

Only one strand of each nucleic acid sequence is shown, but the complementary strand is understood as included by any reference to the displayed strand. As the complement and reverse complement of a primary nucleic acid sequence are necessarily disclosed by the primary sequence, the complementary sequence and reverse complementary sequence of a nucleic acid sequence are included by any reference to the nucleic acid sequence, unless it is explicitly stated to be otherwise (or it is clear to be otherwise from the context in which the sequence appears). Furthermore, as it is understood in the art that the nucleotide sequence of an RNA strand is determined by the sequence of the DNA from which it was transcribed (but for the substitution of uracil (U) nucleobases for thymine (T)), an RNA sequence is included by any reference to the DNA sequence encoding it. In the accompanying sequence listing:

SEQ ID NO:1 shows an exemplary *Euschistus heros* chromatin remodeling gene DNA, referred to herein in some places as brahma.

SEQ ID NO:2 shows the amino acid sequence of a *E. heros* BRAHMA polypeptide encoded by an exemplary *E. heros* chromatin remodeling gene DNA.

SEQ ID NO:3 shows an exemplary *E. heros* chromatin remodeling gene DNA, referred to herein in some places as BSB_brm-1, which is used in some examples for the production of a dsRNA.

SEQ ID NO:4 shows the nucleotide sequence of a T7 phage promoter.

SEQ ID NO:5 shows a segment of an exemplary YFPv2 gene, which is used in some examples for the production of a dsRNA.

SEQ ID NOs:6 and 7 show primers used for PCR amplification of a YFPv2 sequence, used in some examples for dsRNA production.

SEQ ID NO:8 shows a further exemplary *E. heros* chromatin remodeling gene DNA, referred to herein in some places as BSB_mi-2.

SEQ ID NO:9 shows the amino acid sequence of a *E. heros* MI-2 polypeptide encoded by an exemplary *E. heros* chromatin remodeling gene DNA.

SEQ ID NO:10 shows a further exemplary *E. heros* chromatin remodeling gene DNA, referred to herein in some places as BSB_iswi-1.

SEQ ID NO:11 shows the amino acid sequence of a *E. heros* ISWI-1 polypeptide encoded by an exemplary *E. heros* chromatin remodeling gene DNA.

SEQ ID NO:12 shows a further exemplary *E. heros* chromatin remodeling gene DNA, referred to herein in some places as BSB_iswi-2.

SEQ ID NO:13 shows the amino acid sequence of a *E. heros* ISWI-2 polypeptide encoded by an exemplary *E. heros* chromatin remodeling gene DNA.

SEQ ID NO:14 shows a further exemplary *E. heros* chromatin remodeling gene DNA, referred to herein in some places as BSB_chd1.

SEQ ID NO:15 shows the amino acid sequence of a *E. heros* CHD1 polypeptide encoded by an exemplary *E. heros* chromatin remodeling gene DNA.

SEQ ID NO:16 shows an exemplary *E. heros* chromatin remodeling gene DNA, referred to herein in some places as BSB_mi-2-1, which is used in some examples for the production of a dsRNA.

SEQ ID NO:17 shows an exemplary *E. heros* chromatin remodeling gene DNA, referred to herein in some places as BSB_iswi-1-1, which is used in some examples for the production of a dsRNA.

SEQ ID NO:18 shows a further exemplary *E. heros* chromatin remodeling gene DNA, referred to herein in some places as BSB_iswi-2-1, which is used in some examples for the production of a dsRNA.

SEQ ID NO:19 shows a further exemplary *E. heros* chromatin remodeling gene DNA, referred to herein in some places as BSB_chd1-1, which is used in some examples for the production of a dsRNA.

SEQ ID NOs:20-29 show primers used to amplify gene regions of chromatin remodeling genes.

SEQ ID NO:30 shows a further exemplary *E. heros* chromatin remodeling gene DNA, referred to herein in some places as BSB_ino80.

SEQ ID NO:31 shows the amino acid sequence of a *E. heros* INO80 polypeptide encoded by an exemplary *E. heros* chromatin remodeling gene DNA.

SEQ ID NO:32 shows a further exemplary *E. heros* chromatin remodeling gene DNA, referred to herein in some places as BSB_domino.

SEQ ID NO:33 shows the amino acid sequence of a *E. heros* DOMINO polypeptide encoded by an exemplary *E. heros* chromatin remodeling gene DNA.

SEQ ID NOs:34-37 show exemplary DNAs encoding dsRNA sequences for targeting SNF2-Helicase regions of insect (e.g., *Euschistus heros, Diabrotica, Tribolium*, and *Drosophila melanogaster*) chromatin remodeling gene DNA.

SEQ ID NOs:38-41 show exemplary DNAs encoding dsRNA sequences for targeting chromatin remodeling domains (Chromodomain, Bromodomain, or HAND-SLIDE regions) of insect (e.g., *Euschistus heros, Diabrotica, Tribolium*, and *Drosophila melanogaster*) chromatin remodeling gene DNA.

SEQ ID NO:42 shows an exemplary DNA encoding a YFP v2 hairpin-forming RNA; containing sense polynucleotides, a loop polynucleotide (underlined) including an intron, and antisense polynucleotide (bold font):

ATGTCATCTGGAGCACTTCTCTTTCATGGGAAGATTCCTTACGTTGTGGA

GATGGAAGGGAATGTTGATGGCCACACCTTTAGCATACGTGGGAAAGGCT

ACGGAGATGCCTCAGTGGGAAAGGACTAGTACCGGTTGGGAAAGGTATGT

TTCTGCTTCTACCTTTGATATATATATAATAATTATCACTAATTAGTAGT

AATATAGTATTTCAAGTATTTTTTTCAAAATAAAAGAATGTAGTATATAG

CTATTGCTTTTCTGTAGTTTATAAGTGTGTATATTTTAATTTATAACTTT

TCTAATATATGACCAAAACATGGTGATGTGCAGGTTGATCCGCGGTTACT

TTCCCACTGAGGCATCTCCGTAGCCTTTCCCACGTATGCTAAAGGTGTGG

CCATCAACATTCCCTTCCATCTCCACAACGTAAGGAATCTTCCCATGAAA

GAGAAGTGCTCCAGATGACAT

SEQ ID NOs:43-62 show exemplary RNAs transcribed from nucleic acids comprising exemplary chromatin remodeling gene polynucleotides and fragments thereof.

SEQ ID NO:63 shows the open reading frame of an exemplary *E. heros* brahma DNA.

SEQ ID NO:64 shows the open reading frame of an exemplary *E. heros* mi-2 DNA.

SEQ ID NO:65 shows the open reading frame of an exemplary *E. heros* iswi-1 DNA.

SEQ ID NO:66 shows the open reading frame of an exemplary *E. heros* iswi-2 DNA.

SEQ ID NO:67 shows the open reading frame of an exemplary *E. heros* chd1 DNA.

SEQ ID NOs:68-72 show further exemplary RNAs transcribed from nucleic acids comprising exemplary chromatin remodeling gene polynucleotides and fragments thereof.

SEQ ID NO:73 shows the open reading frame of an exemplary muscle actin gene.

SEQ ID NOs:74-91 show oligonucleotides and probes used for BSB probe hydrolysis qPCR assay.

DETAILED DESCRIPTION

I. Overview of Several Embodiments

We developed RNA interference (RNAi) as a tool for insect pest management, using a target pest species for transgenic plants that express dsRNA; the Neotropical brown stink bug. Thus far, most genes proposed as targets for RNAi in particular insects do not achieve their purpose, and those useful targets that have been identified involve typically those that cause lethality in the nymph stage. Herein, we describe RNAi-mediated knockdown of chromatin remodeling genes (e.g., brahma, mi-2, chd1, ino80, and domino) in the Neotropical brown stink bug, which is shown to disrupt embryonic development when, for example, iRNA are molecules are delivered via chromatin remodeling gene-targeting dsRNA fed to adult females. There was almost complete absence of hatching in the eggs collected from females exposed to chromatin remodeling gene-targeting dsRNA. In embodiments herein, the ability to deliver chromatin remodeling gene-targeting dsRNA by feeding to adult insects confers a pRNAi effect that is very useful for insect (e.g., hemipteran) pest management. Furthermore, the potential to affect multiple target sequences in both nymph and adult hemipteran pests may increase opportunities to develop sustainable approaches to insect pest management involving RNAi technologies.

Disclosed herein are methods and compositions for genetic control of hemipteran pest infestations. Methods for identifying one or more gene(s) essential to the lifecycle of a hemipteran pest (e.g., gene(s) essential for normal reproductive capacity and/or embryonic and/or nymph development) for use as a target gene for RNAi-mediated control of a hemipteran pest population are also provided. DNA plasmid vectors encoding an RNA molecule may be designed to suppress one or more target gene(s) essential for growth, survival, development, and/or reproduction. In some embodiments, the RNA molecule may be capable of forming dsRNA molecules. In some embodiments, methods are provided for post-transcriptional repression of expression or inhibition of a target gene via nucleic acid molecules that are complementary to a coding or non-coding sequence of the target gene in a hemipteran pest. In these and further embodiments, a hemipteran pest may ingest one or more dsRNA, siRNA, shRNA, miRNA, and/or hpRNA molecules transcribed from all or a portion of a nucleic acid molecule that is complementary to a coding or non-coding sequence of a target gene, thereby providing a plant-protective effect.

Some embodiments involve sequence-specific inhibition of expression of target gene products, using dsRNA, siRNA, shRNA, miRNA and/or hpRNA that is complementary to coding and/or non-coding sequences of the target gene(s) to achieve at least partial control of a hemipteran pest. Disclosed is a set of isolated and purified nucleic acid molecules comprising a polynucleotide, for example, as set forth in SEQ ID NO:1; SEQ ID NO:8; SEQ ID NO:10; SEQ ID NO:12; SEQ ID NO:14; SEQ ID NO:30; SEQ ID NO:32; SEQ ID NO:63; SEQ ID NO:64; SEQ ID NO:65; SEQ ID NO:66; SEQ ID NO:67; and fragments thereof. In some embodiments, a stabilized dsRNA molecule may be expressed from these polynucleotides, fragments thereof, or a gene comprising one of these polynucleotides, for the post-transcriptional silencing or inhibition of a target gene. In certain embodiments, isolated and purified nucleic acid molecules comprise all or part of any of SEQ ID NO:1; SEQ ID NO:3; SEQ ID NO:8; SEQ ID NO:10; SEQ ID NO:12; SEQ ID NO:14; SEQ ID NO:16; SEQ ID NO:17; SEQ ID NO:18; SEQ ID NO:19; SEQ ID NO:30; SEQ ID NO:32; SEQ ID NO:63; SEQ ID NO:64; SEQ ID NO:65; SEQ ID NO:66; and SEQ ID NO:67.

Some embodiments involve a recombinant host cell (e.g., a plant cell) having in its genome at least one recombinant DNA encoding at least one iRNA (e.g., dsRNA) molecule(s). In particular embodiments, the dsRNA molecule(s) may be produced when ingested by a hemipteran pest to post-transcriptionally silence or inhibit the expression of a target gene in the pest or progeny of the pest. The recombinant DNA may comprise, for example, any of SEQ ID NO:1; SEQ ID NO:8; SEQ ID NO:10; SEQ ID NO:12; SEQ ID NO:14; SEQ ID NO:30; SEQ ID NO:32; SEQ ID NO:63; SEQ ID NO:64; SEQ ID NO:65; SEQ ID NO:66; SEQ ID NO:67; fragments of any of SEQ ID NO:1; SEQ ID NO:8; SEQ ID NO:10; SEQ ID NO:12; SEQ ID NO:14; SEQ ID NO:30; SEQ ID NO:32; SEQ ID NO:63; SEQ ID NO:64; SEQ ID NO:65; SEQ ID NO:66; SEQ ID NO:67 (e.g., SEQ ID NO:3, SEQ ID NO:16, SEQ ID NO:17, SEQ ID NO:18, and SEQ ID NO:19); and a polynucleotide consisting of a partial sequence of a gene comprising one of SEQ ID NO:1; SEQ ID NO:8; SEQ ID NO:10; SEQ ID NO:12; SEQ ID NO:14; SEQ ID NO:30; SEQ ID NO:32; SEQ ID NO:63; SEQ ID NO:64; SEQ ID NO:65; SEQ ID NO:66; SEQ ID NO:67; fragments of any of SEQ ID NO:1; SEQ ID NO:8; SEQ ID NO:10; SEQ ID NO:12; SEQ ID NO:14; SEQ ID NO:30; SEQ ID NO:32; SEQ ID NO:63; SEQ ID NO:64; SEQ ID NO:65; SEQ ID NO:66; SEQ ID NO:67; and/or complements thereof.

Some embodiments involve a recombinant host cell having in its genome a recombinant DNA encoding at least one iRNA (e.g., dsRNA) molecule(s) comprising all or part of SEQ ID NO:43 (e.g., SEQ ID NO:44); all or part of SEQ ID NO:45 (e.g., SEQ ID NO:49); all or part of SEQ ID NO:46 (e.g., SEQ ID NO:50); all or part of SEQ ID NO:47 (e.g., SEQ ID NO:51); all or part of SEQ ID NO:48 (e.g., SEQ ID NO:52); all or part of SEQ ID NO:53; and all or part of SEQ ID NO:54. When ingested by a hemipteran pest, the iRNA molecule(s) may silence or inhibit the expression of a target chromatin remodeling gene (e.g., a DNA comprising all or part of a polynucleotide selected from the group consisting of SEQ ID NO:1; SEQ ID NO:8; SEQ ID NO:10; SEQ ID NO:12; SEQ ID NO:14; SEQ ID NO:30; SEQ ID NO:32; SEQ ID NO:63; SEQ ID NO:64; SEQ ID NO:65; SEQ ID NO:66; and SEQ ID NO:67) in the pest or progeny of the pest, and thereby result in cessation of reproduction in the pest, and/or growth, development, and/or feeding in progeny of the pest.

In some embodiments, a recombinant host cell having in its genome at least one recombinant DNA encoding at least one RNA molecule capable of forming a dsRNA molecule may be a transformed plant cell. Some embodiments involve transgenic plants comprising such a transformed plant cell. In addition to such transgenic plants, progeny plants of any transgenic plant generation, transgenic seeds, and transgenic plant products, are all provided, each of which comprises recombinant DNA(s). In particular embodiments, an RNA molecule capable of forming a dsRNA molecule may be expressed in a transgenic plant cell. Therefore, in these and other embodiments, a dsRNA molecule may be isolated from a transgenic plant cell. In particular embodiments, the transgenic plant is a plant selected from the group comprising corn (*Zea mays*), soybean (*Glycine max*), cotton (*Gossypium* sp.), and plants of the family Poaceae.

Some embodiments involve a method for modulating the expression of a target gene in a hemipteran pest cell. In these and other embodiments, a nucleic acid molecule may be provided, wherein the nucleic acid molecule comprises a polynucleotide encoding an RNA molecule capable of forming a dsRNA molecule. In particular embodiments, a polynucleotide encoding an RNA molecule capable of forming a dsRNA molecule may be operatively linked to a promoter, and may also be operatively linked to a transcription termination sequence. In particular embodiments, a method for modulating the expression of a target gene in a hemipteran pest cell may comprise: (a) transforming a plant cell with a vector comprising a polynucleotide encoding an RNA molecule capable of forming a dsRNA molecule; (b) culturing the transformed plant cell under conditions sufficient to allow for development of a plant cell culture comprising a plurality of transformed plant cells; (c) selecting for a transformed plant cell that has integrated the vector into its genome; and (d) determining that the selected transformed plant cell comprises the RNA molecule capable of forming a dsRNA molecule encoded by the polynucleotide of the vector. A plant may be regenerated from a plant cell that has the vector integrated in its genome and comprises the dsRNA molecule encoded by the polynucleotide of the vector.

Thus, also disclosed is a transgenic plant comprising a vector having a polynucleotide encoding an RNA molecule capable of forming a dsRNA molecule integrated in its genome, wherein the transgenic plant comprises the dsRNA molecule encoded by the polynucleotide of the vector. In particular embodiments, expression of an RNA molecule capable of forming a dsRNA molecule in the plant is sufficient to modulate the expression of a target gene in a cell of a hemipteran pest that contacts the transformed plant or plant cell (for example, by feeding on the transformed plant, a part of the plant (e.g., leaves) or plant cell) or in a cell of a progeny of the hemipteran pest that contacts the transformed plant or plant cell (for example, by parental transmission), such that reproduction of the pest is inhibited. Transgenic plants disclosed herein may display tolerance and/or protection from hemipteran pest infestations. Particular transgenic plants may display protection and/or enhanced protection from one or more pest(s) selected from the group consisting of: *Piezodorus guildinii; Halyomorpha halys; Nezara viridula; Acrosternum hilare; Euschistus heros; Euschistus servus, Chinavia hilare; C. marginatum; Dichelops melacanthus; D. furcatus; Edessa meditabunda; Thyanta perditor; Horcias nobilellus; Taedia stigmosa; Dysdercus peruvianus; Neomegalotomus parvus; Leptoglossus zonatus; Niesthrea sidae; Lygus hesperus*; and *L. lineolaris.*

Also disclosed herein are methods for delivery of control agents, such as an iRNA molecule, to a hemipteran pest. Such control agents may cause, directly or indirectly, an impairment in the ability of a hemipteran pest population to feed, grow or otherwise cause damage in a host. In some embodiments, a method is provided comprising delivery of a stabilized dsRNA molecule to a hemipteran pest to suppress at least one target gene in the pest or its progeny, thereby causing parental RNAi and reducing or eliminating plant damage in a pest host. In some embodiments, a method of inhibiting expression of a target gene in a hemipteran pest may result in cessation of reproduction in the pest, and/or growth, development, and/or feeding in progeny of the pest. In some embodiments, the method may significantly reduce the size of a subsequent pest generation in an infestation, without directly resulting in mortality in the pest(s) that contact the iRNA molecule. In some embodiments, the method may significantly reduce the size of a subsequent pest generation in an infestation, while also resulting in mortality in the pest(s) that contact the iRNA molecule.

In some embodiments, compositions (e.g., a topical composition) are provided that comprise an iRNA (e.g., dsRNA) molecule for use with plants, animals, and/or the environment of a plant or animal to achieve the elimination or reduction of a hemipteran pest infestation. In particular embodiments, the composition may be a nutritional composition or resource, or food source, to be fed to the hemipteran pest. Some embodiments comprise making the nutritional composition or food source available to the pest. Ingestion of a composition comprising iRNA molecules may result in the uptake of the molecules by one or more cells of the hemipteran pest, which may in turn result in the inhibition of expression of at least one target gene in cell(s) of the pest or its progeny. Ingestion of or damage to a plant or plant cell by a hemipteran pest infestation may be limited or eliminated in or on any host tissue or environment in which the pest is present by providing one or more compositions comprising an iRNA molecule in the host of the pest.

The compositions and methods disclosed herein may be used together in combinations with other methods and compositions for controlling damage by hemipteran pests. For example, an iRNA molecule as described herein for protecting plants from hemipteran pests may be used in a method comprising the additional use of one or more chemical agents effective against a hemipteran pest, biopesticides effective against a hemipteran pest, crop rotation, recombinant genetic techniques that exhibit features different from the features of RNAi-mediated methods and RNAi compositions (e.g., recombinant production of proteins in plants that are harmful to a hemipteran pest (e.g., Bt toxins)), and/or recombinant expression of non-parental iRNA molecules (e.g., lethal iRNA molecules that result in the cessation of growth, development, and/or feeding in the hemipteran pest that contacts the iRNA molecule).

II. Abbreviations

BSB Neotropical brown stink bug (*Euschistus heros*)
dsRNA double-stranded ribonucleic acid
GI growth inhibition
NCBI National Center for Biotechnology Information
gDNA genomic Deoxyribonucleic Acid
iRNA inhibitory ribonucleic acid
ISWI Imitation SWI/imitation switch
ORF open reading frame
RNAi ribonucleic acid interference
miRNA micro ribonucleic acid
siRNA small inhibitory ribonucleic acid
hpRNA hairpin ribonucleic acid
shRNA short hairpin ribonucleic acid
pRNAi parental RNA interference
UTR untranslated region
PCR Polymerase chain reaction
qPCR quantitative polymerase chain reaction
RISC RNA-induced Silencing Complex
RH relative humidity
SEM standard error of the mean
YFP yellow fluorescent protein

III. Terms

In the description and tables which follow, a number of terms are used. In order to provide a clear and consistent understanding of the specification and claims, including the scope to be given such terms, the following definitions are provided:

Contact (with an organism): As used herein, the term "contact with" or "uptake by" an organism (e.g., a hemipteran pest), with regard to a nucleic acid molecule, includes internalization of the nucleic acid molecule into the organism, for example and without limitation: ingestion of the molecule by the organism (e.g., by feeding); contacting the organism with a composition comprising the nucleic acid molecule; and soaking of organisms with a solution comprising the nucleic acid molecule.

Contig: As used herein the term "contig" refers to a DNA sequence that is reconstructed from a set of overlapping DNA segments derived from a single genetic source.

Corn plant: As used herein, the term "corn plant" refers to a plant of the species, *Zea mays* (maize). The terms "corn plant" and "maize" are used interchangeably herein.

Cotton plant: As used herein, the term "cotton plant" refers to a plant of the species *Gossypium* sp.; for example, *G. hirsutum.*

Expression: As used herein, "expression" of a coding polynucleotide (for example, a gene or a transgene) refers to the process by which the coded information of a nucleic acid transcriptional unit (including, e.g., gDNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, northern blot, RT-PCR, western blot, or in vitro, in situ, or in vivo protein activity assay(s).

Genetic material: As used herein, the term "genetic material" includes all genes, and nucleic acid molecules, such as DNA and RNA.

Hemipteran pest: As used herein, the term "hemipteran pest" refers to pest insects of the order Hemiptera, including, for example and without limitation, insects in the families Pentatomidae, Miridae, Pyrrhocoridae, Coreidae, Alydidae, and Rhopalidae, which feed on a wide range of host plants and have piercing and sucking mouth parts. In particular examples, a hemipteran pest is selected from the list comprising *Euschistus heros* (Fabr.) (Neotropical Brown Stink Bug), *Nezara viridula* (L.) (Southern Green Stink Bug), *Piezodorus guildinii* (Westwood) (Red-banded Stink Bug), *Halyomorpha halys* (Stål) (Brown Marmorated Stink Bug), *Chinavia hilare* (Say) (Green Stink Bug), *Euschistus servus* (Say) (Brown Stink Bug), *Dichelops melacanthus* (Dallas), *Dichelops furcatus* (F.), *Edessa meditabunda* (F.), *Thyanta perditor* (F.) (Neotropical Red Shouldered Stink Bug), *Chinavia marginatum* (Palisot de Beauvois), *Horcias nobilellus* (Berg) (Cotton Bug), *Taedia stigmosa* (Berg), *Dysdercus peruvianus* (Guérin-Méneville), *Neomegalotomus parvus* (Westwood), *Leptoglossus zonatus* (Dallas), *Niesthrea sidae* (F.), *Lygus hesperus* (Knight) (Western Tarnished Plant Bug), and *Lygus lineolaris* (Palisot de Beauvois).

Inhibition: As used herein, the term "inhibition," when used to describe an effect on a coding polynucleotide (for example, a gene), refers to a measurable decrease in the cellular level of mRNA transcribed from the coding polynucleotide and/or peptide, polypeptide, or protein product of the coding polynucleotide. In some examples, expression of a coding polynucleotide may be inhibited such that expression is approximately eliminated. "Specific inhibition" refers to the inhibition of a target coding polynucleotide without consequently affecting expression of other coding polynucleotides (e.g., genes) in the cell wherein the specific inhibition is being accomplished.

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, gDNA, and synthetic forms and mixed polymers of the above. A nucleotide or nucleobase may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. By convention, the nucleotide sequence of a nucleic acid molecule is read from the 5' to the 3' end of the molecule. The "complement" of a nucleic acid molecule refers to a polynucleotide having nucleobases that may form base pairs with the nucleobases of the nucleic acid molecule (i.e., A-T/U, and G-C).

Some embodiments include nucleic acids comprising a template DNA that is transcribed into an RNA molecule that is the complement of an mRNA molecule. In these embodiments, the complement of the nucleic acid transcribed into the mRNA molecule is present in the 5' to 3' orientation, such that RNA polymerase (which transcribes DNA in the 5' to 3' direction) will transcribe a nucleic acid from the complement that can hybridize to the mRNA molecule. Unless explicitly stated otherwise, or it is clear to be otherwise from the context, the term "complement" therefore refers to a polynucleotide having nucleobases, from 5' to 3', that may form base pairs with the nucleobases of a reference nucleic acid. Similarly, unless it is explicitly stated to be otherwise (or it is clear to be otherwise from the context), the "reverse complement" of a nucleic acid refers to the complement in reverse orientation. The foregoing is demonstrated in the following illustration:

ATGATGATG polynucleotide

TACTACTAC "complement" of the polynucleotide

CATCATCAT "reverse complement" of the polynucleotide

Some embodiments of the invention may include hairpin RNA-forming RNAi molecules. In these RNAi molecules, both the complement of a nucleic acid to be targeted by RNA interference and the reverse complement may be found in the same molecule, such that the single-stranded RNA molecule may "fold over" and hybridize to itself over region comprising the complementary and reverse complementary polynucleotides.

"Nucleic acid molecules" include all polynucleotides, for example: single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), shRNA (small hairpin RNA), mRNA (messenger RNA), miRNA (micro-RNA), hpRNA (hairpin RNA), tRNA (transfer RNAs, whether charged or discharged with a corresponding acylated amino acid), and cRNA (complementary RNA). The term "deoxyribonucleic acid" (DNA) is inclusive of cDNA, gDNA, and DNA-RNA hybrids. The terms "polynucleotide" and "nucleic acid," and "fragments" thereof will be understood by those in the art as a term that includes both gDNAs, ribosomal RNAs, transfer RNAs, messenger RNAs, operons, and smaller engineered polynucleotides that encode or may be adapted to encode, peptides, polypeptides, or proteins.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred bases in length. Because oligonucleotides may bind to a complementary nucleic acid, they may be used as probes for detecting DNA or RNA. Oligonucleotides composed of DNA (oligodeoxyribonucleotides) may be used in PCR, a technique for the amplification of DNAs. In PCR, the oligonucleotide is typically referred to as a "primer," which allows a DNA polymerase to extend the oligonucleotide and replicate the complementary strand.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding polynucleotide," "structural polynucleotide," or "structural nucleic acid molecule" refers to a polynucleotide that is ultimately translated into a polypeptide, via transcription and mRNA, when placed under the control of appropriate regulatory elements. With respect to RNA, the term "coding polynucleotide" refers to a polynucleotide that is translated into a peptide, polypeptide, or protein. The boundaries of a coding polynucleotide are determined by a translation start codon at the 5'-terminus and a translation stop codon at the 3'-terminus. Coding polynucleotides include, but are not limited to: gDNA; cDNA; EST; and recombinant polynucleotides.

As used herein, "transcribed non-coding polynucleotide" refers to segments of mRNA molecules such as 5'UTR, 3'UTR and intron segments that are not translated into a peptide, polypeptide, or protein. Further, "transcribed non-coding polynucleotide" refers to a nucleic acid that is transcribed into an RNA that functions in the cell, for example, structural RNAs (e.g., ribosomal RNA (rRNA) as exemplified by 5S rRNA, 5.8S rRNA, 16S rRNA, 18S rRNA, 23 S rRNA, and 28S rRNA, and the like); transfer RNA (tRNA); and snRNAs such as U4, U5, U6, and the like. Transcribed non-coding polynucleotides also include, for example and without limitation, small RNAs (sRNA), which term is often used to describe small bacterial non-coding RNAs; small nucleolar RNAs (snoRNA); microRNAs; small interfering RNAs (siRNA); Piwi-interacting RNAs (piRNA); and long non-coding RNAs. Further still, "transcribed non-coding polynucleotide" refers to a polynucleotide that may natively exist as an intragenic "linker" in a nucleic acid and which is transcribed into an RNA molecule.

Lethal RNA interference: As used herein, the term "lethal RNA interference" refers to RNA interference that results in death or a reduction in viability of the subject individual to which, for example, a dsRNA, miRNA, siRNA, shRNA, and/or hpRNA is delivered.

Parental RNA interference: As used herein, the term "parental RNA interference" (pRNAi) refers to a RNA interference phenotype that is observable in progeny of the subject (e.g., a hemipteran pest) to which, for example, a dsRNA, miRNA, siRNA, shRNA, and/or hpRNA is delivered. In some embodiments, pRNAi comprises the delivery of a dsRNA to a hemipteran pest, wherein the pest is thereby rendered less able to produce viable offspring. A nucleic acid that initiates pRNAi may or may not increase the incidence of mortality in a population into which the nucleic acid is delivered. In certain examples, the nucleic acid that initiates pRNAi does not increase the incidence of mortality in the population into which the nucleic acid is delivered. For example, a population of hemipteran pests may be fed one or more nucleic acids that initiate pRNAi, wherein the pests survive and mate but produce eggs that are less able to hatch viable progeny than eggs produced by pests of the same species that are not fed the nucleic acid(s). In one mechanism of pRNAi, parental RNAi delivered to a female is able to knockdown zygotic gene expression in offspring embryos of the female. Bucher et al. (2002) Curr. Biol. 12(3):R85-6.

Genome: As used herein, the term "genome" refers to chromosomal DNA found within the nucleus of a cell, and also refers to organelle DNA found within subcellular components of the cell. In some embodiments of the invention, a DNA molecule may be introduced into a plant cell, such that the DNA molecule is integrated into the genome of the plant cell. In these and further embodiments, the DNA molecule may be either integrated into the nuclear DNA of the plant cell, or integrated into the DNA of the chloroplast or mitochondrion of the plant cell. The term "genome," as it applies to bacteria, refers to both the chromosome and plasmids within the bacterial cell. In some embodiments of the invention, a DNA molecule may be introduced into a bacterium such that the DNA molecule is integrated into the genome of the bacterium. In these and further embodiments, the DNA molecule may be either chromosomally-integrated or located as or in a stable plasmid.

Sequence identity: The term "sequence identity" or "identity," as used herein in the context of two polynucleotides or polypeptides, refers to the residues in the sequences of the two molecules that are the same when aligned for maximum correspondence over a specified comparison window.

As used herein, the term "percentage of sequence identity" may refer to the value determined by comparing two optimally aligned sequences (e.g., nucleic acid sequences or polypeptide sequences) of a molecule over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acids with even greater sequence similarity to the sequences of the reference polynucleotides will show increasing percentage identity when assessed by this method.

Specifically hybridizable/Specifically complementary: As used herein, the terms "Specifically hybridizable" and "Specifically complementary" are terms that indicate a sufficient degree of complementarity such that stable and specific binding occurs between the nucleic acid molecule and a target nucleic acid molecule. Hybridization between two nucleic acid molecules involves the formation of an anti-parallel alignment between the nucleobases of the two nucleic acid molecules. The two molecules are then able to form hydrogen bonds with corresponding bases on the opposite strand to form a duplex molecule that, if it is sufficiently stable, is detectable using methods well known in the art. A polynucleotide need not be 100% complementary to its target nucleic acid to be specifically hybridizable. However, the amount of complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acids. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual,* $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, N.Y., 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 20% mismatch between the sequence of the hybridization molecule and a homologous polynucleotide within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize.

The following are representative, non-limiting hybridization conditions.

High Stringency condition (detects polynucleotides that share at least 90% sequence identity): Hybridization in 5×SSC buffer at 65° C. for 16 hours; wash twice in 2×SSC buffer at room temperature for 15 minutes each; and wash twice in 0.5×SSC buffer at 65° C. for 20 minutes each.

Moderate Stringency condition (detects polynucleotides that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (polynucleotides that share at least 50% sequence identity will hybridize): Hybridization in 6×SSC buffer at room temperature to 55° C. for 16-20 hours; wash at least twice in 2×-3×SSC buffer at room temperature to 55° C. for 20-30 minutes each.

As used herein, the term "substantially homologous" or "substantial homology," with regard to a nucleic acid, refers to a polynucleotide having contiguous nucleobases that hybridize under stringent conditions to the reference nucleic acid. For example, nucleic acids that are substantially homologous to a reference nucleic acid of any of SEQ ID NO:1, SEQ ID NO:3, SEQ ID NO:8, SEQ ID NO:10, SEQ ID NO:12, SEQ ID NO:14, SEQ ID NO:16, SEQ ID NO:17, SEQ ID NO:18, SEQ ID NO:19, SEQ ID NO:30, SEQ ID NO:32, SEQ ID NO:63; SEQ ID NO:64; SEQ ID NO:65; SEQ ID NO:66; and SEQ ID NO:67 are those nucleic acids that hybridize under stringent conditions (e.g., the Moderate Stringency conditions set forth, supra) to the reference nucleic acid of SEQ ID NO:1, SEQ ID NO:3, SEQ ID NO:8, SEQ ID NO:10, SEQ ID NO:12, SEQ ID NO:14, SEQ ID NO:16, SEQ ID NO:17, SEQ ID NO:18, SEQ ID NO:19, SEQ ID NO:30, SEQ ID NO:32, SEQ ID NO:63; SEQ ID NO:64; SEQ ID NO:65; SEQ ID NO:66; and SEQ ID NO:67. Substantially homologous polynucleotides may have at least 80% sequence identity. For example, substantially homologous polynucleotides may have from about 80% to 100% sequence identity, such as 79%; 80%; about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target polynucleotides under conditions where specific binding is desired, for example, under stringent hybridization conditions.

As used herein, the term "ortholog" refers to a gene in two or more species that has evolved from a common ancestral nucleic acid, and may retain the same function in the two or more species.

As used herein, two nucleic acid molecules are said to exhibit "complete complementarity" when every nucleotide of a polynucleotide read in the 5' to 3' direction is complementary to every nucleotide of the other polynucleotide when read in the 3' to 5' direction. A polynucleotide that is complementary to a reference polynucleotide will exhibit a sequence identical to the reverse complement of the reference polynucleotide. These terms and descriptions are well defined in the art and are easily understood by those of ordinary skill in the art.

Operably linked: A first polynucleotide is operably linked with a second polynucleotide when the first polynucleotide is in a functional relationship with the second polynucleotide. When recombinantly produced, operably linked polynucleotides are generally contiguous, and, where necessary to join two protein-coding regions, in the same reading frame (e.g., in a translationally fused ORF). However, nucleic acids need not be contiguous to be operably linked.

The term, "operably linked," when used in reference to a regulatory genetic element and a coding polynucleotide, means that the regulatory element affects the expression of the linked coding polynucleotide. "Regulatory elements," or "control elements," refer to polynucleotides that influence the timing and level/amount of transcription, RNA processing or stability, or translation of the associated coding polynucleotide. Regulatory elements may include promoters; translation leaders; introns; enhancers; stem-loop structures; repressor binding polynucleotides; polynucleotides with a termination sequence; polynucleotides with a polyadenylation recognition sequence; etc. Particular regulatory elements may be located upstream and/or downstream of a coding polynucleotide operably linked thereto. Also, particular regulatory elements operably linked to a coding polynucleotide may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding polynucleotide for expression in a cell, or a promoter may be operably linked to a polynucleotide encoding a signal peptide which may be operably linked to a coding polynucleotide for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions or in most tissue or cell types.

Any inducible promoter can be used in some embodiments of the invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that respond to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) Proc. Natl. Acad. Sci. USA 88:0421).

Exemplary constitutive promoters include, but are not limited to: Promoters from plant viruses, such as the 35S promoter from Cauliflower Mosaic Virus (CaMV); promoters from rice actin genes; ubiquitin promoters; pEMU; MAS; maize H3 histone promoter; and the ALS promoter, XbaI/NcoI fragment 5' to the *Brassica napus* ALS3 structural gene (or a polynucleotide similar to said XbaI/NcoI fragment) (International PCT Publication No. WO96/30530).

Additionally, any tissue-specific or tissue-preferred promoter may be utilized in some embodiments of the invention. Plants transformed with a nucleic acid molecule comprising a coding polynucleotide operably linked to a tissue-specific promoter may produce the product of the coding polynucleotide exclusively, or preferentially, in a specific tissue. Exemplary tissue-specific or tissue-preferred promoters include, but are not limited to: A seed-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Soybean plant: As used herein, the term "soybean plant" refers to a plant of the species *Glycine* sp.; for example, *G. max*.

Transformation: As used herein, the term "transformation" or "transduction" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319:791-3); lipofection (Felgner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; and microprojectile bombardment (Klein et al. (1987) Nature 327:70).

Transgene: An exogenous nucleic acid. In some examples, a transgene may be a DNA that encodes one or both strand(s) of an RNA capable of forming a dsRNA molecule that comprises a polynucleotide that is complementary to a nucleic acid molecule found in a hemipteran pest. In further examples, a transgene may be an antisense polynucleotide, wherein expression of the antisense polynucleotide inhibits expression of a target nucleic acid, thereby producing a parental RNAi phenotype. In still further examples, a transgene may be a gene (e.g., a herbicide-tolerance gene, a gene encoding an industrially or pharmaceutically useful compound, or a gene encoding a desirable agricultural trait). In these and other examples, a transgene may contain regulatory elements operably linked to a coding polynucleotide of the transgene (e.g., a promoter).

Vector: A nucleic acid molecule as introduced into a cell, for example, to produce a transformed cell. A vector may include genetic elements that permit it to replicate in the host cell, such as an origin of replication. Examples of vectors include, but are not limited to: a plasmid; cosmid; bacteriophage; or virus that carries exogenous DNA into a cell. A vector may also include one or more genes, including ones that produce antisense molecules, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Yield: A stabilized yield of about 100% or greater relative to the yield of check varieties in the same growing location growing at the same time and under the same conditions. In particular embodiments, "improved yield" or "improving yield" means a cultivar having a stabilized yield of 105% or greater relative to the yield of check varieties in the same growing location containing significant densities of the hemipteran pests that are injurious to that crop growing at the same time and under the same conditions, which are targeted by the compositions and methods herein.

Unless specifically indicated or implied, the terms "a," "an," and "the" signify "at least one," as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin's *Genes X*, Jones & Bartlett Publishers, 2009 (ISBN 10 0763766321); Krebs et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV. Nucleic Acid Molecules Comprising a Hemipteran Pest Polynucleotide

A. Overview

Described herein are nucleic acid molecules useful for the control of hemipteran pests. Described nucleic acid molecules include target polynucleotides (e.g., native genes, and non-coding polynucleotides), dsRNAs, siRNAs, shRNAs, hpRNAs, and miRNAs. For example, dsRNA, siRNA, miRNA, shRNA, and/or hpRNA molecules are described in some embodiments that may be specifically complementary to all or part of one or more nucleic acids in a hemipteran pest. In these and further embodiments, the nucleic acid(s) may be one or more target gene(s), the product of which may be, for example and without limitation: involved in a reproductive process or involved in nymph development. Nucleic acid molecules described herein, when introduced into a cell (e.g., through parental transmission) comprising at least one nucleic acid(s) to which the nucleic acid molecules are specifically complementary, may initiate RNAi in the cell, and consequently reduce or eliminate expression of the native nucleic acid(s). In some examples, reduction or elimination of the expression of a target gene by a nucleic acid molecule specifically complementary thereto may result in reduction or cessation of reproduction in the hemipteran pest, and/or growth, development, and/or feeding in progeny of the pest. These methods may significantly reduce the size of a subsequent pest generation in an infestation, for example, without directly resulting in mortality in the pest(s) that contact the iRNA molecule.

In some embodiments, at least one target gene in a hemipteran pest may be selected, wherein the target gene comprises a chromatin remodeling polynucleotide (e.g., a gene). In particular examples, such a chromatin remodeling gene in a hemipteran pest is selected, wherein the target gene comprises a polynucleotide selected from among BSB_brahma (SEQ ID NO:1 and SEQ ID NO:63); BSB_mi-2 (SEQ ID NO:8 and SEQ ID NO:64); BSB_iswi-1 (SEQ ID NO:10 and SEQ ID NO:65); BSB_chd1 (SEQ ID NO:14 and SEQ ID NO:67); BSB_iswi-2 (SEQ ID NO:12 and SEQ ID NO:66); BSB_ino80 (SEQ ID NO:30); and BSB_domino (SEQ ID NO:32). For example, a target gene in certain embodiments comprises a chromatin remodeling polynucleotide selected from among SEQ ID NO:1, SEQ ID NO: 8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, SEQ ID NO:67; and fragments of any of the foregoing (e.g., SEQ ID NO:3, SEQ ID NO:16, SEQ ID NO:17, SEQ ID NO:18, and SEQ ID NO:19).

In some embodiments, a chromatin remodeling polynucleotide encodes a member of the group of "ATP-dependent remodeling enzymes," a class of ATPases that contain a SNF2 domain (sucrose non-fermenting, originally identified in *Saccharomyces cerevisiae*). ATP-dependent remodeling enzymes include, for example and without limitation, BRAHMA and its orthologs; MI-2 and its orthologs; ISWI, its paralogs, and its orthologs (e.g., ISWI-1 and ISWI-2); CHD1 and its orthologs; INO80 and its orthologs; and DOMINO and its orthologs. Chromatin remodelers (e.g., ATP-dependent remodeling enzymes) exert lasting epigenetic effects by mobilizing nucleosomes and thus changing the access of the transcriptional machinery to DNA.

ATP-dependent remodeling enzymes share the same functional domains and sequence-level conservation. In Pfam (pfam.sanger.ac.uk) searches, ATP-dependent remodeling enzymes can be identified by a combination of SNF2 family N-terminal and Helicase conserved C-terminal (SNF2-Helicase) domains. Thus, RNAi target sites can be designed within the conserved SNF2 family N-terminal and Helicase C-terminal domains (here referred to as SNF2-Helicase) that are common to all chromatin remodelers, as well as chromatin binding or other functional domains that are conserved within each family, which include but are not limited to bromodomain, chromodomain, and HAND-SLIDE domains.

In some embodiments, a target gene may be a nucleic acid molecule comprising a polynucleotide that can be reverse translated in silico to a polypeptide comprising a contiguous amino acid sequence that is at least about 85% identical (e.g., at least 84%, 85%, about 90%, about 95%, about 96%, about 97%, about 98%, about 99%, about 100%, or 100% identical) to the amino acid sequence of a protein product of a chromatin remodeling gene. A target gene may be any nucleic acid in a hemipteran pest, the post-transcriptional inhibition of which has a deleterious effect on the capacity of the pest to produce viable offspring, for example, to provide a protective benefit against the pest to a plant. In particular examples, a target gene is a nucleic acid molecule comprising a polynucleotide that can be reverse translated in silico to a polypeptide comprising a contiguous amino acid sequence that is at least about 85% identical, about 90% identical, about 95% identical, about 96% identical, about 97% identical, about 98% identical, about 99% identical, about 100% identical, or 100% identical to the amino acid sequence that is the in silico translation product of a brahma, mi-2, iswi-1, chd1, iswi-2, ino80, or domino gene. Examples of such translation products include, for example and without limitation: SEQ ID NO:2; SEQ ID NO:9; SEQ ID NO:11; SEQ ID NO:13; SEQ ID NO:15; SEQ ID NO:31; and SEQ ID NO:33.

Provided in some embodiments are DNAs, the expression of which results in an RNA molecule comprising a polynucleotide that is specifically complementary to all or part of a RNA molecule that is encoded by a coding polynucleotide in a hemipteran pest. In some embodiments, after ingestion of the expressed RNA molecule by a hemipteran pest, down-regulation of the coding polynucleotide in cells of the pest, or in cells of progeny of the pest, may be obtained. In particular embodiments, down-regulation of the coding polynucleotide in cells of the hemipteran pest may result in reduction or cessation of reproduction and/or proliferation in the pest, and/or growth, development, and/or feeding in progeny of the pest.

In some embodiments, target polynucleotides include transcribed non-coding RNAs, such as 5'UTRs; 3'UTRs; spliced leaders; introns; outrons (e.g., 5'UTR RNA subsequently modified in trans splicing); donatrons (e.g., non-coding RNA required to provide donor sequences for trans splicing); and other non-coding transcribed RNA of target hemipteran pest genes. Such polynucleotides may be derived from both mono-cistronic and poly-cistronic genes.

Thus, also described herein in connection with some embodiments are iRNA molecules (e.g., dsRNAs, siRNAs, miRNAs, shRNAs, and hpRNAs) that comprise at least one polynucleotide that is specifically complementary to all or part of a target nucleic acid in a hemipteran pest. In some embodiments an iRNA molecule may comprise polynucleotide(s) that are complementary to all or part of a plurality of target nucleic acids; for example, 2, 3, 4, 5, 6, 7, 8, 9, 10, or more target nucleic acids. In particular embodiments, an iRNA molecule may be produced in vitro or in vivo by a genetically-modified organism, such as a plant or bacterium. Also disclosed are cDNAs that may be used for the production of dsRNA molecules, siRNA molecules, miRNA molecules, shRNA molecules, and/or hpRNA molecules that are specifically complementary to all or part of a target nucleic acid in a hemipteran pest. Further described are recombinant DNA constructs for use in achieving stable transformation of particular host targets. Transformed host targets may express effective levels of dsRNA, siRNA, miRNA, shRNA, and/or hpRNA molecules from the recombinant DNA constructs. Therefore, also described is a plant transformation vector comprising at least one polynucleotide operably linked to a heterologous promoter functional in a plant cell, wherein expression of the polynucleotide(s) results in an RNA molecule comprising a string of contiguous nucleobases that are specifically complementary to all or part of a target nucleic acid in a hemipteran pest.

In particular examples, nucleic acid molecules useful for the control of hemipteran pests may include: all or part of a nucleic acid isolated from a hemipteran insect (e.g., BSB) comprising a chromatin remodeling gene polynucleotide (e.g., any of SEQ ID NO:1, SEQ ID NO:3, SEQ ID NO:8, SEQ ID NO:10, SEQ ID NO:12, SEQ ID NO:14, SEQ ID NO:16, SEQ ID NO:17, SEQ ID NO:18, SEQ ID NO:19, SEQ ID NO:30, SEQ ID NO:32, SEQ ID NO:63, SEQ ID NO:64, SEQ ID NO:65, SEQ ID NO:66, and SEQ ID NO:67); DNAs that when expressed result in an RNA molecule comprising a polynucleotide that is specifically complementary to all or part of a RNA molecule that is encoded by chromatin remodeling gene; iRNA molecules (e.g., dsRNAs, siRNAs, miRNAs, shRNAs, and hpRNAs) that comprise at least one polynucleotide that is specifically complementary to all or part of an RNA molecule encoded by a chromatin remodeling gene; cDNAs that may be used for the production of dsRNA molecules, siRNA molecules, miRNA molecules, shRNA molecules, and/or hpRNA molecules that are specifically complementary to all or part of an RNA molecule encoded by a chromatin remodeling gene; and recombinant DNA constructs for use in achieving stable transformation of particular host targets, wherein a transformed host target comprises one or more of the foregoing nucleic acid molecules.

B. Nucleic Acid Molecules

The present invention provides, inter alia, iRNA (e.g., dsRNA, siRNA, miRNA, shRNA, and hpRNA) molecules that inhibit target gene expression in a cell, tissue, or organ of a hemipteran pest; and DNA molecules capable of being expressed as an iRNA molecule in a cell or microorganism to inhibit target gene expression in a cell, tissue, or organ of a hemipteran pest.

Some embodiments of the invention provide an isolated nucleic acid molecule comprising at least one (e.g., one, two, three, or more) polynucleotide(s) selected from the group consisting of: SEQ ID NO:1; SEQ ID NO:63; the complement of SEQ ID NO:1; the complement of SEQ ID NO:63; a fragment of at least 15 contiguous nucleotides (e.g., at least 19 contiguous nucleotides) of SEQ ID NO:1 or SEQ ID NO:63 (e.g., SEQ ID NO:3); the complement of a fragment of at least 15 contiguous nucleotides of SEQ ID NO:1 or SEQ ID NO:63; a coding polynucleotide of a hemipteran insect (e.g., BSB) comprising SEQ ID NO:1 or SEQ ID NO:63; the complement of a coding polynucleotide of a hemipteran insect comprising SEQ ID NO:1 or SEQ ID NO:63; a fragment of at least 15 contiguous nucleotides of a coding polynucleotide of a hemipteran insect comprising SEQ ID NO:1 or SEQ ID NO:63; and the complement of a fragment of at least 15 contiguous nucleotides of a coding polynucleotide of a hemipteran insect comprising SEQ ID NO:1 or SEQ ID NO:63. In particular embodiments, contact with or uptake by a hemipteran pest of the isolated polynucleotide inhibits the growth, development, reproduction and/or feeding of the pest.

Alternative embodiments of the invention provide an isolated nucleic acid molecule comprising at least one (e.g., one, two, three, or more) polynucleotide(s) selected from the group consisting of: SEQ ID NO:8; SEQ ID NO:64; the complement of SEQ ID NO:8; the complement of SEQ ID NO:64; a fragment of at least 15 contiguous nucleotides (e.g., at least 19 contiguous nucleotides) of SEQ ID NO:8 or SEQ ID NO:64 (e.g., SEQ ID NO:16); the complement of a fragment of at least 15 contiguous nucleotides of SEQ ID NO:8 or SEQ ID NO:64; a coding polynucleotide of a hemipteran insect comprising SEQ ID NO:8 or SEQ ID NO:64; the complement of a coding polynucleotide of a hemipteran insect comprising SEQ ID NO:8 or SEQ ID NO:64; a fragment of at least 15 contiguous nucleotides of a coding polynucleotide of a hemipteran insect comprising SEQ ID NO:8 or SEQ ID NO:64; and the complement of a fragment of at least 15 contiguous nucleotides of a coding polynucleotide of a hemipteran insect comprising SEQ ID NO:8 or SEQ ID NO:64. In particular embodiments, contact with or uptake by a hemipteran pest of the isolated polynucleotide inhibits the growth, development, reproduction and/or feeding of the pest.

Particular embodiments of the invention provide an isolated nucleic acid molecule comprising at least one (e.g., one, two, three, or more) polynucleotide(s) selected from the group consisting of: SEQ ID NO:10; SEQ ID NO:65; the complement of SEQ ID NO:10; the complement of SEQ ID NO:65; a fragment of at least 15 contiguous nucleotides (e.g., at least 19 contiguous nucleotides) of SEQ ID NO:10 or SEQ ID NO:65 (e.g., SEQ ID NO:17); the complement of a fragment of at least 15 contiguous nucleotides of SEQ ID NO:10 or SEQ ID NO:65; a coding polynucleotide of a hemipteran insect comprising SEQ ID NO:10 or SEQ ID NO:65; the complement of a coding polynucleotide of a hemipteran insect comprising SEQ ID NO:10 or SEQ ID NO:65; a fragment of at least 15 contiguous nucleotides of a coding polynucleotide of a hemipteran insect comprising SEQ ID NO:10 or SEQ ID NO:65; and the complement of a fragment of at least 15 contiguous nucleotides of a coding polynucleotide of a hemipteran insect comprising SEQ ID NO:10 or SEQ ID NO:65. In particular embodiments, contact with or uptake by a hemipteran pest of the isolated polynucleotide inhibits the growth, development, reproduction and/or feeding of the pest.

Some embodiments of the invention provide an isolated nucleic acid molecule comprising at least one (e.g., one, two, three, or more) polynucleotide(s) selected from the group consisting of: SEQ ID NO:12; SEQ ID NO:66; the complement of SEQ ID NO:12; the complement of SEQ ID NO:66; a fragment of at least 15 contiguous nucleotides (e.g., at least 19 contiguous nucleotides) of SEQ ID NO:12 or SEQ ID NO:66 (e.g., SEQ ID NO:18); the complement of a fragment of at least 15 contiguous nucleotides of SEQ ID NO:12 or SEQ ID NO:66; a coding polynucleotide of a hemipteran insect comprising SEQ ID NO:12 or SEQ ID NO:66; the complement of a coding polynucleotide of a hemipteran insect comprising SEQ ID NO:12 or SEQ ID NO:66; a fragment of at least 15 contiguous nucleotides of a coding polynucleotide of a hemipteran insect comprising SEQ ID NO:12 or SEQ ID NO:66; and the complement of a fragment of at least 15 contiguous nucleotides of a coding polynucleotide of a hemipteran insect comprising SEQ ID NO:12 or SEQ ID NO:66. In particular embodiments, contact with or uptake by a hemipteran pest of the isolated polynucleotide inhibits the growth, development, reproduction and/or feeding of the pest.

Other embodiments of the invention provide an isolated nucleic acid molecule comprising at least one (e.g., one, two, three, or more) polynucleotide(s) selected from the group consisting of: SEQ ID NO:14; SEQ ID NO:67; the complement of SEQ ID NO:14; the complement of SEQ ID NO:67; a fragment of at least 15 contiguous nucleotides (e.g., at least 19 contiguous nucleotides) of SEQ ID NO:14 or SEQ ID NO:67 (e.g., SEQ ID NO:19); the complement of a fragment of at least 15 contiguous nucleotides of SEQ ID NO:14 or SEQ ID NO:67; a coding polynucleotide of a hemipteran insect comprising SEQ ID NO:14 or SEQ ID NO:67; the complement of a coding polynucleotide of a hemipteran insect comprising SEQ ID NO:14 or SEQ ID NO:67; a fragment of at least 15 contiguous nucleotides of a coding polynucleotide of a hemipteran insect comprising SEQ ID NO:14 or SEQ ID NO:67; and the complement of a fragment of at least 15 contiguous nucleotides of a coding polynucleotide of a hemipteran insect comprising SEQ ID NO:14 or SEQ ID NO:67. In particular embodiments, contact with or uptake by a hemipteran pest of the isolated polynucleotide inhibits the growth, development, reproduction and/or feeding of the pest.

Some embodiments of the invention provide an isolated nucleic acid molecule comprising at least one (e.g., one, two, three, or more) polynucleotide(s) selected from the group consisting of: SEQ ID NO:30; the complement of SEQ ID NO:30; a fragment of at least 15 contiguous nucleotides (e.g., at least 19 contiguous nucleotides) of SEQ ID NO:30; the complement of a fragment of at least 15 contiguous nucleotides of SEQ ID NO:30; a coding polynucleotide of a hemipteran insect comprising SEQ ID NO:30; the complement of a coding polynucleotide of a hemipteran insect comprising SEQ ID NO:30; a fragment of at least 15 contiguous nucleotides of a coding polynucleotide of a hemipteran insect comprising SEQ ID NO:30; and the complement of a fragment of at least 15 contiguous nucleotides of a coding polynucleotide of a hemipteran insect comprising SEQ ID NO:30. In particular embodiments, contact with or uptake by a hemipteran pest of the isolated polynucleotide inhibits the growth, development, reproduction and/or feeding of the pest.

Other embodiments of the invention provide an isolated nucleic acid molecule comprising at least one (e.g., one, two, three, or more) polynucleotide(s) selected from the group consisting of: SEQ ID NO:32; the complement of SEQ ID NO:32; a fragment of at least 15 contiguous nucleotides (e.g., at least 19 contiguous nucleotides) of SEQ ID NO:32; the complement of a fragment of at least 15 contiguous nucleotides of SEQ ID NO:32; a coding polynucleotide of a hemipteran insect comprising SEQ ID NO:32; the complement of a coding polynucleotide of a hemipteran insect comprising SEQ ID NO:32; a fragment of at least 15 contiguous nucleotides of a coding polynucleotide of a hemipteran insect comprising SEQ ID NO:32; and the complement of a fragment of at least 15 contiguous nucleotides of a coding polynucleotide of a hemipteran insect comprising SEQ ID NO:32. In particular embodiments, contact with or uptake by a hemipteran pest of the isolated polynucleotide inhibits the growth, development, reproduction and/or feeding of the pest.

In some embodiments, an isolated nucleic acid molecule of the invention may comprise at least one (e.g., one, two, three, or more) polynucleotide(s) selected from the group consisting of: SEQ ID NO:43; the complement of SEQ ID NO:43; SEQ ID NO:44; the complement of SEQ ID NO:44; SEQ ID NO:45; the complement of SEQ ID NO:45; SEQ ID NO:46; the complement of SEQ ID NO:46; SEQ ID NO:47; the complement of SEQ ID NO:47; SEQ ID NO:48; the complement of SEQ ID NO:48; SEQ ID NO:49; the complement of SEQ ID NO:49; SEQ ID NO:50; the complement of SEQ ID NO:50; SEQ ID NO:51; the complement of SEQ ID NO:51; SEQ ID NO:52; the complement of SEQ ID NO:52; SEQ ID NO:53; the complement of SEQ ID NO:53; SEQ ID NO:54; the complement of SEQ ID NO:54; SEQ ID NO:55; the complement of SEQ ID NO:55; SEQ ID NO:56; the complement of SEQ ID NO:56; SEQ ID NO:57; the complement of SEQ ID NO:57; SEQ ID NO:58; the complement of SEQ ID NO:58; SEQ ID NO:59; the complement of SEQ ID NO:59; SEQ ID NO:60; the complement of SEQ ID NO:60; SEQ ID NO:61; the complement of SEQ ID NO:61; SEQ ID NO:62; the complement of SEQ ID NO:62; SEQ ID NO:68; the complement of SEQ ID NO:68; SEQ ID NO:69; the complement of SEQ ID NO:69; SEQ ID NO:70; the complement of SEQ ID NO:70; SEQ ID NO:71; the complement of SEQ ID NO:71; SEQ ID NO:72; the complement of SEQ ID NO:72; a polyribonucleotide transcribed in a hemipteran insect from a gene comprising SEQ ID NO:1, SEQ ID NO:3, SEQ ID NO:8, SEQ ID NO:10, SEQ ID NO:12, SEQ ID NO:14, SEQ ID NO:16, SEQ ID NO:17, SEQ ID NO:18, SEQ ID NO:19, SEQ ID NO:30, SEQ ID NO:32, SEQ ID NO:63, SEQ ID NO:64, SEQ ID NO:65, SEQ ID NO:66, or SEQ ID NO:67; the complement of a polyribonucleotide transcribed in a hemipteran insect from a gene comprising SEQ ID NO:1, SEQ ID NO:3, SEQ ID NO:8, SEQ ID NO:10, SEQ ID NO:12, SEQ ID NO:14, SEQ ID NO:16, SEQ ID NO:17, SEQ ID NO:18, SEQ ID NO:19, SEQ ID NO:30, SEQ ID NO:32, SEQ ID NO:63, SEQ ID NO:64, SEQ ID NO:65, SEQ ID NO:66, or SEQ ID NO:67; a fragment of at least 15 contiguous nucleotides of a polyribonucleotide transcribed in a hemipteran insect from a gene comprising SEQ ID NO:1, SEQ ID NO:3, SEQ ID NO:8, SEQ ID NO:10, SEQ ID NO:12, SEQ ID NO:14, SEQ ID NO:16, SEQ ID NO:17, SEQ ID NO:18, SEQ ID NO:19, SEQ ID NO:30, SEQ ID NO:32, SEQ ID NO:63, SEQ ID NO:64, SEQ ID NO:65, SEQ ID NO:66, or SEQ ID NO:67; and the complement of a fragment of at least 15 contiguous nucleotides of a polyribonucleotide transcribed in a hemipteran insect from a gene comprising SEQ ID NO:1, SEQ ID NO:3, SEQ ID NO:8, SEQ ID NO:10, SEQ ID NO:12, SEQ ID NO:14, SEQ ID NO:16, SEQ ID NO:17, SEQ ID NO:18, SEQ ID NO:19, SEQ ID NO:30, SEQ ID NO:32, SEQ ID NO:63, SEQ ID NO:64, SEQ ID NO:65, SEQ ID NO:66, or SEQ ID NO:67. In particular embodiments, contact with or uptake by a hemipteran pest of the isolated polynucleotide inhibits the growth, development, reproduction and/or feeding of the pest. In some embodiments, contact with or uptake by the insect occurs via feeding on plant material or bait comprising the iRNA. In some embodiments, contact with or uptake by the insect occurs via spraying of a plant comprising the insect with a composition comprising the iRNA.

In some embodiments, a nucleic acid molecule of the invention may comprise at least one (e.g., one, two, three, or more) DNA(s) capable of being expressed as an iRNA molecule in a cell or microorganism to inhibit target gene expression in a cell, tissue, or organ of a hemipteran pest. Such DNA(s) may be operably linked to a promoter that functions in a cell comprising the DNA molecule to initiate or enhance the transcription of the encoded RNA capable of forming a dsRNA molecule(s). In one embodiment, the at least one (e.g., one, two, three, or more) DNA(s) may be derived from the polynucleotide of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67. Derivatives of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67 includes fragments of these polynucleotides. In some embodiments, such a fragment may comprise, for example, at least about 15 contiguous nucleotides of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, or SEQ ID NO:67, or a complement thereof. Thus, such a fragment may comprise, for example, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200 or more contiguous nucleotides of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, or SEQ ID NO:67, or a complement thereof. In some examples, such a fragment may comprise, for example, at least 19 contiguous nucleotides (e.g., 19, 20, 21, 22, 23, 24, 25, 26, 27, 28, 29, or 30 contiguous nucleotides) of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, or SEQ ID NO:67, or a complement thereof.

Some embodiments comprise introducing partially- or fully-stabilized dsRNA molecules into a hemipteran pest to inhibit expression of a target gene in a cell, tissue, or organ of the hemipteran pest. When expressed as an iRNA molecule (e.g., dsRNA, siRNA, miRNA, shRNA, and hpRNA) and taken up by a hemipteran pest, polynucleotides comprising one or more fragments of any of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67; and the complements thereof, may cause one or more of death, developmental arrest, growth inhibition, change in sex ratio, reduction in brood size, cessation of infection, and/or cessation of feeding by a hemipteran pest. In particular examples, polynucleotides comprising one or more fragments (e.g., polynucleotides including about 15 to about 300 nucleotides) of any of S SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67; and the complements thereof, cause a reduction in the capacity of an existing generation of the pest to produce a subsequent generation of the pest.

In certain embodiments, dsRNA molecules provided by the invention comprise polynucleotides complementary to a transcript from a target gene comprising SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67, and/or polynucleotides complementary to a fragment of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67, the inhibition of which target gene in a hemipteran pest results in the reduction or removal of a polypeptide or polynucleotide agent that is essential for the pest's or the pest's progeny's growth, development, or other biological function. A selected polynucleotide may exhibit from about 80% to about 100% sequence identity to SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, or SEQ ID NO:67, a contiguous fragment of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, or SEQ ID NO:67, or the complement of either of the foregoing. For example, a selected polynucleotide may exhibit 79%; 80%; about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; or about 100% sequence identity to SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, or SEQ ID NO:67, a contiguous fragment of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, or SEQ ID NO:67, or the complement of any of the foregoing.

In some embodiments, a DNA molecule capable of being expressed as an iRNA molecule in a cell or microorganism to inhibit target gene expression may comprise a single polynucleotide that is specifically complementary to all or part of a native polynucleotide found in one or more target hemipteran pest species, or the DNA molecule can be constructed as a chimera from a plurality of such specifically complementary polynucleotides.

In some embodiments, a nucleic acid molecule may comprise a first and a second polynucleotide separated by a "linker." A linker may be a region comprising any sequence of nucleotides that facilitates secondary structure formation between the first and second polynucleotides, where this is desired. In one embodiment, the linker is part of a sense or antisense coding polynucleotide for mRNA. The linker may alternatively comprise any combination of nucleotides or homologues thereof that are capable of being linked covalently to a nucleic acid molecule. In some examples, the linker may comprise an intron (e.g., as ST-LS1 intron).

For example, in some embodiments, the DNA molecule may comprise a polynucleotide coding for one or more different RNA molecules, wherein each of the different RNA molecules comprises a first polynucleotide and a second polynucleotide, wherein the first and second polynucleotides are complementary to each other. The first and second polynucleotides may be connected within an RNA molecule by a linker. The linker may constitute part of the first polynucleotide or the second polynucleotide. Expression of an RNA molecule comprising the first and second nucleotide polynucleotides may lead to the formation of a dsRNA molecule of the present invention, by specific intramolecular base-pairing of the first and second nucleotide polynucleotides. The first polynucleotide or the second polynucleotide may be substantially identical to a polynucleotide native to a hemipteran pest (e.g., a target gene, or transcribed non-coding polynucleotide), a derivative thereof, or a complementary polynucleotide thereto.

dsRNA nucleic acid molecules comprise double strands of polymerized ribonucleotides, and may include modifications to either the phosphate-sugar backbone or the nucleoside. Modifications in RNA structure may be tailored to allow specific inhibition. In one embodiment, dsRNA molecules may be modified through a ubiquitous enzymatic process so that siRNA molecules may be generated. This enzymatic process may utilize an RNase III enzyme, such as DICER in eukaryotes, either in vitro or in vivo. See Elbashir et al. (2001) Nature 411:494-8; and Hamilton and Baulcombe (1999) Science 286(5441):950-2. DICER or functionally-equivalent RNase III enzymes cleave larger dsRNA strands and/or hpRNA molecules into smaller oligonucleotides (e.g., siRNAs), each of which is about 19-25 nucleotides in length. The siRNA molecules produced by these enzymes have 2 to 3 nucleotide 3' overhangs, and 5' phosphate and 3' hydroxyl termini. The siRNA molecules generated by RNase III enzymes are unwound and separated into single-stranded RNA in the cell. The siRNA molecules then specifically hybridize with RNAs transcribed from a target gene, and both RNA molecules are subsequently degraded by an inherent cellular RNA-degrading mechanism. This process may result in the effective degradation or removal of the RNA encoded by the target gene in the target organism. The outcome is the post-transcriptional silencing of the targeted gene. In some embodiments, siRNA molecules produced by endogenous RNase III enzymes from heterologous nucleic acid molecules may efficiently mediate the down-regulation of target genes in hemipteran pests.

In some embodiments, a nucleic acid molecule of the invention may include at least one non-naturally occurring polynucleotide that can be transcribed into a single-stranded RNA molecule capable of forming a dsRNA molecule in vivo through intermolecular hybridization. Such dsRNAs typically self-assemble, and can be provided in the nutrition source of a hemipteran pest to achieve the post-transcriptional inhibition of a target gene. In these and further embodiments, a nucleic acid molecule of the invention may comprise two different non-naturally occurring polynucleotides, each of which is specifically complementary to a different target gene in a hemipteran pest. When such a nucleic acid molecule is provided as a dsRNA molecule to a hemipteran pest, the dsRNA molecule inhibits the expression of at least two different target genes in the pest.

C. Obtaining Nucleic Acid Molecules

A variety of polynucleotides in hemipteran pests may be used as targets for the design of nucleic acid molecules of the invention, such as iRNAs and DNA molecules encoding iRNAs. Selection of polynucleotides is not, however, a straight-forward process. Only a small number of polynucleotides in the hemipteran pest will be effective targets. For example, it cannot be predicted with certainty whether a particular polynucleotide can be effectively down-regulated by nucleic acid molecules of the invention, or whether down-regulation of a particular polynucleotide will have a detrimental effect on the growth, viability, proliferation, and/or reproduction of the hemipteran pest. The vast majority of pest polynucleotides, such as ESTs isolated therefrom (e.g., the coleopteran pest polynucleotides listed in U.S. Pat. No. 7,612,194), do not have a detrimental effect on the growth, viability, proliferation, and/or reproduction of the pest. Neither is it predictable which of the polynucleotides that may have a detrimental effect on a hemipteran pest are able to be used in recombinant techniques for expressing nucleic acid molecules complementary to such polynucleotides in a host plant and providing the detrimental effect on the pest upon feeding without causing harm to the host plant.

In some embodiments, nucleic acid molecules of the invention (e.g., dsRNA molecules to be provided in the host plant of a hemipteran pest) are selected to target cDNAs that encode proteins or parts of proteins essential for hemipteran pest reproduction and/or development, such as polypeptides involved in metabolic or catabolic biochemical pathways, cell division, reproduction, energy metabolism, embryonic development, nymph development, transcriptional regulation, and the like. As described herein, contact of compositions by a target organism containing one or more dsRNAs, at least one segment of which is specifically complementary to at least a substantially identical segment of RNA produced in the cells of the target pest organism, can result in failure or reduction of the capacity to mate, lay eggs, or produce viable progeny. A polynucleotide, either DNA or RNA, derived from a hemipteran pest can be used to construct plant cells resistant to infestation by the pests. The host plant of the hemipteran pest (e.g., *Z. mays* or *G. max*), for example, can be transformed to contain one or more of the polynucleotides derived from the hemipteran pest as provided herein. The polynucleotide transformed into the host may encode one or more RNAs that form into a dsRNA structure in the cells or biological fluids within the transformed host, thus making the dsRNA available if/when the pest forms a nutritional relationship with the transgenic host. This may result in the suppression of expression of one or more genes in the cells of the pest, and ultimately inhibition of reproduction and/or development.

Thus, in some embodiments, a gene is targeted that is essentially involved in the growth, development and reproduction of a hemipteran pest. Other target genes for use in the present invention may include, for example, those that play important roles in hemipteran pest viability, movement, migration, growth, development, infectivity, and establishment of feeding sites. A target gene may therefore be a housekeeping gene or a transcription factor. Additionally, a hemipteran pest polynucleotide for use in the present invention may also be derived from a homolog (e.g., an ortholog), of a plant, viral, bacterial or insect gene, the function of which is known to those of skill in the art, and the polynucleotide of which is specifically hybridizable with a target gene in the genome of the target hemipteran pest. Methods of identifying a homolog of a gene with a known nucleotide sequence by hybridization are known to those of skill in the art.

In some embodiments, the invention provides methods for obtaining a nucleic acid molecule comprising a polynucleotide for producing an iRNA (e.g., dsRNA, siRNA, miRNA, shRNA, and hpRNA) molecule. One such embodiment comprises: (a) analyzing one or more target gene(s) for their expression, function, and phenotype upon dsRNA-mediated gene suppression in a hemipteran pest; (b) probing a cDNA or gDNA library with a probe comprising all or a portion of a polynucleotide or a homolog thereof from a targeted hemipteran pest that displays an altered (e.g., reduced) reproduction or development phenotype in a dsRNA-mediated suppression analysis; (c) identifying a DNA clone that specifically hybridizes with the probe; (d) isolating the DNA clone identified in step (b); (e) sequencing the cDNA or gDNA fragment that comprises the clone isolated in step (d), wherein the sequenced nucleic acid molecule comprises all or a substantial portion of the RNA or a homolog thereof; and (f) chemically synthesizing all or a substantial portion of a gene, or an siRNA, miRNA, hpRNA, mRNA, shRNA, or dsRNA.

In further embodiments, a method for obtaining a nucleic acid fragment comprising a polynucleotide for producing a substantial portion of an iRNA (e.g., dsRNA, siRNA, miRNA, shRNA, and hpRNA) molecule includes: (a) synthesizing first and second oligonucleotide primers specifically complementary to a portion of a polynucleotide from a targeted hemipteran pest; and (b) amplifying a cDNA or gDNA insert present in a cloning vector using the first and second oligonucleotide primers of step (a), wherein the amplified nucleic acid molecule comprises a substantial portion of a siRNA, miRNA, hpRNA, mRNA, shRNA, or dsRNA molecule.

Nucleic acids of the invention can be isolated, amplified, or produced by a number of approaches. For example, an iRNA (e.g., dsRNA, siRNA, miRNA, shRNA, and hpRNA) molecule may be obtained by PCR amplification of a target polynucleotide (e.g., a target gene or a target transcribed non-coding polynucleotide) derived from a gDNA or cDNA library, or portions thereof. DNA or RNA may be extracted from a target organism, and nucleic acid libraries may be prepared therefrom using methods known to those ordinarily skilled in the art. gDNA or cDNA libraries generated from a target organism may be used for PCR amplification and sequencing of target genes. A confirmed PCR product may be used as a template for in vitro transcription to generate sense and antisense RNA with minimal promoters. Alternatively, nucleic acid molecules may be synthesized by any of a number of techniques (See, e.g., Ozaki et al. (1992) Nucleic Acids Research, 20: 5205-5214; and Agrawal et al. (1990) Nucleic Acids Research, 18: 5419-5423), including use of an automated DNA synthesizer (for example, a P.E. Biosystems, Inc. (Foster City, Calif.) model 392 or 394 DNA/RNA Synthesizer), using standard chemistries, such as phosphoramidite chemistry. See, e.g., Beaucage et al. (1992) Tetrahedron, 48: 2223-2311; U.S. Pat. Nos. 4,980,460, 4,725,677, 4,415,732, 4,458,066, and 4,973,679. Alternative chemistries resulting in non-natural backbone groups, such as phosphorothioate, phosphoramidate, and the like, can also be employed.

An RNA, dsRNA, siRNA, miRNA, shRNA, or hpRNA molecule of the present invention may be produced chemically or enzymatically by one skilled in the art through manual or automated reactions, or in vivo in a cell comprising a nucleic acid molecule comprising a polynucleotide encoding the RNA, dsRNA, siRNA, miRNA, shRNA, or hpRNA molecule. RNA may also be produced by partial or total organic synthesis; any modified ribonucleotide can be introduced by in vitro enzymatic or organic synthesis. An RNA molecule may be synthesized by a cellular RNA polymerase or a bacteriophage RNA polymerase (e.g., T3 RNA polymerase, T7 RNA polymerase, and SP6 RNA polymerase). Expression constructs useful for the cloning and expression of polynucleotides are known in the art. See, e.g., International PCT Publication No. WO97/32016; and U.S. Pat. Nos. 5,593,874, 5,698,425, 5,712,135, 5,789,214, and 5,804,693. RNA molecules that are synthesized chemically or by in vitro enzymatic synthesis may be purified prior to introduction into a cell. For example, RNA molecules can be purified from a mixture by extraction with a solvent or resin, precipitation, electrophoresis, chromatography, or a combination thereof. Alternatively, RNA molecules that are synthesized chemically or by in vitro enzymatic synthesis may be used with no or a minimum of purification, for example, to avoid losses due to sample processing. The RNA molecules may be dried for storage or dissolved in an aqueous solution. The solution may contain buffers or salts to promote annealing, and/or stabilization of dsRNA molecule duplex strands.

In embodiments, a dsRNA molecule may be formed by a single self-complementary RNA strand or from two complementary RNA strands. dsRNA molecules may be synthesized either in vivo or in vitro. An endogenous RNA polymerase of the cell may mediate transcription of the one or two RNA strands in vivo, or cloned RNA polymerase may be used to mediate transcription in vivo or in vitro. Post-transcriptional inhibition of a target gene in a hemipteran pest may be host-targeted by specific transcription in an organ, tissue, or cell type of the host (e.g., by using a tissue-specific promoter); stimulation of an environmental condition in the host (e.g., by using an inducible promoter that is responsive to infection, stress, temperature, and/or chemical inducers); and/or engineering transcription at a developmental stage or age of the host (e.g., by using a developmental stage-specific promoter). RNA strands that form a dsRNA molecule, whether transcribed in vitro or in vivo, may or may not be polyadenylated, and may or may not be capable of being translated into a polypeptide by a cell's translational apparatus.

D. Recombinant Vectors and Host Cell Transformation

In some embodiments, the invention also provides a DNA molecule for introduction into a cell (e.g., a bacterial cell, a yeast cell, or a plant cell), wherein the DNA molecule comprises a polynucleotide that, upon expression to RNA and ingestion by a hemipteran pest, achieves suppression of a target gene in a cell, tissue, or organ of the pest. Thus, some embodiments provide a recombinant nucleic acid molecule comprising a polynucleotide capable of being expressed as an iRNA (e.g., dsRNA, siRNA, miRNA, shRNA, and hpRNA) molecule in a plant cell to inhibit target gene expression in a hemipteran pest. In order to initiate or enhance expression, such recombinant nucleic acid molecules may comprise one or more regulatory elements, which regulatory elements may be operably linked to the polynucleotide capable of being expressed as an iRNA. Methods to express a gene suppression molecule in plants are known, and may be used to express a polynucleotide of the present invention. See, e.g., International PCT Publication No. WO06/073727; and U.S. Patent Publication No. 2006/0200878 A1)

In specific embodiments, a recombinant DNA molecule of the invention may comprise a polynucleotide encoding an RNA that may form a dsRNA molecule. Such recombinant DNA molecules may encode RNAs that may form dsRNA molecules capable of inhibiting the expression of endogenous target gene(s) in a hemipteran pest cell upon ingestion. In many embodiments, a transcribed RNA may form a dsRNA molecule that may be provided in a stabilized form; e.g., as a hairpin and stem and loop structure.

In alternative embodiments, one strand of a dsRNA molecule may be formed by transcription from a polynucleotide which is substantially homologous to the RNA encoded by a polynucleotide selected from the group consisting of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67; the complement of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67; a fragment of at least 15 contiguous nucleotides of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67; the complement of a fragment of at least 15 contiguous nucleotides of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67; a coding polynucleotide of a hemipteran insect (e.g., BSB) comprising SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67; the complement of a coding polynucleotide of a hemipteran insect comprising SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67; a fragment of at least 15 contiguous nucleotides of a coding polynucleotide of a hemipteran insect comprising SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67; and the complement of a fragment of at least 15 contiguous nucleotides of a coding polynucleotide of a hemipteran insect comprising SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67.

In particular embodiments, a recombinant DNA molecule encoding an RNA that may form a dsRNA molecule may comprise a coding region wherein at least two polynucleotides are arranged such that one polynucleotide is in a sense orientation, and the other polynucleotide is in an antisense orientation, relative to at least one promoter, wherein the sense polynucleotide and the antisense polynucleotide are linked or connected by a linker of, for example, from about five (~5) to about one thousand (~1000) nucleotides. The linker may form a loop between the sense and anti sense polynucleotides. The sense polynucleotide or the antisense polynucleotide may be substantially homologous to an RNA encoded by a target gene (e.g., a chromatin remodeling gene comprising SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, or SEQ ID NO:67) or fragment thereof. In some embodiments, however, a recombinant DNA molecule may encode an RNA that may form a dsRNA molecule without a linker. In embodiments, a sense coding polynucleotide and an antisense coding polynucleotide may be different lengths.

Polynucleotides identified as having a deleterious effect on hemipteran pests or a plant-protective effect with regard to hemipteran pests may be readily incorporated into expressed dsRNA molecules through the creation of appropriate expression cassettes in a recombinant nucleic acid molecule of the invention. For example, such polynucleotides may be expressed as a hairpin with stem and loop structure by taking a first segment corresponding to an RNA encoded by a target gene polynucleotide (e.g., a chromatin remodeling gene comprising SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, or SEQ ID NO:67, and fragments thereof); linking this polynucleotide to a second segment linker region that is not homologous or complementary to the first segment; and linking this to a third segment, wherein at least a portion of the third segment is substantially complementary to the first segment. Such a construct forms a stem and loop structure by intramolecular base-pairing of the first segment with the third segment, wherein the loop structure forms comprising the second segment. See, e.g., U.S. Patent Publication Nos. 2002/0048814 and 2003/0018993; and International PCT Publication Nos. WO94/01550 and WO98/05770. A dsRNA molecule may be generated, for example, in the form of a double-stranded structure such as a stem-loop structure (e.g., hairpin), whereby production of siRNA targeted for a native hemipteran pest polynucleotide is enhanced by co-expression of a fragment of the targeted gene, for instance on an additional plant expressible cassette, that leads to enhanced siRNA production, or reduces methylation to prevent transcriptional gene silencing of the dsRNA hairpin promoter.

Embodiments of the invention include introduction of a recombinant nucleic acid molecule of the present invention into a plant (i.e., transformation) to achieve hemipteran pest-protective levels of expression of one or more iRNA molecules. A recombinant DNA molecule may, for example, be a vector, such as a linear or a closed circular plasmid. The vector system may be a single vector or plasmid, or two or more vectors or plasmids that together contain the total DNA to be introduced into the genome of a host. In addition, a vector may be an expression vector. Nucleic acids of the invention can, for example, be suitably inserted into a vector under the control of a suitable promoter that functions in one or more hosts to drive expression of a linked coding polynucleotide or other DNA element. Many vectors are available for this purpose, and selection of the appropriate vector will depend mainly on the size of the nucleic acid to be inserted into the vector and the particular host cell to be transformed with the vector. Each vector contains various components depending on its function (e.g., amplification of DNA or expression of DNA) and the particular host cell with which it is compatible.

To impart protection from a hemipteran pest to a transgenic plant, a recombinant DNA may, for example, be transcribed into an iRNA molecule (e.g., an RNA molecule that forms a dsRNA molecule) within the tissues or fluids of the recombinant plant. An iRNA molecule may comprise a polynucleotide that is substantially homologous and specifically hybridizable to a corresponding transcribed polynucleotide within a hemipteran pest that may cause damage to the host plant species. The hemipteran pest may contact the iRNA molecule that is transcribed in cells of the transgenic host plant, for example, by ingesting cells or fluids of the transgenic host plant that comprise the iRNA molecule. Thus, expression of a target gene is suppressed by the iRNA molecule within hemipteran pests that infest the transgenic host plant. In some embodiments, suppression of expression of the target gene in the target hemipteran pest may result in the plant being tolerant to attack by the pest.

In order to enable delivery of iRNA molecules to a hemipteran pest in a nutritional relationship with a plant cell that has been transformed with a recombinant nucleic acid molecule of the invention, expression (i.e., transcription) of iRNA molecules in the plant cell is required. Thus, a recombinant nucleic acid molecule may comprise a polynucleotide of the invention operably linked to one or more regulatory elements, such as a heterologous promoter element that functions in a host cell, such as a bacterial cell wherein the nucleic acid molecule is to be amplified, and a plant cell wherein the nucleic acid molecule is to be expressed.

Promoters suitable for use in nucleic acid molecules of the invention include those that are inducible, viral, synthetic, or constitutive, all of which are well known in the art. Non-limiting examples describing such promoters include U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (CaMV 35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. Patent Publication No. 2009/757,089 (maize chloroplast aldolase promoter). Additional promoters include the nopaline synthase (NOS) promoter (Ebert et al. (1987) Proc. Natl. Acad. Sci. USA 84(16):5745-9) and the octopine synthase (OCS) promoters (which are carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-24); the CaMV 35S promoter (Odell et al. (1985) Nature 313:810-2; the figwort mosaic virus 35S-promoter (Walker et al. (1987) Proc. Natl. Acad. Sci. USA 84(19):6624-8); the sucrose synthase promoter (Yang and Russell (1990) Proc. Natl. Acad. Sci. USA 87:4144-8); the R gene complex promoter (Chandler et al. (1989) Plant Cell 1:1175-83); the chlorophyll a/b binding protein gene promoter; CaMV 35S (U.S. Pat. Nos. 5,322,938, 5,352,605, 5,359,142, and 5,530,196); FMV 35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank™ Accession No. V00087; Depicker et al. (1982) J. Mol. Appl. Genet. 1:561-73; Bevan et al. (1983) Nature 304:184-7).

In particular embodiments, nucleic acid molecules of the invention comprise a tissue-specific promoter, such as a leaf-specific promoter or pollen-specific promoter. In some embodiments, a polynucleotide or fragment for hemipteran pest control according to the invention may be cloned between two tissue-specific promoters oriented in opposite transcriptional directions relative to the polynucleotide or fragment, and which are operable in a transgenic plant cell and expressed therein to produce RNA molecules in the transgenic plant cell that subsequently may form dsRNA molecules, as described, supra. The iRNA molecules expressed in plant tissues may be ingested by a hemipteran pest so that suppression of target gene expression is achieved.

Additional regulatory elements that may optionally be operably linked to a nucleic acid molecule of interest include 5'UTRs located between a promoter element and a coding polynucleotide that function as a translation leader element. The translation leader element is present in the fully-processed mRNA, and it may affect processing of the primary transcript, and/or RNA stability. Examples of translation leader elements include maize and petunia heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5'UTRs include GmHsp (U.S. Pat. No. 5,659,122); PhDnaK (U.S. Pat. No. 5,362,865); AtAnt1; TEV (Carrington and Freed (1990) J. Virol. 64:1590-7); and AGRtunos (GenBank™ Accession No. V00087; and Bevan et al. (1983) Nature 304:184-7).

Additional regulatory elements that may optionally be operably linked to a nucleic acid molecule of interest also include 3' non-translated elements, 3' transcription termination regions, or polyadenylation regions. These are genetic elements located downstream of a polynucleotide, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation element can be derived from a variety of plant genes, or from T-DNA genes. A non-limiting example of a 3' transcription termination region is the nopaline synthase 3' region (nos 3; Fraley et al. (1983) Proc. Natl. Acad. Sci. USA 80:4803-7). An example of the use of different 3' nontranslated regions is provided in Ingelbrecht et al., (1989) Plant Cell 1:671-80. Non-limiting examples of polyadenylation signals include one from a *Pisum sativum* RbcS2 gene (Ps.RbcS2-E9; Coruzzi et al. (1984) EMBO J. 3:1671-9) and AGRtu.nos (GenBank™ Accession No. E01312).

Some embodiments may include a plant transformation vector that comprises an isolated and purified DNA molecule comprising at least one of the above-described regulatory elements operatively linked to one or more polynucleotides of the present invention. When expressed, the one or more polynucleotides result in one or more RNA molecule(s) comprising a polynucleotide that is specifically complementary to all or part of a RNA molecule in a hemipteran pest. Thus, the polynucleotide(s) may comprise a segment encoding all or part of a polyribonucleotide present within a targeted hemipteran pest RNA transcript, and may comprise inverted repeats of all or a part of a targeted pest transcript. A plant transformation vector may contain polynucleotides specifically complementary to more than one target polynucleotide, thus allowing production of more than one dsRNA for inhibiting expression of two or more genes in cells of one or more populations or species of target hemipteran pests. Segments of polynucleotides specifically complementary to polynucleotides present in different genes can be combined into a single composite nucleic acid molecule for expression in a transgenic plant. Such segments may be contiguous or separated by a linker.

In some embodiments, a plasmid of the present invention already containing at least one polynucleotide(s) of the invention can be modified by the sequential insertion of additional polynucleotide(s) in the same plasmid, wherein the additional polynucleotide(s) are operably linked to the same regulatory elements as the original at least one polynucleotide(s). In some embodiments, a nucleic acid molecule may be designed for the inhibition of multiple target genes. In some embodiments, the multiple genes to be inhibited can be obtained from the same hemipteran pest species, which may enhance the effectiveness of the nucleic acid molecule. In other embodiments, the genes can be derived from a different insect (e.g., hemipteran) pests, which may broaden the range of pests against which the agent(s) is/are effective. When multiple genes are targeted for suppression or a combination of expression and suppression, a polycistronic DNA element can be engineered.

A recombinant nucleic acid molecule or vector of the present invention may comprise a selectable marker that confers a selectable phenotype on a transformed cell, such as a plant cell. Selectable markers may also be used to select for plants or plant cells that comprise a recombinant nucleic acid molecule of the invention. The marker may encode biocide resistance, antibiotic resistance (e.g., kanamycin, Geneticin (G418), bleomycin, hygromycin, etc.), or herbicide tolerance (e.g., glyphosate, etc.). Examples of selectable markers include, but are not limited to: a neo gene which codes for kanamycin resistance and can be selected for using kanamycin, G418, etc.; a bar gene which codes for bialaphos resistance; a mutant EPSP synthase gene which encodes glyphosate tolerance; a nitrilase gene which confers resistance to bromoxynil; a mutant acetolactate synthase (ALS) gene which confers imidazolinone or sulfonylurea resistance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, streptomycin and tetracycline, and the like. Examples of such selectable markers are illustrated in, e.g., U.S. Pat. Nos. 5,550,318; 5,633,435; 5,780,708; and 6,118,047.

A recombinant nucleic acid molecule or vector of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In $18^{th}$ *Stadler Genetics Symposium*, P. Gustafson and R. Appels, eds. (New York: Plenum), pp. 263-82); a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234:856-9); an xylE gene that encodes a catechol dioxygenase that can convert chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone which in turn condenses to melanin (Katz et al. (1983) J. Gen. Microbiol. 129:2703-14); and an α-galactosidase.

In some embodiments, recombinant nucleic acid molecules, as described, supra, may be used in methods for the creation of transgenic plants and expression of heterologous nucleic acids in plants to prepare transgenic plants that exhibit reduced susceptibility to hemipteran pests. Plant transformation vectors can be prepared, for example, by inserting nucleic acid molecules encoding iRNA molecules into plant transformation vectors and introducing these into plants.

Suitable methods for transformation of host cells include any method by which DNA can be introduced into a cell, such as by transformation of protoplasts (See, e.g., U.S. Pat. No. 5,508,184), by desiccation/inhibition-mediated DNA uptake (See, e.g., Potrykus et al. (1985) Mol. Gen. Genet. 199:183-8), by electroporation (See, e.g., U.S. Pat. No. 5,384,253), by agitation with silicon carbide fibers (See, e.g., U.S. Pat. Nos. 5,302,523 and 5,464,765), by *Agrobacterium*-mediated transformation (See, e.g., U.S. Pat. Nos. 5,563,055; 5,591,616; 5,693,512; 5,824,877; 5,981,840; and 6,384,301) and by acceleration of DNA-coated particles (See, e.g., U.S. Pat. Nos. 5,015,580; 5,550,318; 5,538,880; 6,160,208; 6,399,861; and 6,403,865), etc. Techniques that are particularly useful for transforming corn are described, for example, in U.S. Pat. Nos. 7,060,876 and 5,591,616; and International PCT Publication WO95/06722. Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acids encoding one or more iRNA molecules in the genome of the transgenic plant.

The most widely utilized method for introducing an expression vector into plants is based on the natural transformation system of *Agrobacterium*. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. The Ti (tumor-inducing)-plasmids contain a large segment, known as T-DNA, which is transferred to transformed plants. Another segment of the Ti plasmid, the Vir region, is responsible for T-DNA transfer. The T-DNA region is bordered by terminal repeats. In modified binary vectors, the tumor-inducing genes have been deleted, and the functions of the Vir region are utilized to transfer foreign DNA bordered by the T-DNA border elements. The T-region may also contain a selectable marker for efficient recovery of transgenic cells and plants, and a multiple cloning site for inserting polynucleotides for transfer such as a dsRNA encoding nucleic acid.

Thus, in some embodiments, a plant transformation vector is derived from a Ti plasmid of *A. tumefaciens* (See, e.g., U.S. Pat. Nos. 4,536,475, 4,693,977, 4,886,937, and 5,501,967; and European Patent No. EP 0 122 791) or a Ri plasmid of *A. rhizogenes*. Additional plant transformation vectors include, for example and without limitation, those described by Herrera-Estrella et al. (1983) Nature 303:209-13; Bevan et al. (1983) Nature 304:184-7; Klee et al. (1985) Bio/Technol. 3:637-42; and in European Patent No. EP 0 120 516, and those derived from any of the foregoing. Other bacteria such as *Sinorhizobium, Rhizobium*, and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the transformation vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic medium with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturation.

To confirm the presence of a nucleic acid molecule of interest (for example, a DNA encoding one or more iRNA molecules that inhibit target gene expression in a hemipteran pest) in the regenerating plants, a variety of assays may be performed. Such assays include, for example: molecular biological assays, such as Southern and northern blotting, PCR, and nucleic acid sequencing; biochemical assays, such as detecting the presence of a protein product, e.g., by immunological means (ELISA and/or western blots) or by enzymatic function; plant part assays, such as leaf or root assays; and analysis of the phenotype of the whole regenerated plant.

Integration events may be analyzed, for example, by PCR amplification using, e.g., oligonucleotide primers specific for a nucleic acid molecule of interest. PCR genotyping is understood to include, but not be limited to, polymerase-chain reaction (PCR) amplification of gDNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to gDNA derived from any plant species (e.g., *Z. mays* or *G. max*) or tissue type, including cell cultures.

A transgenic plant formed using *Agrobacterium*-dependent transformation methods typically contains a single recombinant DNA inserted into one chromosome. The polynucleotide of the single recombinant DNA is referred to as a "transgenic event" or "integration event". Such transgenic plants are heterozygous for the inserted exogenous polynucleotide. In some embodiments, a transgenic plant homozygous with respect to a transgene may be obtained by sexually mating (selfing) an independent segregant transgenic plant that contains a single exogenous gene to itself, for example a $T_0$ plant, to produce $T_1$ seed. One fourth of the $T_1$ seed produced will be homozygous with respect to the transgene. Germinating $T_1$ seed results in plants that can be tested for heterozygosity, typically using an SNP assay or a thermal amplification assay that allows for the distinction between heterozygotes and homozygotes (i.e., a zygosity assay).

In particular embodiments, at least 2, 3, 4, 5, 6, 7, 8, 9 or 10 or more different iRNA molecules are produced in a plant cell that have a hemipteran pest-protective effect. The iRNA molecules (e.g., dsRNA molecules) may be expressed from multiple nucleic acids introduced in different transformation events, or from a single nucleic acid introduced in a single transformation event. In some embodiments, a plurality of iRNA molecules are expressed under the control of a single promoter. In other embodiments, a plurality of iRNA molecules are expressed under the control of multiple promoters. Single iRNA molecules may be expressed that comprise multiple polynucleotides that are each homologous to different loci within one or more hemipteran pests (for example, the loci defined by SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67), both in different populations of the same species of hemipteran pest, or in different species of hemipteran pests.

In addition to direct transformation of a plant with a recombinant nucleic acid molecule, transgenic plants can be prepared by crossing a first plant having at least one transgenic event with a second plant lacking such an event. For example, a recombinant nucleic acid molecule comprising a polynucleotide that encodes an iRNA molecule may be introduced into a first plant line that is amenable to transformation to produce a transgenic plant, which transgenic plant may be crossed with a second plant line to introgress the polynucleotide that encodes the iRNA molecule into the second plant line.

The invention also includes commodity products containing one or more of the polynucleotides of the present invention. Particular embodiments include commodity products produced from a recombinant plant or seed containing one or more of the polynucleotides of the present invention. A commodity product containing one or more of the polynucleotides of the present invention is intended to include, but not be limited to, meals, oils, crushed or whole grains or seeds of a plant, or any food product comprising any meal, oil, or crushed or whole grain of a recombinant plant or seed containing one or more of the polynucleotides of the present invention. The detection of one or more of the polynucleotides of the present invention in one or more commodity or commodity products contemplated herein is de facto evidence that the commodity or commodity product is produced from a transgenic plant designed to express one or more of the polynucleotides of the present invention for the purpose of controlling plant pests using dsRNA-mediated gene suppression methods.

In some aspects, seeds and commodity products produced by transgenic plants derived from transformed plant cells are included, wherein the seeds or commodity products comprise a detectable amount of a nucleic acid of the invention. In some embodiments, such commodity products may be produced, for example, by obtaining transgenic plants and preparing food or feed from them. Commodity products comprising one or more of the polynucleotides of the invention includes, for example and without limitation: meals, oils, crushed or whole grains or seeds of a plant, and any food product comprising any meal, oil, or crushed or whole grain of a recombinant plant or seed comprising one or more of the nucleic acids of the invention. The detection of one or more of the polynucleotides of the invention in one or more commodity or commodity products is de facto evidence that the commodity or commodity product is produced from a transgenic plant designed to express one or more of the iRNA molecules of the invention for the purpose of controlling hemipteran pests.

In some embodiments, a transgenic plant or seed comprising a nucleic acid molecule of the invention also may comprise at least one other transgenic event in its genome, including without limitation: a transgenic event from which is transcribed an iRNA molecule targeting a locus in a hemipteran pest other than the ones defined by SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67; a transgenic event from which is transcribed an iRNA molecule targeting a gene in an organism other than a hemipteran pest (e.g., a plant-parasitic nematode); a gene encoding an insecticidal protein (e.g., a *Bacillus thuringiensis* insecticidal protein); an herbicide tolerance gene (e.g., a gene providing tolerance to glyphosate); and a gene contributing to a desirable phenotype in the transgenic plant, such as increased yield, altered fatty acid metabolism, or restoration of cytoplasmic male sterility. In particular embodiments, polynucleotides encoding iRNA molecules of the invention may be combined with other insect control and disease traits in a plant to achieve desired traits for enhanced control of plant disease and insect damage. Combining insect control traits that employ distinct modes-of-action may provide protected transgenic plants with superior durability over plants harboring a single control trait, for example, because of the reduced probability that resistance to the trait(s) will develop in the field.

V. Target Gene Suppression in a Hemipteran Pest

A. Overview

In some embodiments of the invention, at least one nucleic acid molecule useful for the control of hemipteran pests may be provided to a hemipteran pest, wherein the nucleic acid molecule leads to RNAi-mediated gene silencing in the pest(s). In particular embodiments, an iRNA molecule (e.g., dsRNA, siRNA, miRNA, shRNA, and hpRNA) may be provided to the hemipteran host. In some embodiments, a nucleic acid molecule useful for the control of hemipteran pests may be provided to a pest by contacting the nucleic acid molecule with the pest. In these and further embodiments, a nucleic acid molecule useful for the control of hemipteran pests may be provided in a feeding substrate of the pest, for example, a nutritional composition. In these and further embodiments, a nucleic acid molecule useful for the control of a hemipteran pest may be provided through ingestion of plant material comprising the nucleic acid molecule that is ingested by the pest(s). In certain embodiments, the nucleic acid molecule is present in plant material through expression of a recombinant nucleic acid introduced into the plant material, for example, by transformation of a plant cell with a vector comprising the recombinant nucleic acid and regeneration of a plant material or whole plant from the transformed plant cell.

B. RNAi-mediated Target Gene Suppression

In embodiments, the invention provides iRNA molecules (e.g., dsRNA, siRNA, miRNA, shRNA, and hpRNA) that may be designed to target essential polynucleotides (e.g., essential genes) in the transcriptome of a hemipteran (e.g., BSB) pest, for example by designing an iRNA molecule that comprises at least one strand comprising a polynucleotide that is specifically complementary to the target polynucleotide. The sequence of an iRNA molecule so designed may be identical to that of the target polynucleotide, or may incorporate mismatches that do not prevent specific hybridization between the iRNA molecule and its target polynucleotide.

iRNA molecules of the invention may be used in methods for gene suppression in a hemipteran pest, thereby reducing the level or incidence of damage caused by the pest on a plant (for example, a protected transformed plant comprising an iRNA molecule). As used herein the term "gene suppression" refers to any of the well-known methods for reducing the levels of protein produced as a result of gene transcription to mRNA and subsequent translation of the mRNA, including the reduction of protein expression from a gene or a coding polynucleotide including post-transcriptional inhibition of expression and transcriptional suppression. Post-transcriptional inhibition is mediated by specific homology between all or a part of an mRNA transcribed from a gene targeted for suppression and the corresponding iRNA molecule used for suppression. Additionally, post-transcriptional inhibition refers to the substantial and measurable reduction of the amount of mRNA available in the cell for binding by ribosomes.

In embodiments wherein an iRNA molecule is a dsRNA molecule, the dsRNA molecule may be cleaved by the enzyme, DICER, into short siRNA molecules (approximately 20 nucleotides in length). The double-stranded siRNA molecule generated by DICER activity upon the dsRNA molecule may be separated into two single-stranded siRNAs; the "passenger strand" and the "guide strand". The passenger strand may be degraded, and the guide strand may be incorporated into RISC. Post-transcriptional inhibition occurs by specific hybridization of the guide strand with a specifically complementary polynucleotide of an mRNA molecule, and subsequent cleavage by the enzyme, Argonaute (catalytic component of the RISC complex).

In embodiments of the invention, any form of iRNA molecule may be used. Those of skill in the art will understand that dsRNA molecules typically are more stable during preparation and during the step of providing the iRNA molecule to a cell than are single-stranded RNA molecules, and are typically also more stable in a cell. Thus, while siRNA and miRNA molecules, for example, may be equally effective in some embodiments, a dsRNA molecule may be chosen due to its stability.

In particular embodiments, a nucleic acid molecule is provided that comprises a polynucleotide, which polynucleotide may be expressed in vitro to produce an iRNA molecule that is substantially homologous to a nucleic acid molecule encoded by a polynucleotide within the genome of a hemipteran pest. In certain embodiments, the in vitro transcribed iRNA molecule may be a stabilized dsRNA molecule that comprises a stem-loop structure. After a hemipteran pest contacts the in vitro transcribed iRNA molecule, post-transcriptional inhibition of a target gene in the pest (for example, an essential gene) may occur.

In some embodiments of the invention, expression of an iRNA from a nucleic acid molecule comprising at least 15 contiguous nucleotides (e.g., at least 19 contiguous nucleotides) of a polynucleotide are used in a method for post-transcriptional inhibition of a target gene in a hemipteran pest, wherein the polynucleotide is selected from the group consisting of: SEQ ID NO:1; the complement of SEQ ID NO:1; SEQ ID NO:8; the complement of SEQ ID NO:8; SEQ ID NO:10; the complement of SEQ ID NO:10; SEQ ID NO:12; the complement of SEQ ID NO:12; SEQ ID NO:14; the complement of SEQ ID NO:14; SEQ ID NO:30; the complement of SEQ ID NO:30; SEQ ID NO:32; the complement of SEQ ID NO:32; SEQ ID NO:63; the complement of SEQ ID NO:63; SEQ ID NO:64; the complement of SEQ ID NO:64; SEQ ID NO:65; the complement of SEQ ID NO:65; SEQ ID NO:66; the complement of SEQ ID NO:66; SEQ ID NO:67; the complement of SEQ ID NO:67; a fragment of at least 15 contiguous nucleotides of SEQ ID NO:1; the complement of a fragment of at least 15 contiguous nucleotides of SEQ ID NO:1; a fragment of at least 15 contiguous nucleotides of SEQ ID NO:8; the complement of a fragment of at least 15 contiguous nucleotides of SEQ ID NO:8; a fragment of at least 15 contiguous nucleotides of SEQ ID NO:10; the complement of a fragment of at least 15 contiguous nucleotides of SEQ ID NO:10; a fragment of at least 15 contiguous nucleotides of SEQ ID NO:12; the complement of a fragment of at least 15 contiguous nucleotides of SEQ ID NO:12; a fragment of at least 15 contiguous nucleotides of SEQ ID NO:14; the complement of a fragment of at least 15 contiguous nucleotides of SEQ ID NO:14; a fragment of at least 15 contiguous nucleotides of SEQ ID NO:30; the complement of a fragment of at least 15 contiguous nucleotides of SEQ ID NO:30; a fragment of at least 15 contiguous nucleotides of SEQ ID NO:32; the complement of a fragment of at least 15 contiguous nucleotides of SEQ ID NO:32; a fragment of at least 15 contiguous nucleotides of SEQ ID NO:63; the complement of a fragment of at least 15 contiguous nucleotides of SEQ ID NO:63; a fragment of at least 15 contiguous nucleotides of SEQ ID NO:64; the complement of a fragment of at least 15 contiguous nucleotides of SEQ ID NO:64; a fragment of at least 15 contiguous nucleotides of SEQ ID NO:65; the complement of a fragment of at least 15 contiguous nucleotides of SEQ ID NO:65; a fragment of at least 15 contiguous nucleotides of SEQ ID NO:66; the complement of a fragment of at least 15 contiguous nucleotides of SEQ ID NO:66; a fragment of at least 15 contiguous nucleotides of SEQ ID NO:67; the complement of a fragment of at least 15 contiguous nucleotides of SEQ ID NO:67; a coding polynucleotide of a hemipteran insect comprising SEQ ID NO:1; the complement of a coding polynucleotide of a hemipteran insect comprising SEQ ID NO:1; a coding polynucleotide of a hemipteran insect comprising SEQ ID NO:8; the complement of a coding polynucleotide of a hemipteran insect comprising SEQ ID NO:8; a coding polynucleotide of a hemipteran insect comprising SEQ ID NO:10; the complement of a coding polynucleotide of a hemipteran insect comprising SEQ ID NO:10; a coding polynucleotide of a hemipteran insect comprising SEQ ID NO:12; the complement of a coding polynucleotide of a hemipteran insect comprising SEQ ID NO:12; a coding polynucleotide of a hemipteran insect comprising SEQ ID NO:14; the complement of a coding polynucleotide of a hemipteran insect comprising SEQ ID NO:14; a coding polynucleotide of a hemipteran insect comprising SEQ ID NO:30; the complement of a coding polynucleotide of a hemipteran insect comprising SEQ ID NO:30; a coding polynucleotide of a hemipteran insect comprising SEQ ID NO:32; the complement of a coding polynucleotide of a hemipteran insect comprising SEQ ID NO:32; a coding polynucleotide of a hemipteran insect comprising SEQ ID NO:63; the complement of a coding polynucleotide of a hemipteran insect comprising SEQ ID NO:63; a coding polynucleotide of a hemipteran insect comprising SEQ ID NO:64; the complement of a coding polynucleotide of a hemipteran insect comprising SEQ ID NO:64; a coding polynucleotide of a hemipteran insect comprising SEQ ID NO:65; the complement of a coding polynucleotide of a hemipteran insect comprising SEQ ID NO:65; a coding polynucleotide of a hemipteran insect comprising SEQ ID NO:66; the complement of a coding polynucleotide of a hemipteran insect comprising SEQ ID NO:66; a coding polynucleotide of a hemipteran insect comprising SEQ ID NO:67; the complement of a coding polynucleotide of a hemipteran insect comprising SEQ ID NO:67; a fragment of at least 15 contiguous nucleotides of a coding polynucleotide of a hemipteran insect comprising SEQ ID NO:1; the complement of a fragment of at least 15 contiguous nucleotides of a coding polynucleotide of a hemipteran insect comprising SEQ ID NO:1; a fragment of at least 15 contiguous nucleotides of a coding polynucleotide of a hemipteran insect comprising SEQ ID NO:8; the complement of a fragment of at least 15 contiguous nucleotides of a coding polynucleotide of a hemipteran insect comprising SEQ ID NO:8; a fragment of at least 15 contiguous nucleotides of a coding polynucleotide of a hemipteran insect comprising SEQ ID NO:10; the complement of a fragment of at least 15 contiguous nucleotides of a coding polynucleotide of a hemipteran insect comprising SEQ ID NO:10; a fragment of at least 15 contiguous nucleotides of a coding polynucleotide of a hemipteran insect comprising SEQ ID NO:12; the complement of a fragment of at least 15 contiguous nucleotides of a coding polynucleotide of a hemipteran insect comprising SEQ ID NO:12; a fragment of at least 15 contiguous nucleotides of a coding polynucleotide of a hemipteran insect comprising SEQ ID NO:14; the complement of a fragment of at least 15 contiguous nucleotides of a coding polynucleotide of a hemipteran insect comprising SEQ ID NO:14; a fragment of at least 15 contiguous nucleotides of a coding polynucleotide of a hemipteran insect comprising SEQ ID NO:30; the complement of a fragment of at least 15 contiguous nucleotides of a coding polynucleotide of a hemipteran insect comprising SEQ ID NO:30; a fragment of at least 15 contiguous nucleotides of a coding polynucleotide of a hemipteran insect comprising SEQ ID NO:32; and the complement of a fragment of at least 15 contiguous nucleotides of a coding polynucleotide of a hemipteran insect comprising SEQ ID NO:32; a fragment of at least 15 contiguous nucleotides of a coding polynucleotide of a hemipteran insect comprising SEQ ID NO:63; and the complement of a fragment of at least 15 contiguous nucleotides of a coding polynucleotide of a hemipteran insect comprising SEQ ID NO:63; a fragment of at least 15 contiguous nucleotides of a coding polynucleotide of a hemipteran insect comprising SEQ ID NO:64; and the complement of a fragment of at least 15 contiguous nucleotides of a coding polynucleotide of a hemipteran insect comprising SEQ ID NO:64; a fragment of at least 15 contiguous nucleotides of a coding polynucleotide of a hemipteran insect comprising SEQ ID NO:65; and the complement of a fragment of at least 15 contiguous nucleotides of a coding polynucleotide of a hemipteran insect comprising SEQ ID NO:65; a fragment of at least 15 contiguous nucleotides of a coding polynucleotide of a hemipteran insect comprising SEQ ID NO:66; and the complement of a fragment of at least 15 contiguous nucleotides of a coding polynucleotide of a hemipteran insect comprising SEQ ID NO:66; a fragment of at least 15 contiguous nucleotides of a coding polynucleotide of a hemipteran insect comprising SEQ ID NO:67; and the complement of a fragment of at least 15 contiguous nucleotides of a coding polynucleotide of a hemipteran insect comprising SEQ ID NO:67. In certain embodiments, expression of a nucleic acid molecule that is at least about 80% identical (e.g., 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a hemipteran pest.

It is an important feature of some embodiments herein that the RNAi post-transcriptional inhibition system is able to tolerate sequence variations among target genes that might be expected due to genetic mutation, strain polymorphism, or evolutionary divergence. The introduced nucleic acid molecule may not need to be absolutely homologous to either a primary transcription product or a fully-processed mRNA of a target gene, so long as the introduced nucleic acid molecule is specifically hybridizable to either a primary transcription product or a fully-processed mRNA of the target gene. Moreover, the introduced nucleic acid molecule may not need to be full-length, relative to either a primary transcription product or a fully processed mRNA of the target gene.

Inhibition of a target gene using the iRNA technology of the present invention is sequence-specific; i.e., polynucleotides substantially homologous to the iRNA molecule(s) are targeted for genetic inhibition. In some embodiments, an RNA molecule comprising a polynucleotide with a nucleotide sequence that is identical to that of a portion of a target gene may be used for inhibition. In these and further embodiments, an RNA molecule comprising a polynucleotide with one or more insertion, deletion, and/or point mutations relative to a target polynucleotide may be used. In particular embodiments, an iRNA molecule and a portion of a target gene may share, for example, at least from about 80%, at least from about 81%, at least from about 82%, at least from about 83%, at least from about 84%, at least from about 85%, at least from about 86%, at least from about 87%, at least from about 88%, at least from about 89%, at least from about 90%, at least from about 91%, at least from about 92%, at least from about 93%, at least from about 94%, at least from about 95%, at least from about 96%, at least from about 97%, at least from about 98%, at least from about 99%, at least from about 100%, and 100% sequence identity. Alternatively, the duplex region of a dsRNA molecule may be specifically hybridizable with a portion of a target gene transcript. In specifically hybridizable molecules, a less than full length polynucleotide exhibiting a greater homology compensates for a longer, less homologous polynucleotide. The length of the polynucleotide of a duplex region of a dsRNA molecule that is identical to a portion of a target gene transcript may be at least about 25, 50, 100, 200, 300, 400, 500, or at least about 1000 bases. In some embodiments, a polynucleotide of greater than 20-100 nucleotides may be used; for example, a polynucleotide of 100-200 or 300-500 nucleotides may be used. In particular embodiments, a polynucleotide of greater than about 200-300 nucleotides may be used. In particular embodiments, a polynucleotide of greater than about 500-1000 nucleotides may be used, depending on the size of the target gene.

In certain embodiments, expression of a target gene in a hemipteran pest may be inhibited by at least 10%; at least 33%; at least 50%; or at least 80% within a cell of the pest, such that a significant inhibition takes place. Significant inhibition refers to inhibition over a threshold that results in a detectable phenotype (e.g., cessation of reproduction, feeding, development, etc.), or a detectable decrease in RNA and/or gene product corresponding to the target gene being inhibited. Although in certain embodiments of the invention inhibition occurs in substantially all cells of the pest, in other embodiments inhibition occurs only in a subset of cells expressing the target gene.

In some embodiments, transcriptional suppression is mediated by the presence in a cell of a dsRNA molecule exhibiting substantial sequence identity to a promoter DNA or the complement thereof to effect what is referred to as "promoter trans suppression." Gene suppression may be effective against target genes in a hemipteran pest that may ingest or contact such dsRNA molecules, for example, by ingesting or contacting plant material containing the dsRNA molecules. dsRNA molecules for use in promoter trans suppression may be specifically designed to inhibit or suppress the expression of one or more homologous or complementary polynucleotides in the cells of the hemipteran pest. Post-transcriptional gene suppression by antisense or sense oriented RNA to regulate gene expression in plant cells is disclosed in U.S. Pat. Nos. 5,107,065; 5,759,829; 5,283,184; and 5,231,020.

C. Expression of iRNA Molecules Provided to a Hemipteran Pest

Expression of iRNA molecules for RNAi-mediated gene inhibition in a hemipteran pest may be carried out in any one of many in vitro or in vivo formats. The iRNA molecules may then be provided to a hemipteran pest, for example, by contacting the iRNA molecules with the pest, or by causing the pest to ingest or otherwise internalize the iRNA molecules. Some embodiments of the invention include transformed host plants of a hemipteran pest, transformed plant cells, and progeny of transformed plants. The transformed plant cells and transformed plants may be engineered to express one or more of the iRNA molecules, for example, under the control of a heterologous promoter, to provide a pest-protective effect. Thus, when a transgenic plant or plant cell is consumed by a hemipteran pest during feeding, the pest may ingest iRNA molecules expressed in the transgenic plants or cells. The polynucleotides of the present invention may also be introduced into a wide variety of prokaryotic and eukaryotic microorganism hosts to produce iRNA molecules. The term "microorganism" includes prokaryotic and eukaryotic species, such as bacteria and fungi.

Modulation of gene expression may include partial or complete suppression of such expression. In another embodiment, a method for suppression of gene expression in a hemipteran pest comprises providing in the tissue of the host of the pest a gene-suppressive amount of at least one dsRNA molecule formed following transcription of a polynucleotide as described herein, at least one segment of which is complementary to an mRNA within the cells of the hemipteran pest. A dsRNA molecule, including its modified form such as an siRNA, miRNA, shRNA, or hpRNA molecule, ingested by a hemipteran pest in accordance with the invention may be at least from about 80%, 81%, 82%, 83%, 84%, 85%, 86%, 87%, 88%, 89%, 90%, 91%, 92%, 93%, 94%, 95%, 96%, 97%, 98%, 99%, or about 100% identical to an RNA molecule transcribed from a chromatin remodeling gene DNA molecule, for example, comprising a polynucleotide selected from the group consisting of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, and SEQ ID NO:67. Isolated and substantially purified nucleic acid molecules including, but not limited to, non-naturally occurring polynucleotides and recombinant DNA constructs for providing dsRNA molecules of the present invention are therefore provided, which suppress or inhibit the expression of an endogenous coding polynucleotide or a target coding polynucleotide in the hemipteran pest when introduced thereto.

Particular embodiments provide a delivery system for the delivery of iRNA molecules for the post-transcriptional inhibition of one or more target gene(s) in a hemipteran plant pest and control of a population of the plant pest. In some embodiments, the delivery system comprises ingestion of a host transgenic plant cell or contents of the host cell comprising RNA molecules transcribed in the host cell. In these and further embodiments, a transgenic plant cell or a transgenic plant is created that contains a recombinant DNA construct providing a stabilized dsRNA molecule of the invention. Transgenic plant cells and transgenic plants comprising nucleic acids encoding a particular iRNA molecule may be produced by employing recombinant DNA technologies (which basic technologies are well-known in the art) to construct a plant transformation vector comprising a polynucleotide encoding an iRNA molecule of the invention (e.g., a stabilized dsRNA molecule); to transform a plant cell or plant; and to generate the transgenic plant cell or the transgenic plant that contains the transcribed iRNA molecule.

To impart protection from hemipteran pests to a transgenic plant, a recombinant DNA molecule may, for example, be transcribed into an iRNA molecule, such as a dsRNA molecule, an siRNA molecule, a miRNA molecule, a shRNA molecule, or a hpRNA molecule. In some embodiments, an RNA molecule transcribed from a recombinant DNA molecule may form a dsRNA molecule within the tissues or fluids of the recombinant plant. Such a dsRNA molecule may be comprised in part of a polynucleotide that is identical to a corresponding polynucleotide transcribed from a DNA within a hemipteran pest of a type that may infest the host plant. Expression of a target gene within the hemipteran pest is suppressed by the dsRNA molecule, and the suppression of expression of the target gene in the hemipteran pest results in the transgenic plant being resistant to the pest. The modulatory effects of dsRNA molecules have been shown to be applicable to a variety of genes expressed in pests, including, for example, endogenous genes responsible for cell division, chromosomal remodeling, and cellular metabolism or cellular transformation, including housekeeping genes; transcription factors; molting-related genes; and other genes which encode polypeptides involved in cellular metabolism or normal growth and development.

For transcription from a transgene in vivo or an expression construct, a regulatory region (e.g., promoter, enhancer, silencer, and polyadenylation signal) may be used in some embodiments to transcribe the RNA strand (or strands). Therefore, in some embodiments, as set forth, supra, a polynucleotide for use in producing iRNA molecules may be operably linked to one or more promoter elements functional in a plant host cell. The promoter may be an endogenous promoter, normally resident in the host genome. The polynucleotide of the present invention, under the control of an operably linked promoter element, may further be flanked by additional elements that advantageously affect its transcription and/or the stability of a resulting transcript. Such elements may be located upstream of the operably linked promoter, downstream of the 3' end of the expression construct, and may occur both upstream of the promoter and downstream of the 3' end of the expression construct.

In embodiments, suppression of a target gene (e.g., a chromatin remodeling gene) results in a parental RNAi phenotype; a phenotype that is observable in progeny of the subject (e.g., a hemipteran pest) contacted with the iRNA molecule. In some embodiments, the pRNAi phenotype comprises the pest being rendered less able to produce viable offspring. In particular examples of pRNAi, a nucleic acid that initiates pRNAi does not increase the incidence of mortality in a population into which the nucleic acid is delivered. In other examples of pRNAi, a nucleic acid that initiates pRNAi also increases the incidence of mortality in a population into which the nucleic acid is delivered.

In some embodiments, a population of hemipteran pests is contacted with an iRNA molecule, thereby resulting in pRNAi, wherein the pests survive and mate but produce eggs that are less able to hatch viable progeny than eggs produced by pests of the same species that are not provided the nucleic acid(s). In some examples, such pests do not lay eggs or lay fewer eggs than what is observable in pests of the same species that are not contacted with the iRNA molecule. In some examples, the eggs oviposited by such pests do not hatch or hatch at a rate that is significantly less than what is observable in pests of the same species that are not contacted with the iRNA molecule. In some examples, the nymphs that hatch from eggs oviposited by such pests are not viable or are less viable than what is observable in pests of the same species that are not contacted with the iRNA molecule.

Transgenic crops that produce substances that provide protection from insect feeding are vulnerable to adaptation by the target insect pest population reducing the durability of the benefits of the insect protection substance(s). Traditionally, delays in insect pest adaptation to transgenic crops are achieved by (1) the planting of "refuges" (crops that do not contain the pesticidal substances, and therefore allow survival of insects that are susceptible to the pesticidal substance(s)); and/or (2) combining insecticidal substances with multiple modes of action against the target pests, so that individuals that are resistant to one mode of action are killed by a second mode of action.

In some examples, iRNA molecules (e.g., expressed from a transgene in a host plant) represent new modes of action for combining with *Bacillus thuringiensis* insecticidal protein technology (e.g., Cry1A, Cry2A, Cry3A, Cry11A, and Cry51A) and/or lethal RNAi technology in Insect Resistance Management gene pyramids to mitigate against the development of insect populations resistant to either of these control technologies.

Parental RNAi may result in some embodiments in a type of pest control that is different from the control obtained by lethal RNAi, and which may be combined with lethal RNAi to result in synergistic pest control. Thus, in particular embodiments, iRNA molecules for the post-transcriptional inhibition of one or more target gene(s) in a hemipteran plant pest can be combined with other iRNA molecules to provide redundant RNAi targeting and synergistic RNAi effects.

Parental RNAi (pRNAi) that causes egg mortality or loss of egg viability has the potential to bring further durability benefits to transgenic crops that use RNAi and other mechanisms for insect protection. pRNAi prevents exposed insects from producing progeny, and therefore from passing on to the next generation any alleles they carry that confer resistance to the pesticidal substance(s). pRNAi is particularly useful in extending the durability of insect-protected transgenic crops when it is combined with one or more additional pesticidal substances that provide protection from the same pest populations. Such additional pesticidal substances may in some embodiments include, for example, nymph-active dsRNA; insecticidal proteins (such as those derived from *Bacillus thuringiensis, Alcaligenes* spp., *Pseudomonas* spp., or other organisms); and other insecticidal substances. This benefit arises because insects that are resistant to the pesticidal substances occur as a higher proportion of the population in the transgenic crop than in the refuge crop. If a ratio of resistance alleles to susceptible alleles that are passed on to the next generation is lower in the presence of pRNAi than in the absence of pRNAi, the evolution of resistance will be delayed.

For example, pRNAi may not reduce the number of individuals in a first pest generation that are inflicting damage on a plant expressing an iRNA molecule. However, the ability of such pests to sustain an infestation through subsequent generations may be reduced. Conversely, lethal RNAi may kill pests that already are infesting the plant. When pRNAi is combined with lethal RNAi, pests that are contacted with a parental iRNA molecule may breed with pests from outside the system that have not been contacted with the iRNA, however, the progeny of such a mating may be non-viable or less viable, and thus may be unable to infest the plant. At the same time, pests that are contacted with a lethal iRNA molecule may be directly affected. The combination of these two effects may be synergistic; i.e., the combined pRNAi and lethal RNAi effect may be greater than the sum of the pRNAi and lethal RNAi effects independently. pRNAi may be combined with lethal RNAi, for example, by providing a plant that expresses both lethal and parental iRNA molecules; by providing in the same location a first plant that expresses lethal iRNA molecules and a second plant that expresses parental iRNA molecules; and/or by contacting female and/or male pests with the pRNAi molecule, and subsequently releasing the contacted pests into the plant environment, such that they can mate unproductively with the plant pests.

Some embodiments provide methods for reducing the damage to a host plant (e.g., a soybean plant) caused by a hemipteran pest that feeds on the plant, wherein the method comprises providing in the host plant a transformed plant cell expressing at least one nucleic acid molecule of the invention, wherein the nucleic acid molecule(s) functions upon being taken up by the pest(s) to inhibit the expression of a target polynucleotide within the pest(s), which inhibition of expression results in reduced reproduction, for example, in addition to mortality and/or reduced growth of the pest(s), thereby reducing the damage to the host plant caused by the pest. In some embodiments, the nucleic acid molecule(s) comprise dsRNA molecules. In these and further embodiments, the nucleic acid molecule(s) comprise dsRNA molecules that each comprise more than one polynucleotide that is specifically hybridizable to a nucleic acid molecule expressed in a hemipteran pest cell. In some embodiments, the nucleic acid molecule(s) consist of one polynucleotide that is specifically hybridizable to a nucleic acid molecule expressed in a hemipteran pest cell.

In some embodiments, a method for increasing the yield of a corn crop is provided, wherein the method comprises introducing into a corn plant at least one nucleic acid molecule of the invention; and cultivating the corn plant to allow the expression of an iRNA molecule comprising the nucleic acid, wherein expression of an iRNA molecule comprising the nucleic acid inhibits hemipteran pest damage and/or growth, thereby reducing or eliminating a loss of yield due to hemipteran pest infestation. In some embodiments, the iRNA molecule is a dsRNA molecule. In these and further embodiments, the nucleic acid molecule(s) comprise dsRNA molecules that each comprise more than one polynucleotide that is specifically hybridizable to a nucleic acid molecule expressed in a hemipteran pest cell. In some embodiments, the nucleic acid molecule(s) consists of one polynucleotide that is specifically hybridizable to a nucleic acid molecule expressed in a hemipteran pest cell.

In some embodiments, a method for increasing the yield of a plant crop is provided, wherein the method comprises introducing into a female hemipteran pest (e.g., by injection, by ingestion, by spraying, and by expression from a DNA) at least one nucleic acid molecule of the invention; and releasing the female pest into the crop, wherein mating pairs including the female pest are unable or less able to produce viable offspring, thereby reducing or eliminating a loss of yield due to hemipteran pest infestation. In particular embodiments, such a method provides control of subsequent generations of the pest. In similar embodiments, the method comprises introducing the nucleic acid molecule of the invention into a male hemipteran pest, and releasing the male pest into the crop (e.g., wherein pRNAi male pests produce less sperm than untreated controls). In some embodiments, the nucleic acid molecule is a DNA molecule that is expressed to produce an iRNA molecule. In some embodiments, the nucleic acid molecule is a dsRNA molecule. In these and further embodiments, the nucleic acid molecule(s) comprise dsRNA molecules that each comprise more than one polynucleotide that is specifically hybridizable to a nucleic acid molecule expressed in a hemipteran pest cell. In some embodiments, the nucleic acid molecule(s) consists of one polynucleotide that is specifically hybridizable to a nucleic acid molecule expressed in a hemipteran pest cell.

In some embodiments, a method for modulating the expression of a target gene in a hemipteran pest is provided, the method comprising: transforming a plant cell with a vector comprising a polynucleotide encoding at least one iRNA molecule of the invention, wherein the polynucleotide is operatively-linked to a promoter and a transcription termination element; culturing the transformed plant cell under conditions sufficient to allow for development of a plant cell culture including a plurality of transformed plant cells; selecting for transformed plant cells that have integrated the polynucleotide into their genomes; screening the transformed plant cells for expression of an iRNA molecule encoded by the integrated polynucleotide; selecting a transgenic plant cell that expresses the iRNA molecule; and feeding the selected transgenic plant cell to the hemipteran pest. Plants may also be regenerated from transformed plant cells that express an iRNA molecule encoded by the integrated nucleic acid molecule. In some embodiments, the iRNA molecule is a dsRNA molecule. In these and further embodiments, the nucleic acid molecule(s) comprise dsRNA molecules that each comprise more than one polynucleotide that is specifically hybridizable to a nucleic acid molecule expressed in a hemipteran pest cell. In some embodiments, the nucleic acid molecule(s) consists of one polynucleotide that is specifically hybridizable to a nucleic acid molecule expressed in a hemipteran pest cell.

iRNA molecules of the invention can be incorporated within the seeds of a plant species (e.g., soybean), either as a product of expression from a recombinant gene incorporated into a genome of the plant cells, or as incorporated into a coating or seed treatment that is applied to the seed before planting. A plant cell comprising a recombinant gene is considered to be a transgenic event. Also included in embodiments of the invention are delivery systems for the delivery of iRNA molecules to hemipteran pests. For example, the iRNA molecules of the invention may be directly introduced into the cells of a pest(s). Methods for introduction may include direct mixing of iRNA into the diet of the hemipteran pest (e.g., by mixing with plant tissue from a host for the pest), as well as application of compositions comprising iRNA molecules of the invention to host plant tissue. For example, iRNA molecules may be sprayed onto a plant surface. Alternatively, an iRNA molecule may be expressed by a microorganism, and the microorganism may be applied onto the plant surface, or introduced into a root or stem by a physical means such as an injection. As discussed, supra, a transgenic plant may also be genetically engineered to express at least one iRNA molecule in an amount sufficient to kill the hemipteran pests known to infest the plant. iRNA molecules produced by chemical or enzymatic synthesis may also be formulated in a manner consistent with common agricultural practices, and used as spray-on or bait products for controlling plant damage by a hemipteran pest. The formulations may include the appropriate adjuvants (e.g., stickers and wetters) required for efficient foliar coverage, as well as UV protectants to protect iRNA molecules (e.g., dsRNA molecules) from UV damage. Such additives are commonly used in the bioinsecticide industry, and are well known to those skilled in the art. Such applications may be combined with other spray-on insecticide applications (biologically based or otherwise) to enhance plant protection from hemipteran pests.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following Examples are provided to illustrate certain particular features and/or aspects. These Examples should not be construed to limit the disclosure to the particular features or aspects described.

EXAMPLES

Example 1: Identification of Candidate Target Genes

RNAi Target Selection.

In one example, six stages of BSB development were selected for mRNA library preparation. Additional samples were prepared using BSB midgut and salivary glands. Brown stink bug midguts and salivary glands were dissected from 10 and 25 mixed sex adults respectively under a dissecting microscope on a chilled clean glass slide and immediately frozen on dry ice. Total RNA was extracted from insects frozen at −70° C. and homogenized in 10 volumes of Lysis/Binding buffer in Lysing MATRIX A 2 mL tubes (MP BIOMEDICALS, Santa Ana, Calif.) on a FastPrep®-24 Instrument (MP BIOMEDICALS). Total mRNA was extracted using a mirVana™ miRNA Isolation Kit (AMBION; INVITROGEN) according to the manufacturer's protocol. RNA sequencing using an Illumina® HiSeq™ system (San Diego, Calif.) provided candidate target gene sequences for use in RNAi insect control technology. HiSeq™ generated a total of about 378 million reads for the six samples. The reads were assembled individually for each sample using TRINITY assembler software (Grabherr et al. (2011) Nature Biotech. 29:644-652). The assembled transcripts were combined to generate a pooled transcriptome. This BSB pooled transcriptome contains 378,457 sequences.

BSB_Brahma, mi-2, iswi-1, iswi-2, chd1, ino80, and Domino Ortholog Identification.

tBLASTn searches of the BSB pooled transcriptome were performed using sequences of the *Drosophila* BRAHMA (brm-PA, GENBANK Accession No. NP_536745 and NP_536746), MI-2 (Mi-2-PA, GENBANK Accession No. NP_001014591.1, NP_001163476.1, NP_001262078.1, NP_649154.2, and NP_001014591.1), ISWI (Iswi-PA, GENBANK Accession No. NP_523719, NP_725203, and NP_725204), and CHD1 (Chd1-PA, GENBANK Accession No. NP_477197 and NP_001245851) proteins as queries. BSB brahma (SEQ ID NO:1; SEQ ID NO:63), mi-2 (SEQ ID NO:8; SEQ ID NO:64), iswi-1 (SEQ ID NO:10; SEQ ID NO:65), iswi-2 (SEQ ID NO:12; SEQ ID NO:66), chd1 (SEQ ID NO:14; SEQ ID NO:67), ino80 (SEQ ID NO:30), and domino (SEQ ID NO:32) transcripts were identified as BSB candidate target genes.

BSB homology info. The BSB brahma (SEQ ID NO:1) is somewhat (72% identity) related to a fragment of a sequence from *Ciona intestinalis* (GENBANK Accession No. AK116913.1). The closest homolog of the BSB BRAHMA amino acid sequence (SEQ ID NO:2) is a *Camponotus floridanus* protein having GENBANK Accession No. EFN67856.1 (79% similar; 70% identical over the homology region). The BSB mi-2 (SEQ ID NO:8) is somewhat (76% identity) related to a fragment of a sequence from *Acyrthosiphon pisum* (GENBANK Accession No. XM_008186702.1). The closest homolog of the BSB MI-2 amino acid sequence (SEQ ID NO:9) is a *Bombus impatiens* protein having GENBANK Accession No. XP_003493868.1 (79% similar; 71% identical over the homology region). The BSB iswi-1 (SEQ ID NO:10) is somewhat (75% identity) related to a fragment of a sequence from *Bombus impatiens* (GENBANK Accession No. XM_003486758.1). The closest homologs of the BSB ISWI-1 amino acid sequence (SEQ ID NO:11) are a *Megachile rotundata* and *Apis dorsata* proteins having GENBANK Accession Nos. XP_003708682.1 and XP_006615660.1 respectively (91% similar; 84% identical over the homology region). The BSB iswi-2 (SEQ ID NO:12) is somewhat (76% identity) related to a fragment of a sequence from *Latimeria chalumnaw* (GENBANK Accession No. XM_005994941.1). The closest homolog of the BSB ISWI-2 amino acid sequence (SEQ ID NO:13) is a *Cerapachys biroi* protein having GENBANK Accession No. EZA60706.1 (93% similar; 84% identical over the homology region). The BSB chd1 (SEQ ID NO:14) is somewhat (77% identity) related to a fragment of a sequence from *Apis mellifera* (GENBANK Accession No. XM_006565933.1). The closest homolog of the BSB CHD1 amino acid sequence (SEQ ID NO:15) is a *Riptortus pedestris* protein having GENBANK Accession No. BAN20905.1 (94% similar; 88% identical over the homology region). The BSB ino80 (SEQ ID NO:30) is somewhat (79% identity) related to a fragment of a sequence from *Hydra magnipapillata* (GENBANK Accession No. XM_002164516.2). The closest homolog of the BSB INO80 amino acid sequence (SEQ ID NO:31) is a *Zootermopsis nevadensis* protein having GENBANK Accession No. KDR11347.1 (74% similar; 64% identical over the homology region). The BSB domino (SEQ ID NO:32) is somewhat (80% identity) related to a fragment of a sequence from *Apis florea* (GENBANK Accession No. XR_143356.1). The closest homolog of the BSB DOMINO amino acid sequence (SEQ ID NO:33) is a *Nasonia vitripennis* protein having GENBANK Accession No. XP_008210745.1 (71% similar; 58% identical over the homology region).

These genes encode SNF2-type chromatin remodeler proteins, which correspond to a subunit of the chromatin remodeler complexes that play global roles in mobilizing nucleosomes. See, for example, Brizuela et al. (supra); Kal et al. (2000) Genes Devel. 14:1058-71; and Tamkun et al. (1992) Cell 68:561-72. Although they share a SNF2-Helicase domain, most chromatin remodelers within each species have non-redundant functions that are conferred by the additional domains they comprise. These characteristics present chromatin remodeling ATPases as attractive targets for multi-generational/parental RNAi.

Figure 2:
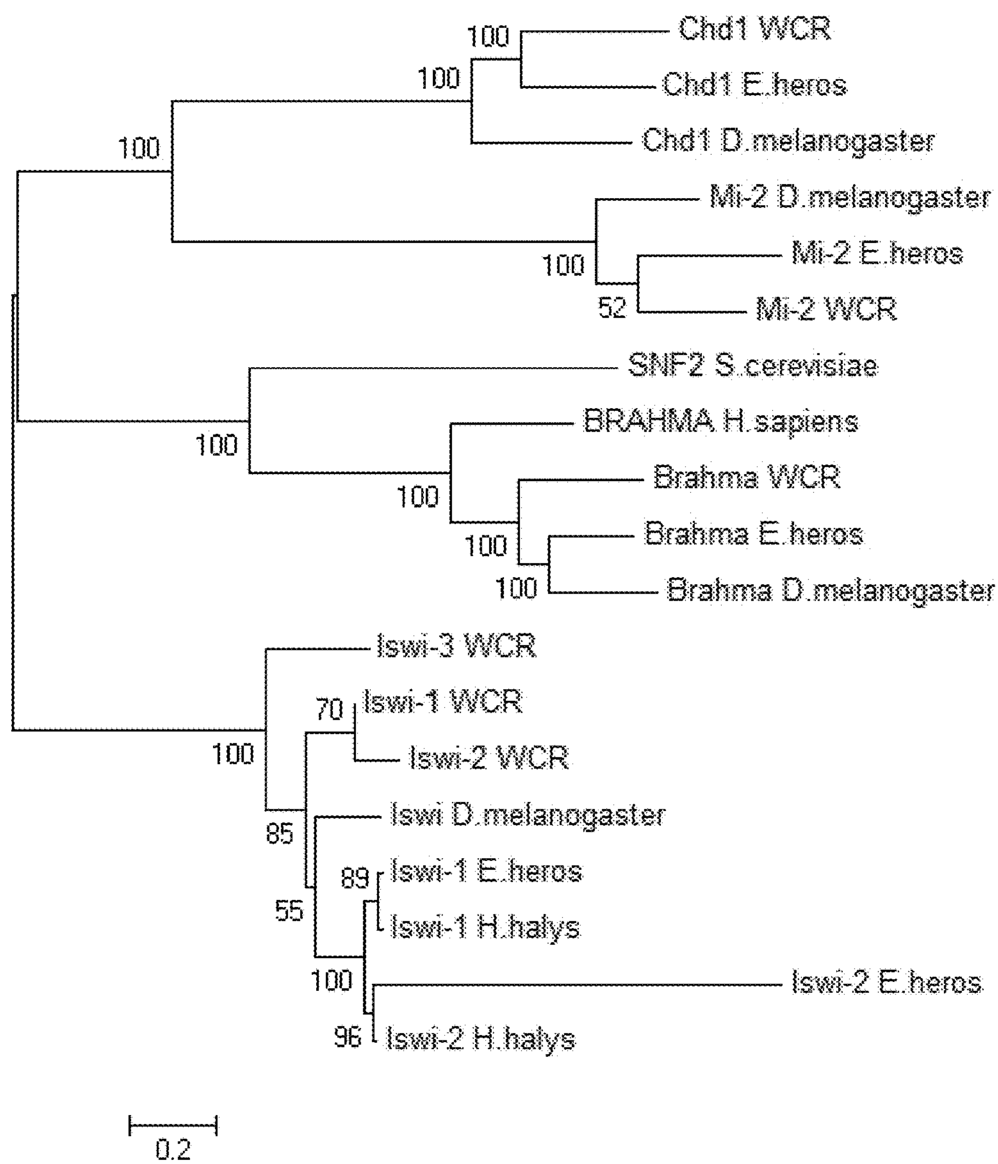
FIG. 2 includes a phylogenetic tree representation of the sequence alignment of ATP-dependent remodelers from *D. v. virgifera* (WCR), *E. heros*, and *Drosophila melanogaster*. For comparison, the tree also contains human BRAHMA, *Saccharomyces cerevisiae* SNF2, and Iswi homologs from the brown marmorated stink bug, *Halyomorpha halys*. The alignment was performed using MUSCLE (100 iterations) in MEGA 6.06. Bootstrap values (MEGA) support the topology of the ATP-dependent remodeler family branches on the maximum likelihood phylogeny tree.
Figure 3A:
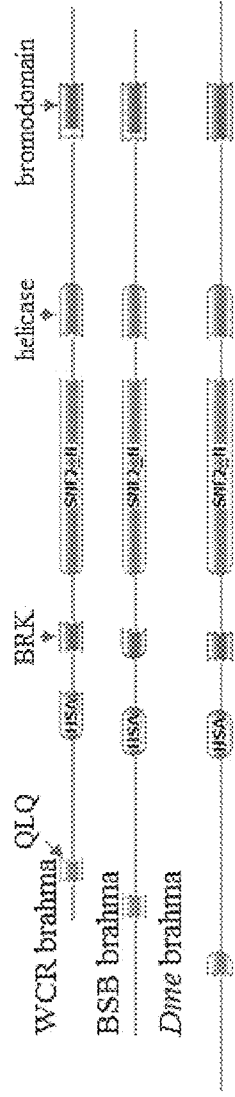
FIGS. 3A-3E includes a representations of the domain architecture of ATP-dependent chromatin remodeling enzymes of *Diabrotica virgifera virgifera* (WCR), *Euschistus heros* (BSB) and *Drosophila melanogaster* (Dme). The graphical representation is of Pfam output, with domains shaded and labeled. The proteins are organized by families and aligned with respect to SNF2 domain. "Squiggly" lines represent truncation/discontinuity for representation purposes.

The SWI2/SNF2 (mating type switch/sucrose non-fermenting) family of the ATP-dependent remodeling enzymes contains a bromodomain, which binds acetylated histones. While yeasts and vertebrates contain several SWI2/SNF2 proteins, only one SWI2/SNF2 protein, BRAHMA, has been identified in *Drosophila*. BRAHMA is well-conserved, and yet distinct, from other insect SNF2-containing proteins, with the putative orthologs clustering closely on a phylogenetic tree. FIG. 2. The human BRAHMA (BRM) as well as the *Saccharomyces cerevisiae* SNF2 protein cluster together with insect BRAHMAs. Furthermore, the orthologs of the *Drosophila* BRAHMA maintain overall protein domain conservation including the SNF2 ATPase/helicase, the bromodomain as well as additional domains: conserved Gln, Leu, Gln motif domain (QLQ), DNA-binding HSA domain, and BRK (brahma and kismet) domain. FIG. 3A.

BRAHMA is known to incorporate into BAP (Brahma Associated Proteins) and PBAP (Polybromo-associated BAP) chromatin remodeling complexes. The loss of *Drosophila* brahma impairs overall transcription by RNA polymerase II (Pol II), suggesting a broad function for the BRAHMA complexes. In *Drosophila*, the maternal contribution of brahma is needed for early embryogenesis, while the zygotic brahma expression is necessary for late embryonic development. In addition to embryogenesis, *Drosophila* brahma is involved in gametogenesis. Brahma RNAi-treated female BSB produce no viable eggs. Table 5. Further, BSB females whose brahma was depleted via RNAi lay no eggs altogether. Tables 3 and 4.

The ISWI (Imitation SWI/imitation switch) family is defined by histone-biding domain that comprises the HAND, SANT, and SLIDE domains in a HAND-SANT-SLIDE architecture (also annotated as HAND-SLIDE). In *Drosophila*, the ISWI family of ATP-dependent remodeling enzymes has only one member, ISWI. The *Drosophila* ISWI can confer multiple functions by integrating into various complexes that include ATP-dependent chromatin assembly and remodeling factor (ACF), nucleosome remodeling factor (NURF), and chromatin accessibility complex (CHRAC). Loss of ISWI in *Drosophila* results in dramatic chromosome condensation defects.

Figure 3B:
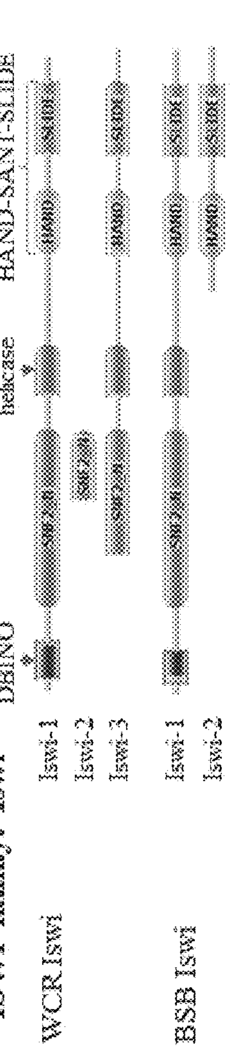

BSB express at least two iswi homologs (SEQ ID NO:10 and SEQ ID NO:12 (with SEQ ID NO:12 being partial sequence). The complete BSB ISWI protein contains the SNF2 ATPase/helicase, HAND-SANT-SLIDE (identified as HAND and SLIDE by Pfam) and DNA-binding domain (DBINO). FIG. 3B. The identified ISWI-2 protein from BSB comprises only HAND-SANT-SLIDE domains. FIG. 3B. The contig that comprises iswi-2 (SEQ ID NO:12) is 1316 nucleotides long; based on the alignment with known *Drosophila* ISWI protein this contig does not contain the first half of the ISWI protein sequence. Therefore, it is reasonable to assume that the current BSB transcriptome assembly contains an incomplete sequence of iswi-2 transcript.

The parental RNAi applications of both BSB_Iswi-1 and BSB_Iswi-2 result in both egg laying and egg hatch defects. Tables 4 and 5.

Figure 3C:
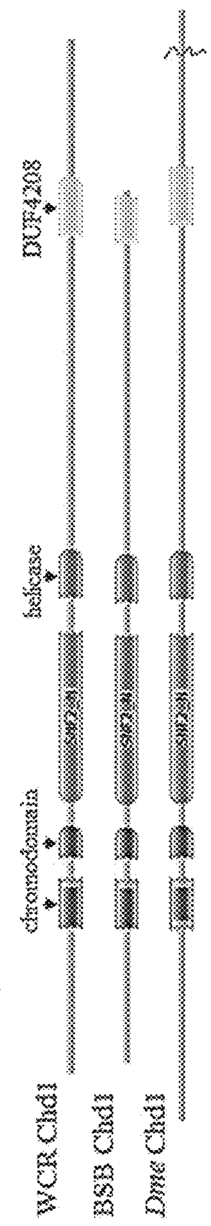

Proteins of the CHD (chromodomain helicase DNA-binding) family of ATP-dependent remodeling enzymes contain two amino-terminal chromodomains [chromatin organization modifier]. FIG. 3C. The *Drosophila* CHD proteins include CHD1, MI-2, CHD3, and KISMET. The CHD family is further subdivided into three subfamilies, herein referred to as subfamilies I, II, and III. The *Drosophila* CHD1 belongs to CHD subfamily I, which has a C-terminal DNA-binding domain. FIG. 1C (DUF4208). In *Drosophila*, CHD1 protein shows similar distribution patterns to BRAHMA, yet chd1 mutant flies are viable. Interestingly, the *Drosophila* chd1 is needed for gametogenesis. BSB females subjected to chd1 RNAi show a significant decrease in both egg production and hatch rates. Tables 4 and 5.

Figure 3D:
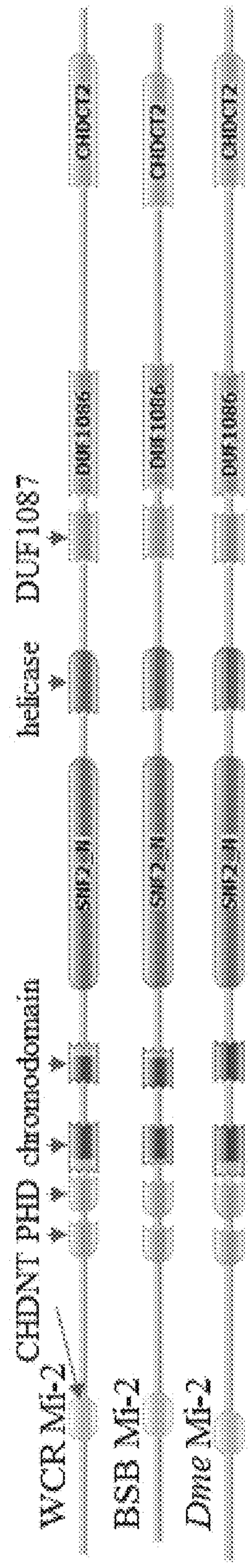

MI-2 and CHD3 belong to subfamily II. Enzymes of the CHD subfamily II have no DNA-binding domain, but have Zn-finger-like domains called PHD (plant homeodomain) fingers. The BSB ortholog of MI-2 mirrors the *Drosophila* domain arrangement, and includes the SNF2 ATPase/helicase domain, the double chromodomain, PHD fingers, and CHDNT domain that is associated with PHD finger-containing chromodomain helicases, as well as other conserved domains of unknown functions, DUF1087 and DUF1086. FIG. 3D. The *Drosophila* MI-2 is known to associate with the NuRD (Nucleosome Remodeling Deacetylase) and dMec (*Drosophila* MEP-1 containing complex) complexes. Maternal expression of mi-2 is necessary for gametogenesis. BSB females whose mi-2 was depleted via RNAi lay very few eggs. Table 4.

Figure 3E:
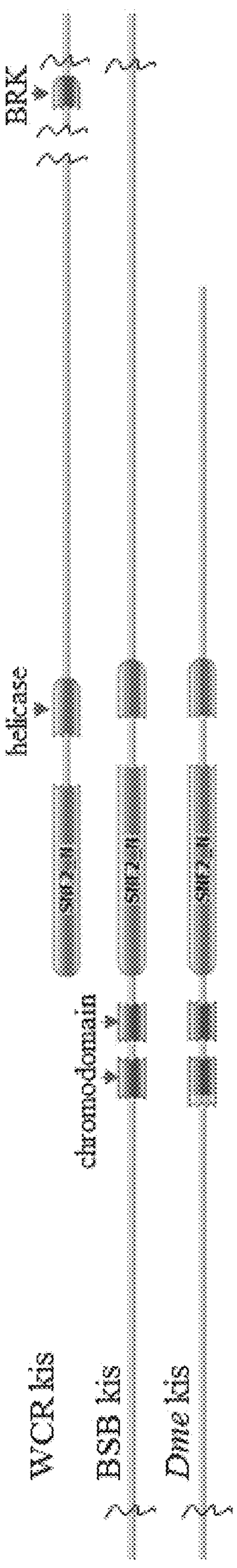

The third subfamily of CHD proteins is represented by KISMET in *Drosophila*; in humans this subfamily comprises CHD5-9. Like other CHD proteins, KISMET contains an SNF2 domain and a chromodomain. FIG. 3E. Unlike other CHD subfamilies, KISMET has characteristics of both CHD and SWI2/SNF2 proteins, in that it has a BRK domain that is common to both BRAHMA and KISMET. Although BRK is a well-established feature of *Drosophila* KISMET, a standard Pfam analysis did not identify this domain in BSB. FIG. 3E. Loss of either maternal or zygotic function of kismet causes defects during *Drosophila* embryogenesis and the insects die during early larval stages, while oogenesis is unaffected.

Example 2: Degenerate Sequences Comprising Chromatin Remodelers

Brahma and its homologs, as well as mi-2 and other chromatin remodelers and their orthologs, share the same functional domains and sequence-level conservation. RNAi target sites were designed within the conserved SNF2 family N-terminal and Helicase C-terminal domains (here referred to as SNF2-Helicase) that are common to all chromatin remodelers, as well as chromatin binding and other functional domains that are conserved within each family (including bromodomain, chromodomain, and HAND-SLIDE domains). RNAi target sequences that are common to *Diabrotica virgifera virgifera, Euschistus heros, Tribolium castaneum*, and *Drosophila melanogaster* were designed. The DNA nucleotides and RNAi nucleotides are listed according to the standard IUPAC code:

A=Adenine
C=Cytosine
G=Guanine
T=Thymine
R=A or G
Y=C or T
S=G or C
W=A or T
K=G or T
M=A or C
B=C or G or T
D=A or G or T
H=A or C or T
V=A or C or G
N=A or C or G or T dsRNA encoding sequences targeting SNF2-Helicase regions (SEQ ID NOs:34-37) and chromatin remodeling domains (SEQ ID NOs:38-41) were designed by aligning the amino acid sequences for each target protein from four species, *Diabrotica v. virgifera, E. heros, Tribolium castaneum*, and *Drosophila melanogaster*, using Vector NTI Align X (Invitrogen, Grand Island, N.Y.). Highly homologous regions of the amino acid sequence containing at least 8 amino acids within the SNF2 domain or chromatin remodeling domain specific to each target protein were selected. The corresponding nucleotide sequence for each species from each target was then aligned also using the Align X program. Where there was a misalignment across the four species the nucleotides were replaced with nucleotides as shown above. Finally, the sequence was aligned against the nucleotide sequence from *Apis mellifera* to determine if the sequence would also target that species. If the sequence could also target the protein from *A. mellifera* either new regions were chosen or the sequence was shortened to at least 21 bases which did not target *A. mellifera* proteins.

Example 3: Preparation of RNAi Molecules

Template Preparation and dsRNA Synthesis.

cDNA was prepared from total BSB RNA extracted from a single young adult insect (about 90 mg) using TRIzol® Reagent (LIFE TECHNOLOGIES, Grand Island, N.Y.). The insect was homogenized at room temperature in a 1.5 mL microcentrifuge tube with 200 μL of TRIzol® using a pellet pestle (FISHERBRAND, Grand Island, N.Y.) and Pestle Motor Mixer (COLE-PARMER, Vernon Hills, Ill.). Following homogenization, an additional 800 μL of TRIzol® was added, the homogenate was vortexed, and then incubated at room temperature for five minutes. Cell debris was removed by centrifugation and the supernatant was transferred to a new tube. Following manufacturer-recommended TRIzol® extraction protocol for 1 mL of TRIzol®, the RNA pellet was dried at room temperature and resuspended in 200 μL Tris Buffer from a GFX PCR DNA AND GEL EXTRACTION KIT (Illustra™; GE HEALTHCARE LIFE SCIENCES, Pittsburgh, Pa.) using Elution Buffer Type 4 (i.e. 10 mM Tris-HCl pH8.0). RNA concentration was determined using a NANODROP™ 8000 spectrophotometer (THERMO SCIENTIFIC, Wilmington, Del.).

cDNA was reverse-transcribed from 5 μg BSB total RNA template and oligo dT primer using a SUPERSCRIPT III FIRST-STRAND SYNTHESIS SYSTEM™ for RT-PCR (INVITROGEN), following the supplier's recommended protocol. The final volume of the transcription reaction was brought to 100 μL with nuclease-free water.

Primers were used to amplify DNA templates for dsRNA transcription. Table 1. The DNA templates were amplified using "touch-down" PCR (annealing temperature lowered from 60° C. to 50° C. in a 1° C./cycle decrease) with 1 μL cDNA (above) as the template. Fragments comprising a 499 bp segment of brahma (i.e., BSB_brm-1; SEQ ID NO:3), a 496 bp segment of mi-2 (i.e., BSB_mi-2-1; SEQ ID NO:16), a 481 bp segment of iswi-1 (i.e., BSB_iswi-1-1; SEQ ID NO:17), a 490 bp segment of iswi-2 (i.e., BSB_iswi-2-1; SEQ ID NO:18), and a 496 bp segment of chd1 (i.e., BSB_chd1-1; SEQ ID NO:19) were generated during 35 cycles of PCR. A 301 pb template for dsRNA termed YFPv2 (SEQ ID NO:5) was synthesized using primers YFPv2_F (SEQ ID NO:6) and YFPv2_R (SEQ ID NO:7). The BSB-specific and YFPv2 primers contained a T7 phage promoter sequence (SEQ ID NO:4) at their 5' ends, enabling the use of the aforementioned BSB DNA fragments for dsRNA transcription.

TABLE 1

Primer pairs used to amplify DNA templates for dsRNA transcription.

Figure 1B:
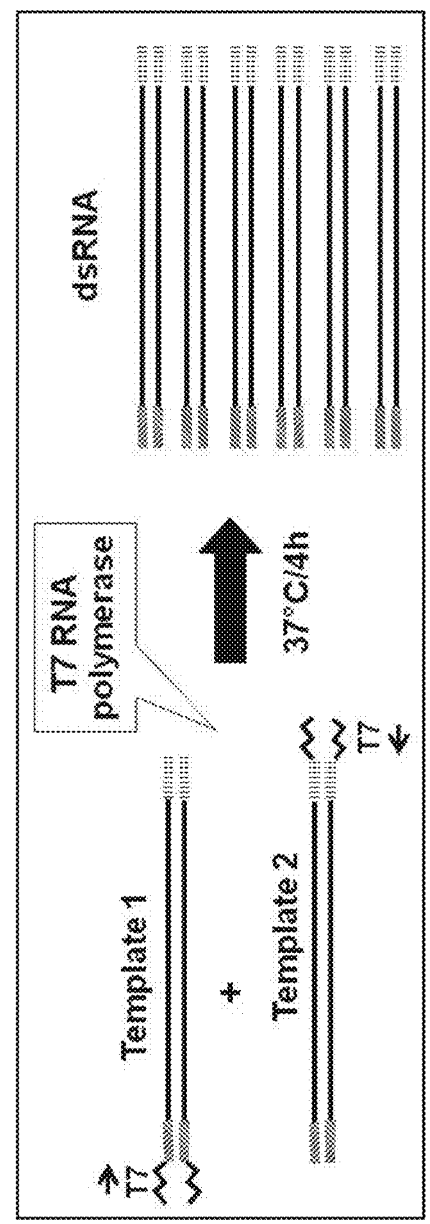

| | Gene (Region) | Primer_ID | Sequence |
|---|---|---|---|
| Pair 1 | Brahma | BSB_brm-1-F | TTAATACGACTCACTATAGGGAGAGATGATGAAGA AGATGCAAGTAC (SEQ ID NO: 20) |
| | | BSB_brm-1-R | TTAATACGACTCACTATAGGGAGACTCCACTCCCT CGGGTC (SEQ ID NO: 21) |
| Pair 2 | mi-2 | BSB_Mi-2-1-F | TTAATACGACTCACTATAGGGAGAGACTACCTCGA GGGTGAAGG (SEQ ID NO: 22) |
| | | BSB_Mi-2-1-R | TTAATACGACTCACTATAGGGAGAGTAATTCTTCA ACAGCTTTATCGTC (SEQ ID NO: 23) |
| Pair 3 | iswi-1 | BSB_Iswi-1-1-F | TTAATACGACTCACTATAGGGAGACAAAAAT TGAA ACTGACCGTTCTAG (SEQ ID NO: 24) |
| | | BSB_Iswi-1-1-R | TTAATACGACTCACTATAGGGAGAGCTAATGTTGA TTTTGGTACGATG (SEQ ID NO: 25) |
| Pair 4 | iswi-2 | BSB_Iswi-2-1-F | TTAATACGACTCACTATAGGGAGAGTTCAAGATTT CCAATTTTTCCCAC (SEQ ID NO: 26) |
| | | BSB_Iswi-2-1-R | TTAATACGACTCACTATAGGGAGAGAAACGGTGCT CTATATCGACTC (SEQ ID NO: 27) |
| Pair 5 | chd1 | BSB_Chd1-1-F | TTAATACGACTCACTATAGGGAGACAGCTGGAACC ATATATTCTACGAC (SEQ ID NO: 28) |
| | | BSB_Chd1-1-R | TTAATACGACTCACTATAGGGAGAGTGAATTTTCA GCATTGAAATGATCG (SEQ ID NO: 29) |
| Pair 6 | YFPv2 | YFPv2_F | TTAATACGACTCACTATAGGGAGAGCATCTGGAGC ACTTCTCTTTCA (SEQ ID NO: 6) |
| | | YFPv2_R | TTAATACGACTCACTATAGGGAGACCATCTCCTTC AAAGGTGATTG (SEQ ID NO: 7) |

dsRNAs were synthesized using 2 μL of PCR product (above) as the template with a MEGAscript™ RNAi kit (AMBION) or HiScribe® T7 In Vitro Transcription Kit, used according to the manufacturer's instructions. See FIG. 1B. dsRNA was quantified on a NANODROP™ 8000 spectrophotometer and diluted to 1 μg/μL in nuclease-free 0.1×TE buffer (1 mM Tris HCL, 0.1 mM EDTA, pH 7.4).

Example 4: Brahma dsRNA Injection of 2nd Instar *Euschistus heros* Nymphs

Insect Rearing.

Neotropical Brown Stink Bugs (BSB; *Euschistus heros*) were reared in a 27° C. incubator, at 65% relative humidity, with 16:8 hour light:dark cycle. One gram of eggs collected over 2-3 days was seeded in 5 L containers with filter paper discs at the bottom; the containers were covered with #18 mesh for ventilation. Each rearing container yielded approximately 300-400 adult BSB. At all stages, the insects were fed fresh green beans three times per week and a sachet of seed mixture containing sunflower seeds, soybeans, and peanuts (3:1:1 by weight ratio) was replaced once a week. Water was supplemented in vials with cotton plugs as wicks. After the initial two weeks, insects were transferred to a new container once a week.

BSB Artificial Diet.

BSB artificial diet was prepared as follows and used within two weeks of preparation. Lyophilized green beans were blended to a fine powder in a MAGIC BULLET® blender while raw (organic) peanuts were blended in a separate MAGIC BULLET® blender. Blended dry ingredients were combined (weight percentages: green beans, 35%; peanuts, 35%; sucrose, 5%; Vitamin complex (e.g. Vanderzant Vitamin Mixture for insects, SIGMA-ALDRICH), 0.9%); in a large MAGIC BULLET® blender, which was capped and shaken well to mix the ingredients. The mixed dry ingredients were then added to a mixing bowl. In a separate container, water and benomyl anti-fungal agent (50 ppm; 25 μL 20,000 ppm solution/50 mL diet solution) were mixed well and then added to the dry ingredient mixture. All ingredients were mixed by hand until the solution was fully blended. The diet was shaped into desired sizes, wrapped loosely in aluminum foil, heated for 4 hours at 60° C., then cooled and stored at 4° C.

Injection of dsRNA into BSB Hemocoel.

BSB were reared on a green bean and seed diet, as the colony described above, in a 27° C. incubator at 65% relative humidity and 16:8 hour light:dark photoperiod. Second instar nymphs (each weighing 1 to 1.5 mg) were gently handled with a small brush to prevent injury and were placed in a Petri dish on ice to chill and immobilize the insects. Each insect was injected with 55.2 nL of a 500 ng/μL dsRNA solution (i.e., 27.6 ng dsRNA; dosage of 18.4 to 27.6 μg/g body weight). Injections were performed using a NANOJECT™ II injector (DRUMMOND SCIENTIFIC, Broomhall, Pa.) equipped with an injection needle pulled from a Drummond 3.5 inch #3-000-203-G/X glass capillary. The needle tip was broken and the capillary was backfilled with light mineral oil, then filled with 2 to 3 μL dsRNA. dsRNA was injected into the abdomen of the nymphs (10 insects injected per dsRNA per trial), and the trials were repeated on three different days. Injected insects (5 per well) were transferred into 32-well trays (Bio-RT-32 Rearing Tray; BIO-SERV, Frenchtown, N.J.) containing a pellet of artificial BSB diet and covered with Pull-N-Peel™ tabs (BIO-CV-4; BIO-SERV). Moisture was supplied by means of 1.25 mL water in a 1.5 mL microcentrifuge tube with a cotton wick. The trays were incubated at 26.5° C., 60% humidity and 16:8 hour light:dark photoperiod. Viability counts and weights were taken on day 7 after the injections.

Injection of dsRNA that Targets Brahma mRNA in BSB $2^{nd}$ Instar Nymphs.

dsRNA that targets segment of YFP coding region, YFPv2, was used as a negative control in BSB injection experiments. As summarized in Table 2, at least ten $2^{nd}$ instar BSB nymphs (1-1.5 mg each) were injected into the hemoceol with 55.2 nL BSB_brm-1 (500 ng/μL) for an approximate final concentration of 18.4-27.6 μg dsRNA/g insect. Percent mortality was scored seven days after dsRNA injection. The mortality determined for BSB_brm-1 dsRNA was not significantly different from that seen with the same amount of injected YFPv2 dsRNA (negative control), with p=0.279 (Student's t-test). There was also no significant difference between the YFPv2 dsRNA injected and not injected treatments.

TABLE 2

Results of BSB_brm-1 dsRNA injection into the hemoceol of $2^{nd}$ instar *E. heros* nymphs seven days after injection. Table shows mean percent mortality, N number of trials, and standard error of the mean (SEM). Means comparisons were performed with YFP dsRNA as control, using a Student's t-test with Dunnett's adjustment in JMP ® Pro 11; p-value shown.

| Treatment | Mean % mortality | SEM | N trials | t-test (p) |
|---|---|---|---|---|
| BSB_brm-1 | 27 | 12.0 | 3 | 0.3039 |
| not injected | 13 | 3.3 | 3 | 0.9384 |
| YFPv2 dsRNA | 10 | 5.8 | 3 | |

*Ten insects injected per trial for each dsRNA.

Example 5: Parental RNAi Effects Following dsRNA Injection in *Euschistus heros*

Injection of dsRNA into BSB Hemocoel.

BSB were reared as described above for the colony. In the following exemplification, young adults (up to one week post adult molt) were collected and chilled in a secondary container on ice. The females and males were separated based on structural dimorphism of the genitalia. Female BSB were handled with Featherweight entomology forceps and injected with dsRNA using a NANOJECT™ II injector (DRUMMOND SCIENTIFIC, Broomhall, Pa.) equipped with an injection needle pulled from a Drummond 3.5 inch #3-000-203-G/X glass capillary. The needle tip was broken and the capillary was backfilled with light mineral oil then filled with 3 μL dsRNA. Ten to twenty females (approximately 90 mg each) per treatment were injected with dsRNA. Each female was injected into the abdomen twice consecutively with 69 nL 1 μg/μL dsRNA for a total of 138 nL (138 ng). Each batch of ten females was moved into a 1 quart (~950 mL) bin with an opening in the lid and #18 mesh for ventilation. Two adult males were added to each bin of ten females. The insects were supplied with a vial of water, green beans, and seeds as described in the rearing procedure. The insects were kept at 26.5° C., 60% humidity and 16:8 light:dark photoperiod.

Surviving female counts, oviposition, and egg hatch numbers were collected on a daily basis starting seven to nine days after injection and continued for up to 16 days. Eggs were removed daily and kept in Petri dishes or multi-well plates on a layer of 1% agarose in water. The adult insects were transferred into bins with fresh water and food every week.

Injections of dsRNA that target brahma, iswi-1, iswi-2, mi-2, and/or chd1 in BSB females decreased egg laying. Females injected with dsRNA that targets a 301 nt sequence of the YFP coding region were used as a negative controls, and compared to un-injected and females injected with BSB_brm-1 dsRNA (SEQ ID NO:3). As summarized in Table 3, un-injected females did not lay statistically different numbers of eggs from YFPv2 controls. On the other hand, BSB_brm-1 dsRNA-injected females oviposited no eggs.

Figure 4A:
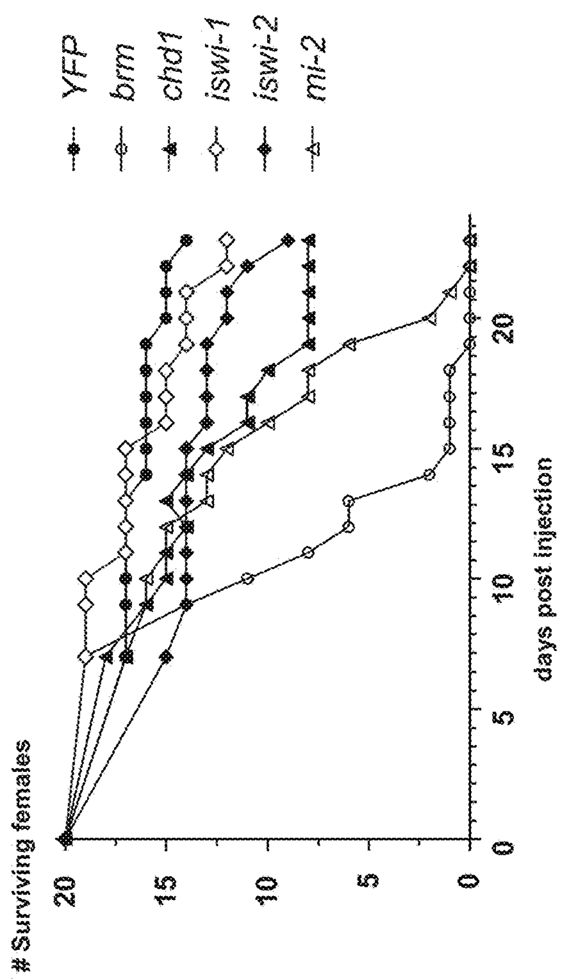
FIGS. 4A-4C includes data regarding *E. heros* adult female survival, oviposition, and egg hatch rates following dsRNA injections that target chromatin remodeling ATPases. Females were injected with dsRNA at 0 to 2 days post adult molt.
Figure 4B:
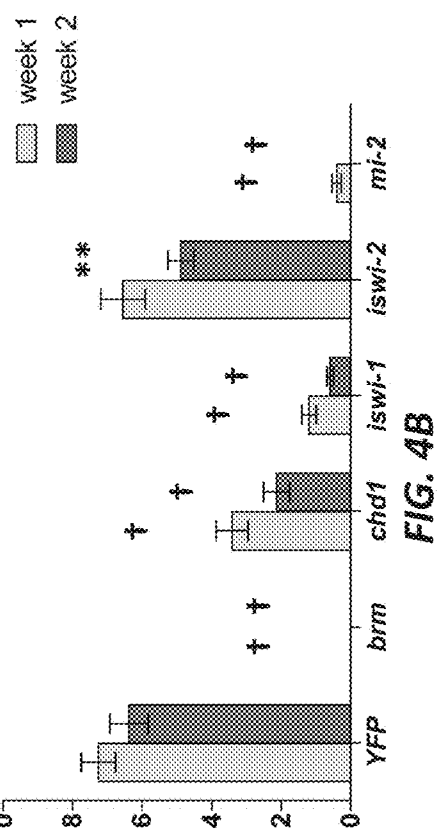
Figure 5:
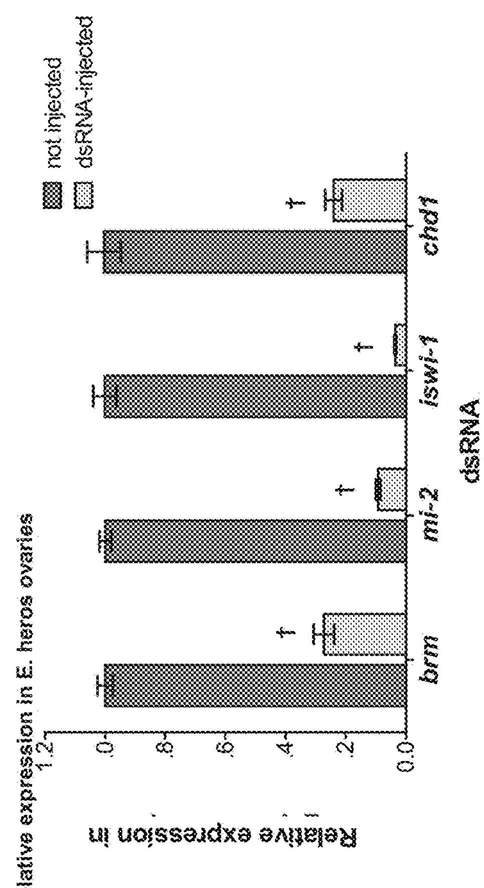
FIG. 5 includes data showing the percent knockdown of chromatin remodeling ATPases in *E. heros* ovaries. Relative expression is represented by $2^{-\Delta\Delta Ct}$. *E. heros* muscle actin transcript was used as a reference gene and ovaries from non-injected females as negative controls. Four sets of ovaries were used in each qRT-PCR experiment. Means comparisons were performed using Student's t-test; † $p<0.001$.

Injection of 138 ng chromatin-remodeling ATPase dsRNA had no effect on viability or no immediate effect on viability of the adult female BSB. FIG. 4A. Injection of BSB brahma dsRNA (BSB_brm-1 (SEQ ID NO:3)) and of dsRNAs that target BSB_mi-2-1 (SEQ ID NO:16), BSB_iswi-1-1 (SEQ ID NO:17), BSB_iswi-2-1 (SEQ ID NO:18), and BSB_chd1-1 (SEQ ID NO:19) of BSB greatly decreased oviposition or eliminated oviposition altogether, as compared to negative YFPv2 dsRNA controls (SEQ ID NO:5) Table 4 and FIG. 4B. Oviposition by BSB females injected with dsRNAs BSB_brm-1 (SEQ ID NO:3), BSB_mi-2-1 (SEQ ID NO:16), BSB_iswi-1-1 (SEQ ID NO:17), BSB_iswi-2-1 (SEQ ID NO:18), and BSB_chd1-1 (SEQ ID NO:19) were significantly different from that observed with the same amount of injected YFPv2 dsRNA (SEQ ID NO:5), with $p<0.05$ (Table 4 and FIG. 4B). No eggs were produced by BSB_brm-1 and very few or none by BSB_mi-2-1 injected females. BSB_brm-1 (SEQ ID NO:3), BSB_mi-2-1 (SEQ ID NO:16), BSB_iswi-1-1 (SEQ ID NO:17), and BSB_chd1-1 (SEQ ID NO:19) dsRNA caused significant knockdown of transcript levels in the BSB ovary. FIG. 5. The transcript of BSB_iswi-2-1 (SEQ ID NO:18) was not readily detected by probe hydrolysis PCR.

Figure 4C:
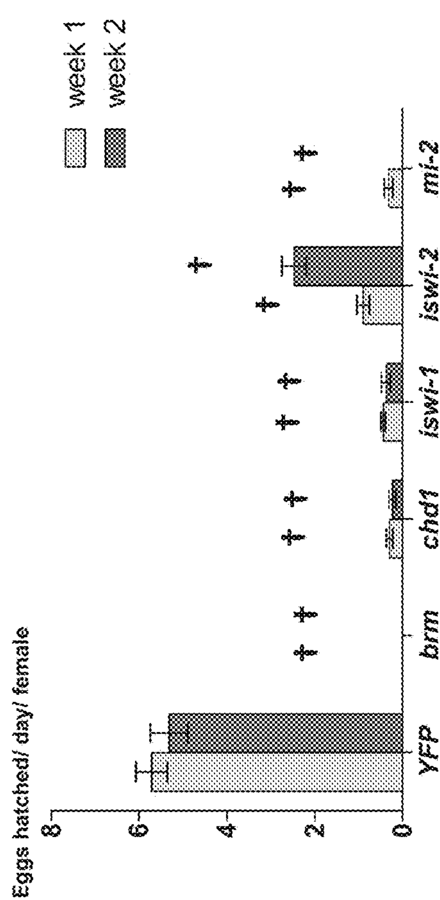

The numbers of eggs hatched in the experiment below shows that the number of offspring produced from females injected with dsRNAs for BSB brahma, mi-2, iswi-1, iswi-2, and chd1 were significantly lower than the control. Table 5 and FIG. 4C. Egg hatch rates of BSB females injected with dsRNAs BSB_brm-1 (SEQ ID NO:3), BSB_mi-2-1 (SEQ ID NO:16), BSB_iswi-1-1 (SEQ ID NO:17), BSB_iswi-2-1 (SEQ ID NO:18), and BSB_chd1-1 (SEQ ID NO:19) were significantly different from those observed with the same amount of injected negative control YFPv2 dsRNA (SEQ ID NO:5), with $p<0.05$ (Student's t-test).

TABLE 3

Brahma pRNAi: number of eggs oviposited per female per day. Ten females were injected with each dsRNA targeted against BSB brahma and negative control, YFPv2. Counts of oviposited eggs were collected starting on day 7 post injection, for up to 15 consecutive days. The N number of days during which eggs were collected varies between treatments due to female mortality impact of some dsRNAs. Means comparisons were performed with YFPv2 dsRNA as control, using a Student's t-test with Dunnett's adjustment in JMP ® Pro 11.

| dsRNA | total # of eggs oviposited in 15 days | mean # of eggs/ day/ female | Std. Deviation | Std. Error | N days | T-test (p) |
|---|---|---|---|---|---|---|
| YFPv2 | 1280 | 8.66 | 1.84 | 0.48 | 15 | |
| not inj. | 1429 | 7.32 | 2.66 | 0.69 | 15 | 0.6697 |
| BSB_brm-1 | 0 | 0 | 0 | 0 | 13 | <0.0001* |

*p-values < 0.05.

TABLE 4

Oviposition by *E. heros* females injected with chromatin remodelers dsRNA. Total numbers of eggs oviposited in 15 days and average numbers of eggs per female injected with negative control YFPv2 dsRNA or chromatin remodeling ATPase dsRNAs. Twenty females were injected with each dsRNA. Egg counts started on day 9 post-injection and continued for 15 consecutive days. The N number of days during which eggs were collected varied between treatments due to female mortality in brm and mi-2 treatments. Means comparisons were performed on average numbers of eggs oviposited by females, using daily oviposition values. YFPv2 dsRNA was used as control for Student t-test with Dunnett's adjustment in JMP.

| dsRNA | Total # of eggs in 15 days | Average # of eggs/ day/female | SEM | N Days | p-Value |
|---|---|---|---|---|---|
| YFPv2 | 1629 | 6.75 | 0.357 | 15 | |
| BSB_brm-1 | 0 | 0.00 | 0.000 | 10 | <0.0001* |
| BSB_chd1-1 | 496 | 2.65 | 0.338 | 15 | <0.0001* |
| BSB_iswi-1-1 | 209 | 0.84 | 0.142 | 15 | <0.0001* |
| BSB_iswi-2-1 | 1097 | 5.54 | 0.433 | 15 | 0.0171* |
| BSB_mi-2-1 | 42 | 0.22 | 0.085 | 13 | <0.0001* |

*significantly different from YFPv2 dsRNA p < 0.05.
N = number of days; SEM = standard error of the mean.

TABLE 5

Total and average numbers of eggs hatched from *E. heros* females injected with chromatin remodelers dsRNA. Total numbers of eggs hatched in 15-day collection and average number of eggs hatched per female per day of oviposition, from females injected with negative control YFPv2 dsRNA or chromatin remodeling dsRNAs. Twenty females were injected with each dsRNA. Nymph emergence was evaluated from eggs oviposited on day 9 post-injection for 15 consecutive days. Means comparisons were performed on numbers of eggs hatched each day per female, using daily values. YFPv2 dsRNA was used as the control for Student-t test with Dunnett's adjustment in JMP.

| dsRNA | Total # of eggs hatched from 15-day collection | Average # of eggs hatched/ female/day | SEM | p-Value |
|---|---|---|---|---|
| YFPv2 | 1321 | 5.47 | 0.257 | |
| BSB_brm-1 | 0 | 0.00 | 0.000 | <0.0001* |
| BSB_chd1-1 | 51 | 0.28 | 0.054 | <0.0001* |
| BSB_iswi-1-1 | 93 | 0.39 | 0.062 | <0.0001* |
| BSB_iswi-2-1 | 312 | 1.63 | 0.253 | <0.0001* |
| BSB_mi-2-1 | 34 | 0.17 | 0.067 | <0.0001* |

*significantly different from YFPv2 dsRNA p < 0.05.
SEM = standard error of the mean.

Figures 6A, 6B:
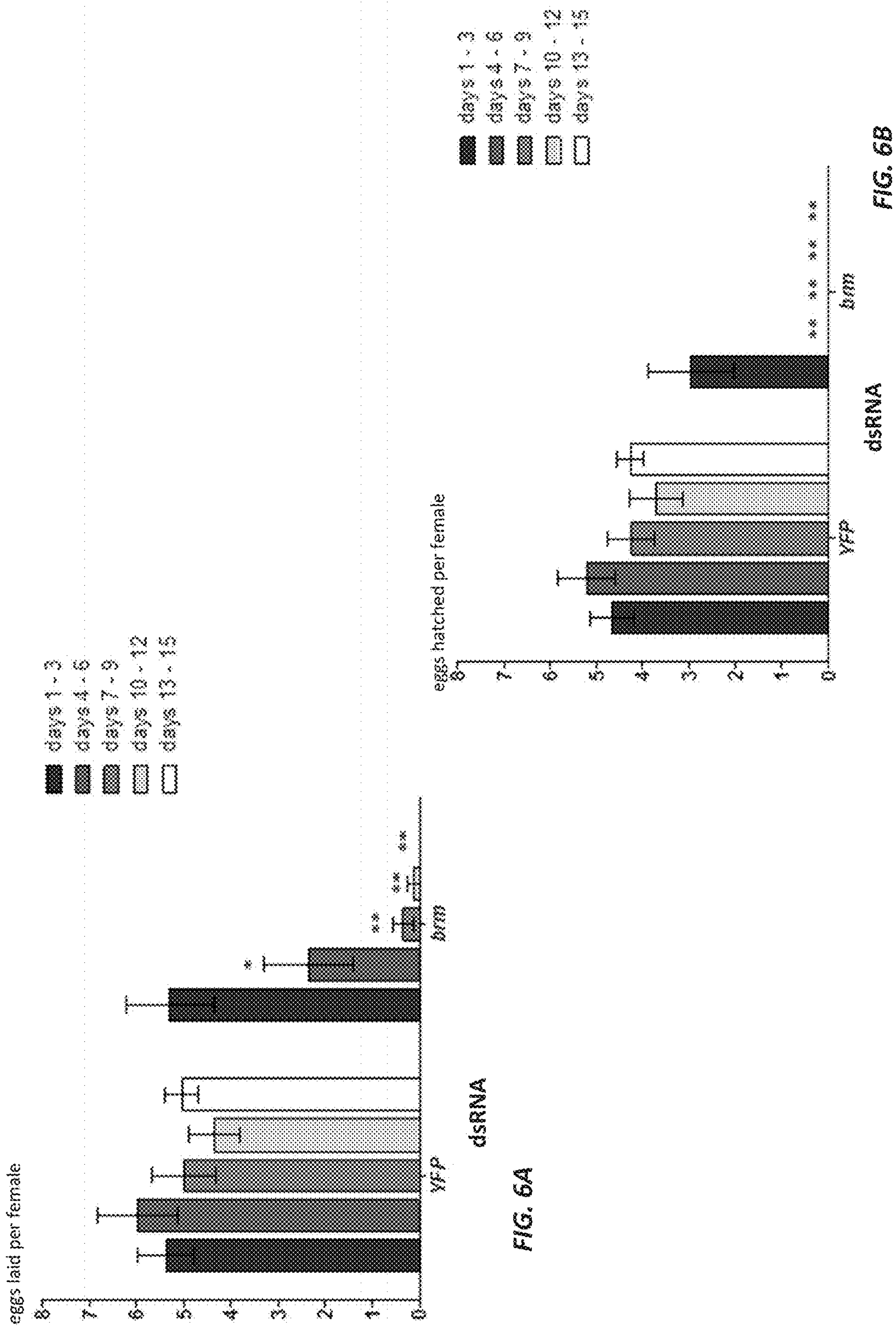
FIGS. 6A-6B includes data showing the development and hatch rates of eggs oviposited by brahma dsRNA-injected *E. heros* females. Ovipositing females were injected with dsRNA at 14 to 16 days post adult molt.

To determine the onset of pRNAi response, oviposting females, 14 to 16 days post adult molt, were injected with BSB_brm-1 (SEQ ID NO:3) dsRNA. FIG. 6 shows that egg hatch was inhibited by day 4 post-injection (FIG. 6B) and oviposition halted by day 7 (FIG. 6A).

Based on the complete lack of oviposition in *E. heros* in response to brahma dsRNA and severe inhibition of oviposition in response to mi-2 dsRNA, we investigated the state of oocyte and ovary development in parent females. The females were examined 9 and 14 days post injection. By day nine after injection, control females began oviposition. Since brm dsRNA injections led to lethality within about two weeks, day 14 was chosen to capture phenotypes from the last surviving females. FIG. 4A. *E. heros* ovaries were dissected in 1×PBS under stereo microscope, and then fixed in 4% paraformaldehyde/1×PBS solution for 2 hours on ice. Trachea surrounding the ovaries was removed with #5 biology forceps. Images of three to four sets of ovaries for each treatment were captured with a Leica M205 FA stereo microscope (WETZLAR, Germany). Mature eggs and developing oocytes were observed in YFP dsRNA-injected females. FIGS. 7C and D. Brahma and mi-2 dsRNA-injected females showed lack of ovary development and ovariole elongation. FIG. 7. These insects showed no maturing oocytes or mature eggs (FIGS. 7E, G, and H), or oocytes that were in a state of decay (FIG. 7F).

Contact with dsRNA molecules encoding sequences targeting SNF2-Helicase regions (SEQ ID NOs:34-37) and chromatin remodeling domains (SEQ ID NOs:38-41) by adult BSB females is demonstrates to a have surprising, dramatic and reproducible effect on egg viability. The mated females exposed to dsRNA produce a lower number of eggs than females exposed to untreated diet or diet treated with YFPv2 dsRNA.

The above results clearly document the systemic nature of RNAi in BSB adults, and the potential to achieve a parental effect where genes associated with embryonic development are knocked down in the eggs of females that are exposed to dsRNA. These observations confirm that the dsRNA can be taken up translocated to tissues (e.g., developing ovarioles) other than the point of contact (e.g., midgut or hemocoel).

The ability to knock down the expression of genes involved with embryonic development such that the eggs do not hatch, offers a unique opportunity to achieve and improve control of BSB. Because adults readily feed on above-ground reproductive tissues, adult BSB can be exposed to iRNA control agents by transgenic expression of dsRNA to achieve plant protection in the subsequent generation by preventing eggs from hatching. Delivery of the dsRNA through transgenic expression of dsRNA in plants, or by contact with surface-applied iRNAs, provides an important stacking partner for other transgenic approaches that target nymphs directly and enhance the overall durability of pest management strategies.

Example 6: Quantitive Real-Time PCR Analysis

*E. heros* tissues for qRT-PCR were collected from zero to three day-old females injected with dsRNA. After seven days, female ovaries were dissected under a stereo microscope in nuclease-free 1×PBS (pH 7.4) and frozen individually on dry ice in collection microtubes. Tissue disruption was performed with the RL lysis buffer and the Klecko™ tissue pulverizer (GARCIA MANUFACTURING, Visalia, Calif.). Following tissue maceration, the total RNA was isolated in high throughput format using the Norgen® Total RNA Purification 96-well kit (NoRGEN BIOTEK CORP., Ontario, Canada) following the manufacturer's protocol using Turbo™ DNase (LIFE TECHNOLOGIES, Carlsbad, Calif.) for 1 hour at 37° C. on the elutant. cDNA synthesis was performed using the high capacity cDNA RT kit (LIFE TECHNOLOGIES, Carlsbad, Calif.) according to the manufacturer's protocol with the following modifications. Total RNA was adjusted to 50 ng/μL with nuclease-free water. RNA samples were heated to 70° C. for 10 minutes and cooled to 4° C. Half reactions were initiated by addition of 5 μL 2× mix. The primer mix, which is supplied solely as random primers, was first spiked with custom synthesized $T_{20}$VN oligo (INTEGRATED DNA TECHNOLOGIES, Coralville, Iowa) to a final concentration of 2 in order to improve the sensitivity of 3'UTR based assays. Following first strand synthesis, the samples were diluted 1:3 with nuclease-free water.

*E. heros* qRT-PCR primers and hydrolysis probes were designed using LightCycler® Probe Design Software 2.0 (ROCHE, Basel, Switzerland) for the reference gene and Primer Express® Software Version 3.0 (APPLIED BIOSYSTEMS, Grand Island, N.Y.) for the target genes. Table 6. Non-injected insects were used as controls. *E. heros* muscle actin (SEQ ID NO:73) was used as the reference gene. Probes were labeled with FAM (6-Carboxy Fluorescein Amidite). The final primer concentration was 0.4 μM, and the final probe concentration was 0.2 μM (in 10 reaction volumes). Relative transcript levels were analyzed by probe hydrolysis qRT-PCR using LightCycler®480. All assays included negative controls of no-template (mix only). For the standard curves, a blank was included in the source plate to check for sample cross-contamination. PCR cycling conditions included a 10 minute target activation incubation at 95° C., followed by 40 cycles of denaturation at 95° C. for 10 seconds, anneal/extend at 60° C. for 40 seconds, and FAM acquisition at 72° C. for 1 second. The reaction was followed by a 10 second cool-down at 40° C. *E. heros* iswi-2 was not detected reliably both in the negative controls and dsRNA exposed females, therefore iswi-2 data was omitted from the final results. The data was analyzed using LightCycler® Software v1.5 and relative changes in expression were calculated using $2^{-\Delta\Delta Ct}$ method (Livak and Schmittgen (2001) Methods 25:402-8).

TABLE 6

Oligonucleotides and probes for BSB probe hydrolysis qPCR assay and primer efficacy results. MGB = Minor Groove Binder probes from Applied Biosystems.

| Reference GENE | NAME | SEQUENCE | Product Length (bp) | Slope | Primer Efficiency (%) |
|---|---|---|---|---|---|
| Actin, muscle | Act42A-F | TCAAGGAAAAACTGTGCTATGT (SEQ ID NO: 74) | 120 | -3.77 | 92 |
| Actin, muscle | Act42A-R | TACCGATGGTGATGACCTGA (SEQ ID NO: 75) | | | |
| Actin, muscle | Act42A-FAM | ACCGCCGCTGCC (SEQ ID NO: 76) | | | |
| **Target GENE** | **NAME** | **SEQUENCE** | | | |
| brahma | brm-F | TCATCAAGGACAAGGCAGT (SEQ ID NO: 77) | 205 | -3.54 | 93.5 |

TABLE 6-continued

Oligonucleotides and probes for BSB probe hydrolysis qPCR assay and primer efficacy results. MGB = Minor Groove Binder probes from Applied Biosystems.

| | | | | | |
|---|---|---|---|---|---|
| brahma | brm-R | GACGGGAGGAGAAAGTTTAGA (SEQ ID NO: 78) | | | |
| brahma | brm-FAM | CGACGAGGGACACAGGATG (SEQ ID NO: 79) | | | |
| mi-2 | mi-2-F | GATGAGGGCTTGCTGTT (SEQ ID NO: 80) | 149 | -3.55 | 95.5 |
| mi-2 | mi-2-R | GAGGCGGGAAGTATTGAC (SEQ ID NO: 81) | | | |
| mi-2 | mi-2-FAM | ATGAGGAAGGAAGCAGAAGTGC (SEQ ID NO: 82) | | | |
| iswi-1 | iswi-1-F | GAGTTCAACGAAGAAGACAGTAA (SEQ ID NO: 83) | 155 | -3.67 | 94.5 |
| iswi-1 | iswi-R | CGATGAGCACGATCCATAG (SEQ ID NO: 84) | | | |
| iswi-1 | iswi-1-FAM | TTAGCCACCGCAGATGTAGTCA (SEQ ID NO: 85) | | | |
| iswi-2 | iswi-2-F_MGB | ACGTAAGGGAGATGGATCTATTTCA (SEQ ID NO: 86) | 65 | -3.96 | 89 |
| iswi-2 | iswi-2-R_MGB | CAGGGCTGCTTTTATCACTCTGT (SEQ ID NO: 87) | | | |
| iswi-2 | iswi-2-FAM_MGB | CTCCACCTGTCTCTG (SEQ ID NO: 88) | | | |
| chd1 | chd1-F | CAACAGTGGCTGGTCCTTCA (SEQ ID NO: 89) | 68 | -3.71 | 93 |
| chd1 | chd1-R | ACCAACTTGTGACATTGACGAAA (SEQ ID NO: 90) | | | |
| chd1 | chd1-FAM | TCTGGTTTCAGCTCTT (SEQ ID NO: 91) | | | |

Example 7: Construction of Plant Transformation Vectors

Entry vectors harboring a target gene construct for dsRNA hairpin formation comprising segments of one of various chromatin remodeling genes (SEQ ID NO:1 or SEQ ID NO:63 (brahma); SEQ ID NO:8 or SEQ ID NO:64 (BSB_mi-2); SEQ ID NO:10 or SEQ ID NO:65 (BSB_iswi-1); SEQ ID NO:12 or SEQ ID NO:66 (BSB_iswi-2); SEQ ID NO:14 or SEQ ID NO:67 (BSB_chd1); SEQ ID NO:30 (BSB_ino80); and SEQ ID NO:32 (BSB_domino)) are assembled using a combination of chemically synthesized fragments (DNA2.0, Menlo Park, Calif.) and standard molecular cloning methods. Intramolecular hairpin formation by RNA primary transcripts is facilitated by arranging (within a single transcription unit) two copies of a target gene segment in opposite orientation to one another, the two segments being separated by a linker sequence (e.g. ST-LS1 intron; Vancanneyt et al. (1990) Mol. Gen. Genet. 220:245-250). Thus, the primary mRNA transcript contains the two brahma or ortholog gene segment sequences as large inverted repeats of one another, separated by the linker sequence. A copy of a promoter (e.g. maize ubiquitin 1, U.S. Pat. No. 5,510,474; 35S from Cauliflower Mosaic Virus (CaMV); promoters from rice actin genes; ubiquitin promoters; pEMU; MAS; maize H3 histone promoter; ALS promoter; phaseolin gene promoter; cab; rubisco; LAT52; Zm13; and/or apg) is used to drive production of the primary mRNA hairpin transcript, and a fragment comprising a 3' untranslated region, for example and without limitation, a maize peroxidase 5 gene (ZmPer5 3'UTR v2; U.S. Pat. No. 6,699,984), AtUbi10, AtEf1, or StPinII is used to terminate transcription of the hairpin-RNA-expressing gene.

The entry vector described above is used in standard GATEWAY® recombination reactions with a typical binary destination vector to produce hairpin RNA expression transformation vectors for *Agrobacterium*-mediated plant embryo transformations.

A negative control binary vector which comprises a gene that expresses a YFP hairpin dsRNA is constructed by means of standard GATEWAY® recombination reactions with a typical binary destination vector and entry vector. The entry vector comprises a YFP hairpin sequence under the expression control of a maize ubiquitin 1 promoter and a fragment comprising a 3' untranslated region from a maize peroxidase 5 gene.

A binary destination vector comprises a herbicide tolerance gene (aryloxyalknoate dioxygenase; (AAD-1 v3, U.S. Pat. No. 7,838,733, and Wright et al. (2010) Proc. Natl. Acad. Sci. U.S.A. 107:20240-5)) under the regulation of a plant operable promoter (e.g., sugarcane bacilliform badnavirus (ScBV) promoter (Schenk et al. (1999) Plant Mol.

Biol. 39:1221-30) or ZmUbi1 (U.S. Pat. No. 5,510,474)). 5' UTR and intron from these promoters, are positioned between the 3' end of the promoter segment and the start codon of the AAD-1 coding region. A fragment comprising a 3' untranslated region from a maize lipase gene (ZmLip 3'UTR; U.S. Pat. No. 7,179,902) is used to terminate transcription of the AAD-1 mRNA.

A further negative control binary vector that comprises a gene that expresses a YFP protein, is constructed by means of standard GATEWAY® recombination reactions with a typical binary destination vector and entry vector. The binary destination vector comprises a herbicide tolerance gene (aryloxyalknoate dioxygenase; AAD-1 v3) (as above) under the expression regulation of a maize ubiquitin 1 promoter and a fragment comprising a 3' untranslated region from a maize lipase gene (ZmLip 3'UTR). The entry vector comprises a YFP coding region under the expression control of a maize ubiquitin 1 promoter and a fragment comprising a 3' untranslated region from a maize peroxidase 5 gene.

Example 8: Transgenic *Zea mays* Comprising Hemipteran Pest Sequences

Ten to 20 transgenic $T_0$ *Zea mays* plants harboring expression vectors for nucleic acids comprising a segment of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, or SEQ ID NO:67 are generated as described in EXAMPLE 5. A further 10-20 $T_1$ *Zea mays* independent lines expressing hairpin dsRNA for an RNAi construct are obtained for BSB challenge. Hairpin dsRNA may be derived comprising a segment of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, or SEQ ID NO:67. These are confirmed through RT-PCR or other molecular analysis methods. Total RNA preparations from selected independent $T_1$ lines are optionally used for RT-PCR with primers designed to bind in the linker of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic *Zea mays* plant. Processing of the dsRNA hairpin of the target genes into siRNA is subsequently optionally confirmed in independent transgenic lines using RNA blot hybridizations.

Moreover, RNAi molecules having mismatch sequences with more than 80% sequence identity to target genes affect hemipterans in a way similar to that seen with RNAi molecules having 100% sequence identity to the target genes. The pairing of mismatch sequence with native sequences to form a hairpin dsRNA in the same RNAi construct delivers plant-processed siRNAs capable of affecting the growth, development, reproduction, and viability of feeding hemipteran pests.

In planta delivery of dsRNA, siRNA, shRNA, hpRNA, or miRNA corresponding to target genes and the subsequent uptake by hemipteran pests through feeding results in down-regulation of the target genes in the hemipteran pest through RNA-mediated gene silencing. When the function of a target gene is important at one or more stages of development, the growth, development, and/or reproduction of the hemipteran pest is affected, and in the case of at least one of *Euschistus heros, Piezodorus guildinii, Halyomorpha halys, Nezara viridula, Chinavia hilare, Euschistus serous, Dichelops melacanthus, Dichelops furcatus, Edessa meditabunda, Thyanta perditor, Chinavia marginatum, Horcias nobilellus, Taedia stigmosa, Dysdercus peruvianus, Neomegalotomus parvus, Leptoglossus zonatus, Niesthrea sidae*, or *Lygus lineolaris* leads to failure to successfully infest, feed, develop, and/or reproduce, or leads to death of the hemipteran pest. The choice of target genes and the successful application of RNAi is then used to control hemipteran pests.

Phenotypic Comparison of Transgenic RNAi Lines and Non-Transformed *Zea mays*.

Target hemipteran pest genes or sequences selected for creating hairpin dsRNA have no similarity to any known plant gene sequence. Hence it is not expected that the production or the activation of (systemic) RNAi by constructs targeting these hemipteran pest genes or sequences will have any deleterious effect on transgenic plants. However, development and morphological characteristics of transgenic lines are compared with non-transformed plants, as well as those of transgenic lines transformed with an "empty" vector having no hairpin-expressing gene. Plant root, shoot, foliage and reproduction characteristics are compared. There is no observable difference in root length and growth patterns of transgenic and non-transformed plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 9: Transgenic *Glycine max* Comprising Hemipteran Pest Sequences

Ten to 20 transgenic $T_0$ *Glycine max* plants harboring expression vectors for nucleic acids comprising a segment of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, or SEQ ID NO:67 are generated as is known in the art, including for example by *Agrobacterium*-mediated transformation, as follows. Mature soybean (*Glycine max*) seeds are sterilized overnight with chlorine gas for sixteen hours. Following sterilization with chlorine gas, the seeds are placed in an open container in a LAMINAR™ flow hood to dispel the chlorine gas. Next, the sterilized seeds are imbibed with sterile $H_2O$ for sixteen hours in the dark using a black box at 24° C.

Preparation of Split-Seed Soybeans.

The split soybean seed comprising a portion of an embryonic axis protocol requires preparation of soybean seed material which is cut longitudinally, using a #10 blade affixed to a scalpel, along the hilum of the seed to separate and remove the seed coat, and to split the seed into two cotyledon sections. Careful attention is made to partially remove the embryonic axis, wherein about ½-⅓ of the embryo axis remains attached to the nodal end of the cotyledon.

Inoculation.

The split soybean seeds comprising a partial portion of the embryonic axis are then immersed for about 30 minutes in a solution of *Agrobacterium tumefaciens* (e.g., strain EHA 101 or EHA 105) containing binary plasmid comprising a segment of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, or SEQ ID NO:67. The *Agrobacterium tumefaciens* solution is diluted to a final concentration of λ=0.6 $OD_{650}$ before immersing the cotyledons comprising the embryo axis.

Co-Cultivation.

Following inoculation, the split soybean seed is allowed to co-cultivate with the *Agrobacterium tumefaciens* strain for 5 days on co-cultivation medium (*Agrobacterium Protocols, vol.* 2, $2^{nd}$ Ed., Wang, K. (Ed.) Humana Press, New Jersey, 2006) in a Petri dish covered with a piece of filter paper.

Shoot Induction.

After 5 days of co-cultivation, the split soybean seeds are washed in liquid Shoot Induction (SI) media consisting of B5 salts, B5 vitamins, 28 mg/L Ferrous, 38 mg/L $Na_2EDTA$, 30 g/L sucrose, 0.6 g/L MES, 1.11 mg/L BAP, 100 mg/L TIMENTIN™, 200 mg/L cefotaxime, and 50 mg/L vancomycin (pH 5.7). The split soybean seeds are then cultured on Shoot Induction I (SII) medium consisting of B5 salts, B5 vitamins, 7 g/L Noble agar, 28 mg/L Ferrous, 38 mg/L $Na_2EDTA$, 30 g/L sucrose, 0.6 g/L MES, 1.11 mg/L BAP, 50 mg/L TIMENTIN™, 200 mg/L cefotaxime, 50 mg/L vancomycin (pH 5.7), with the flat side of the cotyledon facing up and the nodal end of the cotyledon imbedded into the medium. After 2 weeks of culture, the explants from the transformed split soybean seed are transferred to the Shoot Induction II (SI II) medium containing SI I medium supplemented with 6 mg/L glufosinate (LIBERTY®).

Shoot Elongation.

After 2 weeks of culture on SI II medium, the cotyledons are removed from the explants and a flush shoot pad containing the embryonic axis are excised by making a cut at the base of the cotyledon. The isolated shoot pad from the cotyledon is transferred to Shoot Elongation (SE) medium. The SE medium consists of MS salts, 28 mg/L Ferrous, 38 mg/L $Na_2EDTA$, 30 g/L sucrose and 0.6 g/L IVIES, 50 mg/L asparagine, 100 mg/L L-pyroglutamic acid, 0.1 mg/L IAA, 0.5 mg/L GA3, 1 mg/L zeatin riboside, 50 mg/L TIMENTIN™, 200 mg/L cefotaxime, 50 mg/L vancomycin, 6 mg/L glufosinate, 7 g/L Noble agar, (pH 5.7). The cultures are transferred to fresh SE medium every 2 weeks. The cultures are grown in a CONVIRON™ growth chamber at 24° C. with an 18 h photoperiod at a light intensity of 80-90 μmol/$m^2$ sec.

Rooting.

Elongated shoots which developed from the cotyledon shoot pad are isolated by cutting the elongated shoot at the base of the cotyledon shoot pad, and dipping the elongated shoot in 1 mg/L IBA (Indole 3-butyric acid) for 1-3 minutes to promote rooting. Next, the elongated shoots are transferred to rooting medium (MS salts, B5 vitamins, 28 mg/L Ferrous, 38 mg/L $Na_2EDTA$, 20 g/L sucrose and 0.59 g/L IVIES, 50 mg/L asparagine, 100 mg/L L-pyroglutamic acid 7 g/L Noble agar, pH 5.6) in phyta trays.

Cultivation.

Following culture in a CONVIRON™ growth chamber at 24° C., 18 h photoperiod, for 1-2 weeks, the shoots which have developed roots are transferred to a soil mix in a covered sundae cup and placed in a CONVIRON™ growth chamber (models CMP4030 and CMP3244, Controlled Environments Limited, Winnipeg, Manitoba, Canada) under long day conditions (16 hours light/8 hours dark) at a light intensity of 120-150 μmol/$m^2$ sec under constant temperature (22° C.) and humidity (40-50%) for acclimatization of plantlets. The rooted plantlets are acclimated in sundae cups for several weeks before they are transferred to the greenhouse for further acclimatization and establishment of robust transgenic soybean plants.

A further 10-20 $T_1$ *Glycine max* independent lines expressing hairpin dsRNA for an RNAi construct are obtained for BSB challenge. Hairpin dsRNA may be derived comprising a segment of SEQ ID NO:1, SEQ ID NO:8, SEQ ID NO:10, SEQ ID NO:12, SEQ ID NO:14, SEQ ID NO:30, SEQ ID NO:32, SEQ ID NO:63, SEQ ID NO:64, SEQ ID NO:65, SEQ ID NO:66, or SEQ ID NO:67. These are confirmed through RT-PCR or other molecular analysis methods, as known in the art. Total RNA preparations from selected independent $T_1$ lines are optionally used for RT-PCR with primers designed to bind in the linker of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic *Glycine max* plant. Processing of the dsRNA hairpin of the target genes into siRNA is subsequently optionally confirmed in independent transgenic lines using RNA blot hybridizations.

RNAi molecules having mismatch sequences with more than 80% sequence identity to target genes affect BSB in a way similar to that seen with RNAi molecules having 100% sequence identity to the target genes. The pairing of mismatch sequence with native sequences to form a hairpin dsRNA in the same RNAi construct delivers plant-processed siRNAs capable of affecting the growth, development, reproduction, and viability of feeding hemipteran pests.

In planta delivery of dsRNA, siRNA, or miRNA corresponding to target genes and the subsequent uptake by hemipteran pests through feeding results in down-regulation of the target genes in the hemipteran pest through RNA-mediated gene silencing. When the function of a target gene is important at one or more stages of development, the growth, development, and/or reproduction of the hemipteran pest is affected, and in the case of at least one of *Euschistus heros, Piezodorus guildinii, Halyomorpha halys, Nezara viridula, Chinavia hilare, Euschistus servus, Dichelops melacanthus, Dichelops furcatus, Edessa meditabunda, Thyanta perditor, Chinavia marginatum, Horcias nobilellus, Taedia stigmosa, Dysdercus peruvianus, Neomegalotomus parvus, Leptoglossus zonatus, Niesthrea sidae*, or *Lygus lineolaris* leads to failure to successfully infest, feed, develop, and/or reproduce, or leads to death of the hemipteran pest. The choice of target genes and the successful application of RNAi is then used to control hemipteran pests.

Phenotypic comparison of transgenic RNAi lines and non-transformed *Glycine max*. Target hemipteran pest genes or sequences selected for creating hairpin dsRNA have no similarity to any known plant gene sequence. Hence it is not expected that the production or the activation of (systemic) RNAi by constructs targeting these hemipteran pest genes or sequences will have any deleterious effect on transgenic plants. However, development and morphological characteristics of transgenic lines are compared with non-transformed plants, as well as those of transgenic lines transformed with an "empty" vector having no hairpin-expressing gene. Plant root, shoot, foliage and reproduction characteristics are compared. There is no observable difference in root length and growth patterns of transgenic and non-transformed plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 10*: E. heros* Bioassays on Artificial Diet

In dsRNA feeding assays on artificial diet, 32-well trays are set up with an ~18 mg pellet of artificial diet and water, as for injection experiments. dsRNA at a concentration of 200 ng/μL is added to the food pellet and water sample, 100 μL to each of two wells. Five $2^{nd}$ instar *E. heros* nymphs are introduced into each well. Water samples and dsRNA that targets YFP transcript are used as negative controls. The experiments are repeated on three different days. Surviving insects are weighed and the mortality rates are determined after 7 days of treatment.

Feeding bioassays on adult female *E. heros* are performed as 32-well trays as described above. Young (less than one week of adulthood) mated females are introduced into bioassay trays with artificial diet, one per tray. After 7 days of exposure to dsRNA up to ten adult females are moved to containers with green beans, water, seeds, and two males. Female viability as well as the numbers of eggs oviposited and eggs hatched are recorded for the following two weeks. The data shows that the numbers of eggs oviposited and/or hatched are significantly reduced.

Example 11: Transgenic *Arabidopsis thaliana* Comprising Hemipteran Pest Sequences

*Arabidopsis* transformation vectors containing a target gene construct for hairpin formation comprising segments of BSB_brahma (SEQ ID NO:1 or SEQ ID NO:63), BSB_mi-2 (SEQ ID NO:8 or SEQ ID NO:64), BSB_iswi-1 (SEQ ID NO:10 or SEQ ID NO:65), BSB_iswi-2 (SEQ ID NO:12 or SEQ ID NO:66), BSB_chd1 (SEQ ID NO:14 or SEQ ID NO:67), BSB_ino80 (SEQ ID NO:30), and/or BSB_domino (SEQ ID NO:32) are generated using standard molecular methods similar to EXAMPLE 5. *Arabidopsis* transformation is performed using standard *Agrobacterium*-based procedure. $T_1$ seeds are selected with glufosinate tolerance selectable marker. Transgenic $T_1$ *Arabidopsis* plants are generated and homozygous simple-copy T2 transgenic plants are generated for insect studies. Bioassays are performed on growing *Arabidopsis* plants with inflorescences. Five to ten insects are placed on each plant and monitored for survival within 14 days.

Construction of *Arabidopsis* Transformation Vectors.

Entry clones based on an entry vector harboring a target gene construct for hairpin formation comprising a segment of BSB_brahma (SEQ ID NO:1 or SEQ ID NO:63), BSB_mi-2 (SEQ ID NO:8 or SEQ ID NO:64), BSB_iswi-1 (SEQ ID NO:10 or SEQ ID NO:65), BSB_iswi-2 (SEQ ID NO:12 or SEQ ID NO:66), BSB_chd1 (SEQ ID NO:14 or SEQ ID NO:67), BSB_ino80 (SEQ ID NO:30), and/or BSB_domino (SEQ ID NO:32) are assembled using a combination of chemically synthesized fragments (DNA2.0, Menlo Park, Calif.) and standard molecular cloning methods. Intramolecular hairpin formation by RNA primary transcripts is facilitated by arranging (within a single transcription unit) two copies of a target gene segment in opposite orientations, the two segments being separated by an linker sequence (e.g. ST-LS1 intron) (Vancanneyt et al. (1990) Mol. Gen. Genet. 220(2):245-50). Thus, the primary mRNA transcript contains the two chromatin remodeling gene segment sequences as large inverted repeats of one another, separated by the linker sequence. A copy of a promoter (e.g. *Arabidopsis thaliana* ubiquitin 10 promoter (Callis et al. (1990) J. Biological Chem. 265:12486-12493)) is used to drive production of the primary mRNA hairpin transcript, and a fragment comprising a 3' untranslated region from Open Reading Frame 23 of *Agrobacterium tumefaciens* (AtuORF23 3' UTR v1; U.S. Pat. No. 5,428,147) is used to terminate transcription of the hairpin-RNA-expressing gene.

The hairpin clone within the entry vector described above is used in standard GATEWAY® recombination reaction with a typical binary destination vector to produce hairpin RNA expression transformation vectors for *Agrobacterium*-mediated *Arabidopsis* transformation.

The binary destination vector comprises a herbicide tolerance gene, DSM-2v2 (U.S. Patent App. No. 2011/0107455), under the regulation of a Cassava vein mosaic virus promoter (CsVMV Promoter v2, U.S. Pat. No. 7,601,885; Verdaguer et al. (1996) Plant Mol. Biol. 31:1129-39). A fragment comprising a 3' untranslated region from Open Reading Frame 1 of *Agrobacterium tumefaciens* (AtuORF1 3' UTR v6; Huang et al. (1990) J. Bacteriol. 172:1814-22) is used to terminate transcription of the DSM2v2 mRNA.

A negative control binary construct, which comprises a gene that expresses a YFP hairpin RNA, is constructed by means of standard GATEWAY® recombination reactions with a typical binary destination vector and entry vector. An entry construct comprises a YFP hairpin sequence (hpYFP v2, SEQ ID NO:42) under the expression control of an *Arabidopsis* Ubiquitin 10 promoter (as above) and a fragment comprising an ORF23 3' untranslated region from *Agrobacterium tumefaciens* (as above).

Production of Transgenic *Arabidopsis* Comprising Insecticidal Hairpin RNAs: *Agrobacterium*-Mediated Transformation.

Binary plasmids containing hairpin sequences are electroporated into an *Agrobacterium* strain. The recombinant *Agrobacterium* clones are confirmed by restriction analysis of plasmids preparations of the recombinant *Agrobacterium* colonies. A Qiagen Plasmid Max Kit (Qiagen, Cat#12162) is used to extract plasmids from *Agrobacterium* cultures following the manufacture recommended protocol.

*Arabidopsis* Transformation and $T_1$ Selection.

Twelve to fifteen *Arabidopsis* plants (c.v. Columbia) are grown in 4" pots in the green house with light intensity of 250 μmol/m$^2$, 25° C., and 18:6 hours of light:dark conditions. Primary flower stems are trimmed one week before transformation. *Agrobacterium* inoculums are prepared by incubating 10 μL recombinant *Agrobacterium* glycerol stock in 100 mL LB broth (Sigma L3022)+100 mg/L Spectinomycin+50 mg/L Kanamycin at 28° C. and shaking at 225 rpm for 72 hours. *Agrobacterium* cells are harvested and suspended into 5% sucrose+0.04% Silwet-L77 (Lehle Seeds Cat # VIS-02)+10 μg/L benzamino purine (BA) solution to $OD_{600}$ 0.8~1.0 before floral dipping. The above-ground parts of the plant are dipped into the *Agrobacterium* solution for 5-10 minutes, with gentle agitation. The plants are then transferred to the greenhouse for normal growth with regular watering and fertilizing until seed set.

Example 12: Growth and Bioassays of Transgenic *Arabidopsis*

Selection of $T_1$ *Arabidopsis* Transformed with Hairpin RNAi Constructs.

Up to 200 mg of $T_1$ seeds from each transformation are stratified in 0.1% agarose solution. The seeds are planted in germination trays (10.5"×21"×1"; T.O. Plastics Inc., Clearwater, Minn.) with #5 sunshine media. Transformants are selected for tolerance to Ignite® (glufosinate) at 280 g/ha at 6 and 9 days post planting. Selected events are transplanted into 4" diameter pots. Insertion copy analysis is performed within a week of transplanting via hydrolysis quantitative Real-Time PCR (qPCR) using Roche LightCycler480™. The PCR primers and hydrolysis probes are designed against DSM2v2 selectable marker using LightCycler™ Probe Design Software 2.0 (Roche). Plants are maintained at 24° C., with a 16:8 hour light:dark photoperiod under fluorescent and incandescent lights at intensity of 100-150 mE/$m^2$ s.

*E. heros* Nymph Plant Feeding Bioassay.

At least four low copy (1-2 insertions), four medium copy (2-3 insertions), and four high copy (≥4 insertions) events are selected for each construct. Plants are grown to a reproductive stage (plants containing flowers and siliques). The surface of soil is covered with ~50 mL volume of white sand for easy insect identification. Five to ten $2^{nd}$ instar *E. heros* nymphs are introduced onto each plant. The plants are covered with plastic tubes that are 3" in diameter, 16" tall, and with wall thickness of 0.03" (Item No. 484485, Visipack Fenton Mo.); the tubes are covered with nylon mesh to isolate the insects. The plants are kept under normal temperature, light, and watering conditions in a conviron. In 14 days, the insects are collected and weighed; percent mortality as well as growth inhibition (1−weight treatment/weight control) are calculated. YFP hairpin-expressing plants are used as controls.

The pRNAi *Arabidopsis* $T_1$ plants are selected and grown in greenhouse, as described above. One to 5 newly emerged BSB adults are released on each plant and the entire plant is covered as described above to prevent adults from escaping. One week after release, female adults are recovered from each plant and maintained in the laboratory for egg collection. Depending on the parental RNAi target and expected phenotype, parameters such as number of eggs per female, percent egg hatch and nymph mortality are recorded and compared with control plants.

$T_2$ *Arabidopsis* Seed Generation and $T_2$ Bioassays.

T2 seed is produced from selected low copy (1-2 insertions) events for each construct. Plants (homozygous and/or heterozygous) are subjected to *E. heros* nymph and adult feeding bioassay, as described above. $T_3$ seed is harvested from homozygotes and stored for future analysis.

Example 13: Transformation of Additional Crop Species

Cotton is transformed with brahma, mi-2, iswi-1, iswi-2, chd1, ino80, and/or domino (with or without a chloroplast transit peptide) to provide control of stink bugs by utilizing a method known to those of skill in the art, for example, substantially the same techniques previously described in EXAMPLE 14 of U.S. Pat. No. 7,838,733, or Example 12 of PCT International Patent Publication No. WO 2007/053482.

Example 14: pRNAi-Mediated Insect Protection

Parental RNAi that causes egg mortality or loss of egg viability brings further durability benefits to transgenic crops that use RNAi and other mechanisms for insect protection. A basic two-patch model was used to demonstrate this utility.

One patch contained a transgenic crop expressing insecticidal ingredients, and the second patch contained a refuge crop not expressing insecticidal ingredients. Eggs were oviposited in the two modeled patches according to their relative proportions. In this example, the transgenic patch represented 95% of the landscape, and the refuge patch represented 5%. The transgenic crop expressed an insecticidal protein active against the insect.

Pest resistance to the insecticidal protein was modeled as monogenic, with two possible alleles; one (S) conferring susceptibility, and the other (R) conferring resistance. The insecticidal protein was modeled to cause 97% mortality of homozygous susceptible (SS) nymphs that feed on it. There was assumed to be no mortality of nymphs that are homozygous for the resistance allele (RR). Resistance to the insecticidal protein was assumed to be incompletely recessive, whereby the functional dominance is 0.3 (there is 67.9% mortality of nymphs that are heterozygous (RS) for resistance to the protein that feed on the transgenic crop).

The transgenic crop also expressed parentally active dsRNA that, through RNA-interference (pRNAi), causes the eggs of adult female insects that are exposed to the transgenic crop to be non-viable. Insect resistance to the pRNAi was also considered to be monogenic with two possible alleles; one (X) conferring susceptibility of the adult female to RNAi, and the other (Y) conferring resistance of the adult female to RNAi. Assuming a high level of exposure to the dsRNAs, the pRNAi was modeled to cause 99.9% of eggs produced by a homozygous susceptible (XX) female to be non-viable. The model assumed that pRNAi has no effect on the viability of eggs produced by homozygous resistant (YY) females. Resistance to the dsRNA was assumed to be recessive, whereby the functional dominance is 0.01 (98.9% of eggs produced by a female that is heterozygous (XY) for resistance to dsRNA are non-viable).

In the model, there was random mating among surviving adults and random oviposition across the two patches in accordance with their relative proportions. The genotypic frequencies of viable offspring followed Mendelian genetics for a two-locus genetic system.

The effect of pRNAi required the adult females to feed on plant tissue expressing parental active dsRNA. The interference with egg development may be lower for adult females emerging from the refuge crop than from the transgenic crop; adults are expected to feed more extensively in the patch in which they emerged following nymph development. Therefore, the relative magnitude of the pRNAi effect on female adults emerging from the refuge patch was varied, with the proportion of the pRNAi effect ranging from 0 (no effect of pRNAi on adult females emerging from the refuge patch) to 1 (same effect of pRNAi on adult females emerging from the refuge patch as on adult females emerging from the transgenic patch).

This model could be easily adjusted to demonstrate the situation when the effect of pRNAi is also or alternatively achieved by feeding of adult males on plant tissue expressing parental active dsRNA.

Figure 8:
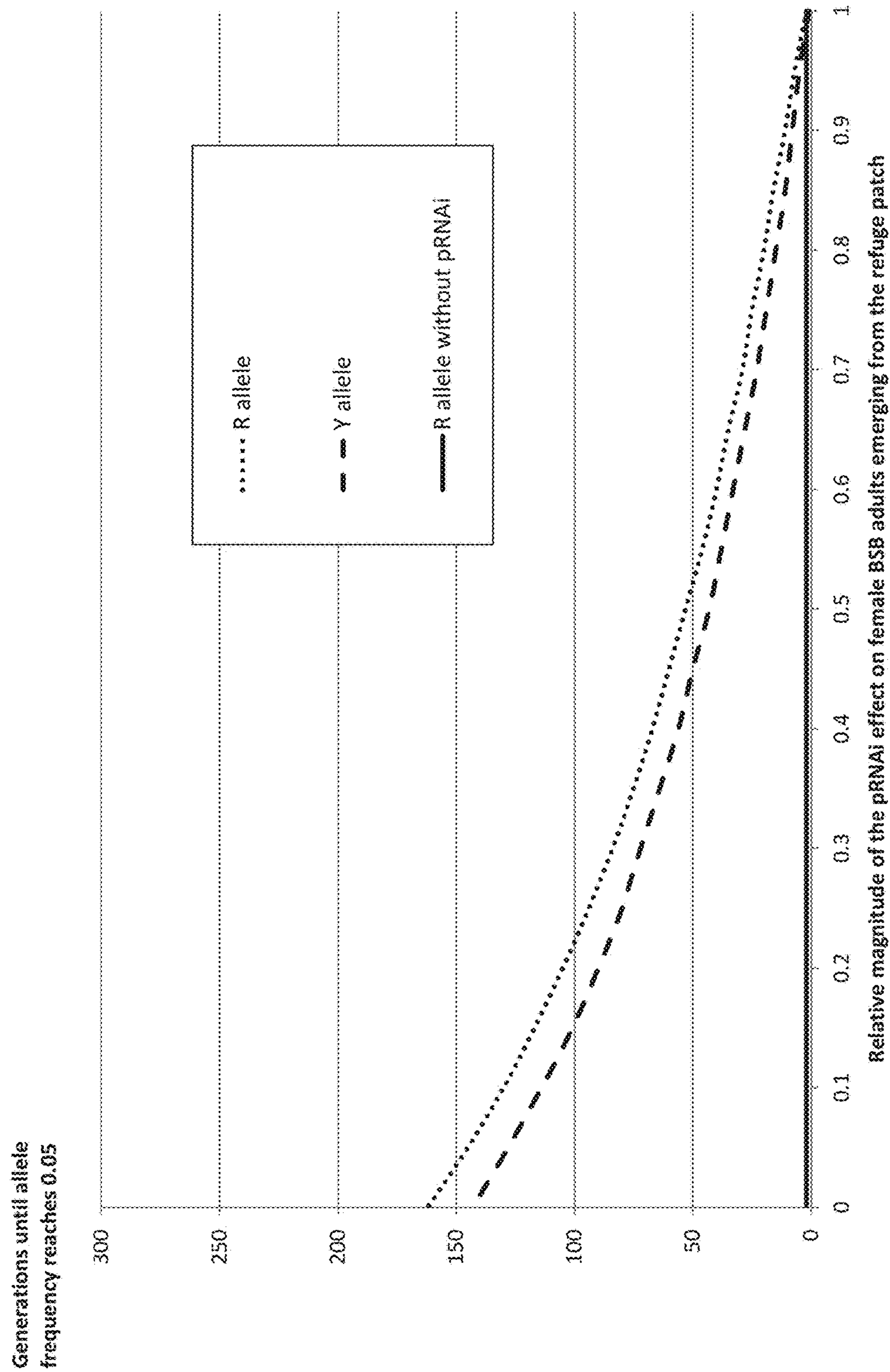
FIG. 8 includes a summary of modeling data showing the relative magnitude of a pRNAi effect on female BSB adults emerging from a "refuge patch" (i.e., that did not express insecticidal iRNAs or recombinant proteins in a transgenic crop).

Frequencies of the two resistance alleles were calculated across generations. The initial frequencies of both of the resistance alleles (R and Y) were assumed to be 0.005. Results were presented as the number of insect generations for the frequencies of each of the resistance alleles to reach 0.05. To examine the resistance delay caused by the pRNAi, simulations that included pRNAi were compared to simulations that did not include pRNAi, but were identical in every other way. FIG. 8.

Figure 9:
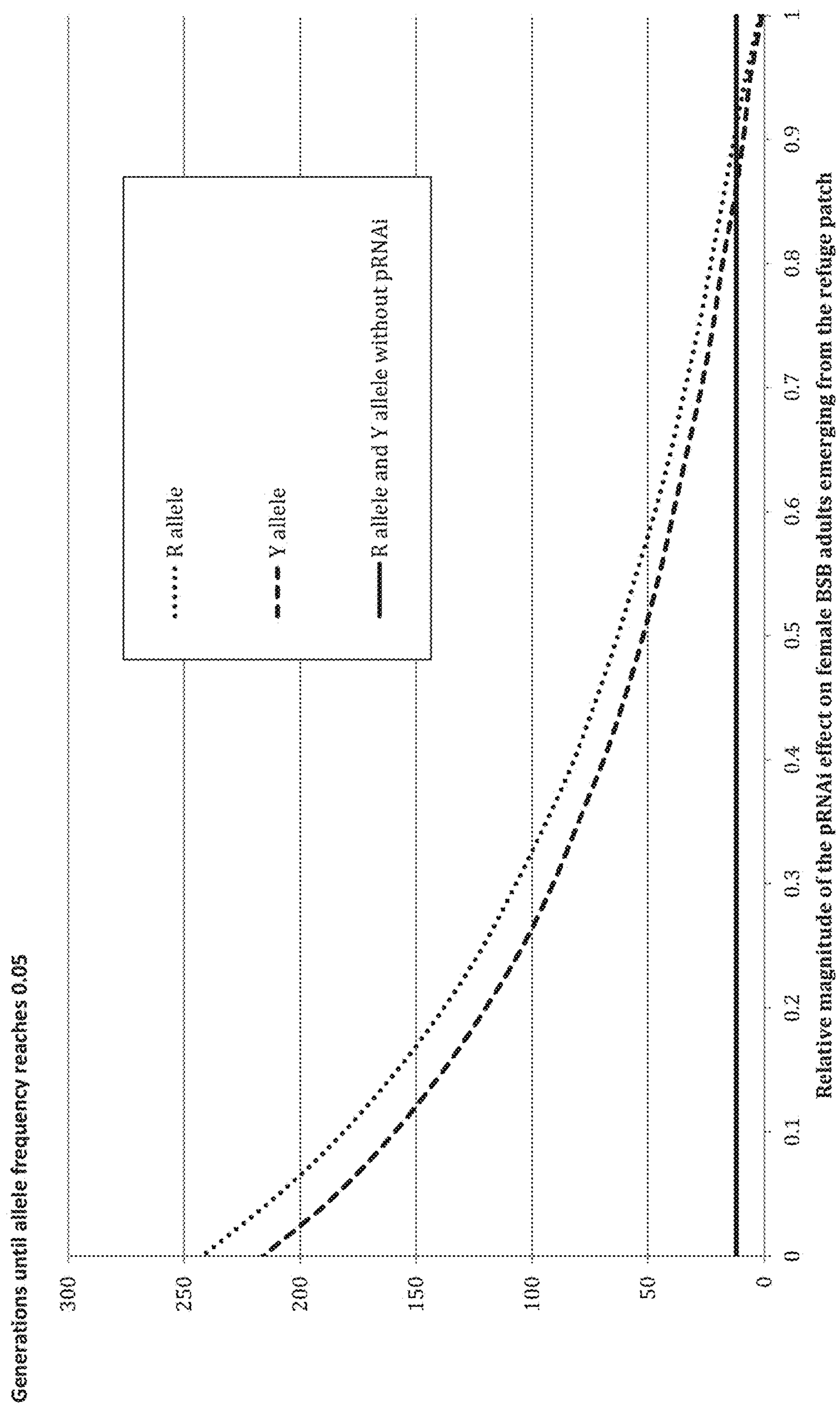
FIG. 9 includes a summary of modeling data showing the relative magnitude of a pRNAi effect on female BSB adults emerging from a "refuge patch" (i.e., that did not express insecticidal iRNAs or recombinant proteins in a transgenic crop of plants comprising BSB nymph-active interfering dsRNA in combination with the BSB-active insecticidal protein in the transgenic crop).

The model was also modified to include nymph-active interfering dsRNA in combination with the BSB-active insecticidal protein in the transgenic crop. Therein, the nymph RNAi was assigned an effect of 97% nymph mortality for homozygous RNAi-susceptible nymphs (genotype XX), and no effect on nymphs that are homozygous RNAi-resistant (YY). There was 67.9% mortality of nymphs that were heterozygous for RNAi-resistance (XY). It was assumed that the same mechanism of resistance applied to both nymph active RNAi and pRNAi. As before, the pRNAi effect on adult females emerging from the refuge patch relative to the effect on adult females emerging from the transgenic patch was varied from 0 to 1. As before, to examine the resistance delay caused by the pRNAi, simulations that included pRNAi were compared to simulations that did not include pRNAi, but were identical in every other way (including nymph RNAi). FIG. 9.

A clear resistance management benefit of pRNAi was observed when the magnitude of the pRNAi effect on egg viability for female adults emerging from the refuge patch was reduced compared with magnitude of the effect for adults emerging from the transgenic patch. The transgenic crops that produced parental active dsRNA in addition to an insecticidal protein were much more durable compared with transgenic crops that produced only an insecticidal protein. Similarly, transgenic crops that produced parental active dsRNA in addition to both an insecticidal protein and a nymph active dsRNA were much more durable compared with transgenic crops that produced only an insecticidal protein and a larval active dsRNA. In the latter case, the durability benefit applied to both the insecticidal protein and the insecticidal interfering dsRNA.

What may be claimed is:

1. An isolated nucleic acid molecule comprising a polynucleotide operably linked to a heterologous promoter, wherein the polynucleotide encode a double-stranded ribonucleic acid (dsRNA) molecule, the polynucleotide comprising:

a first nucleotide sequence selected from the group consisting of: SEQ ID NO:1; SEQ ID NO:63; the complement of SEQ ID NO:1; the complement of SEQ ID NO:63; at least 26 contiguous nucleotides of SEQ ID NO:1; the complement of at least 26 contiguous nucleotides of SEQ ID NO:1; at least 26 contiguous nucleotides of SEQ ID NO:63; the complement of at least 26 contiguous nucleotides of SEQ ID NO:63; at least 26 contiguous nucleotides of a native coding sequence of *Euschistus heros* comprising SEQ ID NO:3; the complement of at least 26 contiguous nucleotides of a native coding sequence of *Euschistus heros* comprising SEQ ID NO:3; at least 23 contiguous nucleotides of SEQ ID NO:3; and the complement of at least 23 contiguous nucleotides of SEQ ID NO:3;

a second nucleotide sequence; and a third nucleotide sequence that is the reverse complement of the first nucleotide sequence, wherein the third nucleotide sequence is linked to the first nucleotide sequence by the second nucleotide sequence.

2. The nucleic acid molecule of claim 1, wherein the heterologous promoter is functional in a plant cell, and wherein the molecule is a plant transformation vector.

3. The nucleic acid molecule of claim 1, wherein the polynucleotide comprises at least 23 contiguous nucleotides of SEQ ID NO:3 or the complement of at least 23 contiguous nucleotides of SEQ ID NO:3.

4. The nucleic acid molecule of claim 1, wherein the heterologous promoter is functional in a plant cell.

5. A double-stranded ribonucleic acid (dsRNA) molecule comprising a first, a second, and a third ribonucleotide sequence, wherein the first ribonucleotide sequence is SEQ ID NO:43; SEQ ID NO:68; the complement of SEQ ID NO:43; the complement of SEQ ID NO:68; at least 26 contiguous nucleotides of SEQ ID NO:43; the complement of at least 26 contiguous nucleotides of SEQ ID NO:43; at least 26 contiguous nucleotides of SEQ ID NO:68; the complement of at least 26 contiguous nucleotides of SEQ ID NO:68; at least 26 contiguous nucleotides of a native messenger RNA (mRNA) of *Euschistus heros* comprising SEQ ID NO:44; the complement of at least 26 contiguous nucleotides of a native mRNA of *Euschistus heros* comprising SEQ ID NO:44; at least 23 contiguous nucleotides of SEQ ID NO:44; and complement of at least 23 contiguous nucleotides of SEQ ID NO:44, wherein the third ribonucleotide sequence is linked to the first ribonucleotide sequence by the second ribonucleotide sequence, and wherein the third ribonucleotide sequence is substantially the reverse complement of the first ribonucleotide sequence, such that the first and the third ribonucleotide sequences hybridize in the stem of a hairpin structure in the molecule.

6. The dsRNA molecule of claim 5, wherein the first ribonucleotide sequence comprises at least 26 contiguous nucleotides of a ribonucleotide sequence selected from the group consisting of SEQ ID NO:43, the complement of SEQ ID NO:43, SEQ ID NO:68, and the complement of SEQ ID NO:68.

7. A prokaryotic cell comprising the nucleic acid molecule of claim 1.

8. A eukaryotic cell comprising the nucleic acid molecule of claim 1.

9. A plant cell comprising the nucleic acid molecule of claim 4.

10. A transgenic plant comprising the plant cell of claim 9.

11. A seed of the plant of claim 10, wherein the seed comprises the polynucleotide.

12. A commodity product produced from the plant of claim 10, wherein the commodity product comprises a detectable amount of the polynucleotide.

13. The plant cell of claim 9, wherein the cell is a *Zea mays* cell, a *Glycine max* cell, or a cell from a *Gossypium* sp.

14. The transgenic plant of claim 10, wherein the plant is maize, soybean, or cotton.

15. A method for controlling a *Euschistus heros* insect pest population, the method comprising feeding an insect of the population with an agent comprising the dsRNA molecule of claim 5.

16. The method according to claim 15, wherein the insect pest is a male *Euschistus heros* insect pest.

17. The method according to claim 15, wherein the insect pest is a female *Euschistus heros* insect pest, the method further comprising releasing the female *Euschistus heros* insect pest into the pest population.

18. The method according to claim 15, wherein the agent is a sprayable formulation.

19. The method according to claim 15, wherein the agent is a *Euschistus heros* host plant or a part thereof, comprising a polynucleotide that is expressed in the plant to produce the dsRNA molecule.

20. A method for improving the yield of a corn, soybean, or cotton crop, the method comprising:

cultivating in the crop the transgenic plant of claim 10.

21. The method according to claim 20, wherein the transgenic plant is a corn, soybean, or cotton plant.

22. A method for producing a transgenic plant cell, the method comprising:

transforming a plant cell with the nucleic acid molecule of claim 4;

culturing the transformed plant cell under conditions sufficient to allow for development of a plant cell culture comprising a plurality of plant cells comprising the polynucleotide; and selecting a transgenic plant cell that has integrated the polynucleotide into its genome, and that expresses the dsRNA molecule.

23. A method for producing a transgenic plant, the method comprising:

regenerating a transgenic plant from the plant cell of claim 9.

24. The nucleic acid molecule of claim 1, further comprising a polynucleotide encoding an insecticidal polypeptide from *Bacillus thuringiensis, Alcaligenes* spp., or *Pseudomonas* spp.

25. The nucleic acid molecule of claim 24, wherein the insecticidal polypeptide is from *B. thuringiensis*, and is selected from a group comprising Cry1A, Cry2A, Cry3A, Cry11A, and Cry51A.

26. The plant cell of claim 9, wherein the cell comprises a polynucleotide encoding an insecticidal polypeptide from *Bacillus thuringiensis, Alcaligenes* spp., or *Pseudomonas* spp.

27. The plant cell of claim 26, wherein the insecticidal polypeptide is from *B. thuringiensis*, and is selected from a group comprising Cry1A, Cry2A, Cry3A, Cry11A, and Cry51A.

28. The transgenic plant of claim 10, wherein the plant comprises a polynucleotide encoding an insecticidal polypeptide from *Bacillus thuringiensis, Alcaligenes* spp., or *Pseudomonas* spp.

29. The transgenic plant of claim 28, wherein the insecticidal polypeptide is from *B. thuringiensis*, and is selected from a group comprising Cry1A, Cry2A, Cry3A, Cry11A, and Cry51A.

30. The method according to claim 15, wherein the method further comprises feeding the insect of the population with an insecticidal polypeptide from *Bacillus thuringiensis, Alcaligenes* spp., or *Pseudomonas* spp.

31. The method according to claim 30, wherein the insecticidal polypeptide is from *B. thuringiensis*, and is selected from a group comprising Cry1A, Cry2A, Cry3A, Cry11A, and Cry51A.

* * * * *